(12) United States Patent
Parsai et al.

US009682246B2

(10) Patent No.: US 9,682,246 B2
(45) Date of Patent: Jun. 20, 2017

(54) SYSTEM FOR CONCURRENT DELIVERY OF THERMOBRACHYTHERAPY IN THE TREATMENT OF CANCERS

(75) Inventors: E. Ishmael Parsai, Sylvania, OH (US); John J. Feldmeier, Monroe, MI (US)

(73) Assignee: The University of Toledo, Toledo, OH (US)

( * ) Notice: Subject to any disclaimer, the term of this patent is extended or adjusted under 35 U.S.C. 154(b) by 496 days.

(21) Appl. No.: 13/126,012

(22) PCT Filed: Oct. 28, 2009

(86) PCT No.: PCT/US2009/062430
§ 371 (c)(1),
(2), (4) Date: Apr. 26, 2011

(87) PCT Pub. No.: WO2010/051322
PCT Pub. Date: May 6, 2010

(65) Prior Publication Data
US 2011/0200526 A1 Aug. 18, 2011

Related U.S. Application Data

(60) Provisional application No. 61/109,105, filed on Oct. 28, 2008.

(51) Int. Cl.
*A61K 51/12* (2006.01)
*A61N 1/40* (2006.01)
*A61N 5/10* (2006.01)

(52) U.S. Cl.
CPC ........... *A61N 1/406* (2013.01); *A61N 5/1027* (2013.01); *A61N 2005/1024* (2013.01)

(58) Field of Classification Search
None
See application file for complete search history.

(56) References Cited

U.S. PATENT DOCUMENTS

| | | | |
|---|---|---|---|
| 5,163,896 A * | 11/1992 | Suthanthiran | A61K 51/1282 600/8 |
| 5,976,067 A | 11/1999 | Tucker et al. | |
| 6,074,337 A | 6/2000 | Tucker et al. | |
| 6,440,058 B1 | 8/2002 | Cutrer | |
| 6,497,647 B1 | 12/2002 | Tucker | |
| 6,746,661 B2 | 6/2004 | Kaplan | |
| 2003/0088145 A1 | 5/2003 | Scott | |
| 2003/0097035 A1 | 5/2003 | Tucker et al. | |
| 2008/0086026 A1 | 4/2008 | Keppel et al. | |

FOREIGN PATENT DOCUMENTS

WO 2010051322 A1 5/2010

OTHER PUBLICATIONS

PCT International Search Report and the Written Opinion, PCT/US09/62430 filed Oct. 28, 2009, dated Dec. 14, 2009, 53-50054.
PCT International Preliminary Report on Patentability, PCT/US09/062430 filed Oct. 28, 2009, dated May 12, 2011, 53-50054.
Parsai et al., "A Quantitative Dose Attenuation Analysis Around Fletcher-Suite Device Due to Stainless Steel Tube for HDR Brachytherapy: Monte Carlo Calculations and MOSFET Measurements", 48th AAPM Annual Meeting, Orlando, FL, Jul. 30, 2006-Aug. 3, 2006, Abstract Information, Meeting Abstract, AbstractID:5539, 2 pages.
Zhang et al., "A Three Dimensional Quantitative Dose Reduction Analysis in MammoSite Balloon Due to Radiopaque Iodine-based Contrast Solution in Ir-192 for HDR Brachytherapy: Monte Carlo Calculations and MOSFET Measurements", 48th AAPM Annual Meeting, Orlando, FL, Jul. 30, 2006-Aug. 3, 2006, Abstract Information, Meeting Abstract, AbstractID:4374, 2 pages.
Shvydka et al., "Investigating Thermal Properties of a Thermobrachytherapy Radioactive Seed for Concurrent Brachytherapy and Hyperthermia Treatments: Design Considerations", 51st AAPM Annual Meeting, Anaheim, California, Jul. 26, 2009-Jul. 30, 2009, Abstract Information, Meeting Abstract, AbstractID:11253, 2 pages.
Khan et al., "Investigating Radiation Properties of a New Radioactive Seed for Concurrent Brachytherapy and Hyperthermia Treatments: A Monte Carlo Study", 51st AAPM Annual Meeting, Anaheim, California, Jul. 26, 2009-Jul. 30, 2009, Abstract Information, Meeting Abstract, AbstractID:11616, 2 pages.
Nadeem Khan, "Dosimetric Calculation of a Thermo Brachytherapy Seed: a Monte Carlo Study", Thesis and Dissertations, The University of Toledo, Paper 1201, dated 2008, released on Dec. 18, 2008, pp. 1-172, and 2 introductory pages.
The University of Toledo Digital Repository, Information and Details, including Summary, re: Nadeem Khan, "Dosimetric Calculation of a Thermo Brachytherapy Seed: a Monte Carlo Study", Thesis and Dissertations, The University of Toledo, Paper 1201, 2008, 4 pages.
Parsai et al., "A Quantitative Three-Dimensional Dose Attenuation Analysis Around Fletcher-Suit-Delclos due to Stainless Steel Tube for High-Dose-Rate Brachytherapy by Monte Carlo Calculations", Brachytherapy, Jul.-Sep. 2009, vol. 8, Issue 3, pp. 318-323, and Abstract, 2 pages.
Zhang et al., "A Three Dimensional Quantitative Dose Reduction Analysis in MammoSite Balloon Due to Radiopaque Iodine-based Contrast Solution in Ir-192 for HDR Brachytherapy: Monte Carlo Calculations and MOSFET Measurements", and Supporting Document, AAPM, 2006, 3 pages.
Parsai et al., "A Quantitative Dose Attenuation Analysis Around Fletcher-Suite Device Due to Stainless Steel Tube for HDR Brachytherapy: Monte Carlo Calculations and MOSFET Measurements", AAPM, Abstract, 2006,1 page.
Shvydka et al.,"Investigating Thermal Properties of a Thermobrachytherapy Radioactive Seed for Concurrent Brachytherapy and Hyhperthermia Treatments: Design Considerations", AAPM, poster, 2009,1 page.

(Continued)

*Primary Examiner* — David J Blanchard
*Assistant Examiner* — Daniel F Coughlin

(57) ABSTRACT

A system combines hyperthermia and radiation treatments in a single treatment modality by using a radioactive seed having magnetic properties.

24 Claims, 43 Drawing Sheets

(56) References Cited

OTHER PUBLICATIONS

Khan et al., Investigating Radiation Properties of a New Radioactive Seed for Concurrent Brachytherapy and Hyperthermia Treatments: A Monte Carlo Study, AAPM, poster, 2009, 1 page.

* cited by examiner

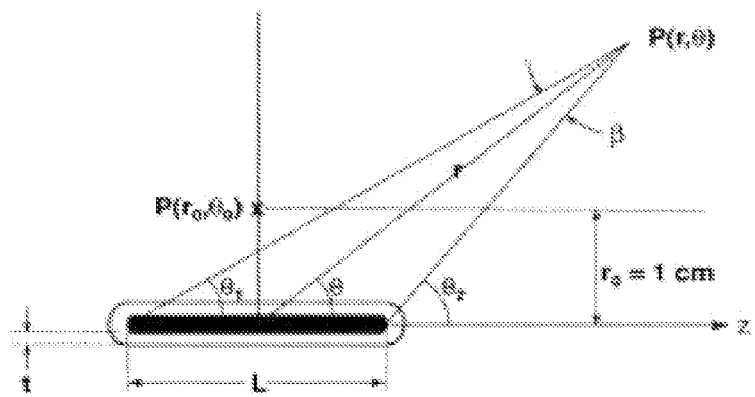
Figure 1
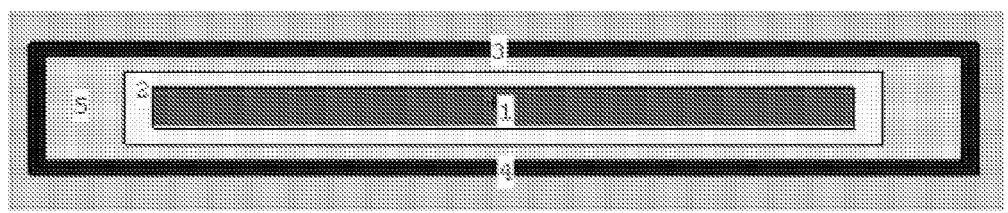
Figure 2 - Prior Art
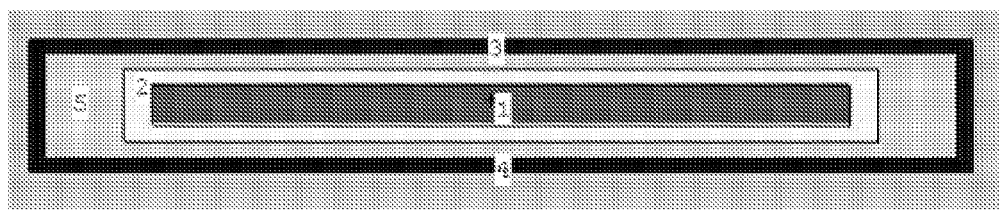
Figure 3
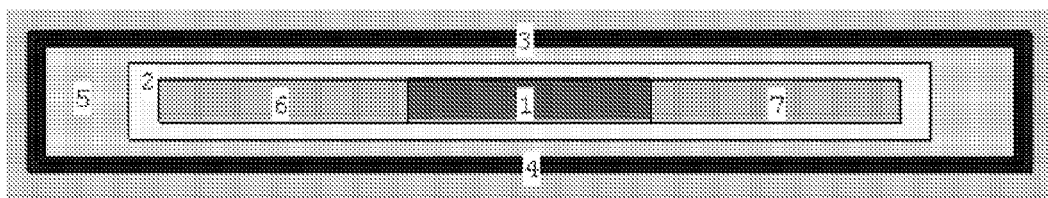
Figure 4

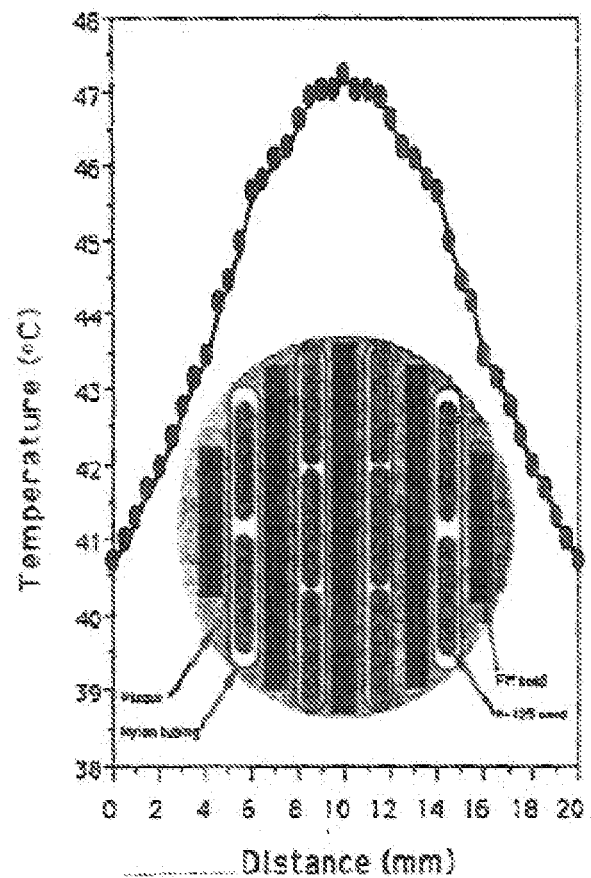
Prior Art Figure 79
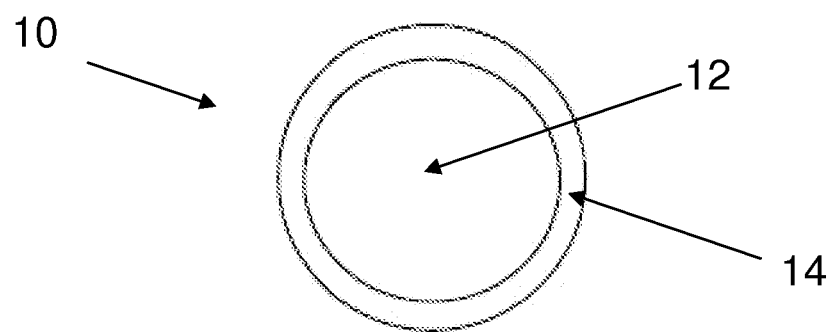
Figure 80

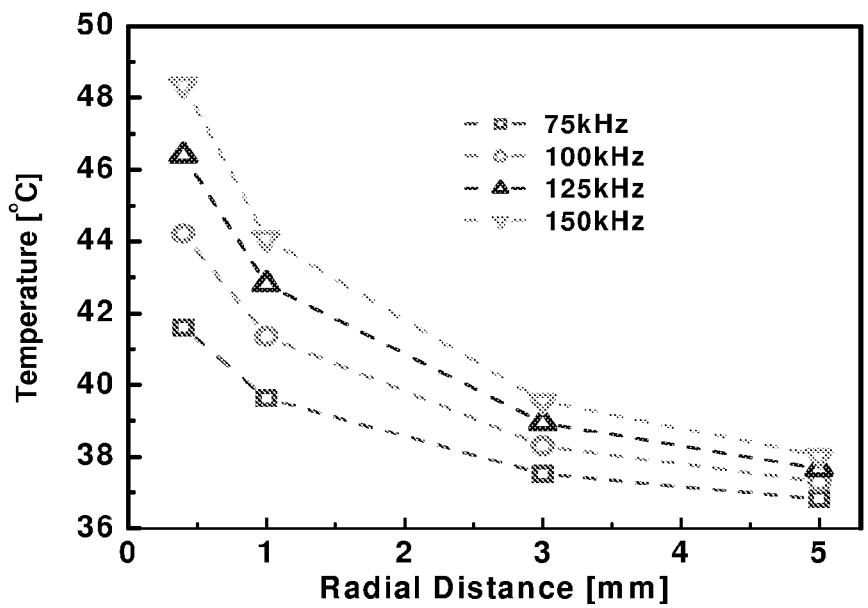
Figure 81
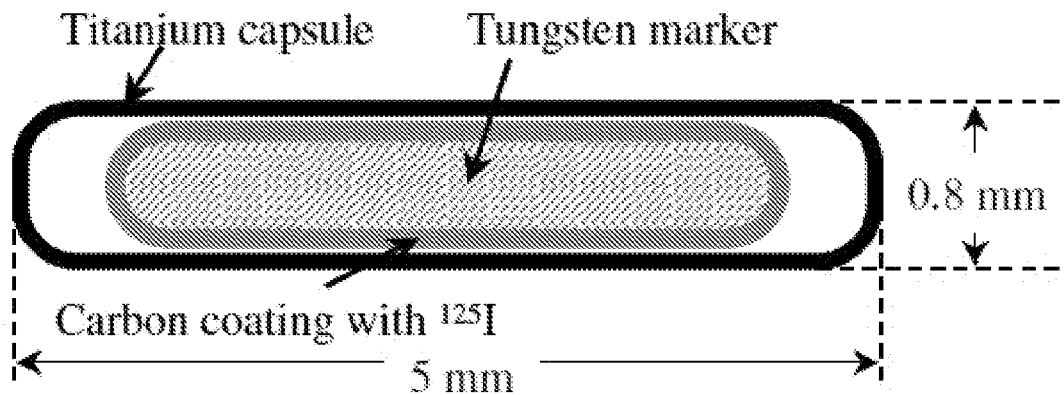
Figure 82A - Prior Art
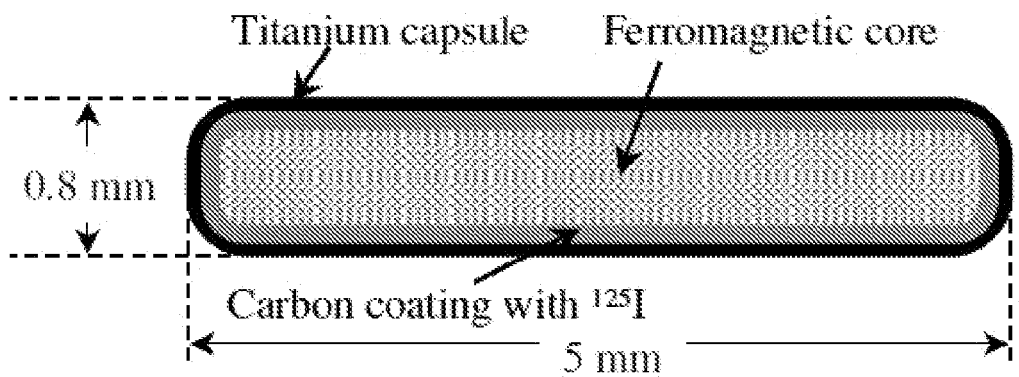
Figure 82B

SYSTEM FOR CONCURRENT DELIVERY OF THERMOBRACHYTHERAPY IN THE TREATMENT OF CANCERS

CROSS-REFERENCE TO RELATED APPLICATIONS AND STATEMENT REGARDING SPONSORED RESEARCH

The present invention claims the benefit of the PCT/US2009/062430 filed Oct. 28, 2009, which claims priority to the provisional patent application Ser. No. 61/109,105 filed Oct. 28, 2008. This invention was not made with government support and the government has no rights in this invention.

BACKGROUND OF THE INVENTION

There is no admission that the background art disclosed in this section legally constitutes prior art.

Brachytherapy, or radiotherapy, is a minimally invasive treatment where radioactive sources, often called seeds, are placed directly in and/or around the tumor site such that a prescribed radiation dose to the defined treatment area.

Hyperthermia, when used in addition to brachytherapy, can have a several folds enhancement in the treatment of certain cancer types. One shortcoming, however, is that such radioactive seeds need to be removed from the patient before being exchanged for the ferromagnetic seeds.

Often, in brachytherapy, the dose of radiation required to give 50% tumor control (with $^{125}$I alone) is about 42 Gy. However, only 9.5 Gy may required to reach the same tumor control (with concurrent $^{125}$I and ferromagnetic hyperthermia) giving a thermal enhancement ratio of 4.4. Furthermore, it has been shown that 29.4 Gy is required to give the 50% tumor control (with I-125 and sequential ferromagnetic hyperthermia) giving a thermal enhancement ratio of 1.4. As can be seen, the concurrent treatments between the two modalities are more than three times more effective than a single treatment modality.

There have been different methods used to deliver such treatments. In one method, a flat plate-style device is used for the delivery of brachytherapy and hyperthermia separately. The plate-style devices are manufactured to contain pathways for radioactive seed trains and non-radioactive ferromagnetic seeds.

Therefore, there is a need for an improved and more efficient and effective system for the delivery of interstitial thermobrachytherapy in the treatment of cancer.

SUMMARY OF THE INVENTION

In a broad aspect, there is provided a system for concurrent delivery of interstitial thermobrachytherapy (including both hyperthermia and brachytherapy) in the treatment of cancers.

In another broad aspect, there is provided herein a seed for combining hyperthermia and radiation treatments in a single treatment modality, comprising a radiation emission material and a magnetic material.

In certain embodiments, the seed comprises within its interior space the magnetic material for hyperthermia, and further comprises at least one layer of the radiation emission material, wherein the at least one layer is provided internally within the seed.

In certain embodiments, the seed has substantially no void between the inner magnetic material and the layer of the radiation emission material.

In certain embodiments, the radiation emission material has an activity in the range of about 0.25 to about 0.5 millicurie.

In certain embodiments, the magnetic material generates a magnetic field in the order of about 5000 A/m and about 50 to about 100 gauss.

In certain embodiments, the radioactive material comprises one or more of I-125, Pd-103, or Cs-131 radionuclides.

In certain embodiments, the seed comprises a NiCu containing material as the magnetic material, and $^{125}$I as the radiation emission source.

In certain embodiments, the seed has at least one outer layer at least partially composed of a platinum or platinum-like materials.

In certain embodiments, the magnetic material comprises Ni—Co.

In certain embodiments, the magnetic material comprises a Ni (70.4%)-Co (29.6%) alloy.

In certain embodiments, the magnetic material comprises a palladium-cobalt (Pd—Co) allow, with concentrations of 93%-7%, correspondingly.

In certain embodiments, the seed exhibits a desired Curie point in a therapeutic range between about 40° C. and about 100° C.

In certain embodiments, the seed has a spherical, cylindrical, conical, frustroconical, ovoid, or bullet shape.

In another broad aspect, there is provided herein a system, comprising:
an implantable medical device,
the implantable medical device including a body having at least one outer surface;
the implantable medical device including one or more magnetic energy-emitting elements configured to at least intermittently deliver a therapeutic dose of heat to at least a portion of tissue proximate the at least one outer surface of the implantable medical device; and
the implantable medical device including one or more radiation-emitting elements configured to deliver a therapeutic dose of radiation to at least a portion of tissue proximate the at least one outer surface of the implantable medical device; and,
a controller configured to apply an electro-magnetic or magnetic field to the one or more implantable medical devices.

In certain embodiments, the one or more energy-emitting elements are configured to provide a sensitizing heat pattern comprising one or more of: a region of tissue treated, intensity of magnetic energy, an ON-pulse duration, an OFF-pulse duration, and pulse frequency.

In certain embodiments, the one or more magnetic energy-emitting elements are operable to emit a sufficient amount of electromagnetic radiation to increase the temperature of at least a portion of the tissue proximate the at least one outer surface of the implantable medical device by about 5° C. to about 20° C.

In certain embodiments, the seed is temperature self-regulating, allowing the power production in the magnetic material to "shut off" once a desired Curie temperature is reached, thus preventing the seed from overheating without a need for complicated feedback system.

In certain embodiments, the magnetic material comprises one or more of: a nickel-copper (Ni—Cu) alloy, comprising 70.4% Ni and 29.6% copper by weight; and, a palladium-cobalt (Pd—Co), with concentrations of 93%-7%, correspondingly.

In another broad aspect, there is provided herein a method for the treatment of a patient in need thereof, comprising: determining one or more precise locations that need to be treated in the patient; and at least temporarily inserting one or more radioactive seeds into the patient.

In certain embodiments, a hyperthermia segment of the treatment is induced through the use of a magnetic field applied to the one or more seeds in the patient.

In certain embodiments, a radiation dose is delivered through brachytherapy as long as the seed is in location in the patient.

In certain embodiments, the patient suffers from one or more cancers, such as, but not limited to: prostate, uterine, vaginal, uveal cancers, and melanoma.

In another broad aspect, there is provided herein a method of treating a patient, comprising:

positioning at least one seed within a patient;

delivering a brachytherapeutic treatment from the seed to the patient; and activating the seed, for at least a period of time, to deliver a hyperthermia treatment to the patient by exposing the seed to a magnetic field.

In certain embodiments, the hyperthermia treatment is intermittently delivered over a set period of time.

In certain embodiments, the magnetic field has a maximum flux density between about 25 gauss and about 100 gauss. In certain embodiments, the magnetic field oscillates within the range of from about 25 kHz to about 200 kHz.

In certain embodiments, the seed exhibits a Curie point in a therapeutic range between about 40° C. and about 60° C.

In certain embodiments, the method includes exposing the seed to one or more oscillating magnetic fields that range between a maximum flux density between about 25 gauss and about 100 gauss. In certain embodiments, the oscillating magnetic field has a range of frequency from about 25 kHz to 200 kHz.

In certain embodiments, the seed is exposed to more than one oscillating magnetic field in more that one treatment.

In another broad aspect, there is provided herein a method for treating a subject, which comprises:

placing proximate to one or more diseased sites within the subject one or more seeds, wherein the activity of the radiation source is not less than 3 curie;

delivering radiation dose to the diseased site; and, at least intermittently exposing the seed to a magnetic force, wherein the activity of the magnetic material increases the temperature of the diseased site.

In another broad aspect, there is provided herein a method of providing brachytherapy and hyperthermia treatment to a tissue comprising:

generating a treatment plan for the tissue to be treated, which treatment plan specifies both:

i) a dose rate of emitted radiation from a brachytherapy source to be administered to the tissue, and ii) a sensitizing heat emitted from a hyperthermia source to be administered to the tissue;

providing one or more therapeutic seeds configured for delivery of both brachytherapy and hyperthermia; and, implanting one or more seeds in or adjacent to the tissue in accordance with the treatment plan.

In certain embodiments, the method includes selectively delivering a particular magnetic force to one or more seeds in accordance with the treatment plan in order to deliver the sensitizing hyperthermia.

In certain embodiments, a radiation dose is effectively administered to a layer of tissue surrounding the seed with a thickness between about 0 mm and about 20 mm.

In certain embodiments, a radiation dose is effectively administered to a layer of tissue surrounding the seed with a thickness of about 10 mm.

In certain embodiments, the radiation dose is delivered as a single dose.

In certain embodiments, the hyperthermia comprises an external stimulus comprised at least one of: electromagnetic energy and magnetic energy. In certain embodiments, the method includes intermittently activating the magnetic material.

Various objects and advantages of this invention will become apparent to those skilled in the art from the following detailed description of the preferred embodiment, when read in light of the accompanying drawings.

BRIEF DESCRIPTION OF THE FIGURE (S)

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1 shows the coordinate system used for AAPM TG-43 factors.

Prior Art FIG. 2 is a schematic diagram of Best Model 2301 $^{125}$I, where 1 is a Tungsten Radio-opaque Marker; 2 is a Carbon containing $^{125}$I; 3 is an Air compartment; 4 is an inner Titanium capsule; and, 5 is an outer Titanium capsule.

FIG. 3 is a schematic diagram of Thermobrachytherapy Seed#1, where 1 is a Ni—Cu Ferromagnetic Material; 2 is a Carbon containing $^{125}$I; 3 is an Air compartment; 4 is an inner Titanium capsule; and 5 is an outer Titanium capsule.

FIG. 4 is a schematic diagram of Thermobrachytherapy Seed#2, where 1 is a Tungsten Radioopaque Marker; 2 is a Carbon containing $^{125}$I; 3 is an Air compartment; 4 is an inner Titanium capsule; 5 is an outer Titanium capsule; 6 is a Left Ni—Cu Ferromagnetic Material; and 7 is a Right Ni—Cu Ferromagnetic Material.

Figure 15:
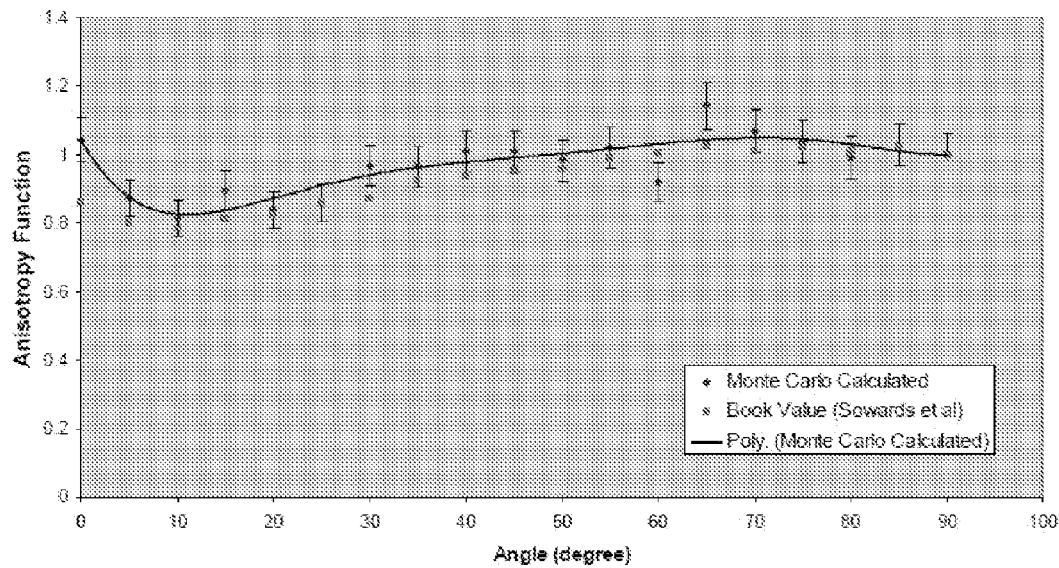

FIG. 15: The Comparison between the calculated and book value data Anisotropy Function for Best Model 2301 $^{125}$I in liquid water at 7 cm radii.

Figure 16:
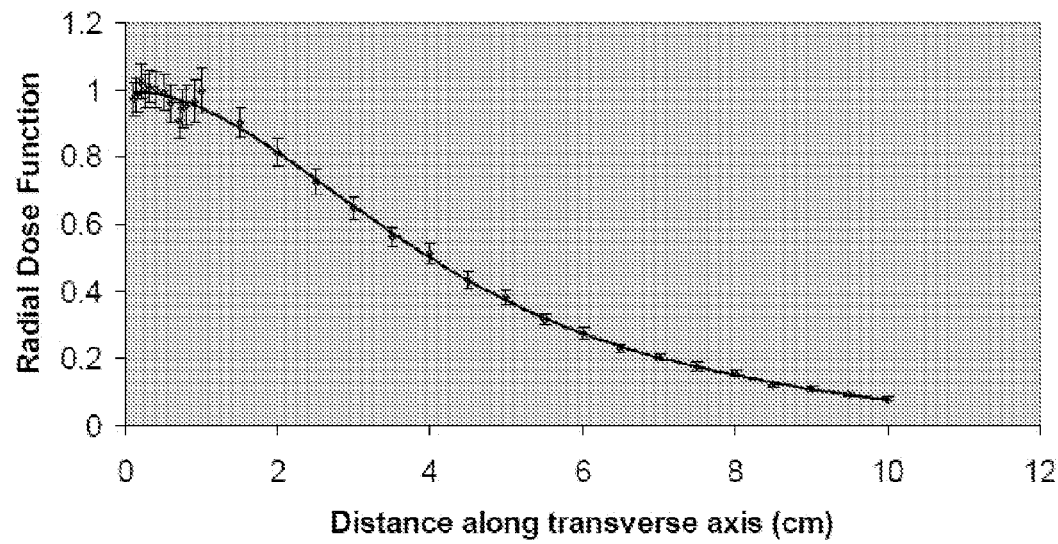

FIG. 16 is a graph for radial dose function versus distance on the transverse plane fits, which illustrates the Radial Dose Function calculated in Solid Water for the Best Model 2301 $^{125}$I Seed.

Figure 17:
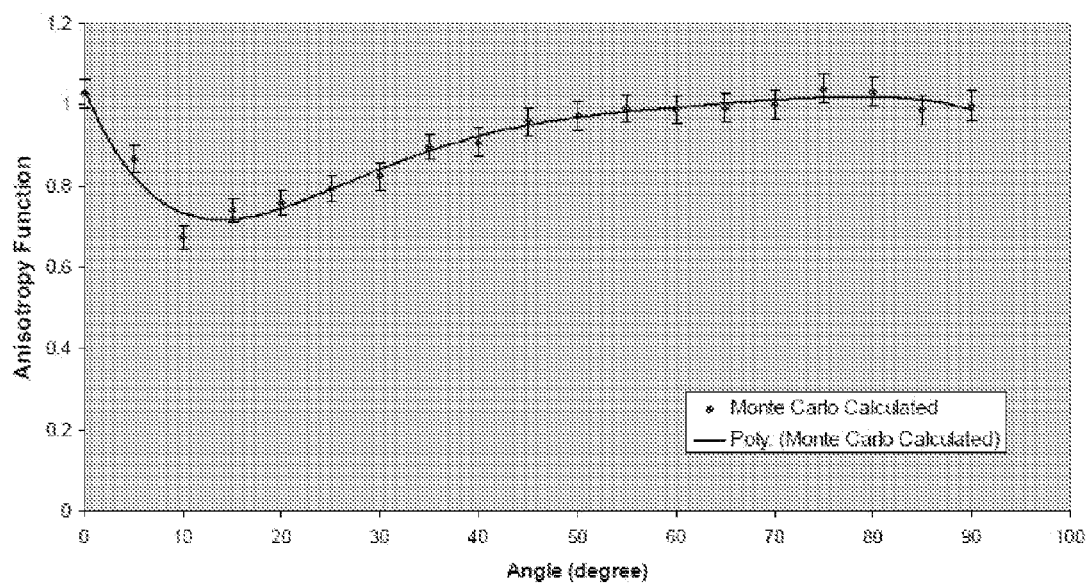

FIG. 17 illustrates Anisotropy Function of Monte Carlo calculated value for Best Model 2301 $^{125}$I in Solid Water at 1 cm radii.

Figure 18:
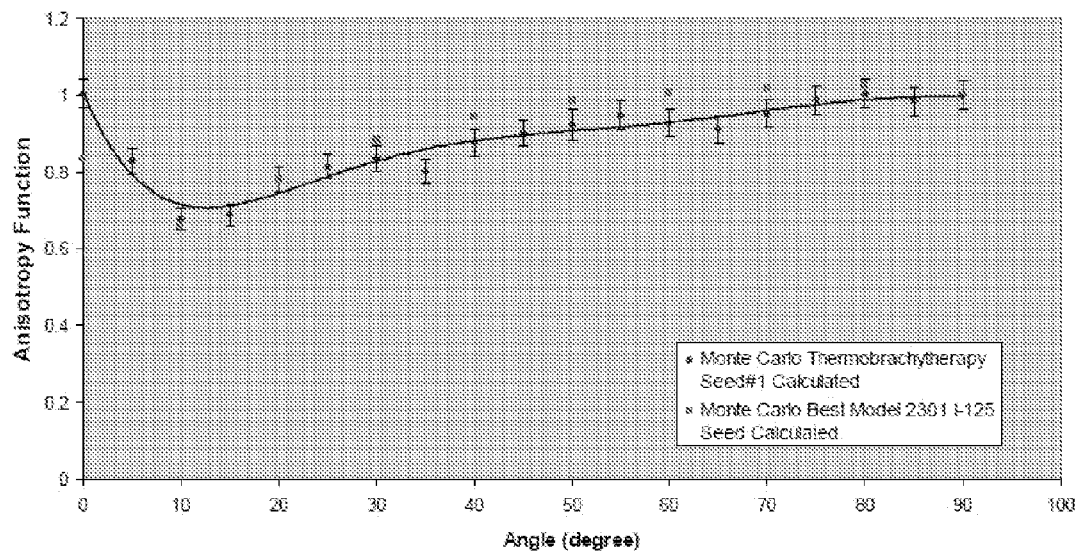

FIG. 18 illustrates the Comparison between the calculated and book value data Anisotropy Function for Best Model 2301 $^{125}$I in Solid Water at 2 cm radii.

Figure 19:
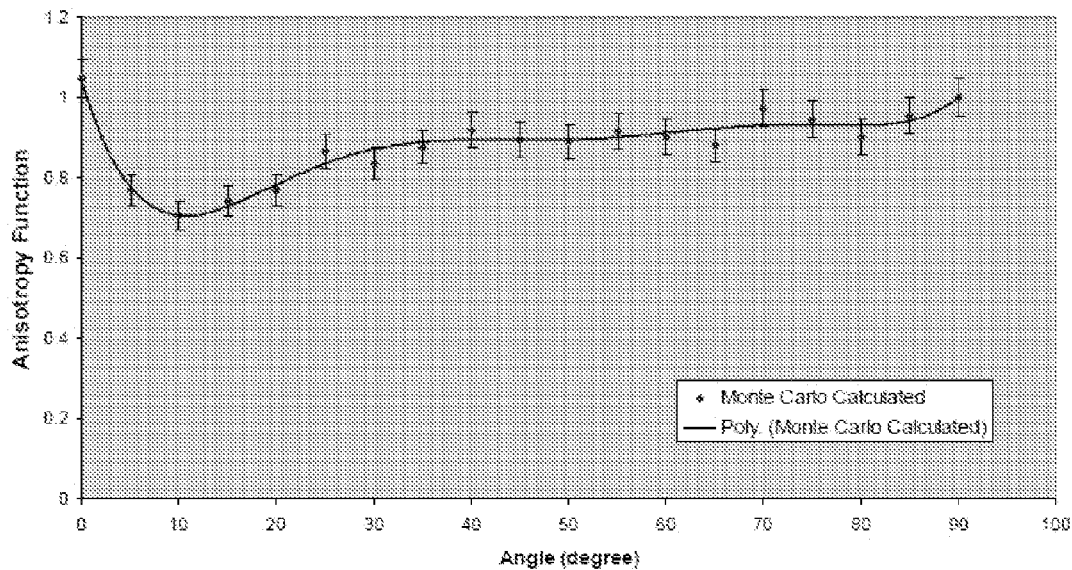

FIG. 19 illustrates Anisotropy Function of Monte Carlo calculated value for Best Model 2301 $^{125}$I in Solid Water at 3 cm radii.

Figure 20:
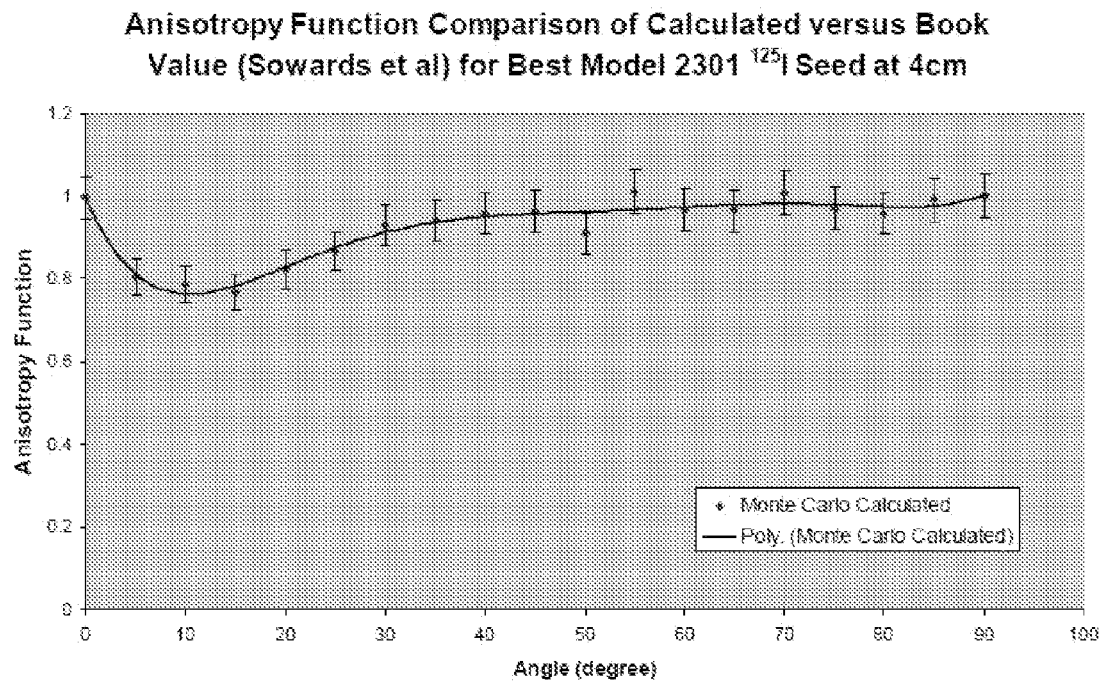

FIG. 20 illustrates Anisotropy Function of Monte Carlo calculated value for Best Model 2301 $^{125}$I in Solid Water at 4 cm radii.

Figure 21A:
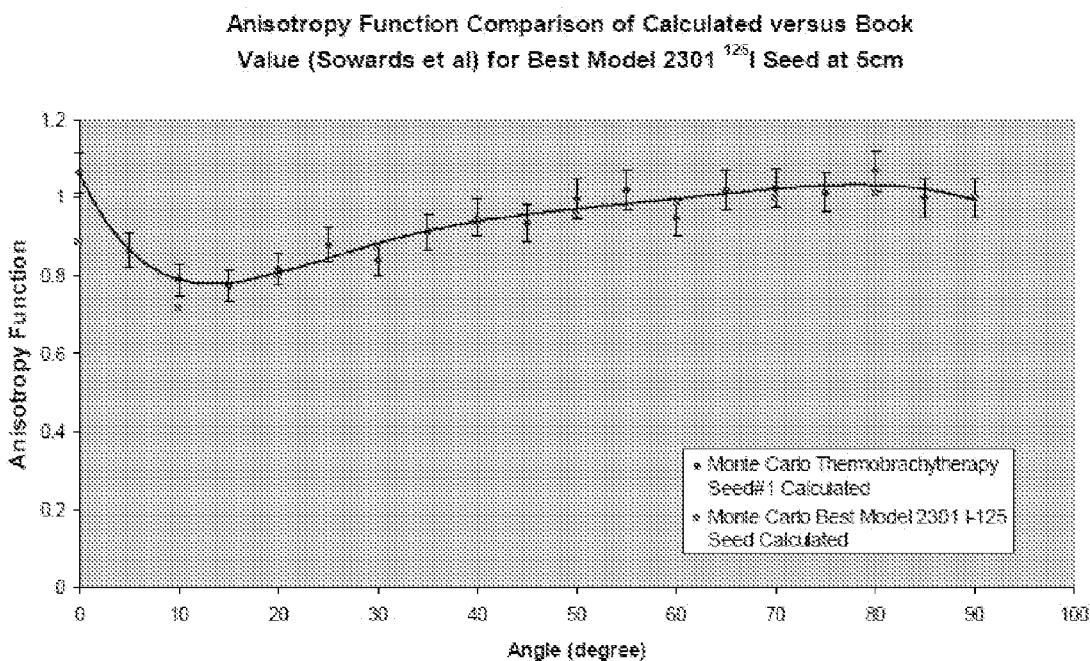

FIG. 21a illustrates the Comparison between the calculated and book value data Anisotropy Function for Best Model 2301 $^{125}$I in Solid water at 5 cm radii.

Figure 21B:
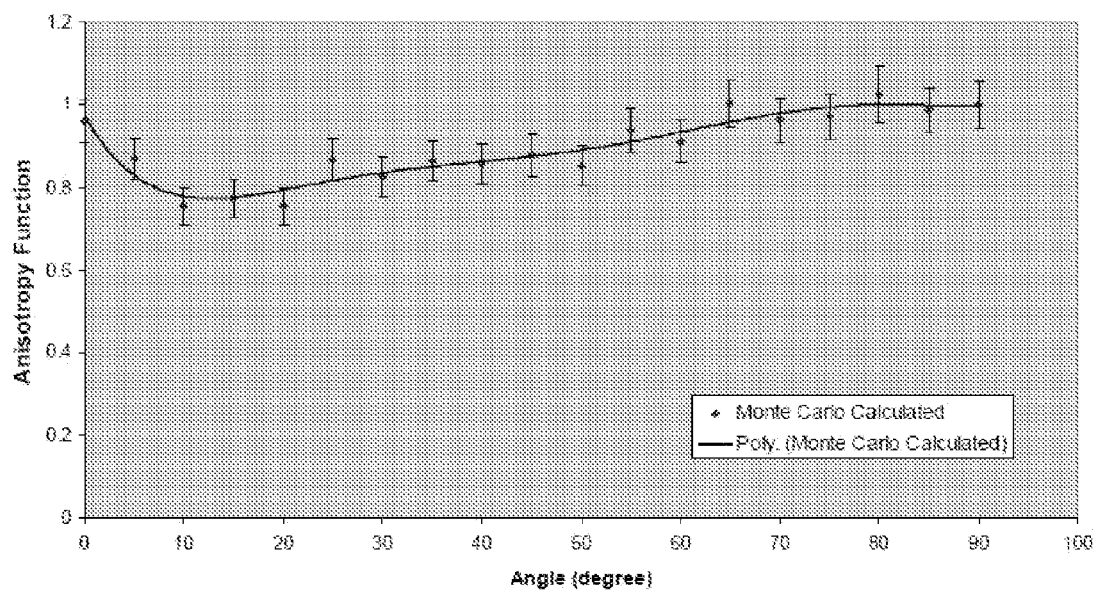

FIG. 21b illustrates Anisotropy Function of Monte Carlo calculated value for Best Model 2301 $^{125}$I in solid water at 6 cm radii.

Figure 22:
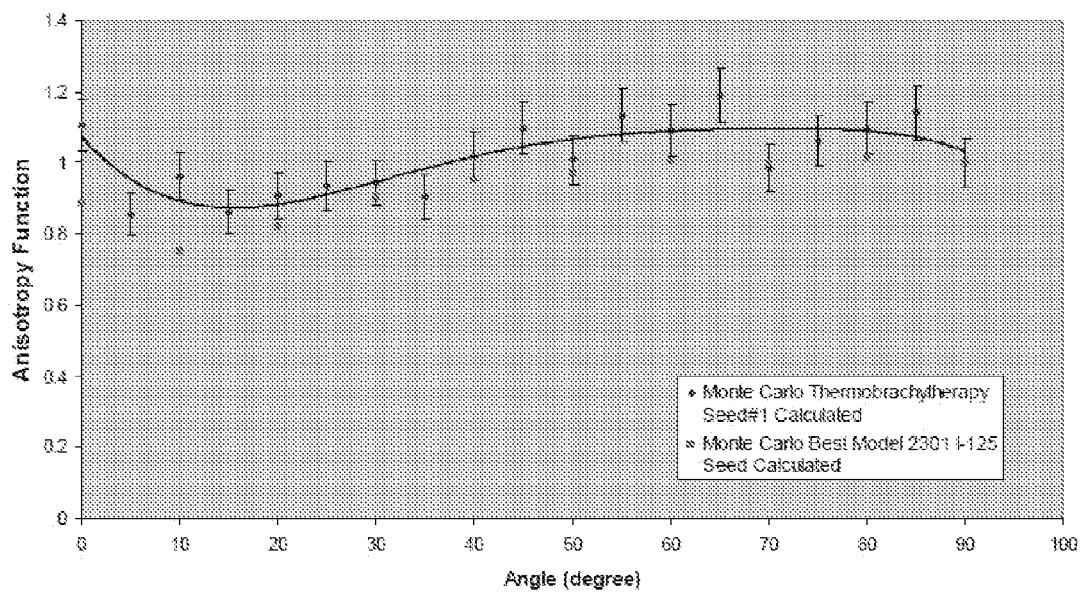

FIG. 22 illustrates Anisotropy Function of Monte Carlo calculated value for Best Model 2301 $^{125}$I in Solid Water at 7 cm radii.

Figure 23:
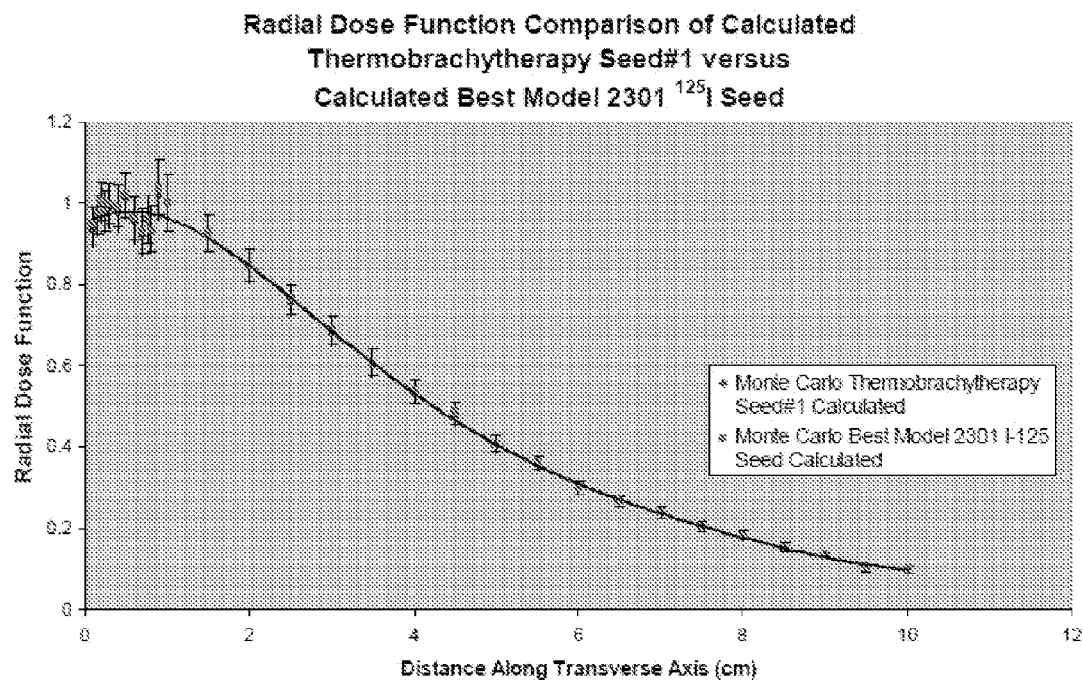

FIG. 23 illustrates the Radial Dose Function of Monte Carlo calculated value for Thermobrachytherapy Seed#1 and the Monte Carlo calculated value for the Best Model 2301 $^{125}$I in liquid water.

Figure 24:
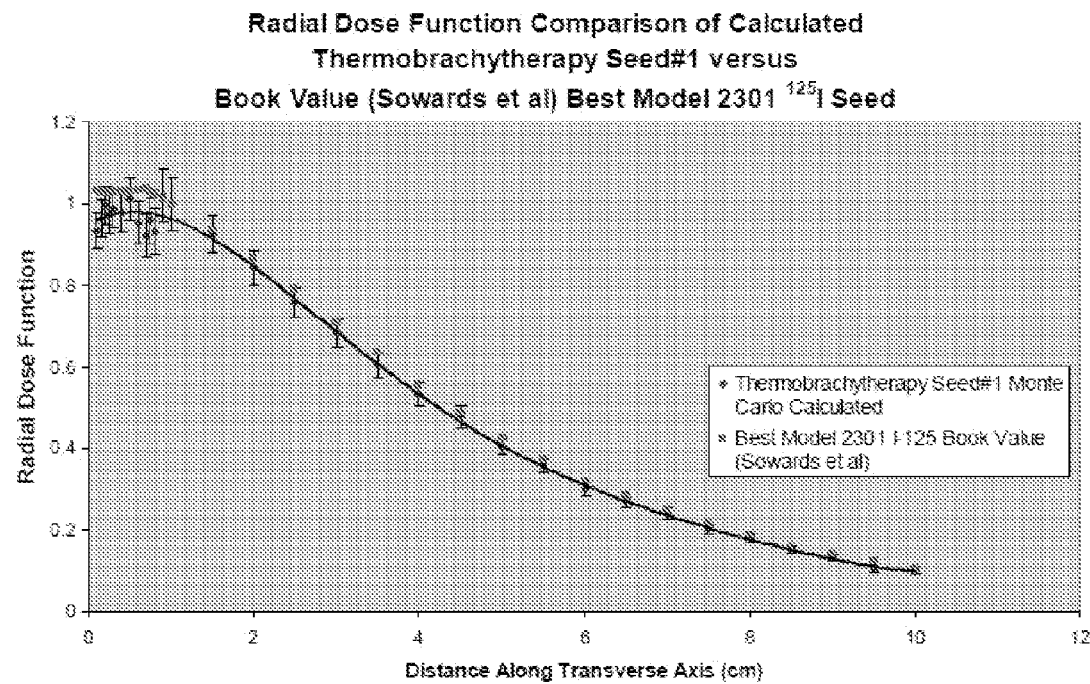

FIG. 24 illustrates the Radial Dose Function of Monte Carlo calculated value for Thermobrachytherapy Seed#1 and the Book Value for the Best Model 2301 $^{125}$I in liquid water.

Figure 25:
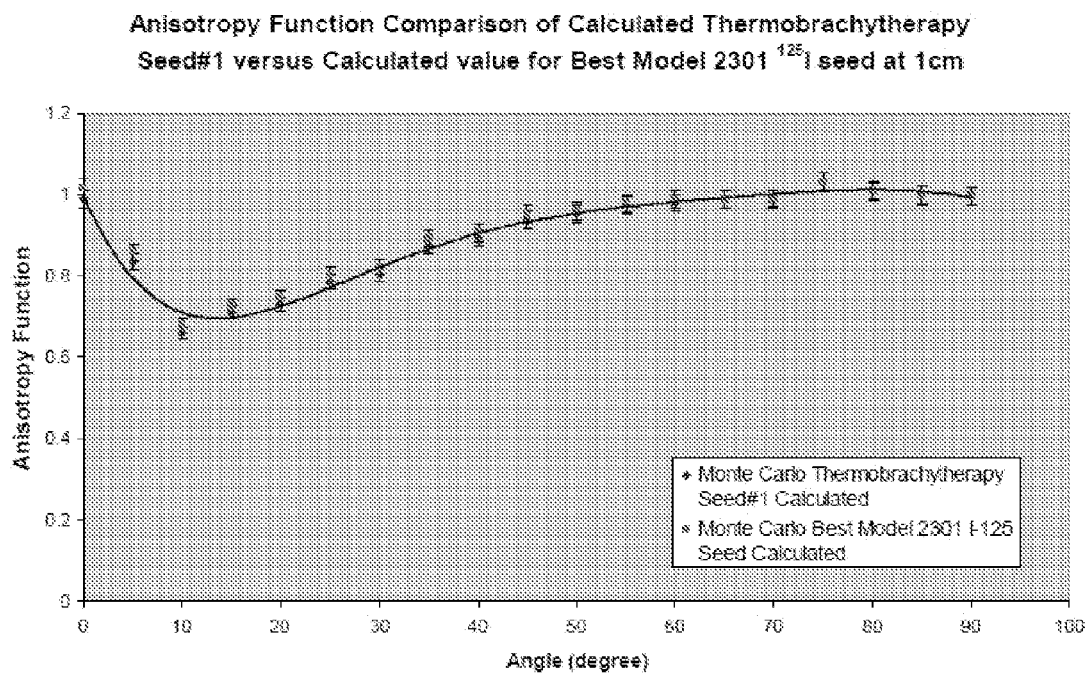

FIG. 25 illustrates the Anisotropy Function of Monte Carlo calculated value for Thermobrachytherapy Seed#1 and the Monte Carlo calculated value for the Best Model 2301 $^{125}$I in liquid water at 1 cm radii.

Figure 26:
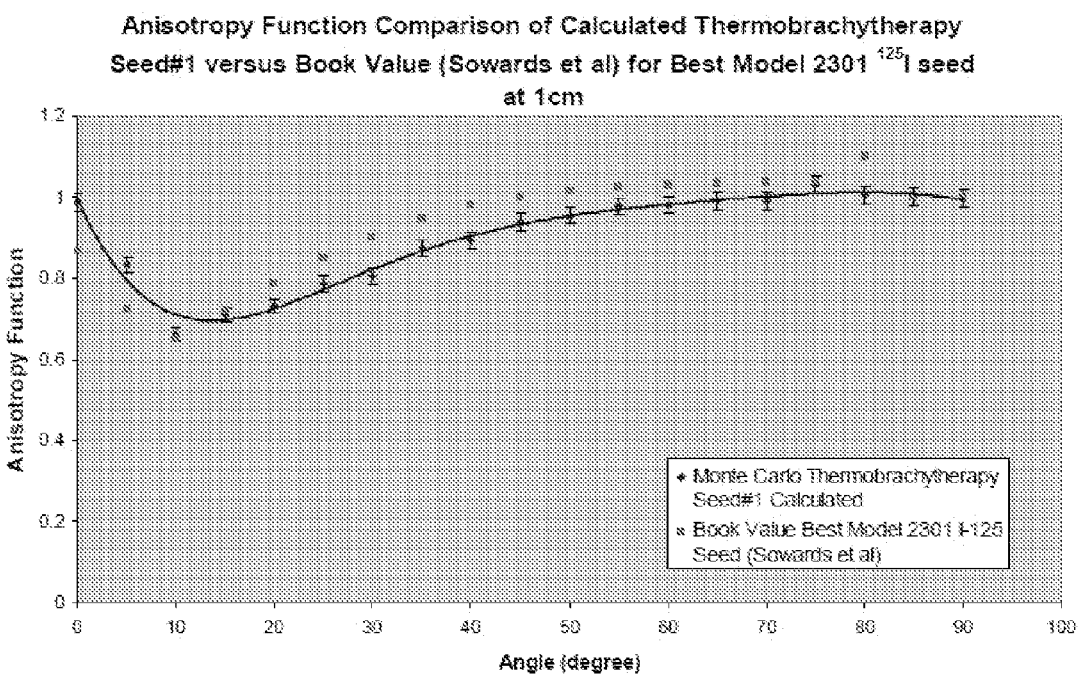

FIG. 26 illustrates the Anisotropy Function of Monte Carlo calculated value for Thermobrachytherapy Seed#1 and the Book Value for the Best Model 2301 $^{125}$I in liquid water at 1 cm radii.

Figure 27:
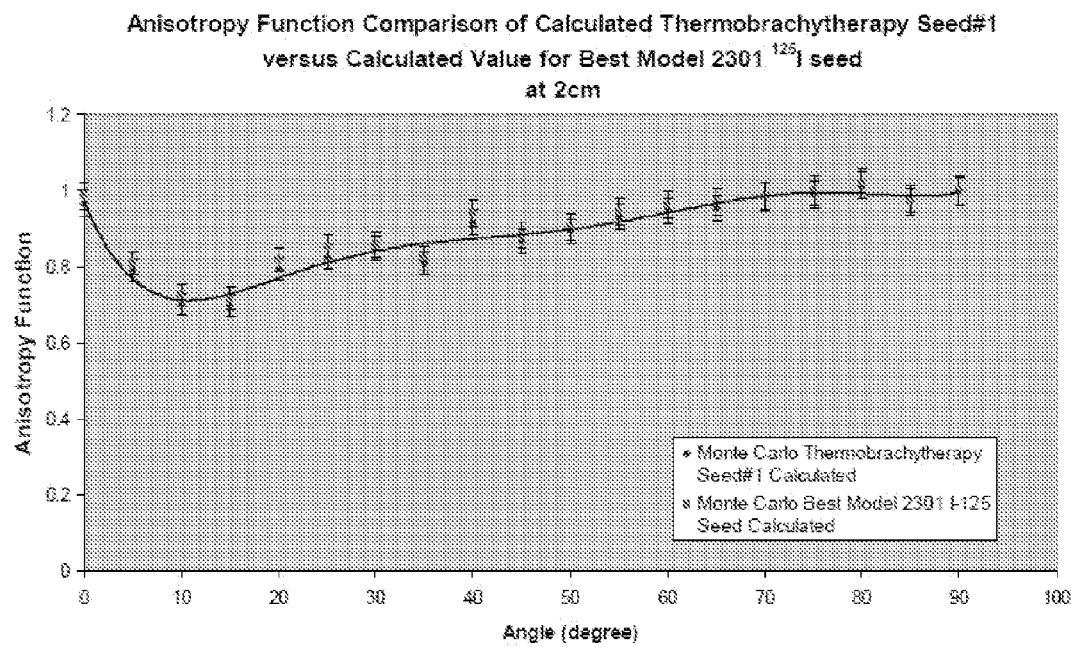

FIG. 27 illustrates the Anisotropy Function of Monte Carlo calculated value for Thermobrachytherapy Seed#1 and the Monte Carlo calculated value for the Best Model 2301 $^{125}$I in liquid water at 2 cm radii.

Figure 28:
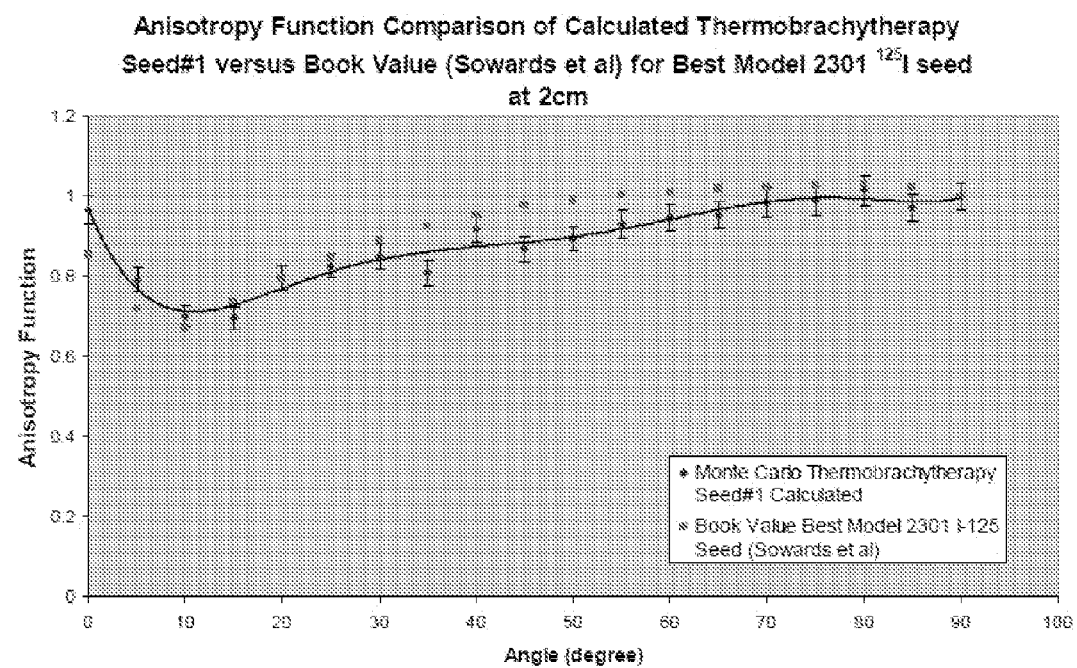

FIG. 28 illustrates the Anisotropy Function of Monte Carlo calculated value for Thermobrachytherapy Seed#1 and the Book Value for the Best Model 2301 $^{125}$I in liquid water at 2 cm radii.

Figure 29:
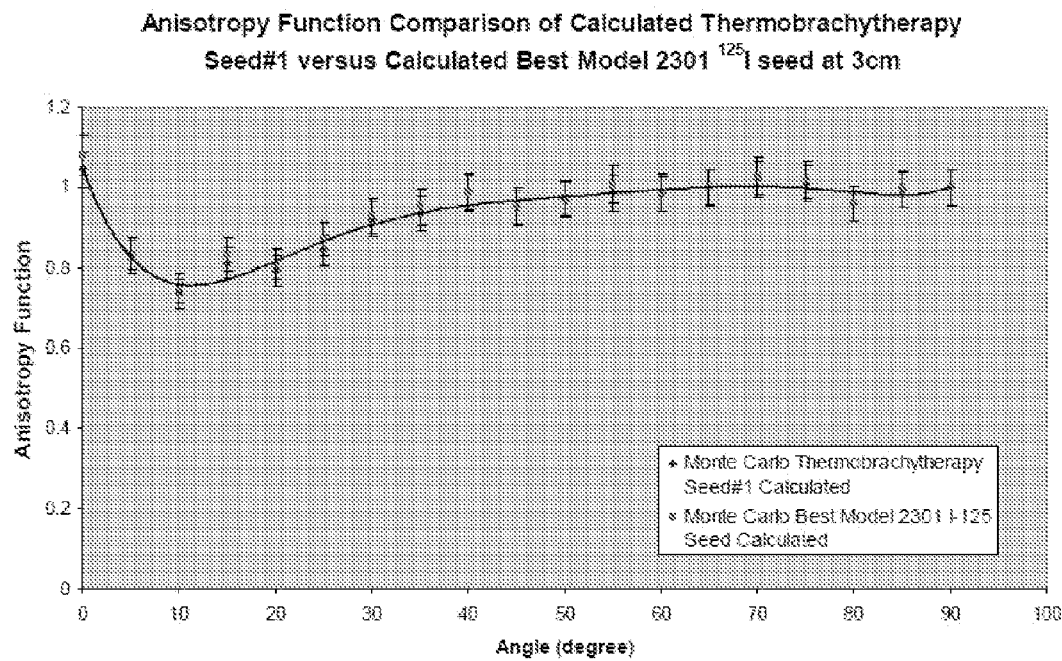

FIG. 29 illustrates the Anisotropy Function of Monte Carlo calculated value for Thermobrachytherapy Seed#1 and the Book Value for the Best Model 2301 $^{125}$I in liquid water at 3 cm radii.

Figure 30:
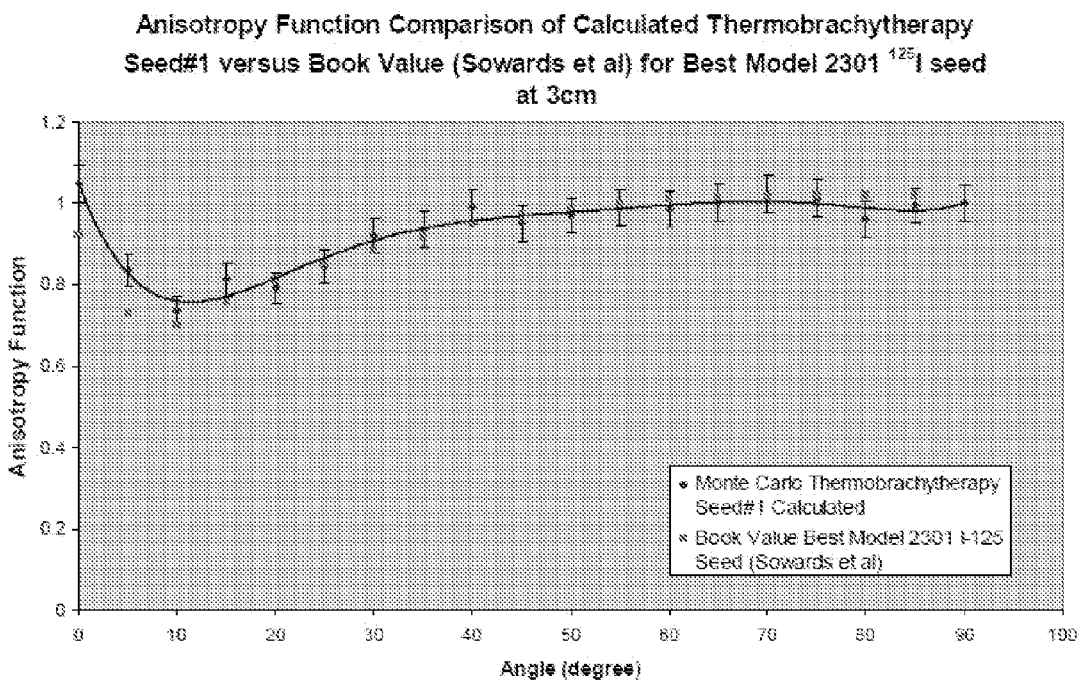

FIG. 30 illustrates the Anisotropy Function of Monte Carlo calculated value for Thermobrachytherapy Seed#1 and the Book Value for the Best Model 2301 $^{125}$I in liquid water at 3 cm radii.

Figure 31:
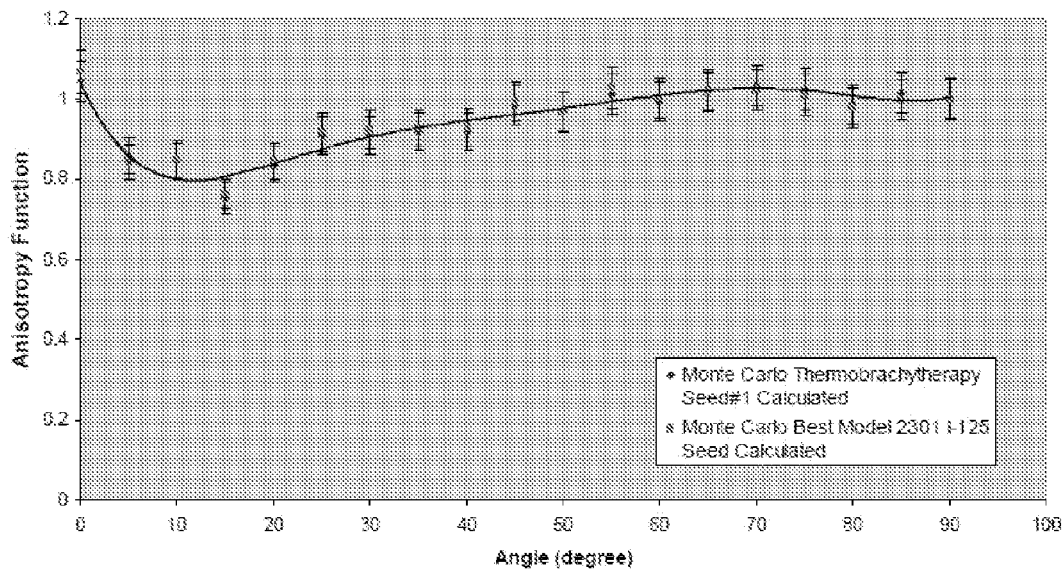

FIG. 31 illustrates the Anisotropy Function of Monte Carlo calculated value for Thermobrachytherapy Seed#1 and the Book Value for the Best Model 2301 $^{125}$I in liquid water at 4 cm radii.

Figure 32:
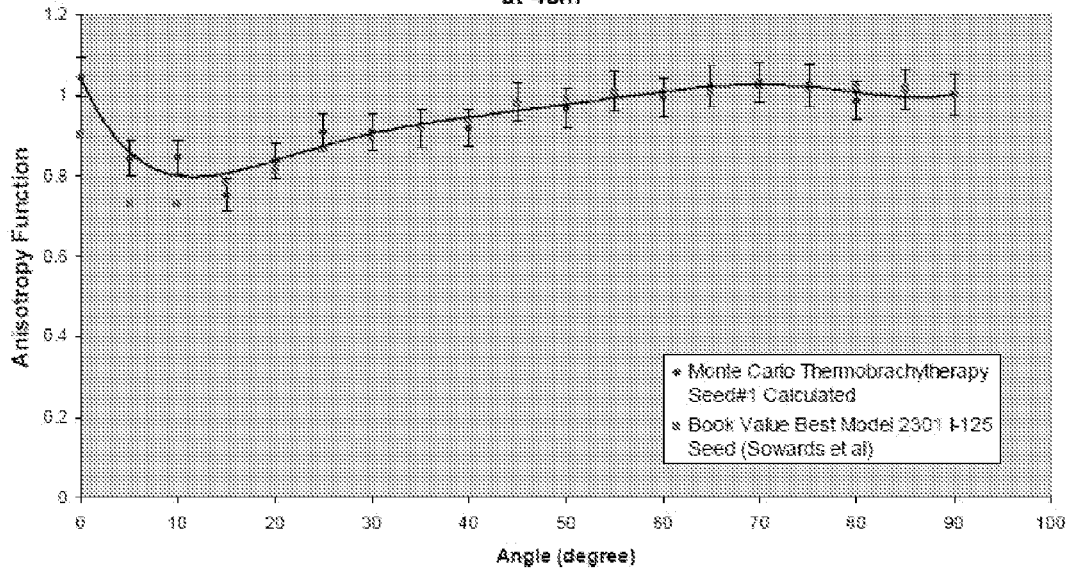

FIG. 32 illustrates the Anisotropy Function of Monte Carlo calculated value for Thermo Brachytherapy Seed#1 and the Book Value for the Best Model 2301 $^{125}$I in liquid water at 4 cm radii.

Figure 33:
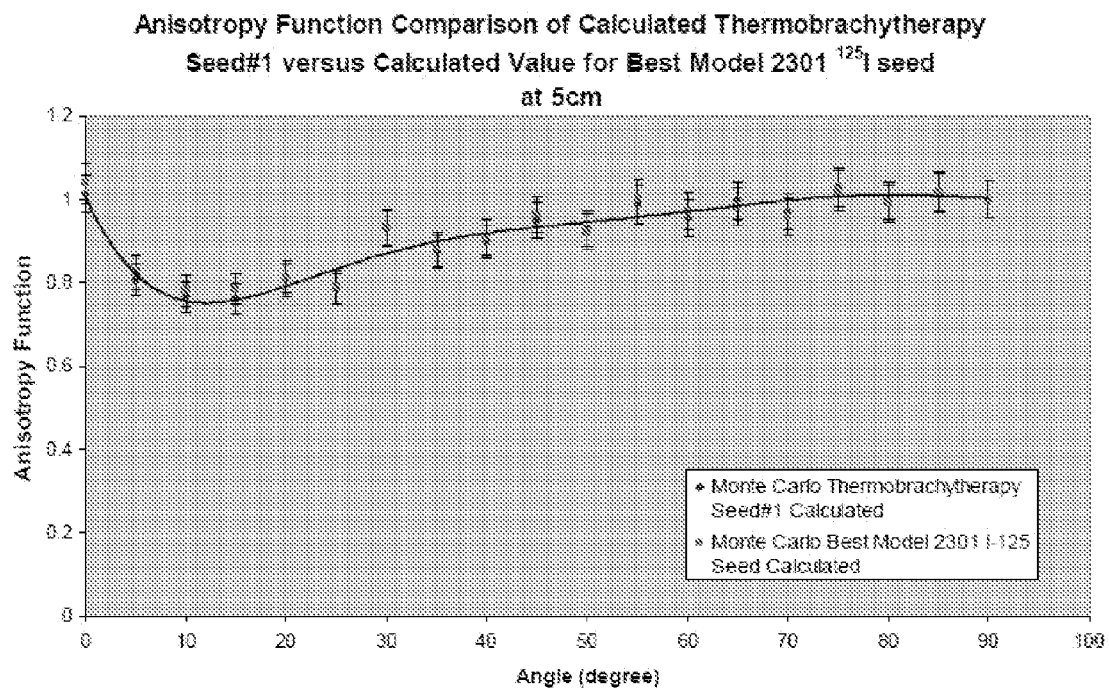

FIG. 33 illustrates the Anisotropy Function of Monte Carlo calculated value for Thermobrachytherapy Seed#1 and the Book Value for the Best Model 2301 $^{125}$I in liquid water at 5 cm radii.

Figure 34:
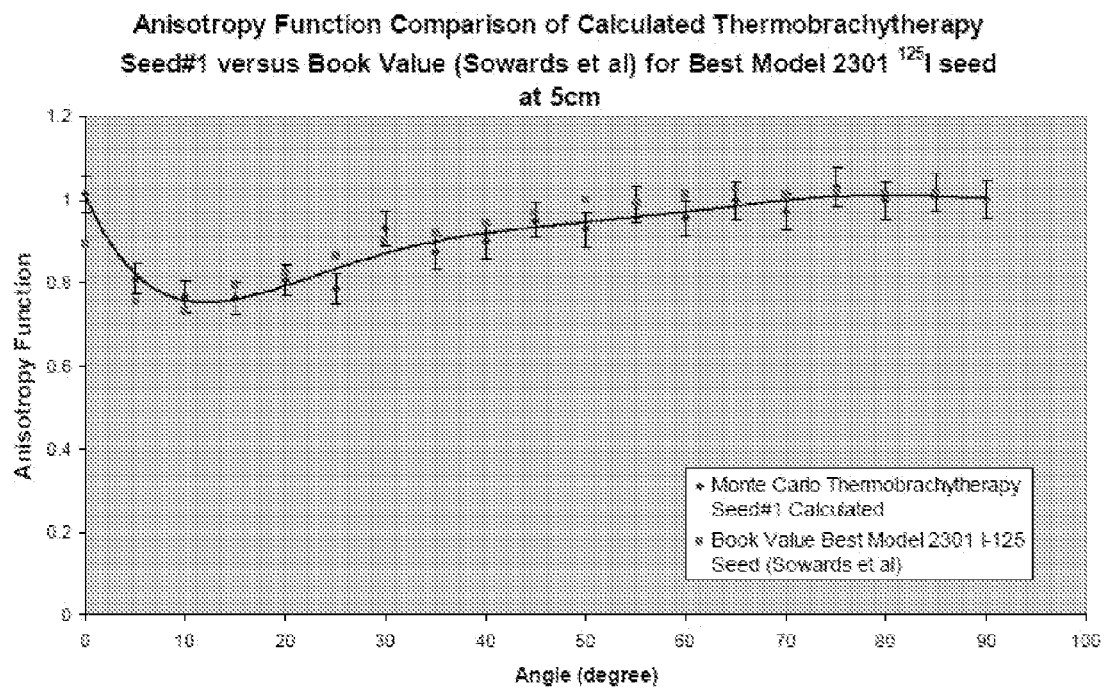

FIG. 34 illustrates the Anisotropy Function of Monte Carlo calculated value for Thermobrachytherapy Seed#1 and the Book Value for the Best Model 2301 $^{125}$I in liquid water at 5 cm radii.

Figure 35:
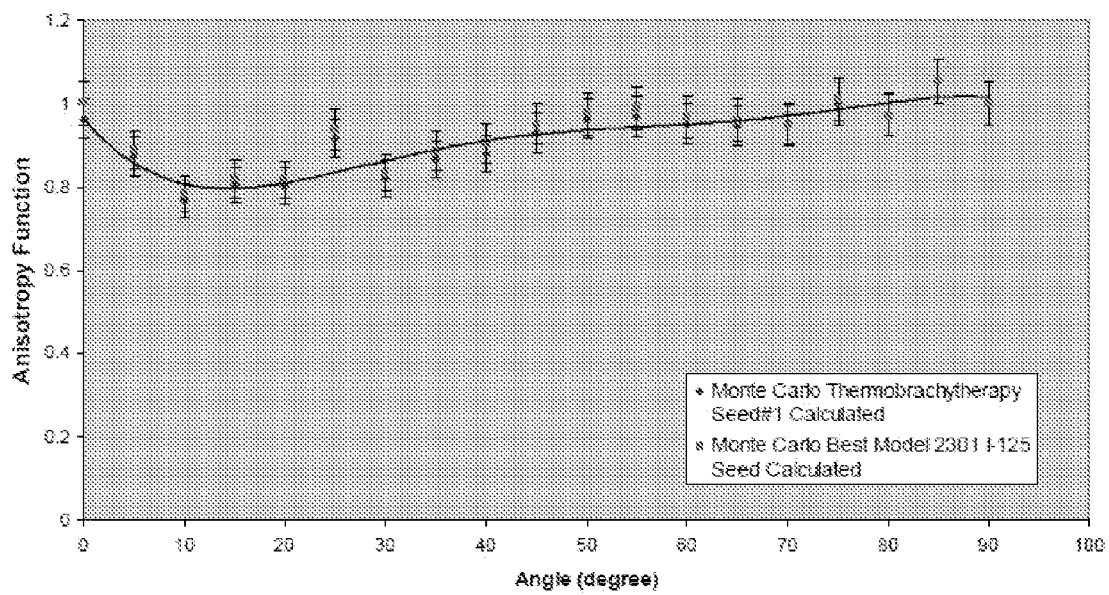

FIG. 35 illustrates the Anisotropy Function of Monte Carlo calculated value for Thermobrachytherapy Seed#1 and the Book Value for the Best Model 2301 $^{125}$I in liquid water at 6 cm radii.

Figure 36:
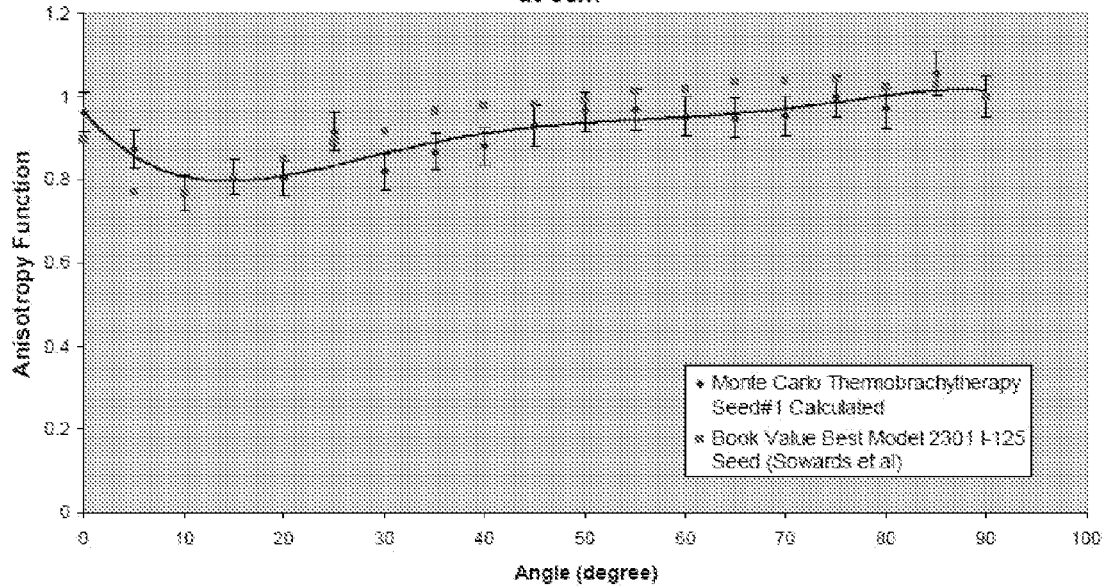

FIG. 36 illustrates the Anisotropy Function of Monte Carlo calculated value for Thermobrachytherapy Seed#1 and the Book Value for the Best Model 2301 $^{125}$I in liquid water at 6 cm radii.

Figure 37:
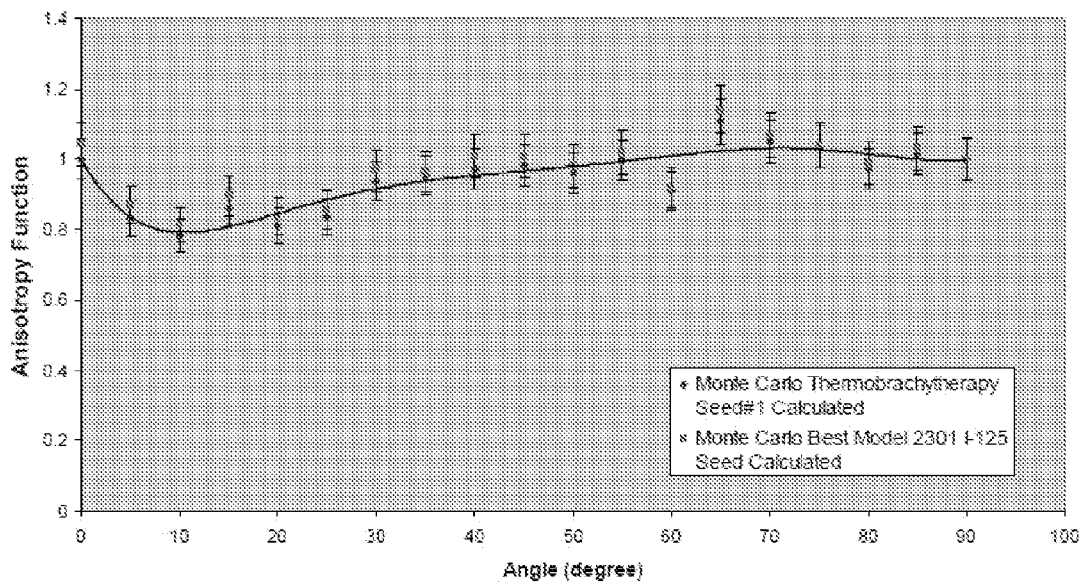

FIG. 37 illustrates the Anisotropy Function of Monte Carlo calculated value for Thermobrachytherapy Seed#1 and the Book Value for the Best Model 2301 $^{125}$I in liquid water at 7 cm radii.

Figure 38:
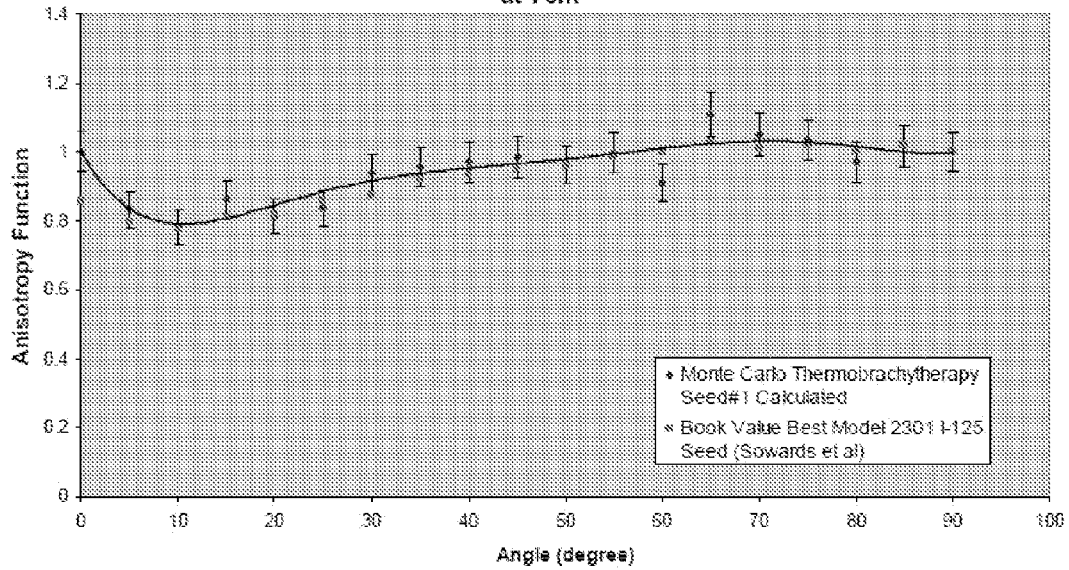

FIG. 38 illustrates the Anisotropy Function of Monte Carlo calculated value for Thermo Brachytherapy Seed#1 and the Book Value for the Best Model 2301 $^{125}$I in liquid water at 7 cm radii.

Figure 39:
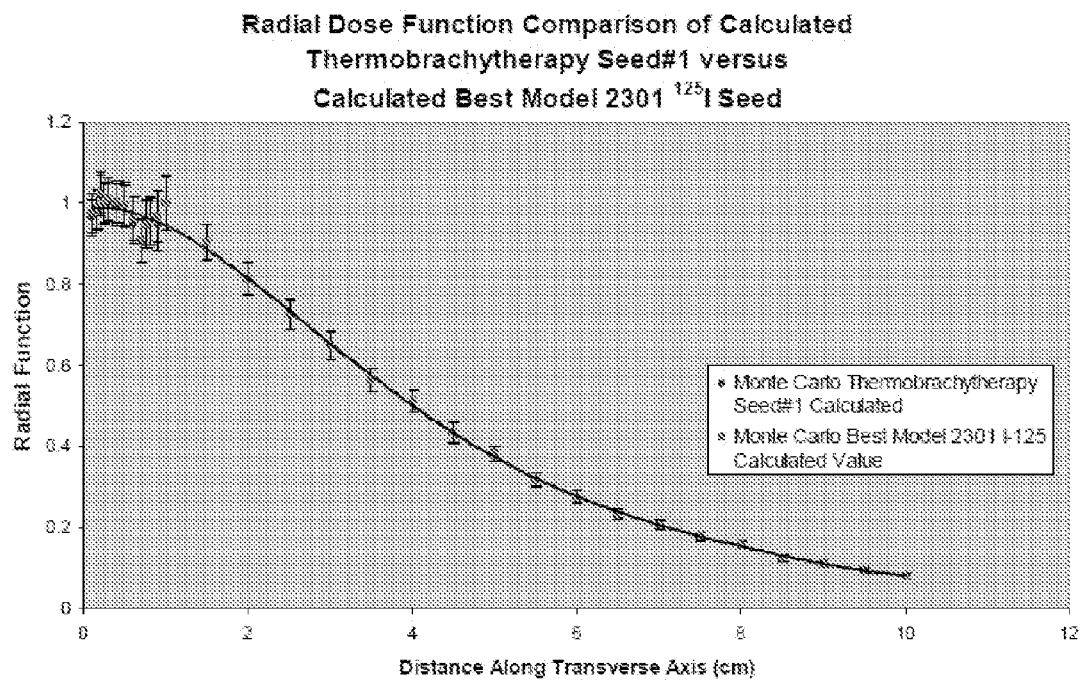

FIG. 39 illustrates the Radial Function of Monte Carlo calculated value for Thermobrachytherapy Seed#1 and the Monte Carlo calculated value for the Best Model 2301 $^{125}$I in Solid Water.

Figure 40:
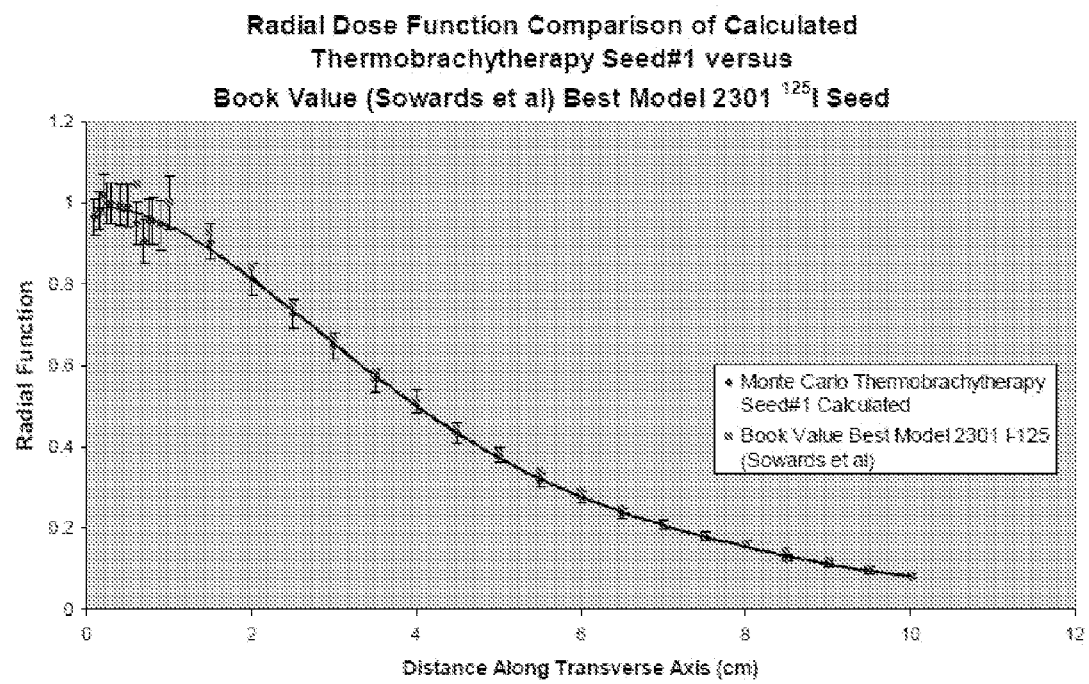

FIG. 40 illustrates the Radial Function of Monte Carlo calculated value for Thermobrachytherapy Seed#1 and the Book Value for the Best Model 2301 $^{125}$I in Solid Water.

Figure 41:
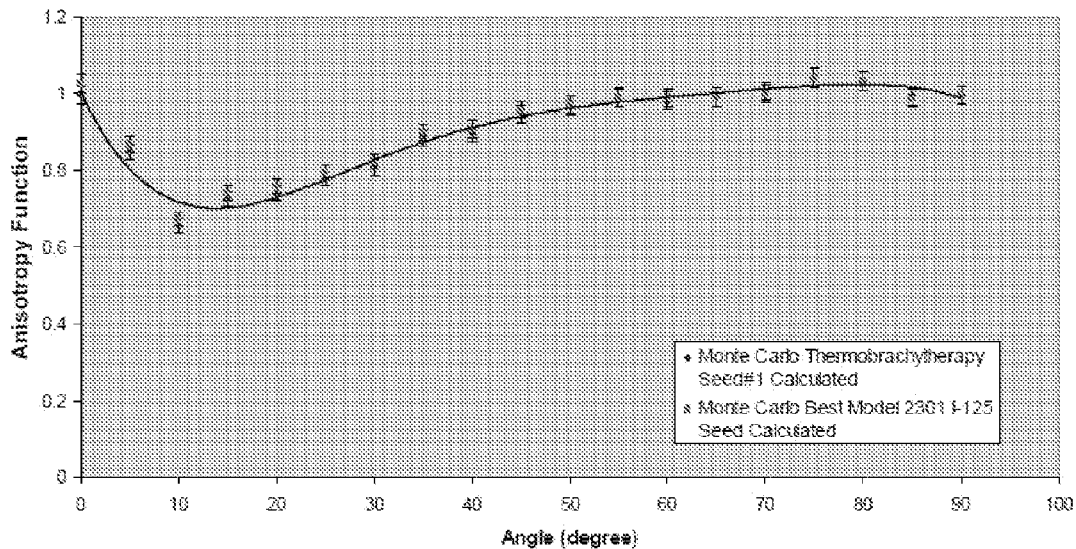

FIG. 41: Anisotropy Function of Monte Carlo calculated value for Thermobrachytherapy Seed#1 and the Monte Carlo for the Best Model 2301 $^{125}$I in Solid Water at 1 cm radii.

Figure 42:
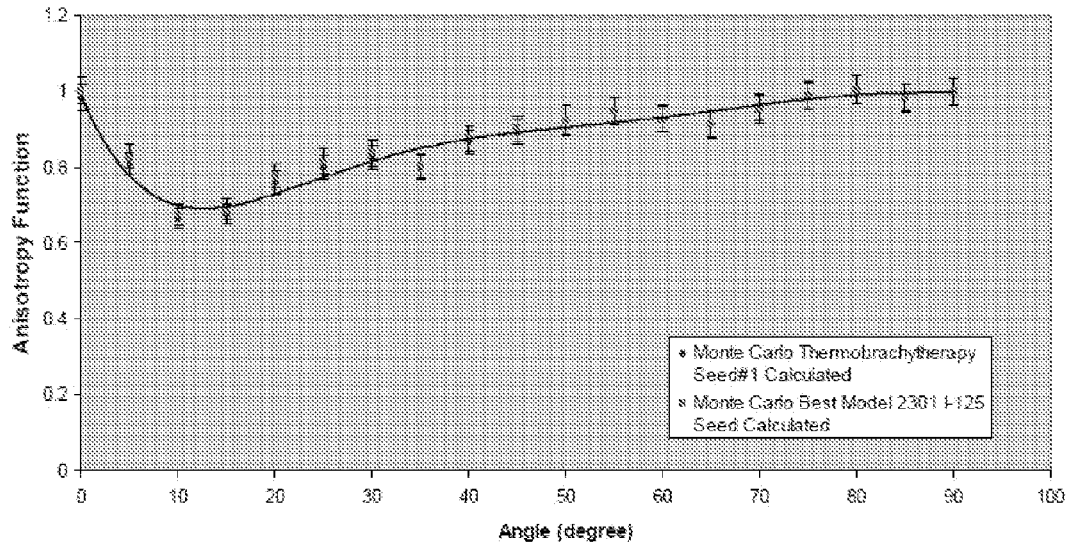

FIG. 42 illustrates the Anisotropy Function of Monte Carlo calculated value for Thermobrachytherapy Seed#1 and the Monte Carlo for the Best Model 2301 $^{125}$I in Solid Water at 2 cm radii.

Figure 43:
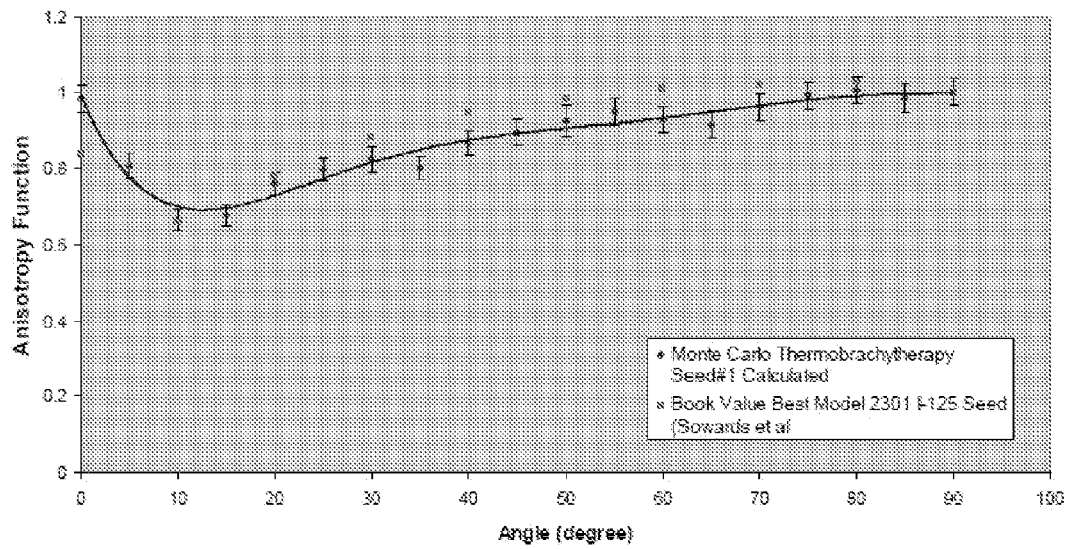

FIG. 43 illustrates the Anisotropy Function of Monte Carlo calculated value for Thermobrachytherapy Seed#1 and the Book value for the Best Model 2301 $^{125}$I in Solid Water at 2 cm radii.

Figure 44:
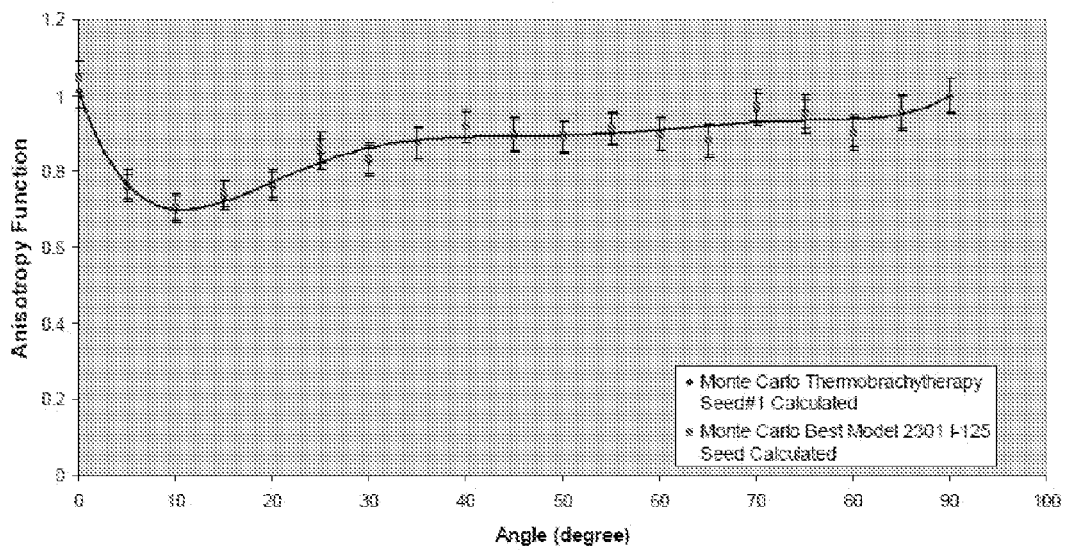

FIG. 44 illustrates the Anisotropy Function of Monte Carlo calculated value for Thermobrachytherapy Seed#1 and the Monte Carlo for the Best Model 2301 $^{125}$I in Solid Water at 3 cm radii.

Figure 45:
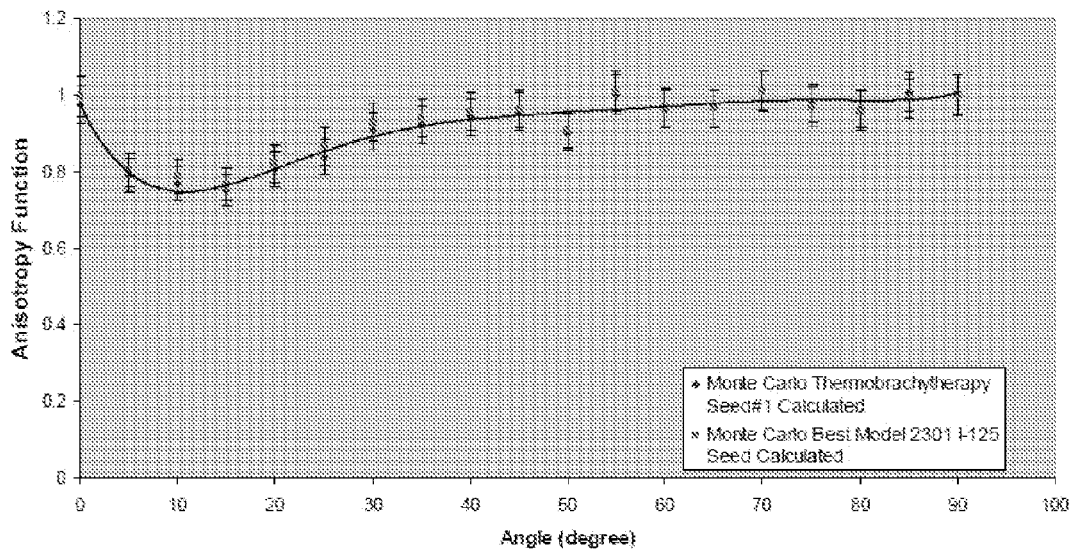

FIG. 45 illustrates the Anisotropy Function of Monte Carlo calculated value for Thermobrachytherapy Seed#1 and the Monte Carlo for the Best Model 2301 $^{125}$I in Solid Water at 4 cm radii.

Figure 46:
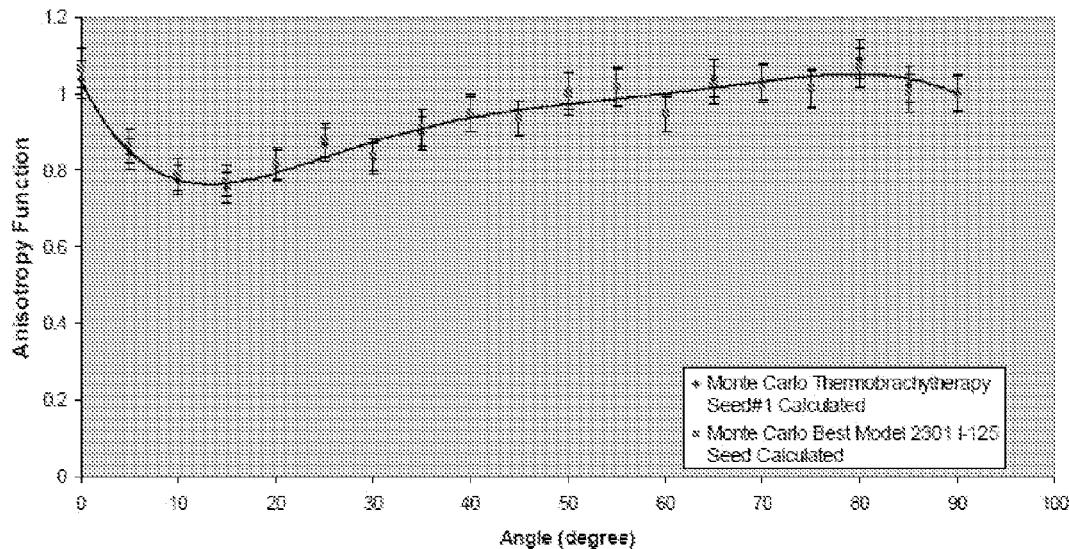

FIG. 46 illustrates the Anisotropy Function of Monte Carlo calculated value for Thermobrachytherapy Seed#1 and the Monte Carlo for the Best Model 2301 $^{125}$I in Solid Water at 5 cm radii.

Figure 47:
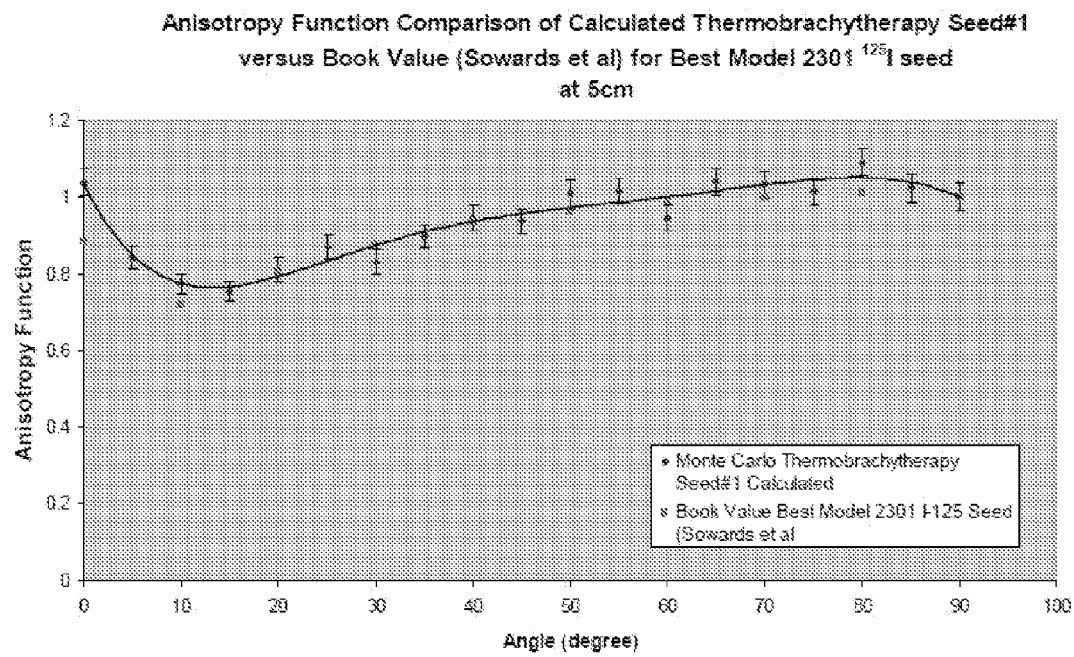

FIG. 47 illustrates the Anisotropy Function of Monte Carlo calculated value for Thermobrachytherapy Seed#1 and the Book value for the Best Model 2301 $^{125}$I in Solid Water at 5 cm radii.

Figure 48:
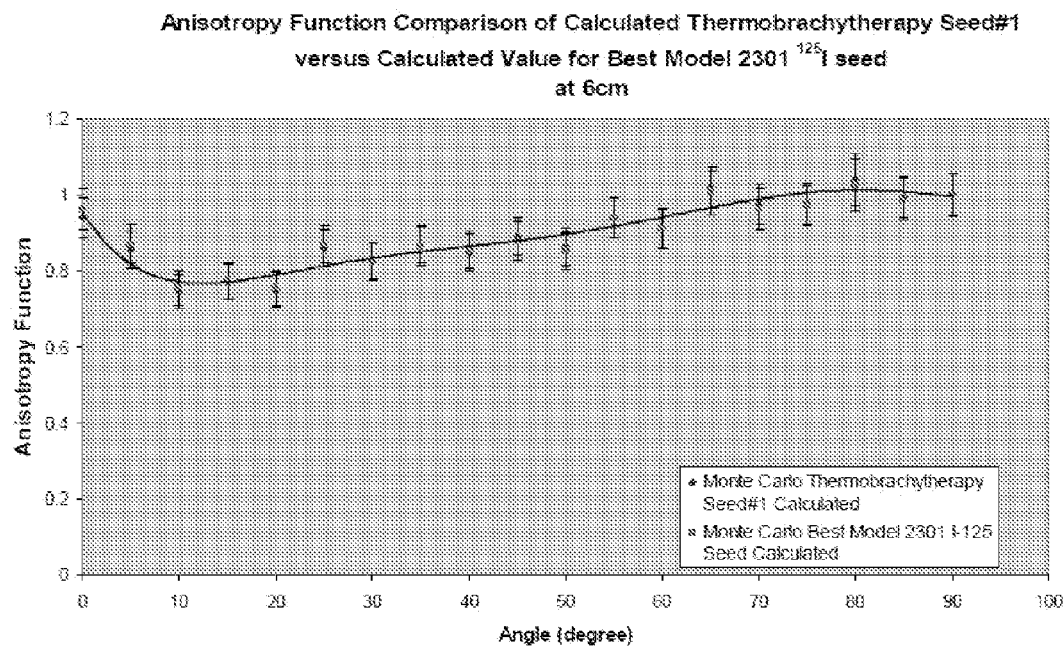

FIG. 48 illustrates the Anisotropy Function of Monte Carlo calculated value for Thermobrachytherapy Seed#1 and the Monte Carlo for the Best Model 2301 $^{125}$I in Solid Water at 6 cm radii.

Figure 49:
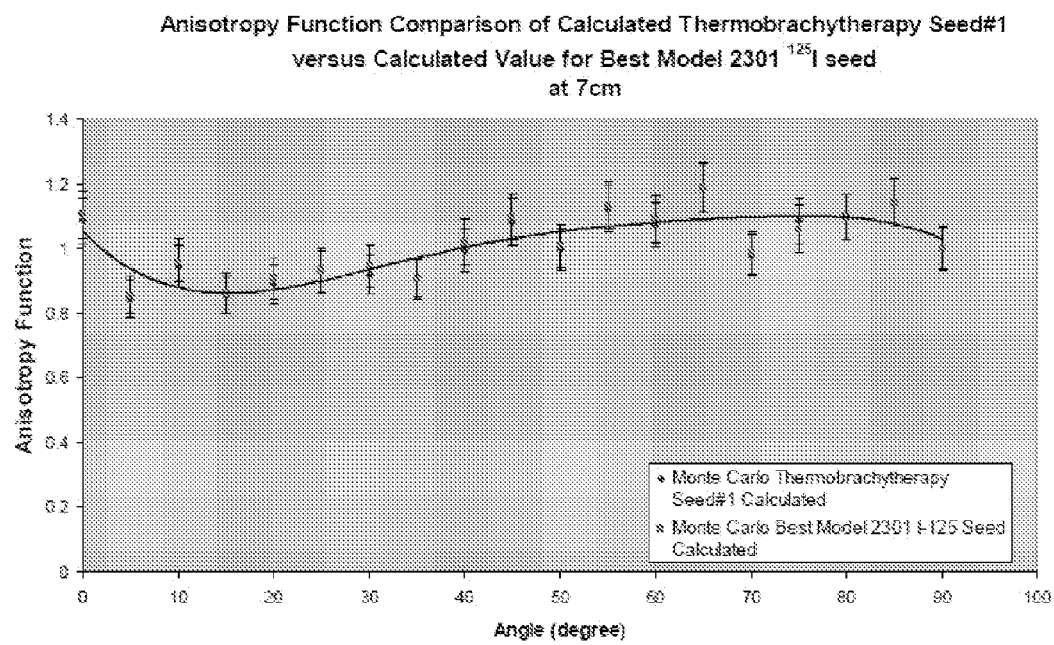

FIG. 49 illustrates the Anisotropy Function of Monte Carlo calculated value for Thermobrachytherapy Seed#1 and the Monte Carlo for the Best Model 2301 $^{125}$I in Solid Water at 7 cm radii.

Figure 50:
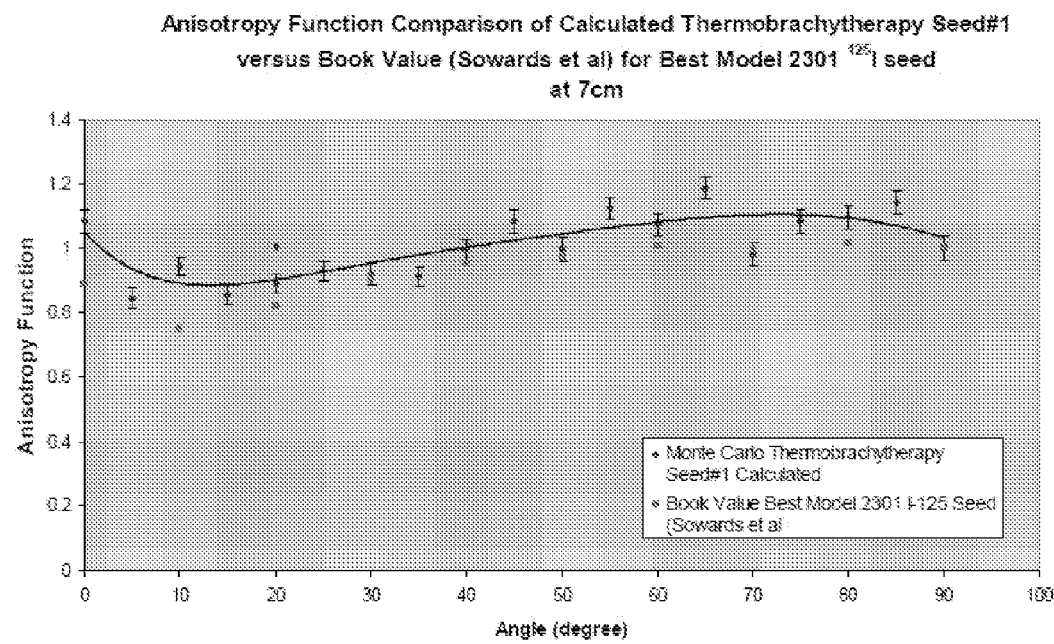

FIG. 50 illustrates the Anisotropy Function of Monte Carlo calculated value for Thermobrachytherapy Seed#1 and the Book value for the Best Model 2301 $^{125}$I in Solid Water at 7 cm radii.

Figure 51:
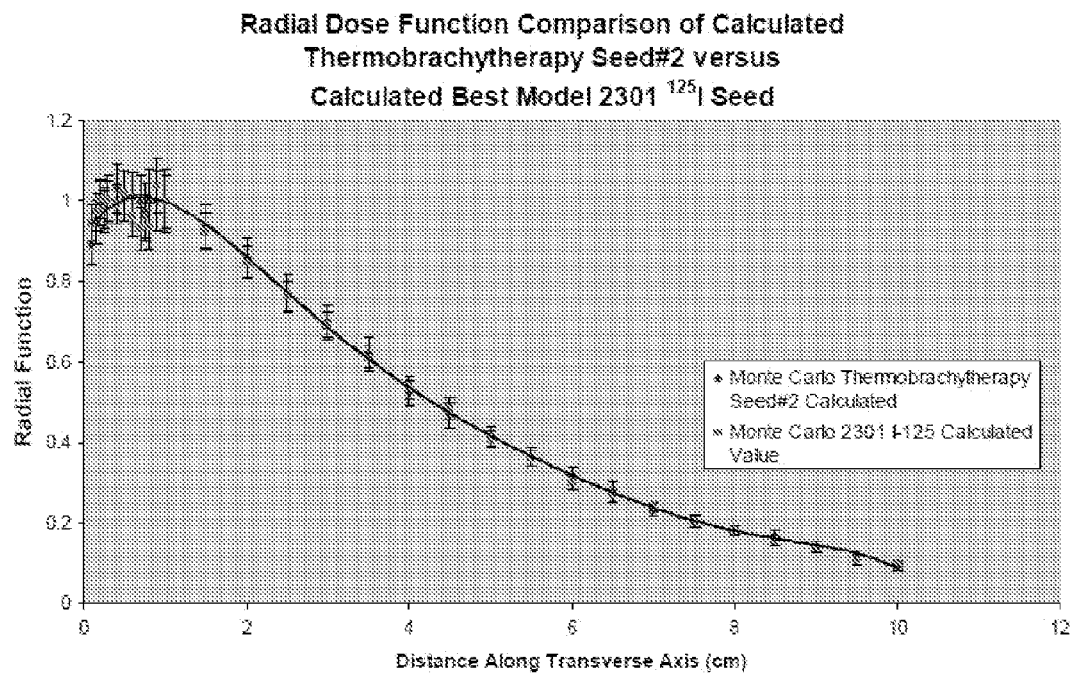

FIG. 51 illustrates the Radial Function of Monte Carlo calculated value for Thermobrachytherapy Seed#2 and the Monte Carlo calculated Value for the Best Model 2301 $^{125}$I in Liquid water.

Figure 52:
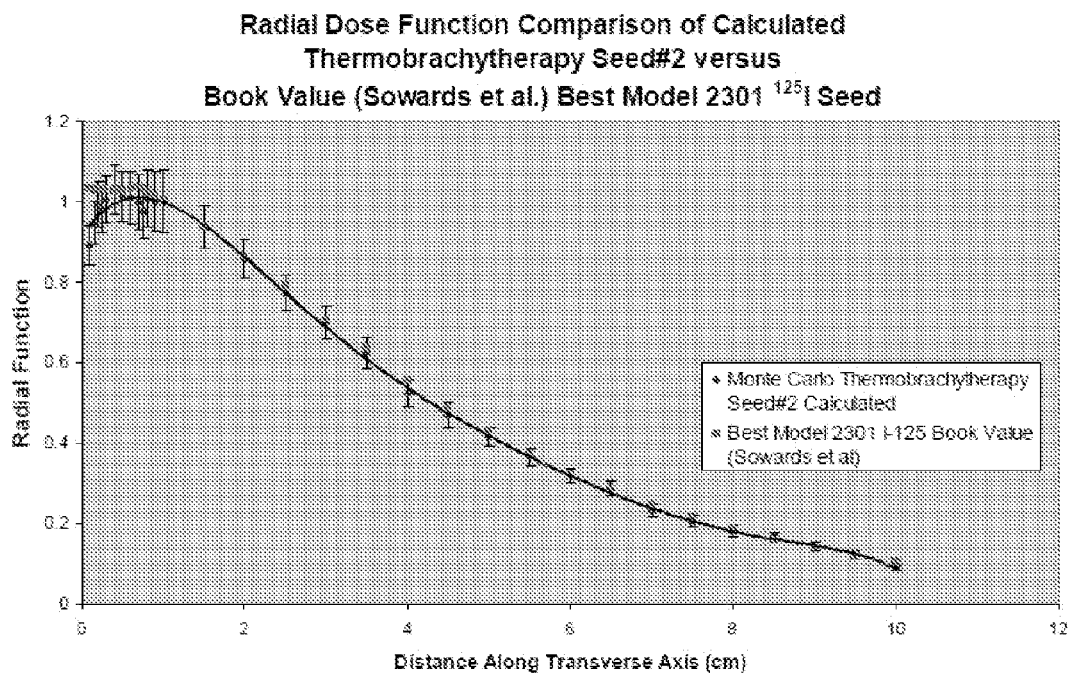

FIG. 52 illustrates the Radial Function of Monte Carlo calculated value for Thermobrachytherapy Seed#2 and the Book Value for the Best Model 2301 $^{125}$I in Liquid water.

Figure 53:
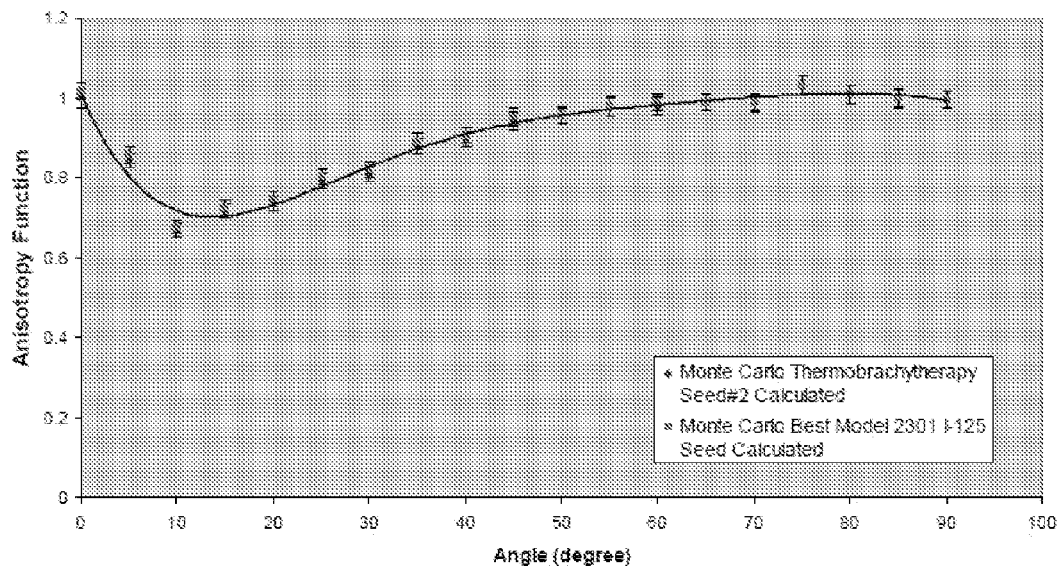

FIG. 53 illustrates the Anisotropy Function of Monte Carlo calculated value for Thermobrachytherapy Seed#2 and the Monte Carlo calculated value for the Best Model 2301 $^{125}$I in liquid water at 1 cm radii.

Figure 54:
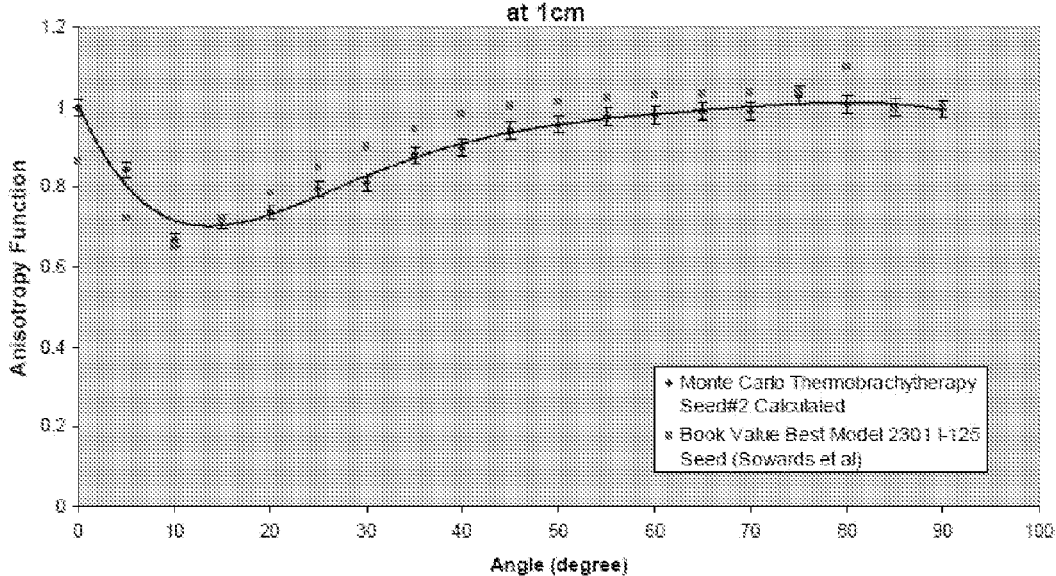

FIG. 54 illustrates the Anisotropy Function of Monte Carlo calculated value for Thermobrachytherapy Seed#2 and the Book Value for the Best Model 2301 $^{125}$I in liquid water at 1 cm radii.

Figure 55:
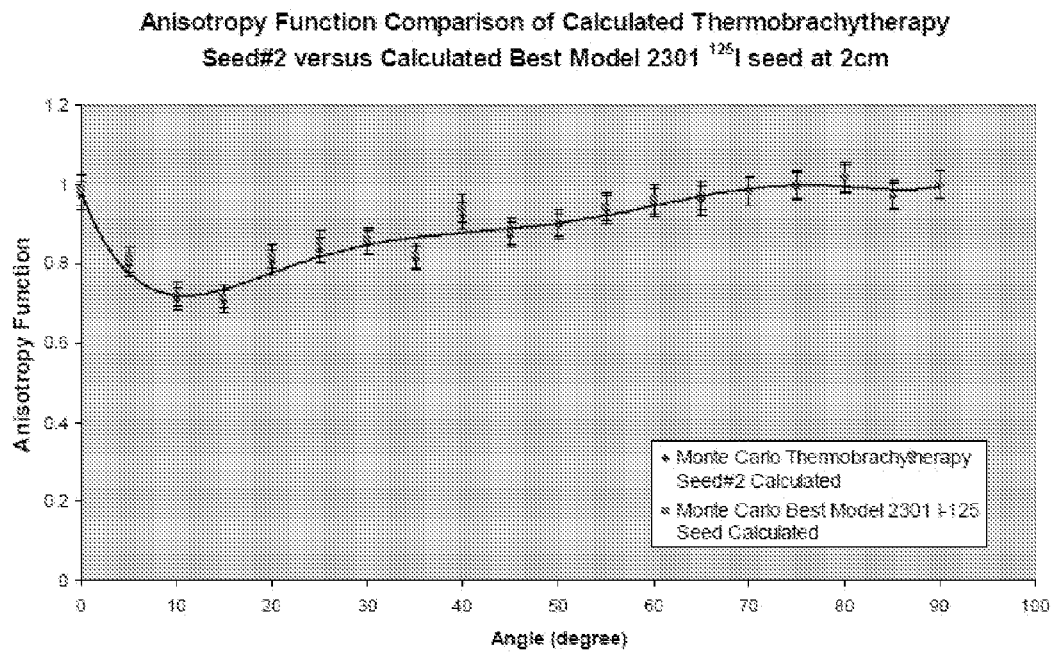

FIG. 55 illustrates the Anisotropy Function of Monte Carlo calculated value for Thermobrachytherapy Seed#2 and the Monte Carlo calculated for the Best Model 2301 $^{125}$I in liquid water at 2 cm radii.

Figure 56:
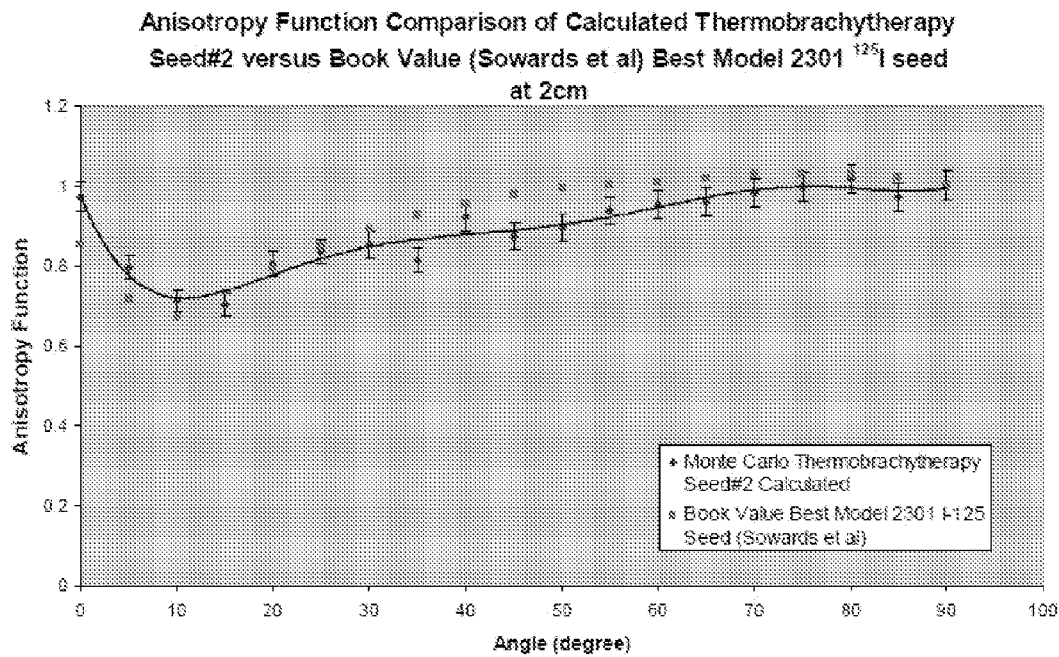

FIG. 56 illustrates the Anisotropy Function of Monte Carlo calculated value for Thermobrachytherapy Seed#2 and the Book Value for the Best Model 2301 $^{125}$I in liquid water at 2 cm radii.

Figure 57:
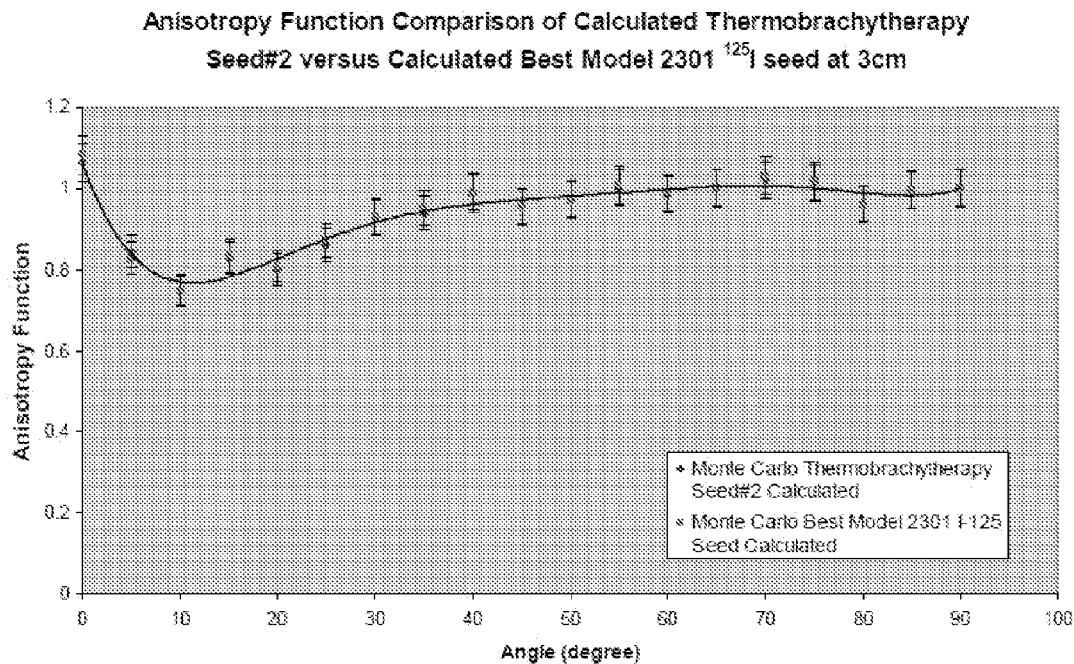

FIG. 57 illustrates the Anisotropy Function of Monte Carlo calculated value for Thermobrachytherapy Seed#2 and the Monte Carlo calculated for the Best Model 2301 $^{125}$I in liquid water at 3 cm radii.

Figure 58:
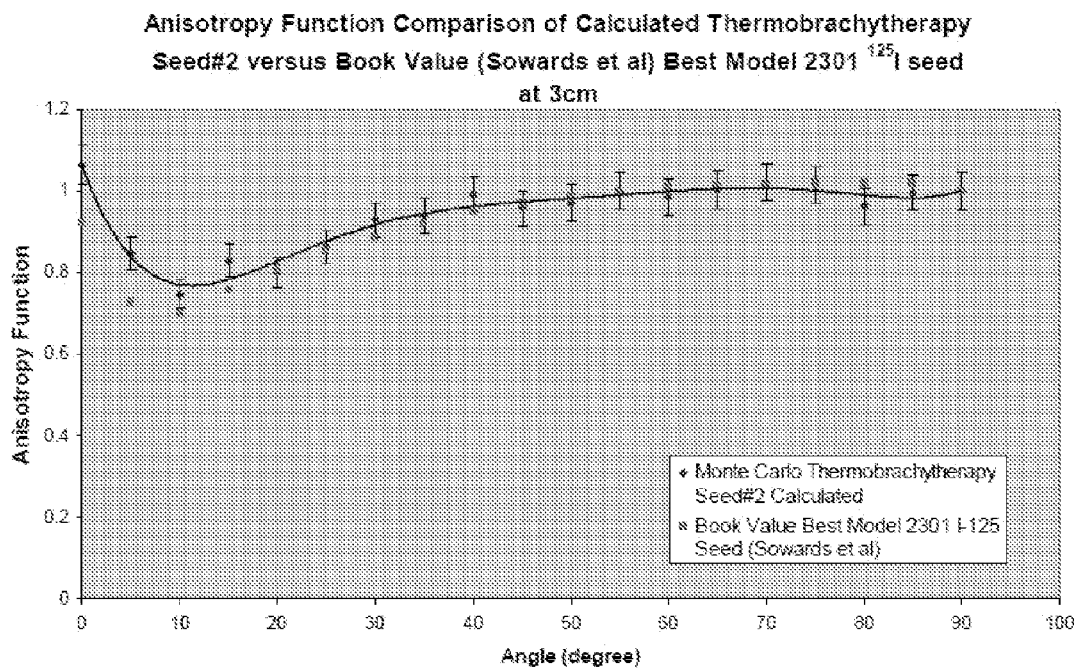

FIG. 58 illustrates the Anisotropy Function of Monte Carlo calculated value for Thermobrachytherapy Seed#2 and the Book value for the Best Model 2301 $^{125}$I in liquid water at 3 cm radii.

Figure 59:
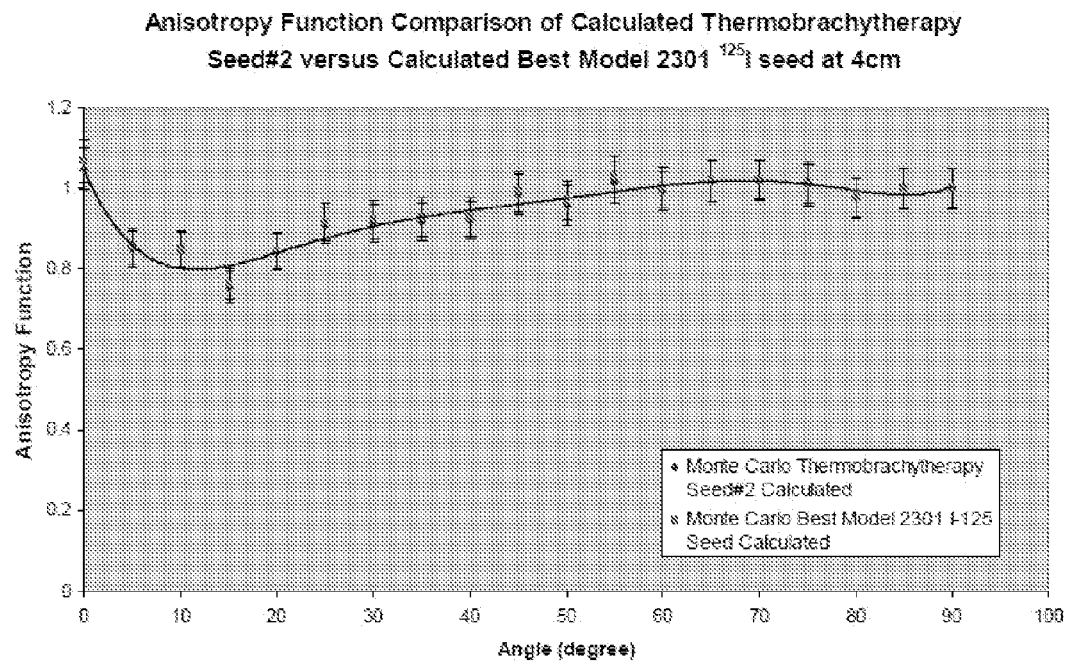

FIG. 59 illustrates the Anisotropy Function of Monte Carlo calculated value for Thermobrachytherapy Seed#2 and the Monte Carlo calculated for the Best Model 2301 $^{125}$I in liquid water at 4 cm radii.

Figure 60:
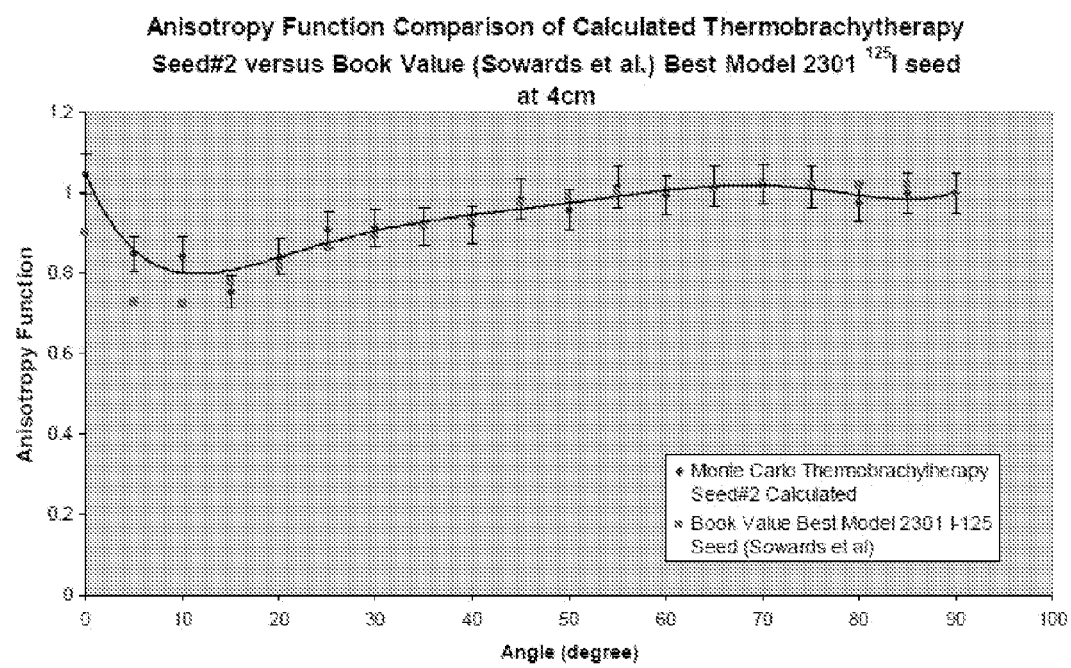

FIG. 60 illustrates the Anisotropy Function of Monte Carlo calculated value for Thermobrachytherapy Seed#2 and the Book Value calculated for the Best Model 2301 $^{125}$I in liquid water at 2 cm radii.

Figure 61:
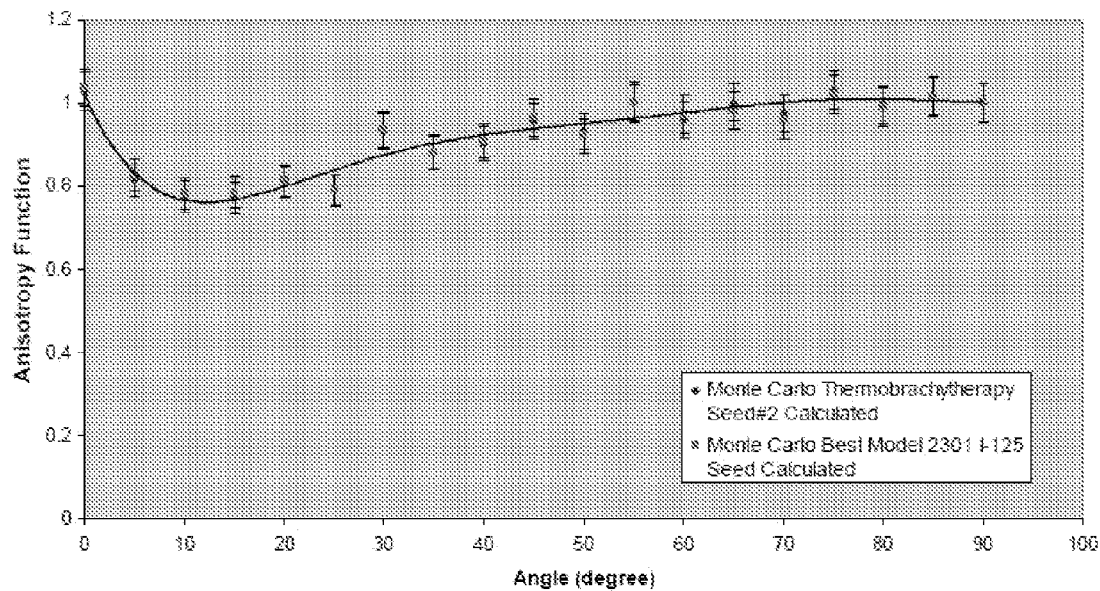

FIG. 61 illustrates the Anisotropy Function of Monte Carlo calculated value for Thermobrachytherapy Seed#2 and the Monte Carlo calculated for the Best Model 2301 $^{125}$I in liquid water at 5 cm radii.

Figure 62:
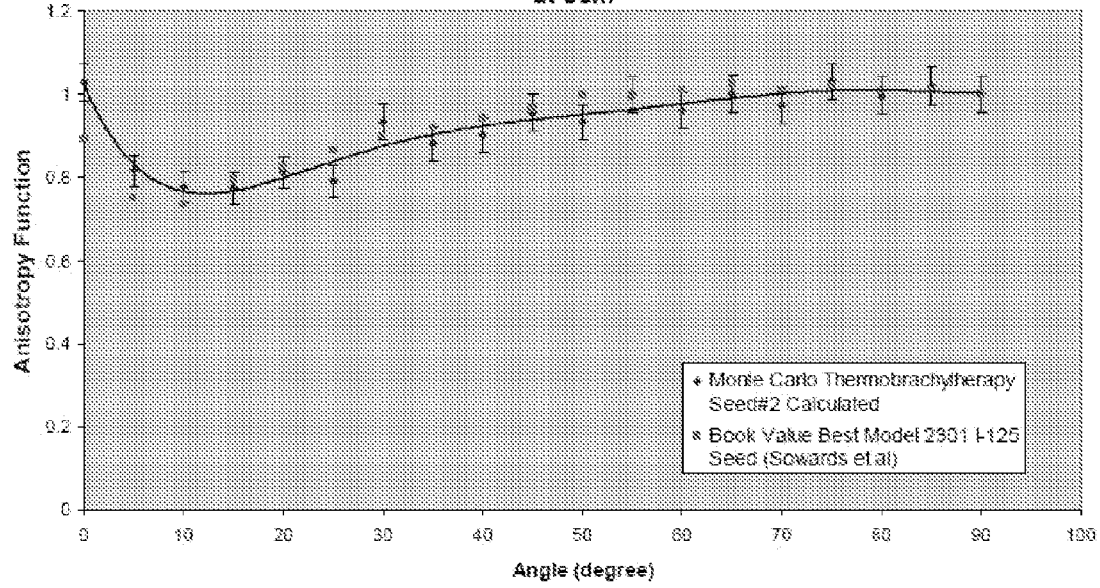

FIG. 62 illustrates the Anisotropy Function of Monte Carlo calculated value for Thermobrachytherapy Seed#2 and the Book Value for the Best Model 2301 $^{125}$I in liquid water at 5 cm radii.

Figure 63:
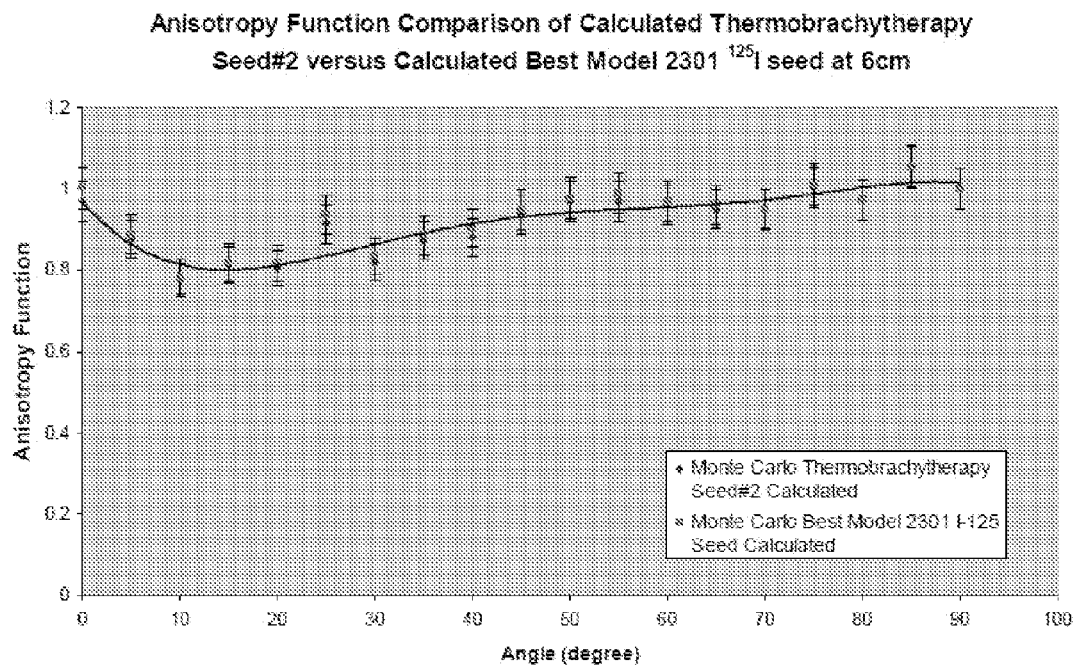

FIG. 63 illustrates the Anisotropy Function of Monte Carlo calculated value for Thermobrachytherapy Seed#2 and the Monte Carlo calculated for the Best Model 2301 $^{125}$I in liquid water at 6 cm radii.

Figure 64:
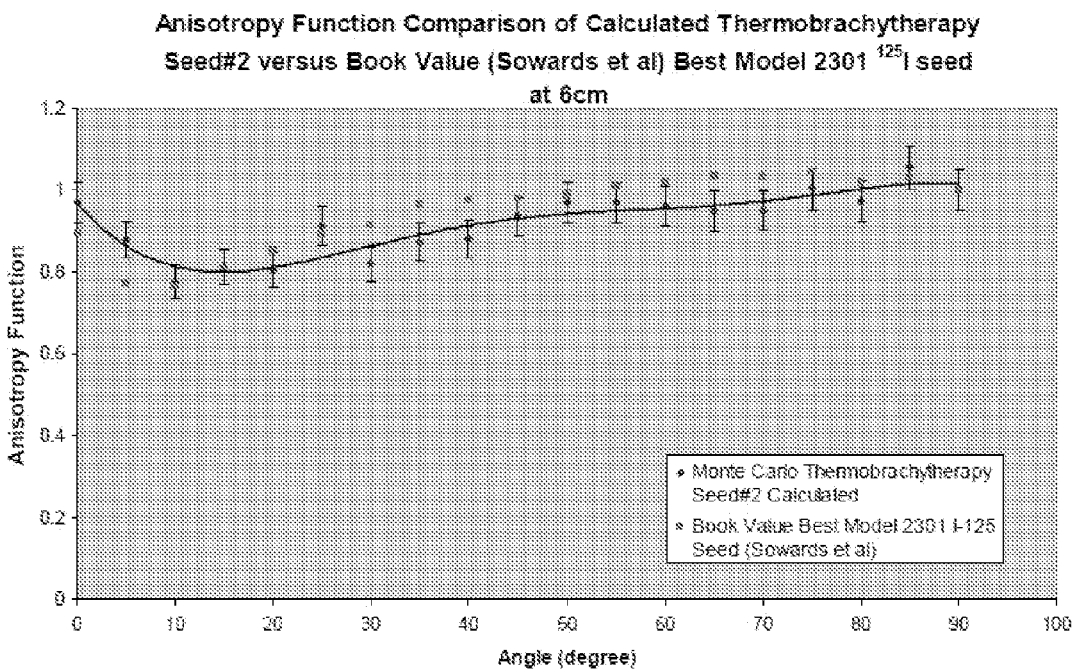

FIG. 64 illustrates the Anisotropy Function of Monte Carlo calculated value for Thermobrachytherapy Seed#2 and the Book value for the Best Model 2301 $^{125}$I in liquid water at 6 cm radii.

Figure 65:
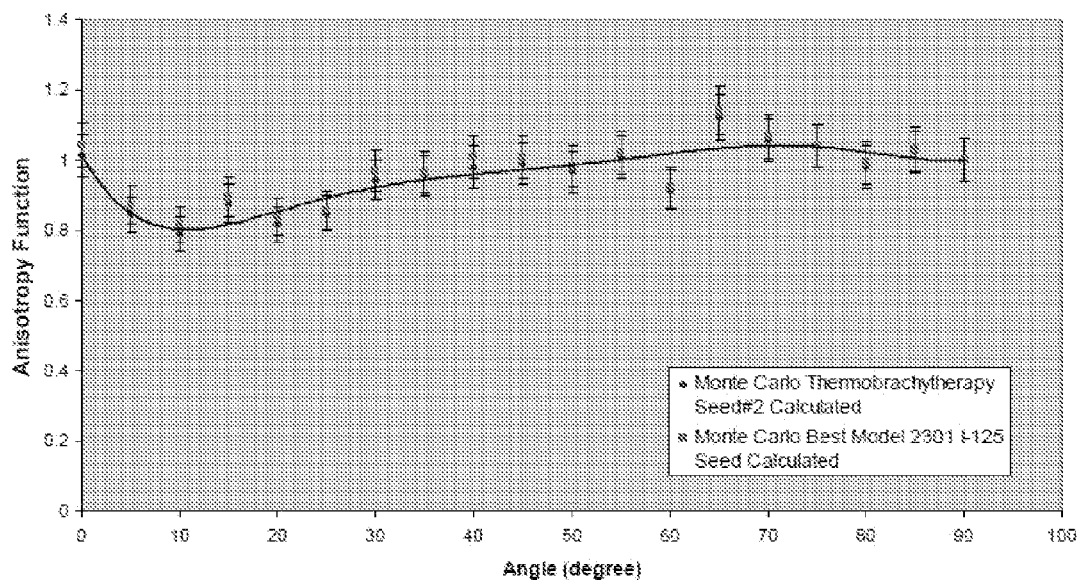

FIG. 65 illustrates the Anisotropy Function of Monte Carlo calculated value for Thermobrachytherapy Seed#2 and the Monte Carlo calculated for the Best Model 2301 $^{125}$I in liquid water at 7 cm radii.

Figure 66:
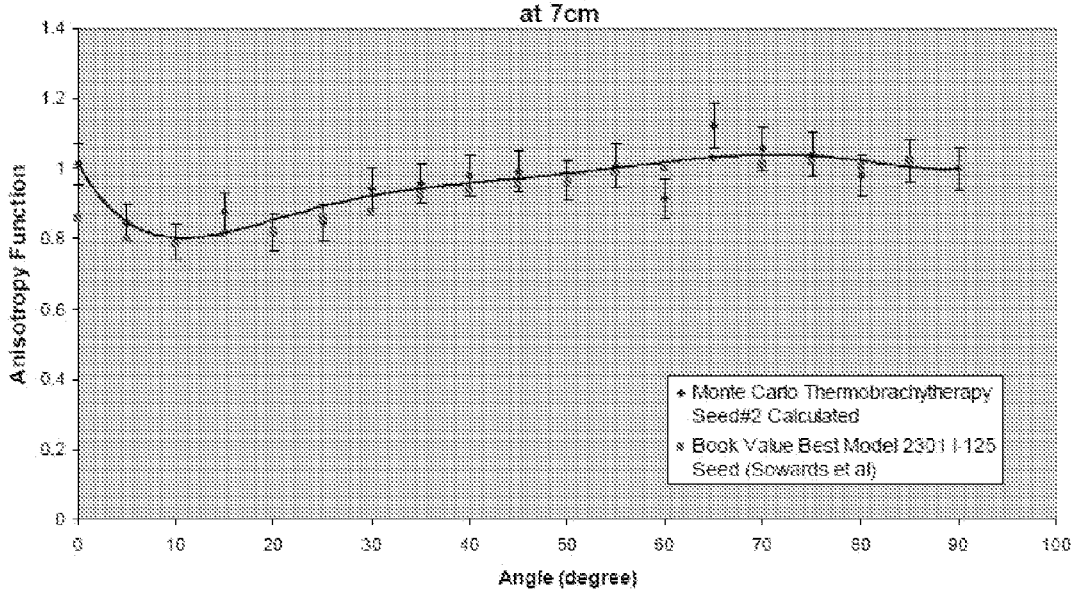

FIG. 66 illustrates the Anisotropy Function of Monte Carlo calculated value for Thermobrachytherapy Seed#2 and the Book value calculated for the Best Model 2301 $^{125}$I in liquid water at 7 cm radii.

Figure 67:
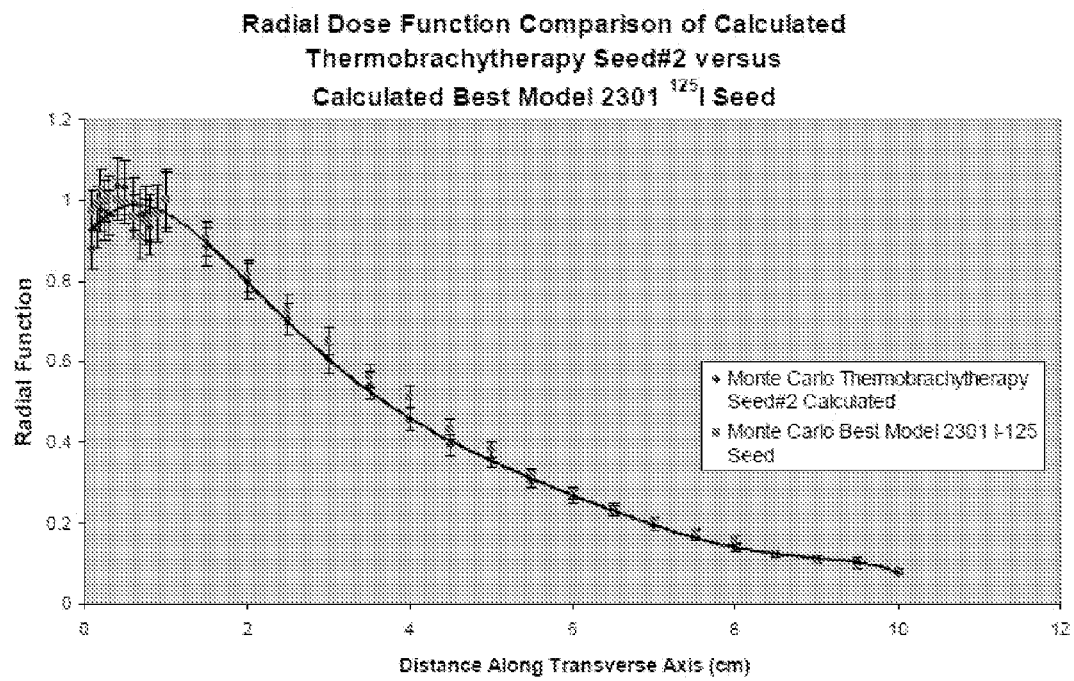

FIG. 67 illustrates the Radial Function of Monte Carlo calculated value for Thermobrachytherapy Seed#2 and the Monte Carlo calculated value for the Best Model 2301 $^{125}$I in Solid Water.

Figure 68:
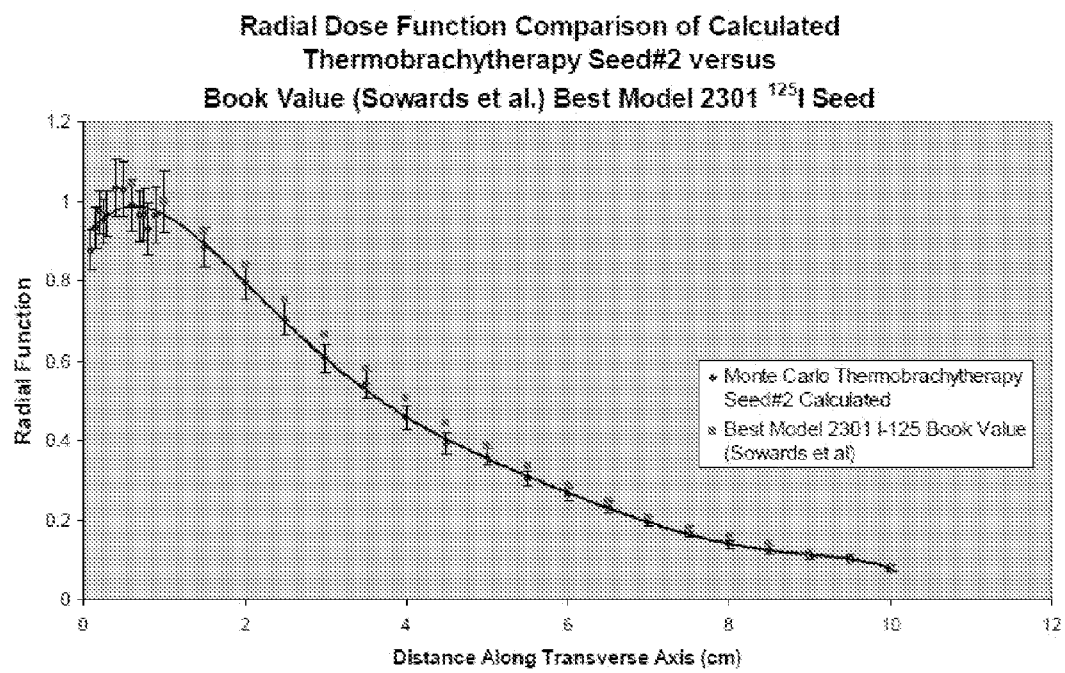

FIG. 68 illustrates the Radial Function of Monte Carlo calculated value for Thermobrachytherapy Seed#2 and the Book Value for the Best Model 2301 $^{125}$I in Solid Water.

Figure 69:
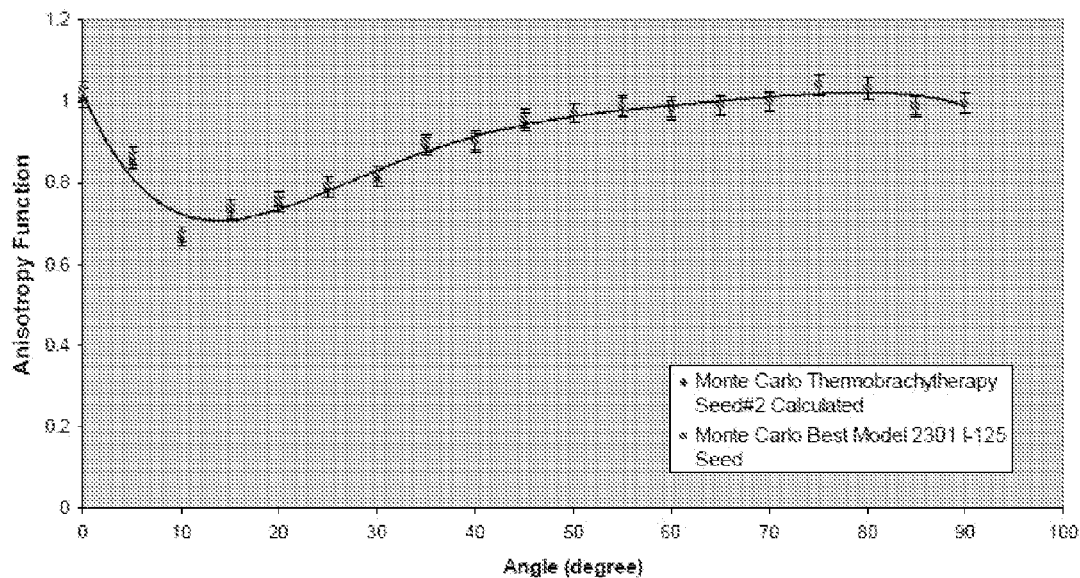

FIG. 69 illustrates the Anisotropy Function of Monte Carlo calculated value for Thermobrachytherapy Seed#2 and the Monte Carlo calculated for the Best Model 2301 $^{125}$I in Solid Water at 1 cm radii.

Figure 70:
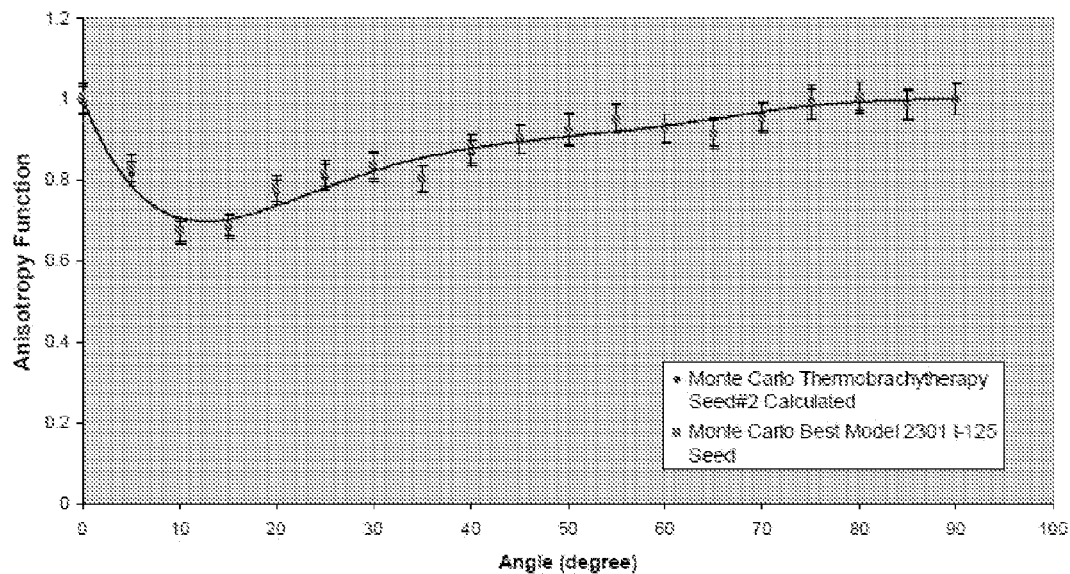

FIG. 70 illustrates the Anisotropy Function of Monte Carlo calculated value for Thermobrachytherapy Seed#2 and the Monte Carlo calculated for the Best Model 2301 $^{125}$I in Solid Water at 2 cm radii.

Figure 71:
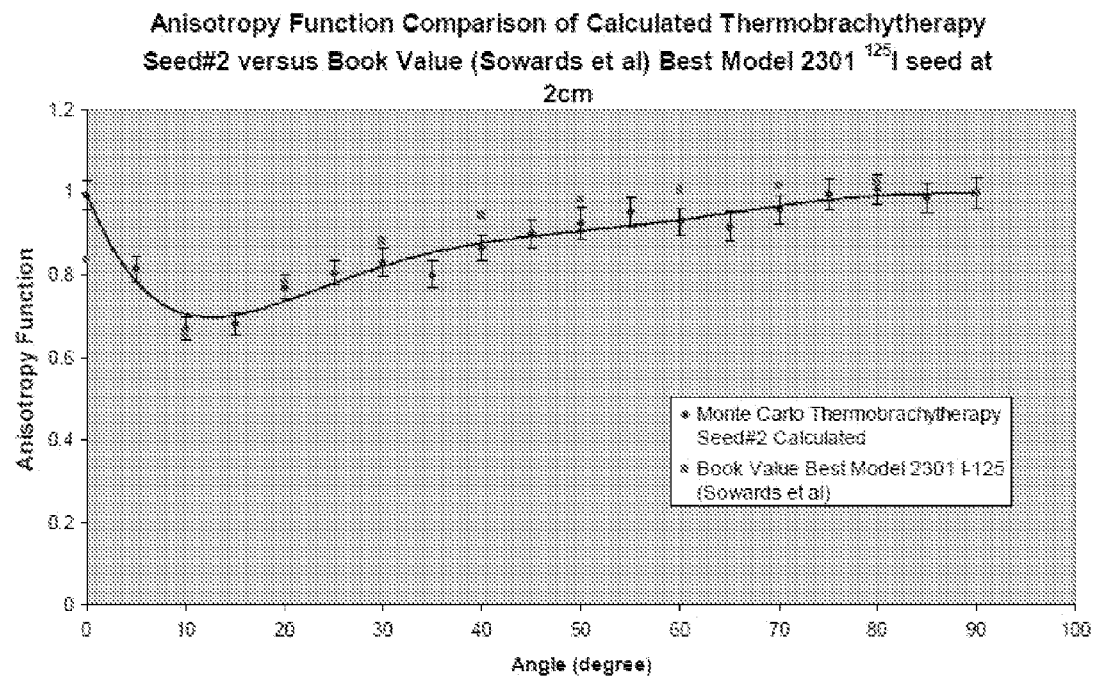

FIG. 71 illustrates the Anisotropy Function of Monte Carlo calculated value for Thermobrachytherapy Seed#2 and the Book value for the Best Model 2301 $^{125}$I in Solid Water at 2 cm radii.

Figure 72:
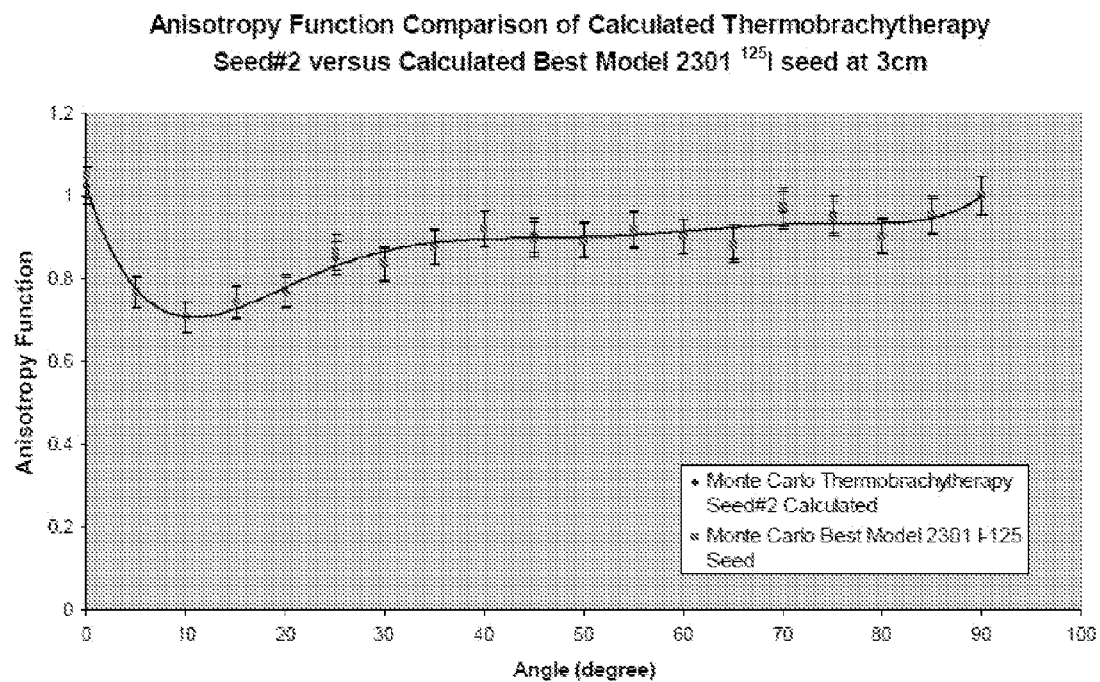

FIG. 72 illustrates the Anisotropy Function of Monte Carlo calculated value for Thermobrachytherapy Seed#2 and the Monte Carlo calculated for the Best Model 2301 $^{125}$I in Solid Water at 3 cm radii.

Figure 73:
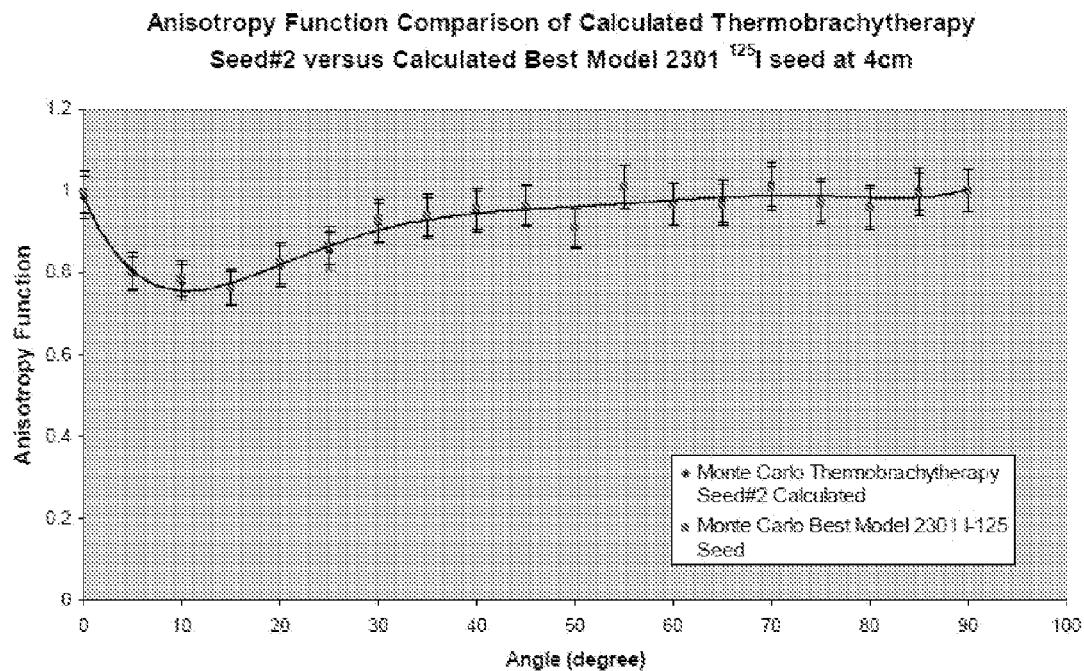

FIG. 73 illustrates the Anisotropy Function of Monte Carlo calculated value for Thermobrachytherapy Seed#2 and the Monte Carlo calculated for the Best Model 2301 $^{125}$I in Solid Water at 4 cm radii.

Figure 74:
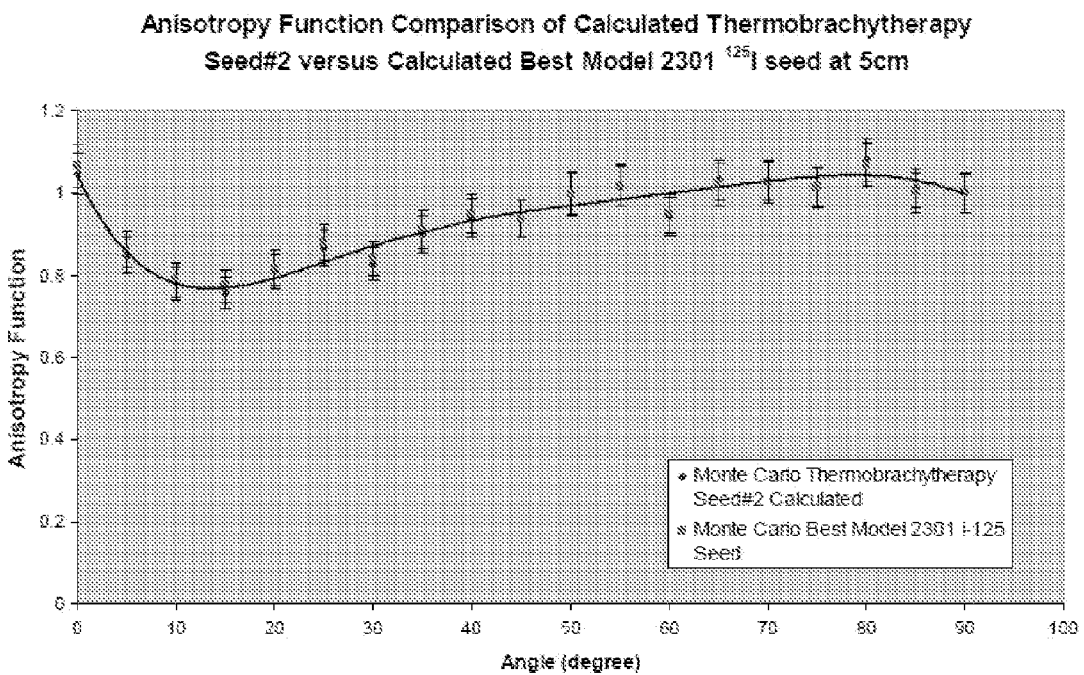

FIG. 74 illustrates the Anisotropy Function of Monte Carlo calculated value for Thermobrachytherapy Seed#2 and the Monte Carlo calculated for the Best Model 2301 $^{125}$I in Solid Water at 5 cm radii.

Figure 75:
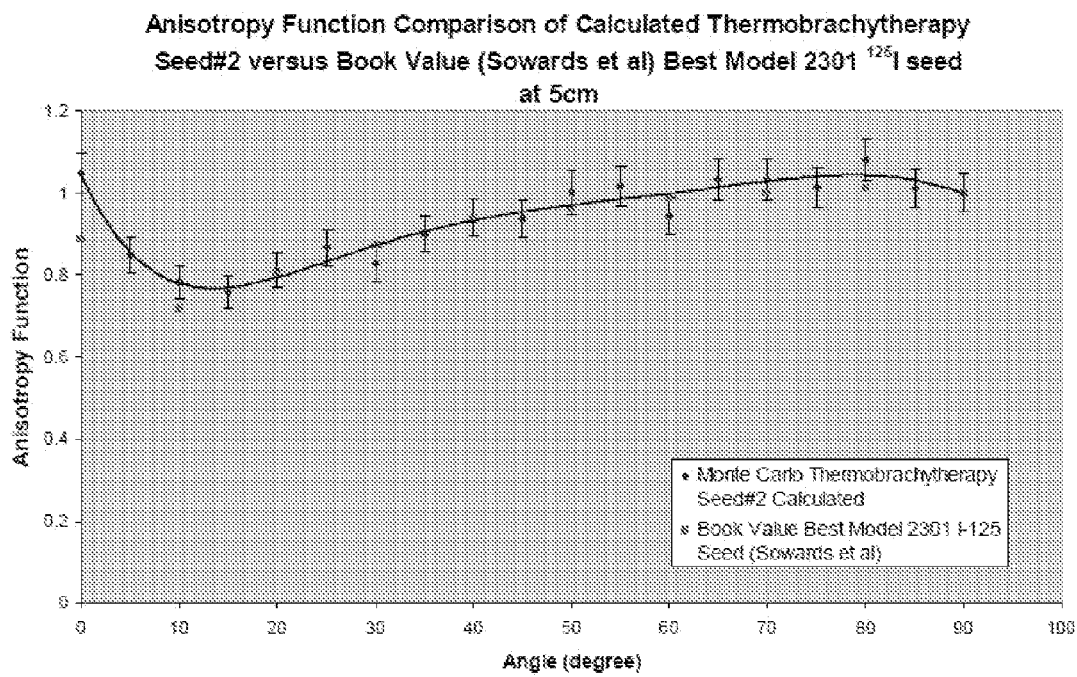

FIG. 75 illustrates the Anisotropy Function of Monte Carlo calculated value for Thermobrachytherapy Seed#2 and the Book value for the Best Model 2301 $^{125}$I in Solid Water at 1 cm radii.

Figure 76:
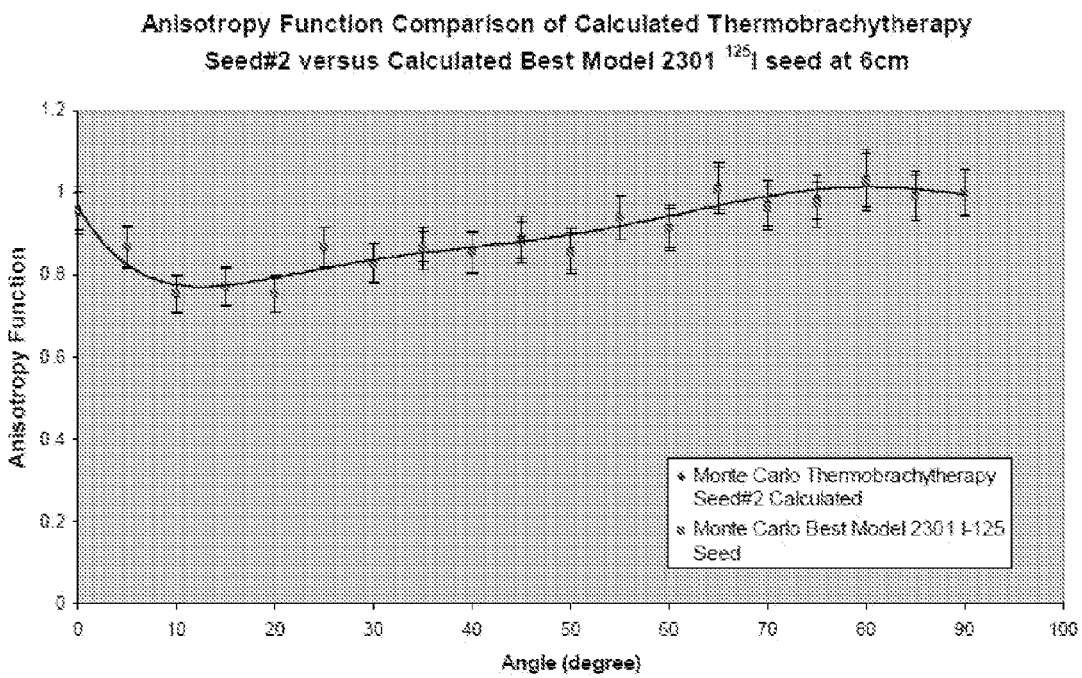

FIG. 76 illustrates the Anisotropy Function of Monte Carlo calculated value for Thermobrachytherapy Seed#2 and the Monte Carlo calculated for the Best Model 2301 $^{125}$I in Solid Water at 6 cm radii.

Figure 77:
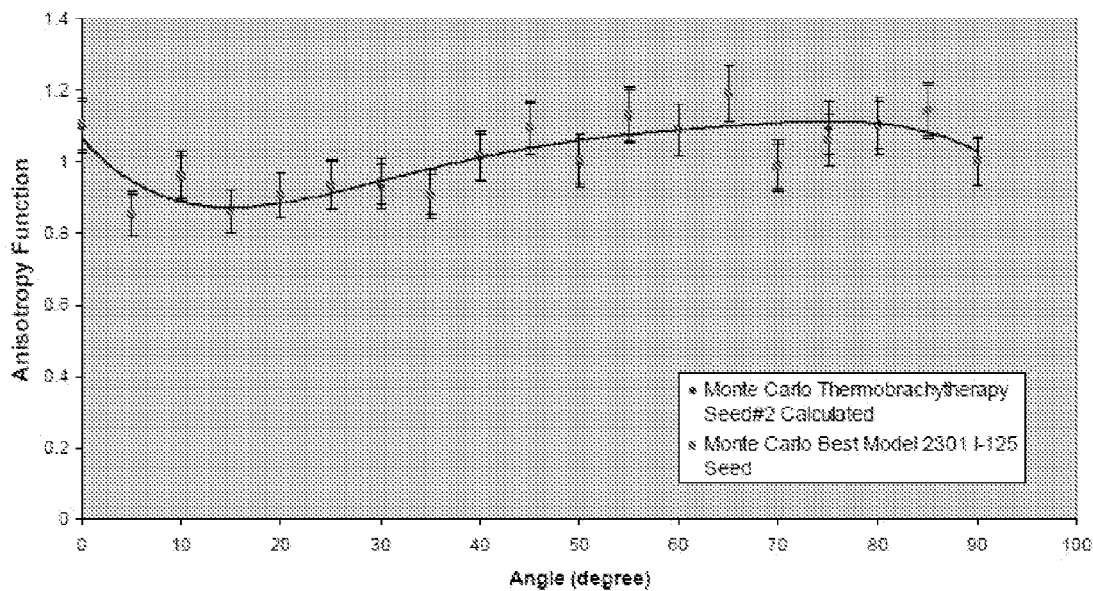

FIG. 77 illustrates the Anisotropy Function of Monte Carlo calculated value for Thermobrachytherapy Seed#2 and the Monte Carlo calculated for the Best Model 2301 $^{125}$I in Solid Water at 7 cm radii.

Figure 78:
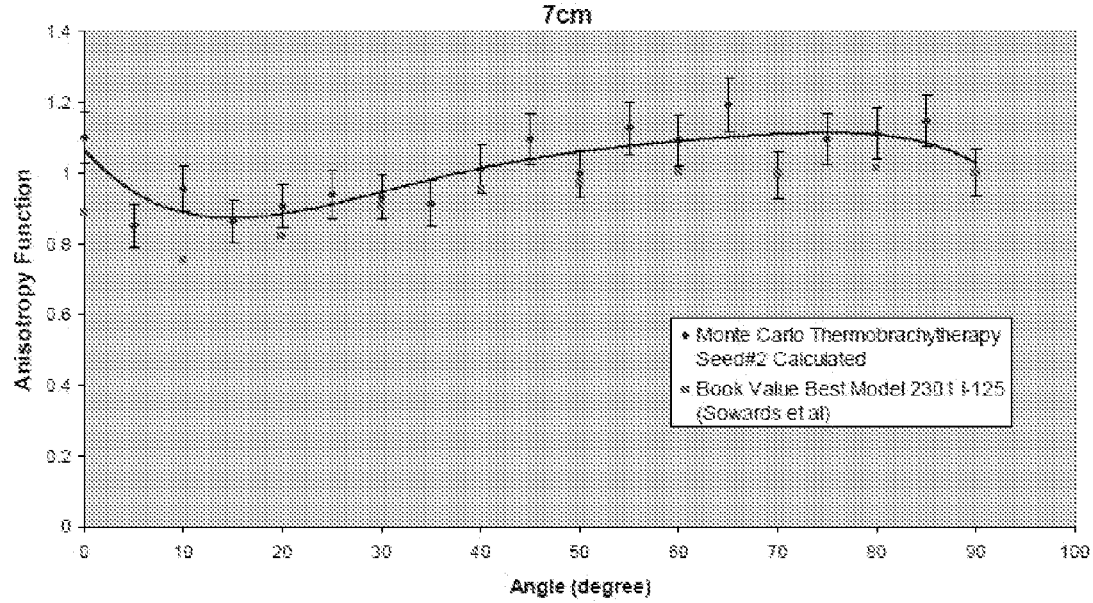

FIG. 78 illustrates the Anisotropy Function of Monte Carlo calculated value for Thermobrachytherapy Seed#2 and the Book value for the Best Model 2301 $^{125}$I in Solid Water at 7 cm radii.

Prior Art FIG. 79 illustrates a Prior Art seed where a middle of the seed has fairly larger temperature profile than the peripheral areas.

FIG. 80 is a schematic illustration of a radioactive interstitial thermobrachytherapeutic delivery system having magnetic properties.

FIG. 81 is a graph showing the modeled temperature distribution (in ° C.) at the seed middle point for different frequencies of EM field.

FIG. 82A-PRIOR ART is a schematic illustration of a BEST $^{125}$I, Model 2301 brachytherapy seed.

FIG. 82B is a schematic illustration of a Thermo-brachytherapy seed.

Figure 83:
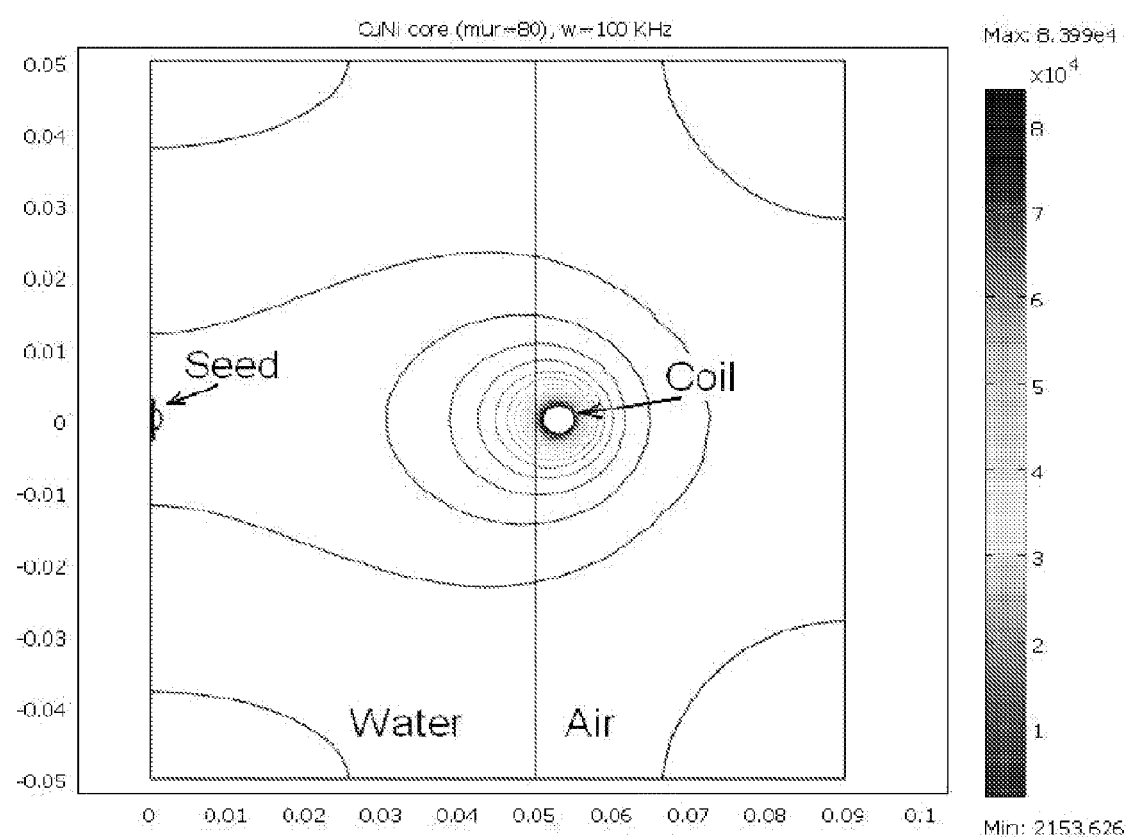

FIG. 83 shows a model layout and resulting magnetic field distribution for 1 seed with ferromagnetic cores in alternating electro-magnetic field of w=100 kHz.

Figure 84:
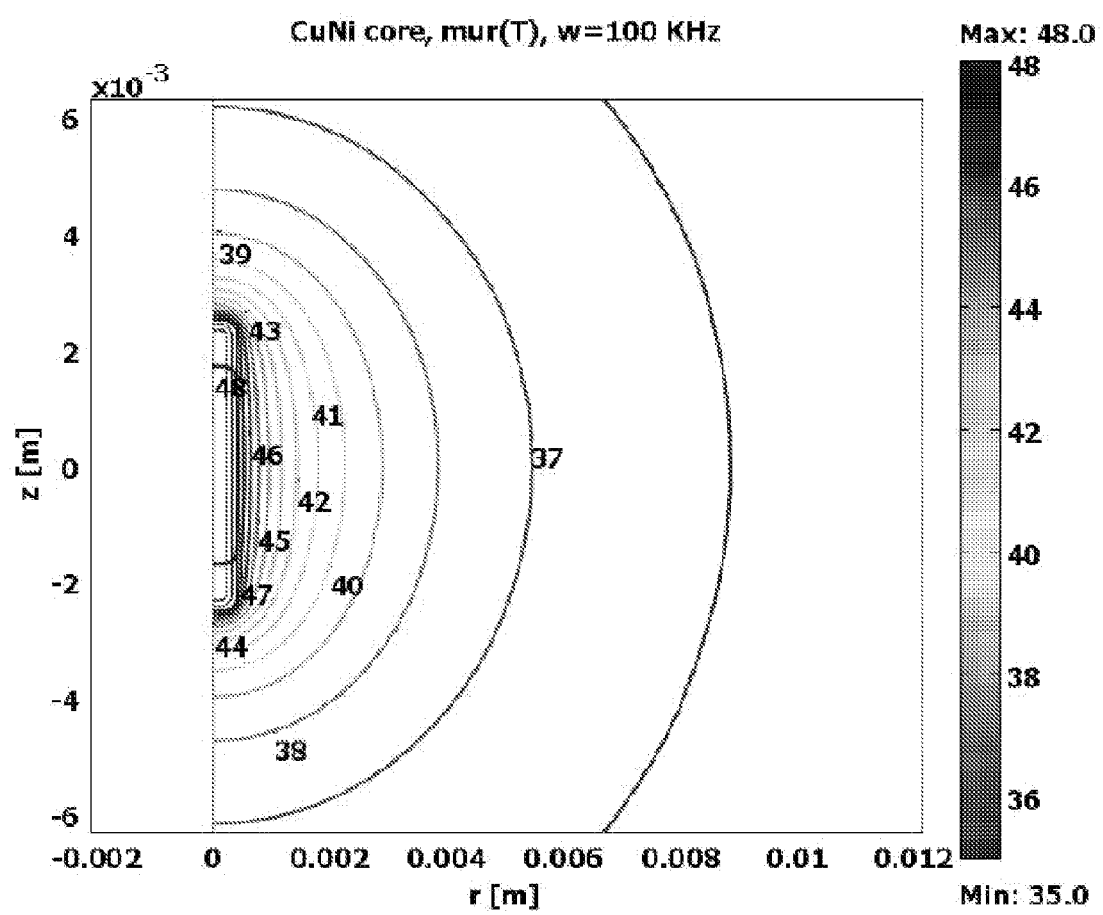

FIG. 84 shows a modeled temperature distribution (in ° C.) near the seed with ferromagnetic self-regulating core.

Figure 85:
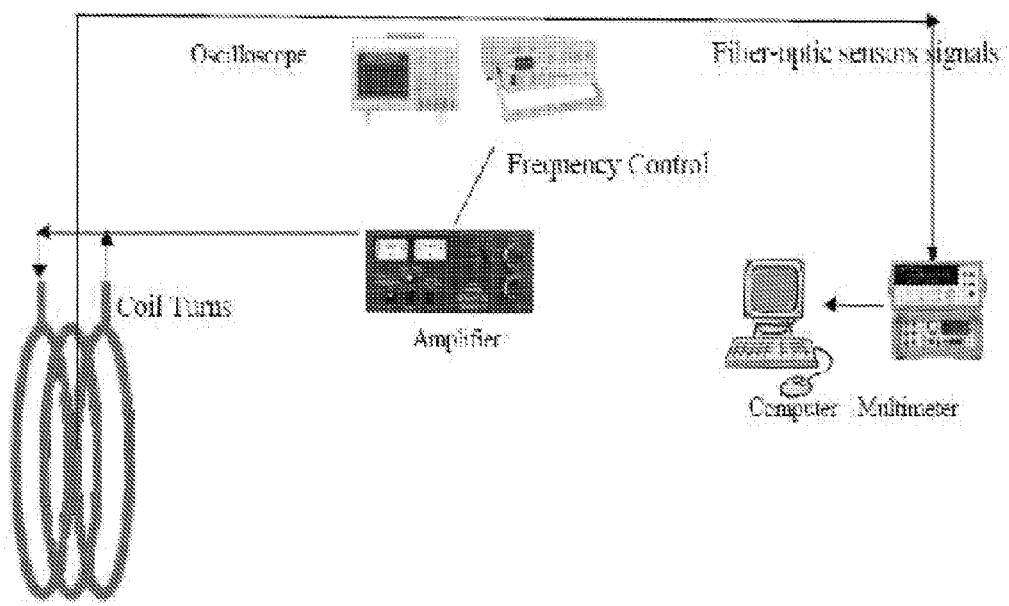

FIG. 85 is a schematic illustration of a system for the use in delivering a thermo-brachytherapeutic treatment.

DETAILED DESCRIPTION OF THE PREFERRED EMBODIMENT(S)

In one aspect, there is provided a system for combining hyperthermia and radiation treatments in a single treatment modality.

In a first broad aspect, there is provided herein a therapeutic seed for combining hyperthermia and radiation treatments in a single treatment modality, comprising a radioactive material having magnetic properties.

In certain embodiments, the seed includes one or more materials that possess ferromagnetic properties configured for hyperthermia delivery.

In certain embodiments, the seed has an inner section at least partially comprised of a magnetic material, and an outer layer that can be at least partially composed of platinum or platinum-like materials. In certain embodiments, the outer layer comprises palladium. In certain embodiments, the outer layer has a thickness from about 0.1 micron to about 20 microns. In certain embodiments, the seed has a spherical, cylindrical, conical, frustroconical, ovoid, or bullet shape or other suitable shape.

In certain embodiments, the magnetic material comprises Ni—Co. In certain embodiments, the magnetic material comprises a Ni (70.4%)-Co (29.6%) ferromagnetic alloy.

In another broad aspect, there is provided herein a method for the treatment of a patient in need thereof, comprising: determining one or more precise locations that need to be treated in the patient; and at least temporarily inserting one or more radioactive seeds described herein into the patient.

In certain embodiments, a radiation dose is delivered through brachytherapy as long as the seed is in location in the patient and/or as long as the seed remains radioactive.

In certain embodiments, the method includes providing a concurrent delivery of radiation dose and/or heat, and a substantially uniform distribution of temperature in a therapeutic regimen substantially suited for the patient.

In another broad aspect, there is provided herein a method of treating a patient, comprising: positioning at least one seed within a patient; delivering a brachytherapeutic treatment from the seed to the patient; and simultaneously activating the seed, for at least a period of time, to deliver a hyperthermia treatment to the patient by exposing the seed to a magnetic field.

In certain embodiments, the hyperthermia treatment is intermittently delivered over a set period of time.

In another broad aspect, there is provided herein a method of treating a patient, comprising: positioning a seed capable of delivering a dose of radiation within the patient; and at least intermittently exposing the seed to a magnetic field sufficient to deliver heat to the patient in an area surrounding the seed.

In certain embodiments, the method includes exposing the seed to one or more oscillating magnetic fields that range between a maximum flux density between about 25 gauss and about 100 gauss. In certain embodiments, the seed is exposed to more than one oscillating magnetic field in more that one treatment period of time.

In certain embodiments, the magnetic field oscillates within the range of from about 25 kHz to about 200 kHz.

In certain embodiments, the seed exhibits a Curie point in a therapeutic range between about 41.5° C. and about 100° C.

In a particular aspect, the system described herein includes the use of a dual-seed system, that is, a radioactive seed having magnetic properties. In one embodiment, the dual-seed system can contain a radioactive material suitable for permanent seed such as I-125, Pd-103, or Cs-131 or other similar (in energy and half life) radionuclides. In one embodiment the dual-seed system can include one or more materials that possess ferromagnetic properties for hyperthermia delivery.

One advantage of the dual-seed system is that two modalities of treatment can be combined in one delivery vehicle. The dual-seed system provides a more efficient method since two modalities can be designed to work in synergy with one another.

Another advantage of the dual-seed system is that there can now be a method for concurrent delivery of radiation dose and/or heat, a substantially uniform distribution of temperature, and substantially optimal design particularly suited for each individual patient.

In an additional aspect, there is provided herein a method for the treatment of cancers, such as, but not limited to: prostate cancer, vaginal cancer, choroidal melanoma, uveal melanoma, and other cancers.

The dual-seed delivery system also provides the clinician with an advanced technology in order to provide heat distribution and a monitoring system using the dual-system seeds.

In another aspect, there is provided herein a treatment planning method that can be used to determine the precise location and the number of dual-seed systems that need to be inserted in the target volume.

In certain embodiments, a hyperthermia segment of the treatment can be induced through the use of a strong magnetic field in the order of about 5000 A/m. In certain embodiments, useful ranges of 50-100 gauss can be used.

In use, one or more thermometers (placed in multiple locations) can be introduced to record the temperatures in the patient. In one embodiment, radiation dose is delivered through brachytherapy as long as the dual-seed systems are in place. It is to be understood that the uniformity and effectiveness of heat and dose distribution can depend, in part, on the treatment prescribed for the patient in need thereof.

Also, in certain embodiments, the dual-seed system can be used for permanent implantation in a patient in need thereof. In such embodiments, the radiation dose can be delivered continuously, while the hyperthermia can be delivered at determined segments, including times and dosages.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only.

Example 1

Materials and Methods

American Association of Physicists in Medicine Task Group-43 (AAPM TG-43). The AAPM TG-43 Report published in March 2004 is a revised AAPM protocol for brachytherapy dose calculations. The revised model is different from the original model in the following ways:

Air Kerma Strength (SK):

The new model has a revised definition of air-kerma strength. The original AAPM definition of the air kerma strength did not account for a low-energy cutoff (S).

The lower energy parameter is needed to discriminate against low energy photons, mostly characteristic x-rays from exterior capsules, that increase the air kerma rate (Ks(d)) without contributing significantly to doses at distances greater than 0.1 cm in tissue. The cut-off is usually 5 keV for low-energy brachytherapy source. This correction was necessary to ensure that the dose rate being recorded was accurately representative of the energy contribution from the radioactive sources.

Apparent Activity ($A_{app}$):

The new model eliminated apparent activity for specification of the strength of a source. Apparent activity is the activity from an unfiltered point source that has the same air-kerma strength as an encapsulated source. It was found that using $A_{app}$ for reporting source strength specification suffers from problems. In order to specify source strength, vendors had used $A_{app}$. Vendors convert air kerma strength to $A_{app}$ by dividing it by an assumed exposure rate constant r6 (x). The vendor supplied $A_{app}$ is multiplied by the assumed r6 (x) to get Absorbed Dose. r6 (x) has no meaningful physical role in the dosimetry of output calibrated source. Thus, quantities such as this might mislead the user if they use the wrong r6 (x). Therefore, Aapp is no longer used for specifying source strength. Air Kerma Strength has taken its place and is used for all aspects of dose calculations.

Anisotropy Constant ($\Phi$an) Versus One-Dimensional Anisotropy Function ($\Phi_{an}(r)$)

The earlier anisotropy constant was eliminated in favor of distance dependent one-dimensional anisotropy function. ($\Phi_{an}$ (r) is the ratio of the solid angle-weighted dose rate, averaged over the entire 47C steradian space, to the dose rate at the same distance 'r' on the transverse plane.

$$\Phi_{an}(r) = \frac{\int_0^\pi \dot{D}(r,\theta)\sin(\theta)\,d\theta}{2\dot{D}(r,\theta_0)} \quad (1)$$

The change from $^{(D}$an to $\Phi_{an}(r)$ was suggested to compensate for inadequacies in the treatment planning system. It is important to use the $\Phi_{an}(r)$ to minimize dose-calculation errors at small distances, for example, r<1 cm.

Recommendations on extrapolating data to varied distances:

The revised TG43 Report listed that care must be taken in evaluating dose rates at distances falling outside the range of tabulated data (especially at r<0.5 cm). At shorter radii, points at small polar angles near 0° and 180° are located inside the source capsule. The outcome from this is that the anisotropy function cannot be defined over the full interval from 0° to 90°. The TG-43 formalism breaks down at r<L/2. It has been recommended that it is essential when working with small distances to use the same geometry function and length of the source for evaluating absorbed dose as when used in the Monte Carlo data. Often the anisotropy function and radial function will exhibit nonphysical properties due to breaking down of the line source very near the source.

Correction in Minor Inconsistencies in the Original Protocol:

There are now consistent guidelines for use of point- and line-source geometries as applicable. Also, the report recommends a unified approach to compare reference dose distributions derived from different investigators to develop a single evaluated consensus data.

FIG. 1 shows the coordinate system used for AAPM TG-43 factors.

P(r0, 00)=>Reference Point of interest at r0=1 cm 00=90°
P(r, 0)=>Point of interest
L=>Length of the source
0=>Angle from the center of the source to the point of interest
$\theta_1$ and $\theta_2$=>Angles from the end of the source to the point of interest
β=>Angle formed at the Point of Interest by the tips of the source
r=>radii from center of the source to the Point of Interest
t=>Thickness of the Titanium capsule.

The AAPM TG-43 Report is a task group report recommending the various factors required in commissioning a clinical seed. There are several factors that have been recommended that ensure the dose function and anisotropy factors for seeds used in clinical trials.

Air-Kerma Strength (SK):

Air Kerma Strength is the air kerma rate (Ks(d)) due to photons greater than the cut-off energy (S) at distance (d), multiplied by the square of this distance ($d^2$)

$$SK = Ks(d)d2 \quad (2)$$

An important designation to be noted is that the term "d" is the distance from the source center to the point where the dose rate is being measured. This distance is required to be on the transverse plane of the source.

Dose-Rate (D):

Dose rate, per se, is not a highlighted parameter in the TG 43 factors. However, it is used in the calculation of the dose rate constant Dose rate, like air kerma strength, is measured at reference positions (0=90°, r=1 cm) on the transverse plane. These measurements are taken in the medium designated by the phantom (water or solid water).

$$\dot{D} = \frac{D}{\text{time}} \quad (3)$$

Dose-Rate Constant (Λ):

Dose rate constant in water is the ratio of dose-rate at the reference position, [P(r0, 00)] and the air kerma strength [SK].

$$\Lambda = \frac{\dot{D}(r_0, \theta_0)}{S_K} \quad (4)$$

Dose-rate constant depends on both the radionuclide being used and the source model being considered. It is also affected by the internal design of the source.

Geometry Function (G(r,θ)):

The purpose of the geometry function is for improving accuracy for dose rates when discrete points are used for interpolating the data.

This is done using the inverse square law correction that takes into account an approximate model of the distribution of radioactivity within the source.

$$G_P(r, \theta) = r^{-2} \quad (5) \rightarrow \text{for point source approximation}$$

$$G_L(r, \theta) = \frac{\beta}{Lr\sin\theta} \text{ if } \theta \neq 0° \text{ or,} \quad (6) \rightarrow \text{for line source approximation}$$

$$= (r^2 - L^2/4)^{-1} \text{ if } \theta = 0° \quad (7) \rightarrow \text{for line source approximation}$$

Units of $G_P$ or $G_L$ are $cm^{-2}$

Radial Dose Function g(r):

The need for the radial dose function is to account for dose fall-off on the transverse-plane due to photon scatter and attenuation. This does not include the dose fall-off that has already been included by the geometry function.

$$gx(r) = \frac{\dot{D}(r, \theta_0) * Gx(r_0, \theta_0)}{\dot{D}(r_0, \theta_0) * Gx(r, \theta_0)} \quad (8)$$

The subscript X refers to either point-source (P) or line-source (L). Most commercial treatment planning systems use a fifth order polynomial fit to the collected g (r) data.

2D Anisotropy Function F (r,θ):

2D anisotropy function is important to understand the variation in dose as the polar angle changes to the transverse plane.

$$F(r, \theta) = \frac{\dot{D}(r, \theta) * Gx(r, \theta_0)}{\dot{D}(r, \theta_0) * Gx(r, \theta)} \quad (9)$$

The value of F (r, 0) usually decreases as a) r decreases, b) as θ approaches 0° C. or 180° C.) as encapsulation thickness increases and/or d) as photon energy decreases.

Correction Factor and Wide Angle Free-Air Chamber (WAFAC) Anomaly

National Institute of Standards and Technology (NIST) located a shift in well chamber coefficients for certain batch of seeds. Further investigations led to more seeds having a downward in the air kerma strengths of several sources. NIST completed a number of measurements comparing the results in WAFAC and in the re-entrant chamber. The results indicate a combined ratio for the sources of 0.897±0.028. The conclusion is that the WAFAC air-kerma strengths measured in 1999 were too large by 2% to 7%, and required dose rate constant measurements normalized to NIST 1999 SK calibrations to be revised accordingly.

General Monte Carlo N-Particle Transport Code (MCNP) Version 5 (MCNP5)

In the MCNP5 code there are options for the operator to select from a choice of tallies that pertain to the particular problem that is being dealt with. They are normalized to be per starting particle except for a few special cases with criticality sources. It is important to note that tallies can be made for any cells and surfaces and do not require special geometry to be created. Any quantity in the form below can be tallied.

$$C = \int \Phi(E) f(E) d(E) \quad (10)$$

Where, Φ(E) is the energy dependent fluence, f(E) is any product or summation of quantities in the cross sectional libraries or a response function provided by the user. The basic MCNP tallies depends on the final answer that individual is interested in.

The Table 1 below lists some of the tallies and their uses.

TABLE 1

Tallies used in MCNP5 designate depend on the point of interest for the user

| Tally#1 | Tally#2 | Tally#3 | Description |
|---|---|---|---|
| F1:N or | F1:P or | F1:E | Surface current |
| F2:N or | F2:P or | F2:E | Surface flux |
| F4:N or | F4:P or | F4:E | Track length estimate of cell flux |
| F5a:N or | F5a:P or | | Flux at a point or ring detector |
| F6:N or | F6:P or | F1:N, P | Track length estimate of energy deposition |
| F7:N | | | Track length estimate of fission energy deposition |
| F68:N or | F8:P or | F8:E or F8:P, E | Pulse height tally |

For the purposes described herein, the F6 tally type is used. This tally directly calculates the dose at a given point per photon by determining the average energy deposition over a tally cell in the unit Mev/g.

$$H_t = \frac{\rho_a}{m} \int de \int dt \int dV \int d\Omega \sigma_t(E) H(E) \psi(\vec{r}\vec{\Omega}, E, t) \quad (11)$$

Where, $H_t$=total energy deposition in a cell (MeV/g)

$\rho_a$=atom density (atom/barn-cm) m=cell mass (g)

r,n,E,t=particle position vector (cm), direction vector, energy (MeV) and time (sh, sh=$10^{-9}$ s)

σt=microscopic total cross-section (barns)

H(E)=heating number (MeV/collision)

Monte Carlo results are obtained by sampling possible random walks and assigning a value for each walk. Random walks produce a range of score depending on the tally selected and the variance reduction chosen. There is also an important distinction between the precision and accuracy chosen in Monte Carlo calculations. Precision is the uncertainty in mean caused by statistical uncertainty. Accuracy is a measure of how close the expected value of the mean is to the true value being estimated. Uncertainties in Monte Carlo calculations refer only to the precision of the result and not to the accuracy. In order to get good statistical results, it is imperative to use a significant number of histories. Increasing the number of interactions, improves the statistical score. However, in doing so, the time required for computations also increases and increases the duration of the computations.

An introduction of the procedure involved in the development of the MCNP output data follows. An input file needs to be created in order to produce the output file with the dose values. There are 5 different steps that need to be created:

1—Cell Cards

This card creates the cells based on different surfaces. The cell card allows the orientation of different surfaces to one another and allows in the formation of the overall geometry. This is also the card where the density of the atom/compound/mixture of the surface is designated.

2—Surface Cards

The surface card creates surfaces and promotes the dimensions of the different materials being used in the creation of the cells. Dimensions of the detector are also added here.

3—Material Cards

This is where the different materials are designated and the atomic number and atomic masses recorded. A negative sign before an atomic fraction suggests fraction designation by weight and a positive sign indicates fraction by atomic number.

4—Data Cards

Data card is where the source is specified, including the radius and length of the source, the axis it is placed on and the probability of the detection. Energy along with the probability from the radioactive source is also designated here.

5—Tally Cards

The tally card follows the data card and it accounts for the Multiplier (FM6) in this project. Also, the number of histories or the number of particles to be started is recorded in this section. MCNP5 is a versatile program that is easy to use. It includes a powerful general source, geometry tally plotters, variance reduction techniques, a flexible tally structure and an extensive collection of cross-section data. It is an important code that creates a particle and tracks it's interaction through different materials, through cells composed of varied surfaces, as it ventures it ways through the geometry under question. It should also be noted that the MCNP5 code can be used for various reasons and uses. The code in this project is used to detect dose rate at selected distances and angles from the source.

The Three Modeled Seeds: a) Best Model 2301 $^{125}$I seed:

This seed has an inner radio-opaque Tungsten marker, followed by a Carbon containing $^{125}$I. The outer layer consists of an inner and outer Titanium capsule.

Prior Art FIG. 2 is a schematic diagram of Best Model 2301 $^{125}$I where 1 is a Tungsten Radio-opaque Marker; 2 is a Carbon containing $^{125}$I; 3 is an Air compartment; 4 in an inner Titanium capsule; and, 5—is an outer Titanium capsule.

Dimensions for the seed are as follows:

Tungsten marker (cell 1): length—3.7 mm, diameter—0.25 mm

Carbon containing $^{125}$I(cell 2)—length—4 mm, diameter—0.45 mm, thickness—0.1 mm (0.15 mm at edges)

Air compartment (cell 3)—length—4.84 mm, diameter—0.64 mm, thickness—0.095 mm (0.42 mm at edges)

Inner Titanium Capsule (cell 4)—length—4.92 mm, diameter—0.72 mm, thickness—0.04 mm Outer Titanium Capsule (cell 5)—length—5.0 mm, diameter—0.8 mm, thickness—0.04 mm After the overall values were compared and were within an acceptable (5-6%), two models of thermobrachytherapy seeds were created. It is also important to note that the vendor's Best Model seed has a slight curvature to the I-125 compartment at the ends. However, the dimensions for the curvature are unavailable in any literature and therefore, the curvature was not incorporated into the calculated modeled seeds. This will cause very slight deviation in the results from the calculated values at the ends of the seed.

Thermobrachytherapy Seed#1

Thermobrachytherapy Seed#1 is similar in geometry to the Best Model 2301 $^{125}$I seed with the radiographic marker replaced by a ferromagnetic material. The ferromagnetic material is 70.4% Nickel and 29.6% Copper. The dimensions stay the same.

FIG. 3 is a schematic diagram of Thermobrachytherapy Seed#1, where 1 is a Ni—Cu Ferromagnetic Material; 2 is a Carbon containing $^{125}$I; 3 is an Air compartment; 4 is an inner Titanium capsule; and 5 is an outer Titanium capsule.

Dimensions for the seed are as follows:

Ferromagnetic marker (cell 1): length—3.7 mm, diameter—0.25 mm

Carbon containing $^{125}$I— length (cell 2)—4 mm, diameter—0.45 mm, thickness—0.1 mm (0.15 mm at edges)

Air compartment (cell 3)—length—4.84 mm, diameter—0.64 mm, thickness—0.095 mm (0.42 mm at edges)

Inner Titanium Capsule (cell 4)—length—4.92 mm, diameter—0.72 mm, thickness—0.04 mm Outer Titanium Capsule (cell 5)—length—5.0 mm, diameter—0.8 mm, thickness—0.04 mm Thermobrachytherapy Seed#2

Thermobrachytherapy Seed#2 has both a ferromagnetic component and radio-opaque Tungsten marker in the seed. The ferromagnetic seed is similar to thermobrachytherapy seed#2 with 70.4% Nickel and 29.6% Copper.

The outer compartments are the same as previous two seeds. However, the inner radio-opaque marker is smaller in size covering the middle of the seed and two ferromagnetic components are added to the two ends of the seed. The dimension of the ferromagnetic-radio-opaque-ferromagnetic component stays the same as the original radio-opaque (Best Model 2301 $^{125}$I) or the ferromagnetic component (thermobrachytherapy seed#1).

FIG. 4 is a schematic diagram of Thermobrachytherapy Seed#1, where 1 is a Tungsten Radioopaque Marker; 2 is a Carbon containing $^{125}$I; 3 is an Air compartment; 4 is an inner Titanium capsule; 5 is an outer Titanium capsule; 6 is a Left Ni—Cu Ferromagnetic Material; and 7 is a Right Ni—Cu Ferromagnetic Material.

Dimensions for the seed are as follows:

Tungsten marker (cell 1): length—1.23 mm, diameter—0.25 mm

Left Ferromagnetic marker (cell 6): length—1.23 mm, diameter—0.25 mm

Right Ferromagnetic marker (cell 7): length—1.23 mm, diameter—0.25 mm

Carbon containing $^{125}$I— length (cell 2)—4 mm, diameter—0.45 mm, thickness—0.1 mm (0.15 mm at edges)

Air compartment (cell 3)—length—4.84 mm, diameter—0.64 mm, thickness—0.095 mm (0.42 mm at edges)

Figure 5:
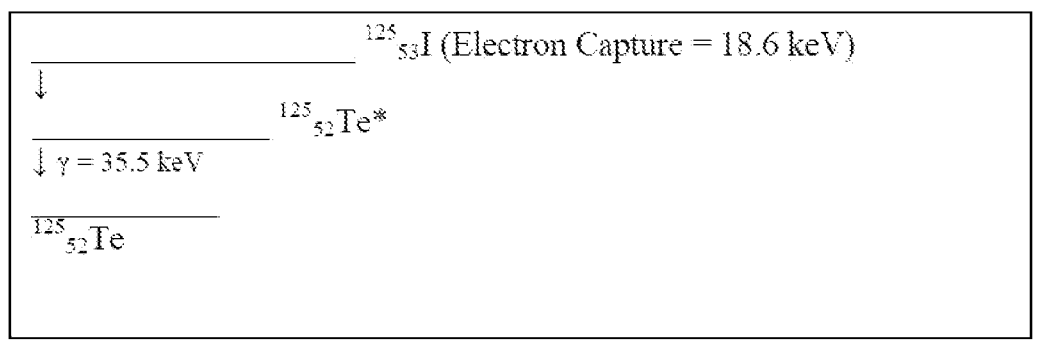
FIG. 5 is a diagram detailing the disintegration of $^{125}$I is shown in which shows the disintegration of $^{125}_{53}$I to $^{125}_{52}$Te releasing characteristic x-rays and γ-emission.

Inner Titanium Capsule (cell 4)—length—4.92 mm, diameter—0.72 mm, thickness—0.04 mm Outer Titanium Capsule (cell 5)—length—5.0 mm, diameter—0.8 mm, thickness—0.04 mm Radioactive Material:

$^{125}$I is used as the radioactive material. It is useful because of its short half life with a T1/2 of 59.4 days. As a result it is convenient for storage. Furthermore, its low 28 keV energy allows for less shielding. A diagram detailing the disintegration of $^{125}$I is shown in FIG. 5 which shows the disintegration of $^{125}_{53}$I to $^{125}_{52}$Te releasing characteristic x-rays and γ-emission.

$^{125}$I Decays via electron capture (100% of the time) to first excited state of $^{125}$Te. This in turn de-excites spontaneously to the ground state with the emission of a 35.5-keV γ-emission accounting for 7% of the released x-rays, the production of characteristic x-rays, in the range of 27-35 keV, account for the other 93% produced to electron capture and internal conversion. On an average, 1.4 photons are emitted per disintegration of $^{125}$I The low energy electrons (maximum energy of 35 keV) emitted can be filtered by iodine and by the thin encapsulation materials. The nuclear data for $^{125}$I brachytherapy sources are listed in Table 2.

TABLE 2[11]

Nuclear Data for $^{125}$I for brachytherapy dosimetry

| Photon energy (keV) | Photons per disintegration |
|---|---|
| 27.202 | 0.406 |
| 27.472 | 0.757 |
| 30.98 | 0.202 |
| 31.71 | 0.0439 |
| 35.492 | 0.0668 |

The Gamma Constant $(\Gamma_{5skev})=0.0355~\mu Gym^2h^{-1}Bq^{-1}$

It should be noted that, as stated in AAPM TG-43 report, the tungsten k-shell binding energy exceeds the maximum energy emitted during $^{125}$I decay and therefore, no characteristic k-shell x-rays are produced and L-shell x-rays are absorbed in the encapsulation.

Ferromagnetic Material

The ferromagnetic material is an alloy of 70.4% Nickel and 29.6% Copper. This alloy has a curie temperature of 48.2° C. Nickel has an atomic number of 28, atomic mass of 59 amu while Copper's atomic number 29 and atomic mass 64 amu. Together, the density of the material is 8.92 g/cm³.

The density of the material is higher than the bone. Therefore, it is deciphered that the Ni—Cu alloy will show under kilo-voltage beams as an identifier and could possibly replace the radio-opaque marker.

Methods:

Hyperthermia and Brachytherapy have a synergy effect; this property was introduced to be combined together to kill cancer cells.

General Monte Carlo N-Particle Transport Code version 5 (MCNP5) was undertaken as a useful resource to create and simulate the seed. This program allows the creation and tracking of particle(s) from their initiation to their transportation through materials.

An in-depth study of the MCNP5 code was performed. This took the form of understanding the various commands associated with creating the files, comprehending the cell, surface and data commands and becoming aware of the various atomic mixtures and material commands. Understanding the input and output files was also extensively studied. This started by creating one generic cell with one compartment, followed by a seed with several sub-compartments (or cells). After perfecting this method, method for two and then multiple seeds, at a required distance from one another, was learned. It was also ensured that the system, as created, did produce particle or particles. It was also imperative to confirm that the particles were being created in the source and not from any other compartments. Detectors were also created and methods to form multiple detectors were learned through the Transfer (TRCL) command at the required coordinates, distances and angles. This proved to be vital during the course of simulating dose rates from the modeled seeds.

The Best Model 2301 $^{125}$I Seed was modeled. After modeling the seed, the TG-43 factors were measured for the seed in the simulated program. The values were compared to Book values. This was done to ensure that the modeling of the seed was done accurately. When the values were within an acceptable range of 5-6% for both solid and liquid water, two thermobrachytherapy seeds were modeled and TG-43 factors were calculated for the models to study the closeness of the newly developed seed to the Best Model seed already in clinical practice. The values for the two thermobrachytherapy seeds were calculated in both liquid water and liquid water phantoms.

Calculating Geometry Function for the Anisotropy Function at Different Angles θ:

Cosine Law:

$$a^2=b^2+c^2-2bc\cos(\alpha) \quad (12)$$

where, b=Radial Distance

α=θ

Sine Law:

$$\frac{\sin\alpha}{a} = \frac{\sin\beta}{b} = \frac{\sin\gamma}{c} \quad (13)$$

a=>get froth cosine law c=>length of half of the source (L/2)

Figure 6:
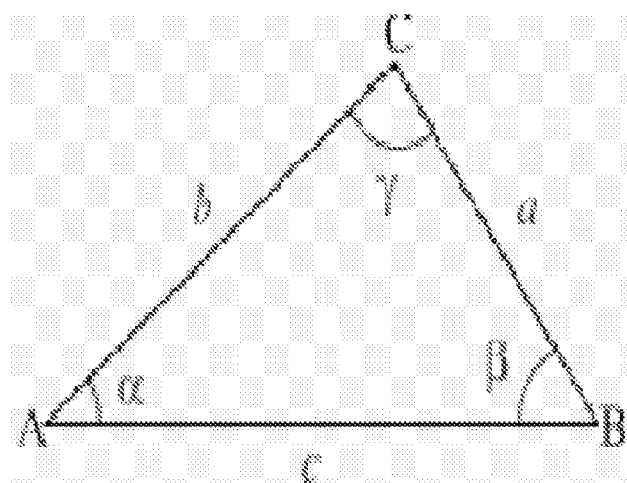
FIG. 6 is a schematic illustration showing the β covers two triangles and has to be repeated for the second triangle.

This will give angle γ for one triangle. The β covers two triangles and has to be repeated for the second triangle, as shown in FIG. 6.

Figure 7:
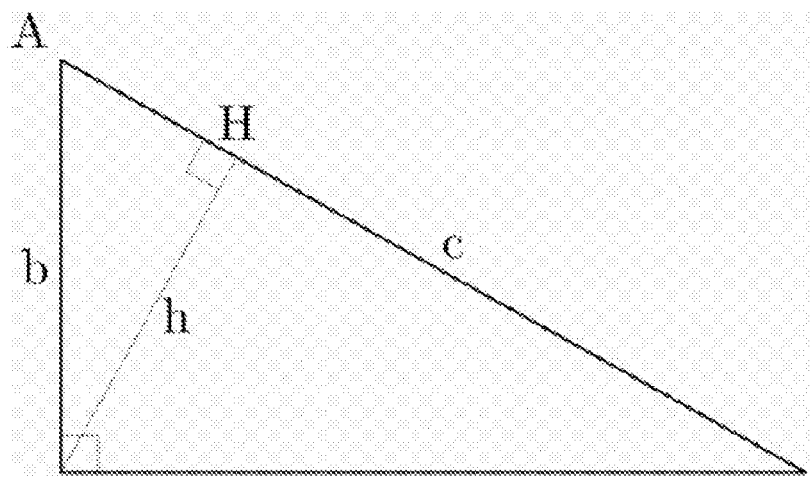
FIG. 7 is a schematic illustration used to calculate the coordinates of the detectors.

Calculating Coordinates for the Placements of Detectors at Varied Angles:

$$x~\text{coordinate}=r^*\sin\theta \quad (14)$$

$$z~\text{coordinate}=r^*\cos\theta \quad (15)$$

where, r=radial distance (or h from FIG. 7 used to calculate the coordinates of the detectors).

θ=angle (taken from center of the source) at which the detectors are placed

Error Calculations:

The T-43 discusses three sources of error: a) uncertainty due to uncertainty of the cross-sections; b) Uncertainty from the seed geometric model; and, c) Statistical uncertainty due to the Monte Carlo technique. However, in the present example, the statistical uncertainty is the uncertainty that is taken into account for all measurements. Two different error calculations are done Calculating Error Percentage:

Error percentage is taken between two values to find out how one deviates from the other.

$$\text{Error Percentage} = \frac{(\text{Calculated Value} - \text{Book Value})}{\text{Book Value}} \quad (16)$$

Calculating Standard Deviation:

Standard Deviation is required to add the error bars on the data points and to provide the error range for the values.

$$\left(\frac{\sigma_Z}{Z}\right)^2 = \left(\frac{\sigma_X}{X}\right)^2 + \left(\frac{\sigma_Y}{Y}\right)^2 \quad (17)$$

where,

X=>value in the numerator

σX=>standard deviation for X

Y=>value in the denominator

σY=>standard deviation for Y

Z=>Final answer from X/Y

σZ=>standard deviation for Z

Results

The three sets of seeds (Best Model 2301 $^{125}$I seed, Thermobrachytherapy seed#1, Thermobrachytherapy seed#2) were modeled on MCNP5. TG-43 factors were calculated in both liquid and solid water and recorded for the three sets and exported to Excel for further computations.

1) Best Model 2301 $^{125}$I Seed in Liquid Water.
i) Dose Rate (D):
Dose Rate was calculated for seed at 1 cm on the transverse plane (θ=90°) of the source (from the center of the source) in water. Therefore, for this measurement the phantom was taken to be liquid water since it is the liquid water measurement.
Table 3 shows the Dose Rate for Best Model 2301 $^{125}$I Seed in liquid water calculated using Monte Carlo. The dose rate recorded is $0.237 \pm 4.84 \times 10^{-3}$ cGy*sec$^{-1}$*Ci$^{-1}$.

TABLE 3

Dose Rate for Best Model 2301 $^{125}$I Seed in liquid water calculated using Monte Carlo

| Calculated Dose Rate (cGy*sec$^{-1}$*Ci$^{-1}$) | Book Value (Meigooni et al) | Error |
|---|---|---|
| 0.236993 | N/A | N/A | ii) Air Kerma Strength (SK):
Air Kerma Strength was calculated for the seed again at 1 cm on the transverse plane of the source (from the center of the source) but it was measured in air. Therefore, the material inside the phantom was taken as air.
Also, the 0.897 WAFAC correction factor (as discussed in the Materials and Methods section) is used for SK. Table 4 shows the Air Kerma Strength for Best Model 2301 $^{125}$I Seed in Air calculated using Monte Carlo. The Air Kerma Strength recorded is $0.224 \pm 4.98 \times 10^{-3}$ cGy*cm$^2$sec$^{-1}$*Ci$^{-1}$.

TABLE 4

Air Kerma Strength for Best Model 2301 $^{125}$I Seed in Air calculated using Monte Carlo

| Calculated Air Kerma Strength (cGy*cm$^2$sec$^{-1}$*Ci$^{-1}$) | Book Value (Meigooni et al) | Error |
|---|---|---|
| 0.224332 | N/A | N/A | iii) Dose Rate Constant (Λ):
Dose rate constant is calculated using equation #4. In order to calculate it, the ratio of the dose rate and air kerma strength is taken. Table 5 shows the Monte Carlo calculated Dose Rate Constant for Best Model 2301 $^{125}$I Seed in liquid water. The error is calculated by using equation #16. Therefore, the error between the measured value and the book value is 4.6%. The measured value of Dose Rate Constant is $1.056 \pm 0.0055$ cGy*h$^{-1}$*U$^{-1}$.

TABLE 5

Monte Carlo calculated Dose Rate Constant for Best Model 2301 $^{125}$I Seed in liquid water

| Calculated Dose Rate (Gy*h$^{-1}$*U$^{-1}$) | Book Value (Meigooni et al) (Gy*h$^{-1}$*U$^{-1}$) | Error |
|---|---|---|
| 1.05644 | 1.01 | 0.04598 | iv) Radial Function:
Calculation of the radial function is a two fold process.
a) Geometry Function
Using equations #6 and #7 the geometry function was calculated for each distance along the transverse plane from the center of the seed at varied distances.
Table 6 shows the Geometry Function calculated for the seeds where the Geometry Function is independent of the components of the seed. It depends on the geometry/dimensions of the source component of the seed.

TABLE 6

Geometry Function calculated for the seeds (Please note that Geometry Function is independent of the components of the seed. It depends on the geometry/dimensions of the source component of the seed.)

| Transverse distance (r) cm | Geometry Function G(r, θ) cm$^{-2}$ |
|---|---|
| 0.1 | 55.34268 |
| 0.15 | 30.90395 |
| 0.2 | 19.63125 |
| 0.25 | 13.48885 |
| 0.3 | 9.801083 |
| 0.4 | 5.795581 |
| 0.5 | 3.8041 |
| 0.6 | 2.680029 |
| 0.7 | 1.988054 |
| 0.75 | 1.736857 |
| 0.8 | 1.531238 |
| 0.9 | 1.214714 |
| 1 | 0.986798 |
| 1.5 | 0.441485 |
| 2 | 0.249099 |
| 2.5 | 0.159493 |
| 3 | 0.110808 |
| 3.5 | 0.081516 |
| 4 | 0.062384 |
| 4.5 | 0.049248 |
| 5 | 0.039961 |
| 5.5 | 0.032996 |
| 6 | 0.027775 |
| 6.5 | 0.023625 |
| 7 | 0.020441 |
| 7.5 | 0.017799 |
| 8 | 0.015596 |
| 8.5 | 0.013857 |
| 9 | 0.012312 |
| 9.5 | 0.011113 |
| 10 | 0.010034 | b) Radial Dose Function Using the Geometry Function
Radial Dose Function was calculated using equation #8 incorporating the geometry function calculated in part a) above. Table 7 shows the Radial Dose Function calculated at the transverse plane for the Best Model 2301 $^{125}$I Seed in liquid water using Monte Carlo.

TABLE 7

Radial Dose Function calculated at the transverse plane for the Best Model 2301 $^{125}$I Seed in liquid water using Monte Carlo

| Transverse distance (r) cm | Radial Dose Function g(r) | Book Value | Error |
|---|---|---|---|
| 0.1 | 0.945629 | 1.033 | −0.08458 |
| 0.15 | 0.972143 | 1.029 | −0.05525 |
| 0.2 | 1.004325 | 1.028 | −0.02303 |
| 0.25 | 0.978685 | 1.027 | −0.04704 |
| 0.3 | 0.999578 | 1.027 | −0.0267 |
| 0.4 | 0.99135 | 1.027 | −0.03471 |
| 0.5 | 1.02054 | 1.028 | −0.00726 |
| 0.6 | 0.963113 | 1.034 | −0.06856 |
| 0.7 | 0.931244 | 1.036 | −0.10112 |
| 0.75 | 0.959788 | 1.03 | −0.06817 |
| 0.8 | 0.935891 | 1.024 | −0.08604 |
| 0.9 | 1.038878 | 1.013 | 0.025546 |
| 1 | 1.000001 | 1 | 5.07E−07 |
| 1.5 | 0.926622 | 0.938 | −0.01213 |
| 2 | 0.847695 | 0.866 | −0.02114 |
| 2.5 | 0.762436 | 0.79 | −0.03489 |
| 3 | 0.688111 | 0.707 | −0.02672 |
| 3.5 | 0.607313 | 0.635 | −0.0436 |
| 4 | 0.536531 | 0.555 | −0.03328 |

TABLE 7-continued

Radial Dose Function calculated at the transverse plane for the Best Model 2301 $^{125}$I Seed in liquid water using Monte Carlo

| Transverse distance (r) cm | Radial Dose Function g(r) | Book Value | Error |
|---|---|---|---|
| 4.5 | 0.482933 | 0.488 | −0.01038 |
| 5 | 0.407078 | 0.427 | −0.04666 |
| 5.5 | 0.360958 | 0.372 | −0.02968 |
| 6 | 0.299346 | 0.32 | −0.06454 |
| 6.5 | 0.268061 | 0.285 | −0.05944 |
| 7 | 0.239495 | 0.248 | −0.0343 |
| 7.5 | 0.203286 | 0.215 | −0.05448 |
| 8 | 0.181816 | 0.187 | −0.02772 |
| 8.5 | 0.154299 | 0.16 | −0.03563 |
| 9 | 0.132667 | 0.142 | −0.06573 |
| 9.5 | 0.10157 | 0.123 | −0.17422 |
| 10 | 0.099486 | 0.103 | −0.03412 |

Figure 8:
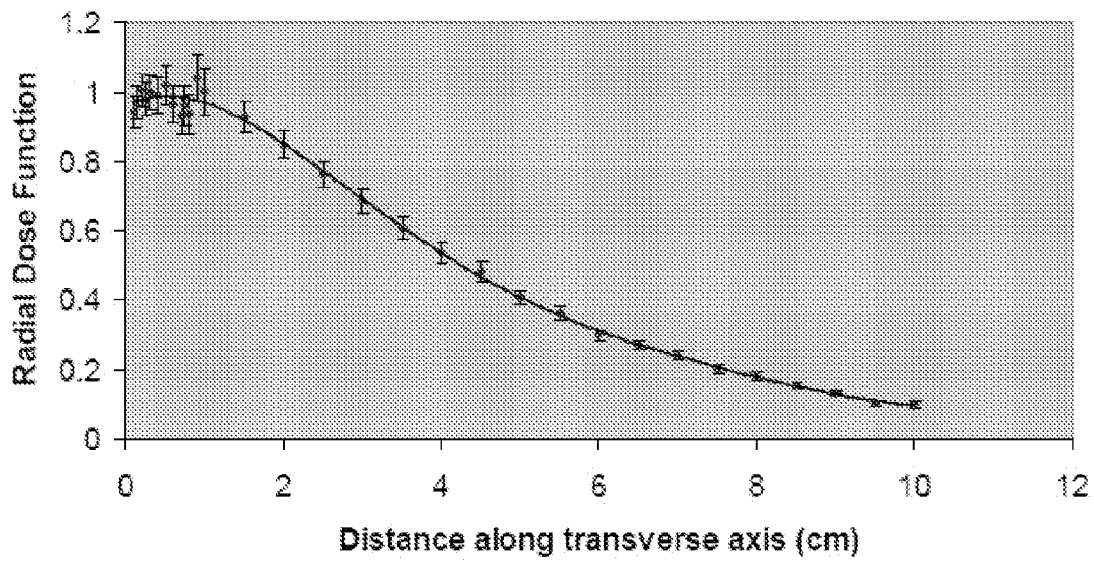
FIG. 8 is a graph for radial dose function versus distance on the transverse plane fits, in which illustrates Radial Dose Function calculated in Liquid Water for the Best Model 2301 $^{125}$I Seed.

The graph for radial dose function versus distance on the transverse plane fits as show in FIG. 8 which illustrates Radial Dose Function calculated in Liquid Water for the Best Model 2301 $^{125}$I Seed. The curve is fitted to 5th order polynomial Function.

iv) Anisotropy Function:

Calculation of the radial function is a three fold process.

a) Calculating Geometry Function

Equations #12 and #13 is used to calculate β for the various angles which in turn is used to calculate the Geometry Function at various angles.

Table 8a shows the Geometry Function calculated for the various angles for the Best Model 2301 $^{125}$I Seed at 1, 2, 3 and 4 cm where the Geometry Function is independent of the components of the seed.

TABLE 8a

Geometry Function calculated for the various angles for the Best Model 2301 $^{125}$I Seed at 1, 2, 3 and 4 cm (Please note that Geometry Function is independent of the components of the seed)

| Angle | GF at 1 cm | GF at 2 cm | GF at 3 cm | GF at 4 cm |
|---|---|---|---|---|
| 0 | 1.0416667 | 0.25252525 | 0.111607 | 0.06265 |
| 5 | 1.041096617 | 0.250143349 | 0.111730696 | 0.062535837 |
| 10 | 1.040481322 | 0.253225575 | 0.11115182 | 0.062679598 |
| 15 | 1.037567568 | 0.251812259 | 0.111729408 | 0.062742519 |
| 20 | 1.035774854 | 0.251927997 | 0.111826267 | 0.062822551 |
| 25 | 1.031323877 | 0.251643026 | 0.111382979 | 0.062652926 |
| 30 | 1.0391475 | 0.2521525 | 0.111389167 | 0.06282 |
| 35 | 1.022223432 | 0.251565767 | 0.111469222 | 0.062511433 |
| 40 | 1.017690513 | 0.251030327 | 0.11149365 | 0.062757582 |
| 45 | 1.012568953 | 0.250828324 | 0.111273574 | 0.06262995 |
| 50 | 1.008045039 | 0.250587467 | 0.111055809 | 0.062646867 |
| 55 | 1.003534799 | 0.250084707 | 0.111148759 | 0.062454594 |
| 60 | 0.999445727 | 0.249861432 | 0.11116147 | 0.062465358 |
| 65 | 0.995767108 | 0.249904801 | 0.111068801 | 0.0624762 |
| 70 | 0.992700798 | 0.249451463 | 0.111073582 | 0.062536902 |
| 75 | 0.989917184 | 0.249285714 | 0.111546325 | 0.06243433 |
| 80 | 0.988538071 | 0.249127538 | 0.110870981 | 0.06244797 |
| 85 | 0.98813253 | 0.249223143 | 0.110960509 | 0.062415286 |
| 90 | 0.99072375 | 0.24909875 | 0.1108075 | 0.06238375 |

Table 8b shows the Geometry Function calculated for the various angles for the Best Model 2301 $^{125}$I Seed at 5, 6 and 7 cm where the Geometry Function is independent of the components of the seed.

TABLE 8b

Geometry Function calculated for the various angles for the Best Model 2301 $^{125}$I Seed at 5, 6 and 7 cm (Please note that Geometry Function is independent of the components of the seed)

| Angle | GF at 5 cm | GF at 6 cm | GF at 7 cm |
|---|---|---|---|
| 0 | 0.0401 | 0.02781 | 0.020425 |
| 5 | 0.040022936 | 0.027599149 | 0.020726163 |
| 10 | 0.041117816 | 0.027579023 | 0.02041564 |
| 15 | 0.040087838 | 0.027791988 | 0.020452978 |
| 20 | 0.04030848 | 0.027637671 | 0.020591583 |
| 25 | 0.040221631 | 0.027673857 | 0.020479146 |
| 30 | 0.0399605 | 0.02792 | 0.020441429 |
| 35 | 0.039976916 | 0.027867305 | 0.020411896 |
| 40 | 0.04002916 | 0.027816874 | 0.020450733 |
| 45 | 0.04010785 | 0.027766973 | 0.020362447 |
| 50 | 0.039980091 | 0.027811412 | 0.020421251 |
| 55 | 0.039949634 | 0.027698413 | 0.020393337 |
| 60 | 0.039997979 | 0.027790368 | 0.020437974 |
| 65 | 0.039965508 | 0.0277672 | 0.020429872 |
| 70 | 0.039912234 | 0.027845745 | 0.020353913 |
| 75 | 0.040012164 | 0.02777368 | 0.02038672 |
| 80 | 0.039948985 | 0.027754653 | 0.020436367 |
| 85 | 0.039945783 | 0.027813128 | 0.020398379 |
| 90 | 0.0399605 | 0.027774583 | 0.020441429 | b) Calculating Coordinates for Detectors

Equations #14 and #15 are used to calculate the x and z coordinates in order to place detectors for measuring the dose rates at various angles. Table 9 shows the Coordinates for detectors as calculated for the listed angles.

TABLE 9

Coordinates for detectors as calculated for the listed angles

| Angle | Axis | 1 cm | 2 cm | 3 cm | 4 cm | 5 cm | 6 cm | 7 cm |
|---|---|---|---|---|---|---|---|---|
| 0 | x | 0 | 0 | 0 | 0 | 0 | 0 | 0 |
| 0 | z | 1 | 2 | 3 | 4 | 5 | 6 | 7 |
| 5 | x | 0.087 | 0.174 | 0.261 | 0.348 | 0.435 | 0.522 | 0.609 |
| 5 | z | 0.996 | 1.992 | 2.988 | 3.948 | 4.98 | 5.976 | 6.972 |
| 10 | x | 0.1736 | 0.348 | 0.5208 | 0.6944 | 0.868 | 1.044 | 1.218 |
| 10 | z | 0.985 | 1.97 | 2.955 | 3.94 | 4.925 | 5.91 | 6.895 |
| 15 | x | 0.259 | 0.518 | 0.777 | 1.036 | 1.295 | 1.554 | 1.813 |
| 15 | z | 0.966 | 1.932 | 2.898 | 3.864 | 4.83 | 5.796 | 6.762 |
| 20 | x | 0.342 | 0.684 | 1.026 | 1.368 | 1.71 | 2.052 | 2.394 |
| 20 | z | 0.94 | 1.88 | 2.82 | 3.76 | 4.7 | 5.64 | 6.58 |
| 25 | x | 0.4226 | 0.8452 | 1.2678 | 1.6904 | 2.113 | 2.5356 | 2.9582 |
| 25 | z | 0.906 | 1.812 | 2.718 | 3.624 | 4.53 | 5.436 | 6.342 |
| 30 | x | 0.5 | 1 | 1.5 | 2 | 2.5 | 3 | 3.5 |

TABLE 9-continued

Coordinates for detectors as calculated for the listed angles

| Angle | Axis | 1 cm | 2 cm | 3 cm | 4 cm | 5 cm | 6 cm | 7 cm |
|---|---|---|---|---|---|---|---|---|
| 30 | z | 0.866 | 1.732 | 2.598 | 3.464 | 4.33 | 5.196 | 6.062 |
| 35 | x | 0.574 | 1.148 | 1.722 | 2.296 | 2.87 | 3.444 | 4.018 |
| 35 | z | 0.819 | 1.638 | 2.4597 | 3.276 | 4.095 | 4.914 | 5.733 |
| 40 | x | 0.643 | 1.286 | 1.929 | 2.572 | 3.215 | 3.858 | 4.501 |
| 40 | z | 0.766 | 1.532 | 2.298 | 3.064 | 3.83 | 4.596 | 5.362 |
| 45 | x | 0.707 | 1.414 | 2.121 | 2.828 | 3.535 | 4.242 | 4.949 |
| 45 | z | 0.707 | 1.414 | 2.121 | 2.828 | 3.535 | 4.242 | 4.949 |
| 50 | x | 0.766 | 1.532 | 2.298 | 3.064 | 3.83 | 4.596 | 5.362 |
| 50 | z | 0.643 | 1.286 | 1.929 | 2.572 | 3.215 | 3.858 | 4.501 |
| 55 | x | 0.819 | 1.638 | 2.4597 | 3.276 | 4.095 | 4.914 | 5.733 |
| 55 | z | 0.574 | 1.148 | 1.722 | 2.296 | 2.87 | 3.444 | 4.018 |
| 60 | x | 0.866 | 1.732 | 2.598 | 3.464 | 4.33 | 5.196 | 6.062 |
| 60 | z | 0.5 | 1 | 1.5 | 2 | 2.5 | 3 | 3.5 |
| 65 | x | 0.906 | 1.812 | 2.718 | 3.624 | 4.53 | 5.436 | 6.342 |
| 65 | z | 0.4226 | 0.8452 | 1.2678 | 1.6904 | 2.113 | 2.5356 | 2.9582 |
| 70 | x | 0.94 | 1.88 | 2.82 | 3.76 | 4.7 | 5.64 | 6.58 |
| 70 | z | 0.342 | 0.684 | 1.026 | 1.368 | 1.71 | 2.052 | 2.394 |
| 75 | x | 0.966 | 1.932 | 2.898 | 3.864 | 4.83 | 5.796 | 6.762 |
| 75 | z | 0.259 | 0.518 | 0.777 | 1.036 | 1.295 | 1.554 | 1.813 |
| 80 | x | 0.985 | 1.97 | 2.955 | 3.94 | 4.925 | 5.91 | 6.895 |
| 80 | z | 0.174 | 0.348 | 0.5208 | 0.6944 | 0.868 | 1.044 | 1.218 |
| 85 | x | 0.996 | 1.992 | 2.988 | 3.948 | 4.98 | 5.976 | 6.972 |
| 85 | z | 0.087 | 0.174 | 0.261 | 0.348 | 0.435 | 0.522 | 0.609 |
| 90 | x | 1 | 2 | 3 | 4 | 5 | 6 | 7 |
| 90 | z | 0 | 0 | 0 | 0 | 0 | 0 | 0 | c) Calculating Anisotropy Function Using the Data Accumulated in Tables 7 and 8

The Anisotropy Function was calculated using all the factors listed in equation #9. Tables 8a and 8b were used to calculate the Geometry Function at various angles. Table 9 was used to find the coordinates needed to place the detectors at the various angles and radial distances. Table 10a shows the Monte Carlo calculated Anisotropy Function of the Best Model 2301 $^{125}$I Seed in liquid water for Radial Distances of 1 cm and 2 cm. A comparison between book values is also calculated.

TABLE 10a

Monte Carlo calculated Anisotropy Function of the Best Model 2301 $^{125}$I Seed in liquid water for Radial Distances of 1 cm and 2 cm. A comparison between book values is also calculated

| Angle | AF at 1 cm | Book Value | Error | AF at 2 cm | Book Value | Error |
|---|---|---|---|---|---|---|
| 0 | 1.016857 | 0.867 | 0.172846 | 0.986817 | 0.854 | 0.155523 |
| 5 | 0.857865 | 0.724 | 0.184896 | 0.810992 | 0.72 | 0.126377 |
| 10 | 0.677306 | 0.653 | 0.037222 | 0.724824 | 0.671 | 0.080214 |
| 15 | 0.725931 | 0.721 | 0.006839 | 0.718106 | 0.734 | −0.021655 |
| 20 | 0.7474 | 0.785 | −0.047899 | 0.819861 | 0.794 | 0.03257 |
| 25 | 0.803672 | 0.85 | −0.054504 | 0.853352 | 0.847 | 0.007499 |
| 30 | 0.821182 | 0.9 | −0.087576 | 0.858304 | 0.89 | −0.035614 |
| 35 | 0.890772 | 0.946 | −0.05838 | 0.821552 | 0.926 | −0.112794 |
| 40 | 0.906355 | 0.982 | −0.077032 | 0.940464 | 0.954 | −0.014189 |
| 45 | 0.953106 | 1.001 | −0.047847 | 0.883125 | 0.978 | −0.09701 |
| 50 | 0.959333 | 1.014 | −0.053913 | 0.903854 | 0.992 | −0.088857 |
| 55 | 0.978387 | 1.024 | −0.044544 | 0.944112 | 1.003 | −0.058712 |
| 60 | 0.98857 | 1.03 | −0.040223 | 0.963059 | 1.01 | −0.046476 |
| 65 | 0.988487 | 1.033 | −0.043091 | 0.971319 | 1.019 | −0.046792 |
| 70 | 0.986962 | 1.036 | −0.047334 | 0.984718 | 1.026 | −0.040236 |
| 75 | 1.031196 | 1.039 | −0.007511 | 1.000409 | 1.029 | −0.027786 |
| 80 | 1.009489 | 1.1 | −0.082283 | 1.019994 | 1.03 | −0.009715 |
| 85 | 0.998686 | 1 | −0.001314 | 0.976201 | 1.022 | −0.044813 |
| 90 | 0.996037 | 1 | −0.003963 | 1 | 1 | 0 |

Figure 9:
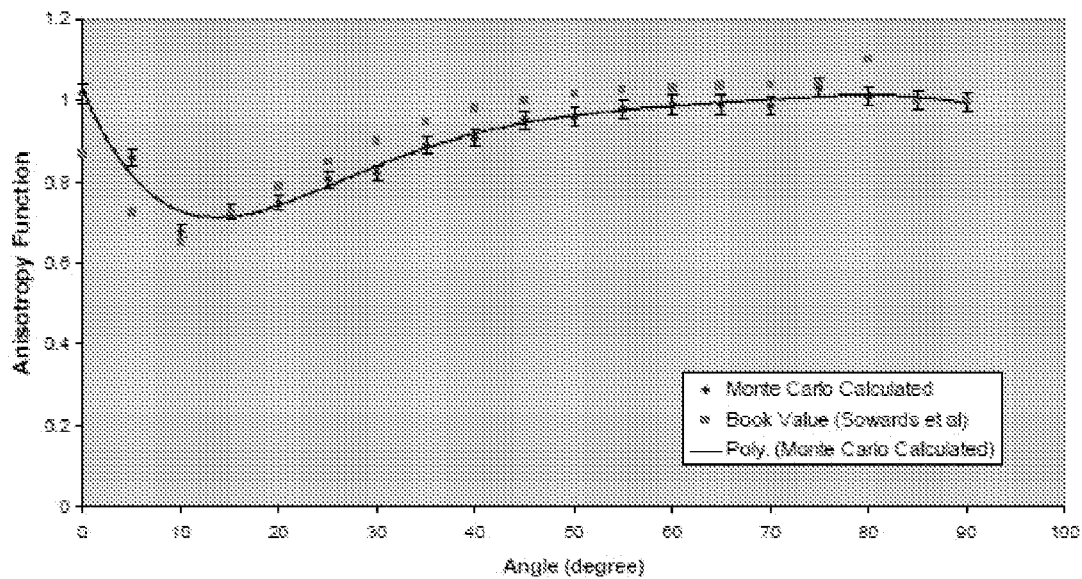
FIG. 9 shows the Comparison between the calculated and book value data Anisotropy Function for Best Model 2301 $^{125}$I in liquid water at 1 cm radii.

FIG. 9 shows the Comparison between the calculated and book value data Anisotropy Function for Best Model 2301 $^{125}$I in liquid water at 1 cm radii. The plot is fitted with a 6th order polynomial function.

Figure 10:
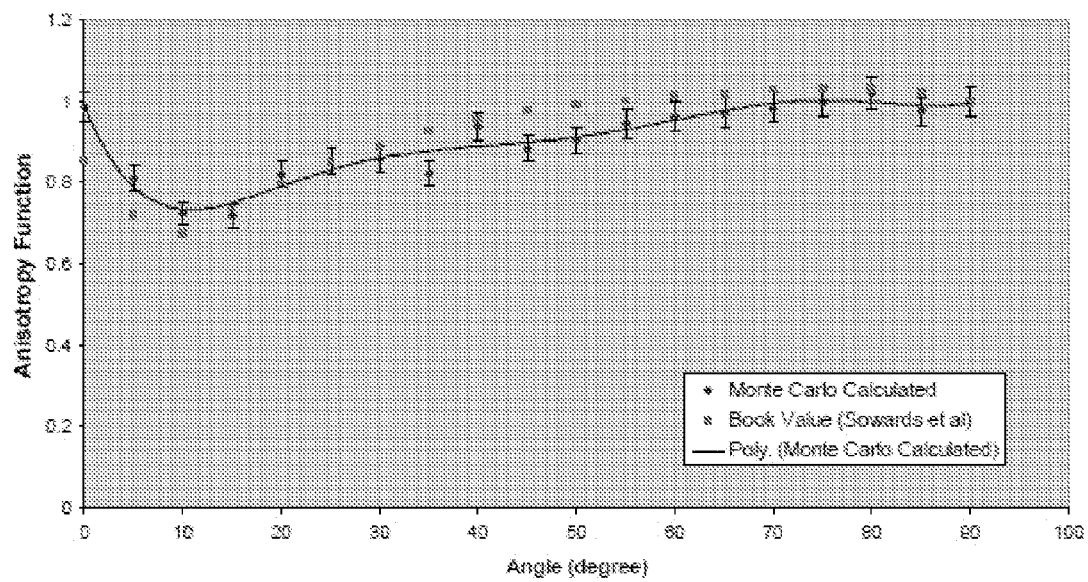
FIG. 10 shows the Comparison between the calculated and book value data Anisotropy Function for Best Model 2301 $^{125}$I in liquid water at 2 cm radii.

FIG. 10 shows the Comparison between the calculated and book value data Anisotropy Function for Best Model 2301 $^{125}$I in liquid water at 2 cm radii. The plot is fitted with a 6th order polynomial function Table 10b shows the Monte Carlo calculated Anisotropy Function of the Best Model 2301 $^{125}$I Seed in liquid water for Radial Distances of 3 cm and 4 cm. A comparison between book values is also calculated.

Table 10c shows the Monte Carlo calculated Anisotropy Function of the Best Model 2301 $^{125}$I Seed in liquid water for Radial Distances of 5 cm and 6 cm. A comparison between book values is also calculated.

Figure 13:
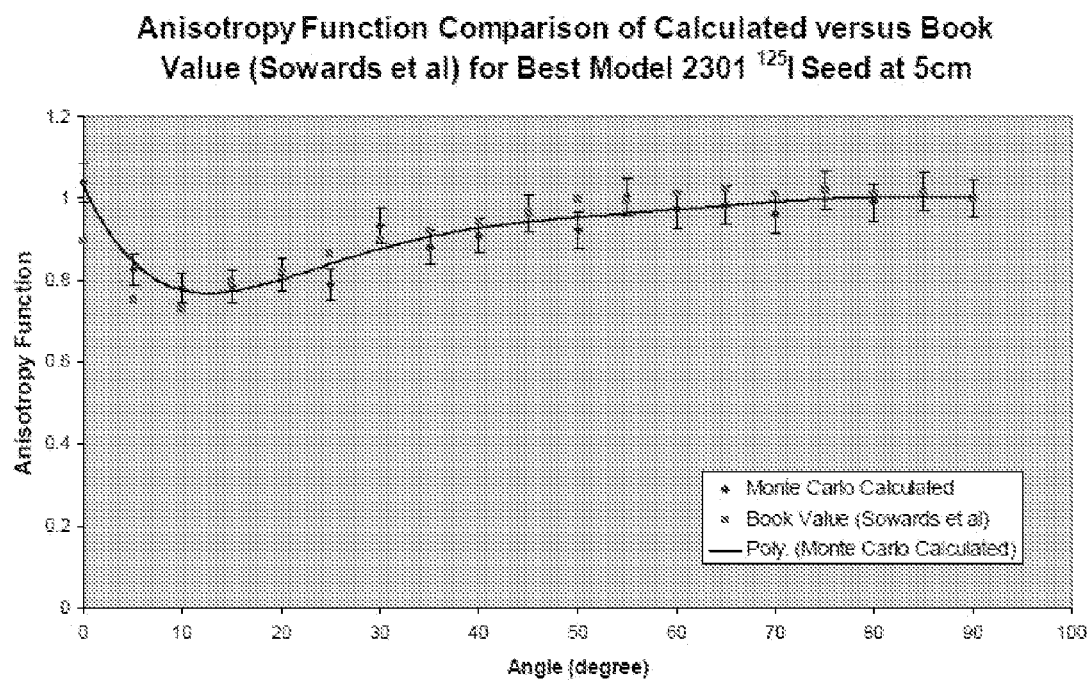
FIG. 13 shows the Comparison between the calculated and book value data Anisotropy Function for Best Model 2301 $^{125}$I in liquid water at 5 cm radii.

FIG. 13 shows the Comparison between the calculated and book value data Anisotropy Function for Best Model 2301 $^{125}$I in liquid water at 5 cm radii. The plot is fitted with a 6th order polynomial function TABLE 10b Monte Carlo calculated Anisotropy Function of the Best Model 2301 $^{125}$I Seed in liquid water for Radial Distances of 3 cm and 4 cm. A comparison between book values is also calculated.

| Angle | AF at 3 cm | Book Value | Error | AF at 4 cm | Book Value | Error |
| --- | --- | --- | --- | --- | --- | --- |
| 0 | 1.081703 | 0.922 | 0.173213 | 1.067157 | 0.902 | 0.183101 |
| 5 | 0.827588 | 0.726 | 0.139928 | 0.856189 | 0.728 | 0.176084 |
| 10 | 0.750467 | 0.699 | 0.07363 | 0.849553 | 0.727 | 0.168574 |
| 15 | 0.833466 | 0.756 | 0.102468 | 0.762809 | 0.779 | −0.020784 |
| 20 | 0.808948 | 0.809 | −6.37E−05 | 0.843573 | 0.814 | 0.03633 |
| 25 | 0.872956 | 0.852 | 0.024597 | 0.917008 | 0.863 | 0.062582 |
| 30 | 0.930988 | 0.885 | 0.051963 | 0.921985 | 0.892 | 0.033615 |
| 35 | 0.953275 | 0.919 | 0.037296 | 0.927006 | 0.918 | 0.009811 |
| 40 | 0.987268 | 0.947 | 0.042521 | 0.928846 | 0.939 | −0.010813 |
| 45 | 0.95516 | 0.968 | −0.013264 | 0.992994 | 0.976 | 0.017412 |
| 50 | 0.973073 | 0.985 | −0.012109 | 0.968645 | 0.991 | −0.022558 |
| 55 | 1.008446 | 0.997 | 0.011481 | 1.028106 | 1.004 | 0.02401 |
| 60 | 0.988973 | 1.009 | −0.019849 | 1.000959 | 1.007 | −0.005999 |
| 65 | 1.000178 | 1.012 | −0.011682 | 1.017048 | 1.009 | 0.007976 |
| 70 | 1.030136 | 1.016 | 0.013913 | 1.020551 | 1.023 | −0.002394 |
| 75 | 1.018382 | 1.018 | 0.000375 | 1.009032 | 1.017 | −0.007835 |
| 80 | 0.960588 | 1.019 | −0.057323 | 0.975997 | 1.017 | −0.040317 |
| 85 | 0.996809 | 1.019 | −0.021788 | 0.998651 | 1.018 | −0.019007 |
| 90 | 1 | 1 | 0 | 0.999983 | 1 | −1.73E−50 |

Figure 11:
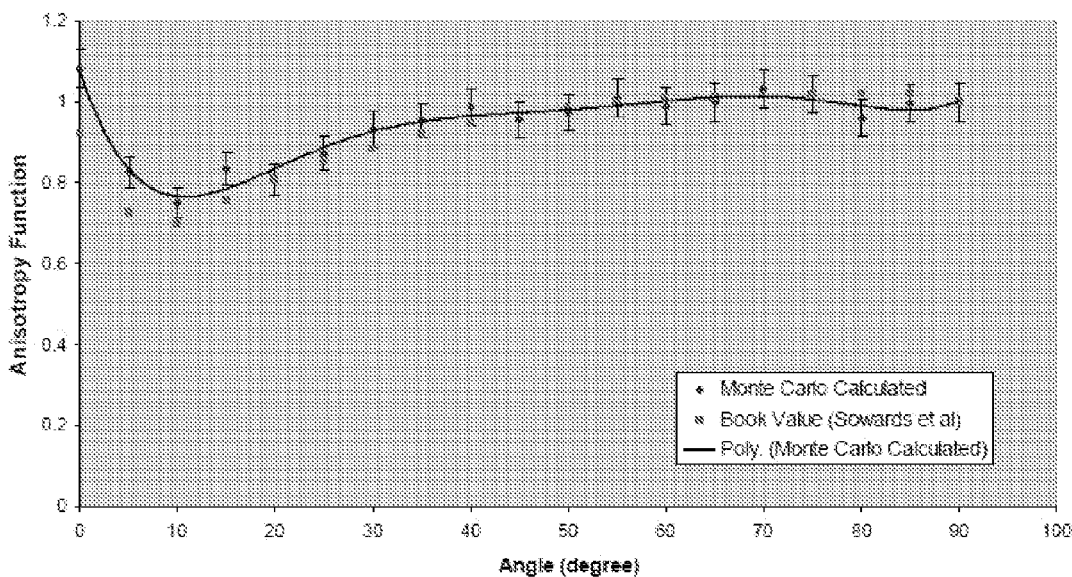
FIG. 11 shows the Comparison between the calculated and book value data Anisotropy Function for Best Model 2301 $^{125}$I in liquid water at 3 cm radii.

FIG. 11 shows the Comparison between the calculated and book value data Anisotropy Function for Best Model 2301 $^{125}$I in liquid water at 3 cm radii. The plot is fitted with a 6th order polynomial function.

Figure 12:
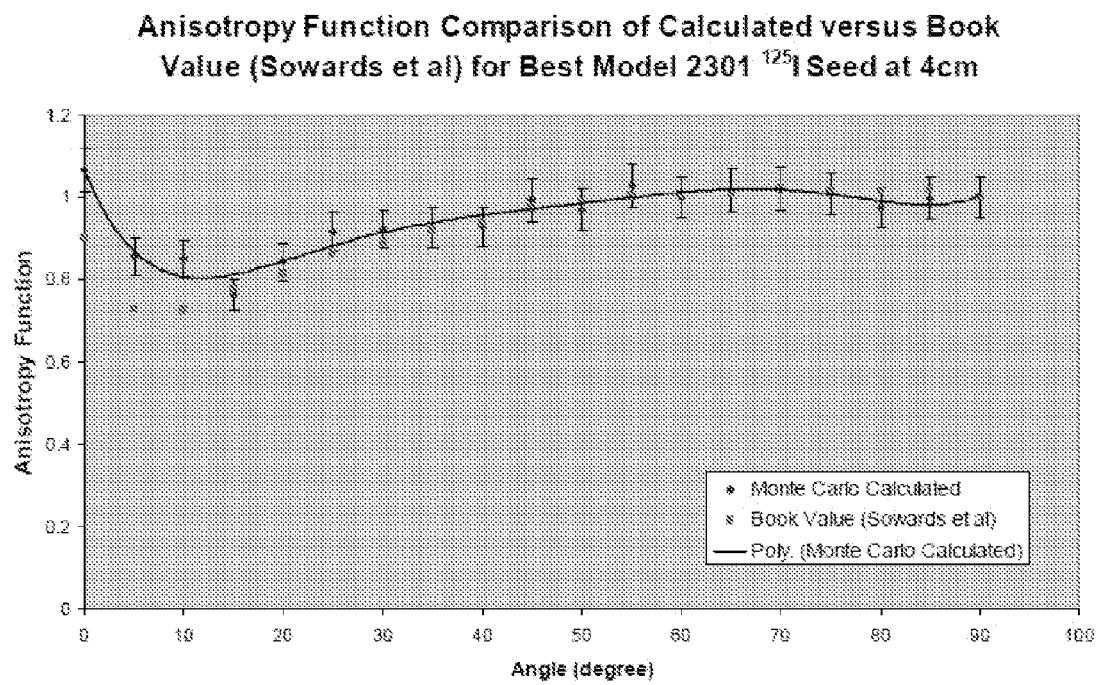
FIG. 12 shows the Comparison between the calculated and book value data Anisotropy Function for Best Model 2301 $^{125}$I in liquid water at 4 cm radii.

FIG. 12 shows the Comparison between the calculated and book value data Anisotropy Function for Best Model 2301 $^{125}$I in liquid water at 4 cm radii. The plot is fitted with a 6th order polynomial function.

Figure 14:
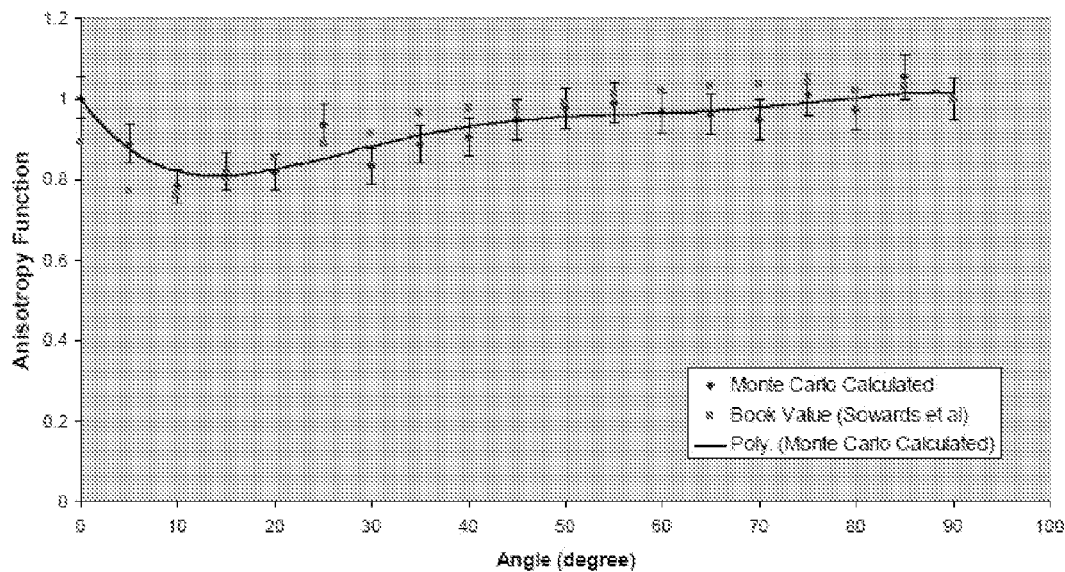
FIG. 14 shows the Comparison between the calculated and book value data Anisotropy Function for Best Model 2301 $^{125}$I in liquid water at 6 cm radii.

FIG. 14 shows the Comparison between the calculated and book value data Anisotropy Function for Best Model 2301 $^{125}$I in liquid water at 6 cm radii. The plot is fitted with a 6th order polynomial function.

Table 10d shows the Monte Carlo calculated Anisotropy Function of the Best Model 2301 $^{125}$I Seed in liquid water for Radial Distance of 7 cm. A comparison between book values is also calculated.

TABLE 10c

Monte Carlo calculated Anistropy Function of the Best Model 2301 $^{125}$I Seed in liquid water for Radial Distances of 5 cm and 6 cm. A comparison between book values is also calculated

| Angle | AF at 5 cm | Book Value | Error | AF at 6 cm | Book Value | Error |
| --- | --- | --- | --- | --- | --- | --- |
| 0 | 1.037909 | 0.894 | 0.160972 | 1.002815 | 0.893 | 0.122973 |
| 5 | 0.826259 | 0.753 | 0.097289 | 0.888127 | 0.771 | 0.151915 |
| 10 | 0.781112 | 0.732 | 0.067093 | 0.782999 | 0.764 | 0.024867 |
| 15 | 0.785625 | 0.795 | −0.011792 | 0.819448 | 0.805 | 0.017947 |
| 20 | 0.814253 | 0.825 | −0.013026 | 0.817894 | 0.852 | −0.040031 |
| 25 | 0.790151 | 0.865 | −0.08653 | 0.936581 | 0.89 | 0.052338 |
| 30 | 0.93407 | 0.899 | 0.03901 | 0.833299 | 0.915 | −0.089291 |
| 35 | 0.880933 | 0.92 | −0.042464 | 0.886202 | 0.964 | −0.080703 |
| 40 | 0.909002 | 0.943 | −0.036053 | 0.904777 | 0.976 | −0.072974 |
| 45 | 0.965222 | 0.968 | −0.00287 | 0.948816 | 0.979 | −0.030831 |
| 50 | 0.921762 | 0.997 | −0.075464 | 0.976859 | 0.989 | −0.012276 |
| 55 | 1.00322 | 0.993 | 0.010292 | 0.98898 | 1.011 | −0.02178 |
| 60 | 0.972524 | 1.01 | −0.037105 | 0.967874 | 1.019 | −0.050173 |
| 65 | 0.982562 | 1.024 | −0.040466 | 0.960829 | 1.034 | −0.070765 |
| 70 | 0.959269 | 1.011 | −0.051168 | 0.948077 | 1.035 | −0.083983 |

TABLE 10c-continued

Monte Carlo calculated Anistropy Function of the Best Model 2301 $^{125}$I Seed in liquid water for Radial Distances of 5 cm and 6 cm. A comparison between book values is also calculated

| Angle | AF at 5 cm | Book Value | Error | AF at 6 cm | Book Value | Error |
|---|---|---|---|---|---|---|
| 75 | 1.020911 | 1.02 | 0.000894 | 1.01108 | 1.043 | −0.030604 |
| 80 | 0.991336 | 1.01 | −0.018479 | 0.972717 | 1.02 | −0.046356 |
| 85 | 1.015815 | 1.011 | 0.004762 | 1.053106 | 1.031 | 0.021441 |
| 90 | 1 | 1 | 0 | 1 | 1 | 0 |

FIG. 15: The Comparison between the calculated and book value data Anisotropy Function for Best Model 2301 $^{125}$I in liquid water at 7 cm radii. The plot is fitted with a 6th order polynomial function.

Average Anisotropy Function:

The average anisotropy constant is taken by taking an average of the calculated anisotropy functions for all the angles.

Table 11a shows the Average Anisotropy Constant calculated for radial distances of 1 cm and 2 cm in liquid water.

TABLE 11a

Average Anisotropy Constant calculated for radial distances of 1 cm and 2 cm in liquid water

| | 1 cm | Book value | Error | 2 cm | Book value | Error |
|---|---|---|---|---|---|---|
| Avg. Anisotropy Constant $\Phi_{an}$ (r) | 0.913 | 0.986 | −0.0745 | 0.904 | 0.976 | −0.0735 |

Table 11b shows the Average Anisotropy Constant calculated for radial distances of 3 cm and 4 cm in liquid water.

TABLE 11b

Average Anisotropy Constant calculated for radial distances of 3 cm and 4 cm in liquid water

| | 3 cm | Book value | Error | 4 cm | Book value | Error |
|---|---|---|---|---|---|---|
| Avg. Anisotropy Constant $\Phi_{an}$ (r) | 0.946 | 0.968 | −0.0224 | 0.952 | 0.971 | −0.0197 |

Table 11c shows the Average Anisotropy Constant calculated for radial distances of 5 cm and 6 cm in liquid water.

TABLE 11c

Average Anisotropy Constant calculated for radial distances of 5 cm and 6 cm in liquid water

| | 5 cm | Book value | Error | 6 cm | Book value | Error |
|---|---|---|---|---|---|---|
| Avg. Anisotropy Constant $\Phi_{an}$ (r) | 0.926 | 0.969 | −0.0445 | 0.932 | 0.991 | −0.0599 |

Table 11d shows the Average Anisotropy Constant calculated for radial distance of 7 cm in liquid water.

TABLE 11d

Average Anisotropy Constant calculated for radial distance of 7 cm in liquid water

| | 7 cm | Book value | Error |
|---|---|---|---|
| Avg. Anisotropy Constant $\Phi_{an}$ (r) | 0.972 | 0.969 | 0.003 |

Source Anisotropy Constant:

The Source Anisotropy Constant is taken by averaging all the average Anisotropy Constants. Table 12 shows the Source Anisotropy Constant for Best Model 2301 $^{125}$I Seed in liquid water. The Source Anisotropy Constant is 0.935 and deviates from the book value by 4.6%

TABLE 12

Source Anisotropy Constant for Best Model 2301 $^{125}$I Seed in liquid water.

| | Calculated value | Book value | Error |
|---|---|---|---|
| Source Anisotropy Constant $\overline{\Phi_{an}}$ (r) | 0.935 | 0.98 | −0.0459 |

1) Best Model 2301 $^{125}$I Seed in Solid Water i) Dose Rate (D):

Dose Rate was calculated for seed at 1 cm on the transverse plane (θ=90°) of the source (from the center of the source) in Solid Water. Therefore, for this measurement the phantom was taken to be Solid Water since it is the Solid Water measurement. Table 13 shows the Dose Rate for Best Model 2301 $^{125}$I Seed in Solid Water calculated using Monte Carlo. The dose rate recorded is $0.231 \pm 4.78 \times 10^{-3}$ cGy*sec$^{-1}$*Ci$^{-1}$.

TABLE 13

Dose Rate for Best Model 2301 $^{125}$I Seed in Solid Water calculated using Monte Carlo

| Calculated Dose Rate (cGy*sec$^{-1}$*Ci$^{-1}$) | Book Value (Meigooni et al) | Error |
|---|---|---|
| 0.230994 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials and Methods section) is used for SK. Table 14 shows the Air Kerma Strength for Best Model 2301 $^{125}$I Seed in Air calculated using Monte Carlo. The Air Kerma Strength recorded is $0.224 \pm 4.98 \times 10^{-3}$ cGy*cm$^2$sec$^{-1}$*Ci$^{-1}$.

TABLE 14

Air Kerma Strength for Best Model 2301 $^{125}$I
Seed in Air calculated using Monte Carlo

| Calculated Air Kerma Strength (cGy*cm$^2$sec$^{-1}$*Ci$^{-1}$) | Book Value (Meigooni et al) | Error |
|---|---|---|
| 0.224332 | N/A | N/A | iii) Dose Rate Constant (Λ):

Dose rate constant is calculated using equation #4. In order to calculate it, the ratio of the dose rate and air kerma strength is taken. Table 15 shows the Monte Carlo calculated Dose Rate Constant for Best Model 2301 $^{125}$I Seed in Solid Water. The error is calculated by using equation #16. Therefore, the error between the measured value and the book value is 5.1%. The measured value of Dose Rate Constant is 1.03±0.031 cGy*h$^{-1}$*U$^{-1}$.

TABLE 15

Monte Carlo calculated Dose Rate Constant for
Best Model 2301 $^{125}$I Seed in Solid Water

| Calculated Dose Rate Constant (cGy*h$^{-1}$*U$^{-1}$) | Book Value (Meigooni et al) (cGy*h$^{-1}$*U$^{-1}$) | Error |
|---|---|---|
| 1.02969 | 0.98 | 0.05071 | iv) Correction/Multiplicative Factor:

Meigooni et al calculated that a conversion factor of 1.05 was needed to convert the dose rate constant in solid water to liquid water.

The calculated Correction/Multiplicative factor obtained is 1.026.

v) Radial Dose Function:

Calculation of the radial function is a two fold process.

a) Geometry Function

The Geometry function is independent of the material content of the phantom and therefore, the geometry factor from Table 6 is applicable here.

b) Radial Dose Function Using the Geometry Function

The Radial Function was calculated using equation#8 incorporating the geometry function calculated in part a) above. Table 16* shows the Radial Dose Function calculated at the transverse plane for the Best Model 2301 $^{125}$I Seed in Solid Water using Monte Carlo. *Note that the empty cells refer to unavailable book values (and hence no error to calculate).

TABLE 16*

Radial Dose Function calculated at the transverse plane for the
Best Model 2301 $^{125}$I Seed in Solid Water using Monte Carlo.

| Transverse distance (r) cm | Radial Dose Function g(r) | Book Value | Error |
|---|---|---|---|
| 0.1 | 0.974085 | | |
| 0.15 | 0.987273 | | |
| 0.2 | 1.024577 | | |
| 0.25 | 0.997152 | | |
| 0.3 | 1.010615 | | |
| 0.4 | 1.002436 | | |
| 0.5 | 0.996278 | | |
| 0.6 | 0.960112 | 1.044 | −0.08035 |
| 0.7 | 0.907923 | | |
| 0.75 | 0.946739 | | |
| 0.8 | 0.955411 | | |
| 0.9 | 0.966749 | | |
| 1 | 1.000001 | 1 | 5.07E−07 |
| 1.5 | 0.904062 | 0.926 | −0.02369 |
| 2 | 0.812967 | 0.842 | −0.03448 |
| 2.5 | 0.728075 | 0.752 | −0.03182 |
| 3 | 0.650595 | 0.666 | −0.02313 |
| 3.5 | 0.563531 | 0.581 | −0.03007 |
| 4 | 0.512549 | 0.509 | 0.006973 |
| 4.5 | 0.43286 | 0.443 | −0.02289 |
| 5 | 0.381773 | 0.386 | −0.01095 |
| 5.5 | 0.317848 | 0.336 | −0.05402 |
| 6 | 0.275389 | 0.286 | −0.0371 |
| 6.5 | 0.230972 | 0.245 | −0.05726 |
| 7 | 0.204101 | 0.207 | −0.014 |
| 7.5 | 0.176629 | 0.178 | −0.0077 |
| 8 | 0.157109 | 0.159 | −0.0119 |
| 8.5 | 0.124603 | 0.14 | −0.10998 |
| 9 | 0.109814 | 0.116 | −0.05333 |
| 9.5 | 0.093497 | 0.097 | −0.03611 |
| 10 | 0.079492 | 0.08 | −0.00635 |

The graph for radial dose function versus distance on the transverse plane fits as shown in FIG. 16 which illustrates the Radial Dose Function calculated in Solid Water for the Best Model 2301 $^{125}$I Seed. The curve is fitted to 5th order polynomial function.

iv) Anisotropy Function:

Calculation of the Anisotropy function is a three fold process.

a) Calculating Geometry Function

The Geometry function is independent of the material content of the phantom and therefore, the geometry function from Tables 8a and 8b is applicable here.

b) Calculating Coordinates for Detectors

The coordinates are independent of the material content of the phantom and therefore, the coordinates from Table 9 are applicable here.

c) Calculating Anisotropy Function Using the Data Accumulated in Tables 8a, 8b and 9

The Anisotropy Function was calculated using all the factors listed in equation #9. Tables 8a and 8b were used to calculate the Geometry Function at various angles. Table 9 was used to find the coordinates needed to place the detectors at the various angles (and radial distances). Table 17a shows the Monte Carlo calculated Anisotropy Function of the Best Model 2301 $^{125}$I Seed in Solid Water for Radial Distances of 1 cm, 2 cm, 3 cm and 4 cm. A comparison between book values is also calculated. *Note that there are no any book values (and hence no error to calculate) **Empty cells refer to no book values (and hence no error to calculate).

TABLE 17a

Monte Carlo calculated Anisotropy Function of the Best Model 2301 $^{125}$I
Seed in Solid Water for Radial Distances of 1 cm, 2 cm, 3 cm and 4 cm. A comparison
between book values is also calculated

| Angle | AF at 1 cm* | AF at 2 cm | Book Value** | Error | AF at 3 cm* | AF at 4 cm* |
|---|---|---|---|---|---|---|
| 0 | 1.026252 | 1.002986 | 0.837 | 0.198311 | 1.045494 | 0.996217 |
| 5 | 0.866304 | 0.829332 | | | 0.767353 | 0.804645 |
| 10 | 0.672536 | 0.677051 | 0.659 | 0.027391 | 0.706056 | 0.786272 |
| 15 | 0.739002 | 0.689879 | | | 0.742168 | 0.766287 |
| 20 | 0.75897 | 0.779294 | 0.782 | −0.003461 | 0.769965 | 0.821381 |
| 25 | 0.793086 | 0.81592 | | | 0.864285 | 0.865759 |
| 30 | 0.822657 | 0.83656 | 0.882 | −0.05152 | 0.835925 | 0.928838 |
| 35 | 0.897361 | 0.803188 | | | 0.876294 | 0.940615 |
| 40 | 0.906809 | 0.876187 | 0.946 | −0.073798 | 0.919709 | 0.956302 |
| 45 | 0.957336 | 0.901717 | | | 0.893813 | 0.963304 |
| 50 | 0.971523 | 0.924023 | 0.985 | −0.061905 | 0.89036 | 0.909226 |
| 55 | 0.989839 | 0.948227 | | | 0.916484 | 1.009165 |
| 60 | 0.987353 | 0.928041 | 1.007 | −0.078411 | 0.900548 | 0.967434 |
| 65 | 0.99135 | 0.912797 | | | 0.880534 | 0.964955 |
| 70 | 0.998792 | 0.952063 | 1.02 | −0.066605 | 0.97229 | 1.007641 |
| 75 | 1.038309 | 0.987641 | | | 0.944857 | 0.970099 |
| 80 | 1.032288 | 1.004358 | 1.027 | −0.022046 | 0.899939 | 0.956987 |
| 85 | 0.986828 | 0.984115 | | | 0.95404 | 0.990027 |
| 90 | 0.996037 | 1 | 1 | 0 | 1 | 1 |

The comparison of the graph for Anisotropy Function versus Angle was fitted to a 6th order polynomial. The Anisotropy Function at 1 cm, 2 cm, 3 cm and 4 cm (calculated and measured) for Best Model 2301 $^{125}$I are plotted in the FIGS. 17-20.

FIG. 17 illustrates Anisotropy Function of Monte Carlo calculated value for Best Model 2301 $^{125}$I in Solid Water at 1 cm radii. The plot is fitted with a 6th order polynomial function.

FIG. 18 illustrates the Comparison between the calculated and book value data Anisotropy Function for Best Model 2301 $^{125}$I in Solid Water at 2 cm radii. The plot is fitted with a 6th order polynomial function.

FIG. 19 illustrates Anisotropy Function of Monte Carlo calculated value for Best Model 2301 $^{125}$I in Solid Water at 3 cm radii. The plot is fitted with a 6th order polynomial function.

FIG. 20 illustrates Anisotropy Function of Monte Carlo calculated value for Best Model 2301 $^{125}$I in Solid Water at 4 cm radii. The plot is fitted with a 6th order polynomial function.

Table 17b shows the Monte Carlo calculated Anisotropy Function of the Best Model 2301 $^{125}$I Seed in Solid Water for Radial Distances of 5 cm, 6 cm and 7 cm. A comparison between book values is also calculated. *Note that there are no any book values (and hence no error to calculate). **Empty cells refer to no book values (and hence no error to calculate).

TABLE 17b

Monte Carlo calculated Anisotropy Function of the Best Model 2301 $^{125}$I
Seed in Solid Water for Radial Distances of 5 cm, 6 cm and 7 cm. A comparison
between book values is also calculated.

| Angle | AF at 5 cm | Book Value** | Error | AF at 6 cm* | AF at 7 cm | Book Value | Error |
|---|---|---|---|---|---|---|---|
| 0 | 1.06538 | 0.886 | 0.20246 | 0.961176 | 1.106333 | 0.888 | 0.24587 |
| 5 | 0.863781 | | | 0.869443 | 0.855329 | | |
| 10 | 0.788669 | 0.719 | 0.096898 | 0.754599 | 0.96212 | 0.751 | 0.281119 |
| 15 | 0.773249 | | | 0.77439 | 0.860677 | | |
| 20 | 0.817595 | 0.801 | 0.020717 | 0.754773 | 0.907204 | 0.82 | 0.106346 |
| 25 | 0.879567 | | | 0.868662 | 0.933333 | | |
| 30 | 0.840307 | 0.873 | −0.037449 | 0.82609 | 0.944759 | 0.905 | 0.043933 |
| 35 | 0.911502 | | | 0.864491 | 0.904032 | | |
| 40 | 0.949538 | 0.938 | 0.012301 | 0.85658 | 1.018978 | 0.952 | 0.070355 |
| 45 | 0.936324 | | | 0.878697 | 1.095808 | | |
| 50 | 0.99784 | 0.962 | 0.037255 | 0.853307 | 1.006513 | 0.972 | 0.035507 |
| 55 | 1.018567 | | | 0.938518 | 1.133607 | | |
| 60 | 0.948673 | 0.99 | −0.041745 | 0.912431 | 1.091072 | 1.004 | 0.086725 |
| 65 | 1.02104 | | | 1.005409 | 1.189276 | | |
| 70 | 1.024804 | 1.001 | 0.02378 | 0.962483 | 0.984267 | 0.999 | −0.014748 |
| 75 | 1.013883 | | | 0.972179 | 1.061721 | | |
| 80 | 1.06825 | 1.011 | 0.056627 | 1.025741 | 1.096051 | 1.015 | 0.079853 |
| 85 | 1.000983 | | | 0.987695 | 1.141173 | | |
| 90 | 1 | 1 | 0 | 1 | 0.999979 | 1 | −2.1E−05 |

FIG. 21a illustrates the Comparison between the calculated and book value data Anisotropy Function for Best Model 2301 $^{125}$I in Solid water at 5 cm radii. The plot is fitted with a 6th order polynomial function.

FIG. 21b illustrates Anisotropy Function of Monte Carlo calculated value for Best Model 2301 $^{125}$I in solid water at 6 cm radii. The plot is fitted with a 6th order polynomial function.

FIG. 22 illustrates Anisotropy Function of Monte Carlo calculated value for Best Model 2301 $^{125}$I in Solid Water at 7 cm radii. The plot is fitted with a 6th order polynomial function.

Average Anisotropy Function:

The average anisotropy function is taken by taking an average of the calculated anisotropy functions for all the angles. Table 18a illustrates the Average Anisotropy Function calculated for radial distances of 1 cm, 2 cm, 3 cm, 4 cm in Solid Water.

TABLE 18a

Average Anisotropy Function calculated for radial distances of 1 cm, 2 cm, 3 cm, 4 cm in Solid Water

|  | 1 cm | 2 cm | Book value | Error | 3 cm | 4 cm |
|---|---|---|---|---|---|---|
| Avg. Anisotropy Constant $\Phi_{an}$ (r) | 0.917 | 0.898 | 0.975 | −0.0789 | 0.883 | 0.926 |

Table 18b illustrates the Average Anisotropy Function calculated for radial distances of 5 cm and 6 cm in Solid Water.

TABLE 18b

Average Anisotropy Function calculated for radial distances of 5 cm and 6 cm in Solid Water

|  | 5 cm | Book value | Error | 6 cm |
|---|---|---|---|---|
| Avg. Anisotropy Constant $\Phi_{an}$ (r) | 0.950 | 0.965 | −0.015 | 0.898 |

Table 18c illustrates the Average Anisotropy Function calculated for radial distance of 7 cm in Solid Water.

TABLE 18c

Average Anisotropy Function calculated For radial distance of 7 cm in Solid Water

|  | 7 cm | Book value | Error |
|---|---|---|---|
| Avg. Anisotropy Constant $\Phi_{an}$ (r) | 1.01 | 0.977 | 0.0355 |

Source Anisotropy Constant:

The Source Anisotropy Constant is taken by averaging all the average Anisotropy Constants.

Table 19 illustrates the Source Anisotropy Constant for Best Model 2301 $^{125}$I Seed in Solid Water. The Source Anisotropy Constant is 0.926 and deviates from the book value by 4.5%

TABLE 19

Source Anisotropy Constant for Best Model 2301 $^{125}$I Seed in Solid Water.

|  | Calculated value | Book value | Error |
|---|---|---|---|
| Source Anisotropy Constant $\overline{\Phi_{an}}$ (r) | 0.926 | 0.97 | −0.0453 |

1) Thermobrachytherapy Seed#1 in liquid water i) Dose Rate (D):

Dose Rate was calculated for seed at 1 cm on the transverse plane (θ=90°) of the source (from the center of the source) in water. Therefore, for this measurement the phantom was taken to be liquid water since it is the liquid water measurement.

Table 20 illustrates the Dose Rate for Thermobrachytherapy Seed#1 in liquid water calculated using Monte Carlo. The error is calculated by using equation #16. Therefore, the error between the calculated thermobrachytherapy seed#1 value and the calculated Best Model 2301 $^{125}$I seed is 6.1%. The measured value of Dose Rate is 0.25±4.98*10$^{-3}$ cGy*sec$^{-1}$*Ci$^{-1}$.

TABLE 20

Dose Rate for Thermobrachytherapy Seed#1 in liquid water calculated using Monte Carlo

| Calculated Dose Rate (cGy*sec$^{-1}$*Ci$^{-1}$) | Calculated Best Model 2301 $^{125}$I Seed (cGy*sec$^{-1}$*Ci$^{-1}$) | Error | Book Value (Meigooni et al) | Error |
|---|---|---|---|---|
| 0.251432 | 0.236993 | 0.06093 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials and Methods section) is used for SK. Table 21 illustrates the Air Kerma Strength for Thermobrachytherapy Seed#1 in Air calculated using Monte Carlo. The error is calculated by using equation #16. Therefore, the error between the calculated thermobrachytherapy value and the calculated Best Model 2301 $^{125}$I seed is 6.0%. The measured value of Air Kerma Strength is 0.238±5.14*10$^{-3}$ cGy*cm$^2$ sec$^{-1}$*Ci$^{-1}$.

TABLE 21

Air Kerma Strength for Thermobrachytherapy
Seed#1 in Air calculated using Monte Carlo

| Calculated Air Kerma Strength (cGy*cm² sec⁻¹*Ci⁻¹) | Calculated Best Model 2301 ¹²⁵I Seed (cGy*cm² sec⁻¹*Ci⁻¹) | Error | Book Value (Meigooni et al) | Error |
|---|---|---|---|---|
| 0.237773 | 0.224332 | 0.0599 | N/A | N/A | iii) Dose Rate Constant ($\Lambda$):

Dose rate constant is calculated using equation #4. In order to calculate it, the ratio of the dose rate and air kerma strength is taken. Table 22 illustrates the Monte Carlo calculated Dose Rate Constant for Thermobrachytherapy Seed#1 in liquid water. The error is calculated by using equation #16. Therefore, the error between the calculated thermobrachytherapy value and the calculated Best Model 2301 ¹²⁵I seed is 0.091%. Also, the error between the calculated thermobrachytherapy value and the Book Value for Best Model 2301 ¹²⁵I seed is 4.69%. The measured value of Dose Rate Constant is 1.057±0.031 cGy*h⁻¹U⁻¹

TABLE 22

Monte Carlo calculated Dose Rate Constant for
Thermobrachytherapy Seed#1 in liquid water

| Calculated Dose Rate Constant (cGy*h⁻¹U⁻¹) | Best Model 2301 ¹²⁵I Seed Dose Rate Consant (cGy*h⁻¹U⁻¹) | Error | Book Value (Meigooni et al) (cGy*h⁻¹U⁻¹) | Error |
|---|---|---|---|---|
| 1.0574 | 1.05644 | 0.00091 | 1.01 | 0.04693 | iv) Radial Dose Function:

Calculation of the radial dose function is a two fold process.

a) Geometry Function

The Geometry function is independent of the material content of the phantom. And also, the geometry (and dimension) of the source cell remains the same. Therefore, the geometry factor from Table 6 is applicable here.

b) Radial Dose Function Using the Geometry Function

Radial Dose Function was calculated using equation#8 incorporating the geometry function calculated in part a) above. Table 23 illustrates the Radial Dose Function calculated at the transverse plane for the Thermobrachytherapy Seed#1 in liquid water using Monte Carlo.

TABLE 23

Radial Dose Function calculated at the transverse plane for the
Thermobrachytherapy Seed#1 in liquid water using Monte Carlo

| Transverse distance (r) cm | Radial Dose Function g(r) | Best Model 2301 ¹²⁵I Seed | Error | Book Value (Meigooni et al) | Error |
|---|---|---|---|---|---|
| 0.1 | 0.934737 | 0.9456286 | −0.01152 | 1.033 | −0.09512 |
| 0.15 | 0.963187 | 0.972143 | −0.00921 | 1.029 | −0.06396 |
| 0.2 | 0.996078 | 1.0043252 | −0.00821 | 1.028 | −0.03105 |
| 0.25 | 0.973889 | 0.9786852 | −0.0049 | 1.027 | −0.05171 |
| 0.3 | 0.986499 | 0.9995776 | −0.01308 | 1.027 | −0.03944 |
| 0.4 | 0.978327 | 0.9913498 | −0.01314 | 1.027 | −0.04739 |
| 0.5 | 1.012846 | 1.0205403 | −0.00754 | 1.028 | −0.01474 |
| 0.6 | 0.953455 | 0.9631128 | −0.01003 | 1.034 | −0.0779 |
| 0.7 | 0.922393 | 0.9312438 | −0.0095 | 1.036 | −0.10966 |
| 0.75 | 0.95948 | 0.9597881 | −0.00032 | 1.03 | −0.06847 |
| 0.8 | 0.931838 | 0.9358905 | −0.00433 | 1.024 | −0.09 |
| 0.9 | 1.019078 | 1.0388782 | −0.01906 | 1.013 | 0.006 |
| 1 | 1.000001 | 1.0000005 | 2.22E−16 | 1 | 5.07E−07 |
| 1.5 | 0.923599 | 0.9266222 | −0.00326 | 0.938 | −0.01535 |
| 2 | 0.842546 | 0.8476955 | −0.00607 | 0.866 | −0.02708 |
| 2.5 | 0.757101 | 0.7624361 | −0.007 | 0.79 | −0.04164 |
| 3 | 0.682296 | 0.6881108 | −0.00845 | 0.707 | −0.03494 |
| 3.5 | 0.60327 | 0.6073126 | −0.00666 | 0.635 | −0.04997 |
| 4 | 0.532988 | 0.5365308 | −0.0066 | 0.555 | −0.03966 |
| 4.5 | 0.478261 | 0.4829325 | −0.00967 | 0.488 | −0.01996 |
| 5 | 0.405112 | 0.4070779 | −0.00483 | 0.427 | −0.05126 |
| 5.5 | 0.359484 | 0.3609578 | −0.00408 | 0.372 | −0.03365 |
| 6 | 0.299933 | 0.2993458 | 0.001961 | 0.32 | −0.06271 |
| 6.5 | 0.268552 | 0.2680607 | 0.001832 | 0.285 | −0.05771 |
| 7 | 0.240006 | 0.2394946 | 0.002136 | 0.248 | −0.03223 |
| 7.5 | 0.202435 | 0.2032859 | −0.00418 | 0.215 | −0.05844 |
| 8 | 0.179735 | 0.1818156 | −0.01144 | 0.187 | −0.03885 |
| 8.5 | 0.152857 | 0.1542993 | −0.00935 | 0.16 | −0.04464 |
| 9 | 0.133356 | 0.1326667 | 0.005198 | 0.142 | −0.06087 |

TABLE 23-continued

Radial Dose Function calculated at the transverse plane for the Thermobrachytherapy Seed#1 in liquid water using Monte Carlo

| Transverse distance (r) cm | Radial Dose Function g(r) | Best Model 2301 $^{125}$I Seed | Error | Book Value (Meigooni et al) | Error |
|---|---|---|---|---|---|
| 9.5 | 0.102986 | 0.1015704 | 0.013935 | 0.123 | −0.16272 |
| 10 | 0.101814 | 0.0994859 | 0.0234 | 0.103 | −0.01152 |

FIG. 23 illustrates the Radial Dose Function of Monte Carlo calculated value for Thermobrachytherapy Seed#1 and the Monte Carlo calculated value for the Best Model 2301 $^{125}$I in liquid water. The plot is fitted with a 5th order polynomial function.

FIG. 24 illustrates the Radial Dose Function of Monte Carlo calculated value for Thermobrachytherapy Seed#1 and the Book Value for the Best Model 2301 $^{125}$I in liquid water. The plot is fitted with a 5th order polynomial function.

iv) Anisotropy Function:

Calculation of the radial function is a three fold process.

a) Calculating Geometry Function

The Geometry function is independent of the material content of the phantom and therefore, the geometry function from Tables 8a & 8b is applicable here.

b) Calculating Coordinates for Detectors

The coordinates are independent of the material content of the phantom and therefore, the coordinates from Table 9 are applicable here.

c) Calculating Anisotropy Function Using the Data Accumulated in Tables 8a, 8b and 9

The Anisotropy Function was calculated using all the factors listed in equation #9. Table 8a & 8b was used to calculate the Geometry Function at various angles. Table 9 was used to find the coordinates needed to place the detectors at the various angles (and radial distances). Table 24a illustrates the Monte Carlo calculated Anisotropy Function of the Thermobrachytherapy Seed#1 in liquid water for Radial Distances of 1 cm. A comparison between calculated and book values of the Best Model 2301 $^{125}$I Seed is also calculated.

TABLE 24a

Monte Carlo calculated Anisotropy Function of the Thermobrachytherapy Seed#1 in liquid water for Radial Distances of 1 cm. A comparison between calculated and book values of the Best Model 2301 $^{125}$I Seed is also calculated

| Angle | AF at 1 cm | Best Model 2301 $^{125}$I Seed | Error | Book Value (Meigooni et al) | Error |
|---|---|---|---|---|---|
| 0 | 0.987793 | 1.016857 | −0.02942 | 0.867 | 0.139323 |
| 5 | 0.834117 | 0.857865 | −0.02847 | 0.724 | 0.152096 |
| 10 | 0.660437 | 0.677306 | −0.02554 | 0.653 | 0.011389 |
| 15 | 0.710819 | 0.725931 | −0.02126 | 0.721 | −0.01412 |
| 20 | 0.730699 | 0.7474 | −0.02286 | 0.785 | −0.06917 |
| 25 | 0.785677 | 0.803672 | −0.0229 | 0.85 | −0.07567 |
| 30 | 0.80466 | 0.821182 | −0.02053 | 0.9 | −0.10593 |
| 35 | 0.87556 | 0.890772 | −0.01737 | 0.946 | −0.07446 |
| 40 | 0.89236 | 0.906355 | −0.01568 | 0.982 | −0.09128 |
| 45 | 0.9378 | 0.953106 | −0.01632 | 1.001 | −0.06314 |
| 50 | 0.953471 | 0.959333 | −0.00615 | 1.014 | −0.05969 |
| 55 | 0.976016 | 0.978387 | −0.00243 | 1.024 | −0.04686 |
| 60 | 0.979357 | 0.98857 | −0.00941 | 1.03 | −0.04917 |
| 65 | 0.988796 | 0.988487 | 0.000312 | 1.033 | −0.04279 |
| 70 | 0.989097 | 0.986962 | 0.002158 | 1.036 | −0.04527 |
| 75 | 1.030016 | 1.031196 | −0.00115 | 1.039 | −0.00865 |
| 80 | 1.00686 | 1.009489 | −0.00261 | 1.1 | −0.08467 |
| 85 | 1.000187 | 0.998686 | 0.001501 | 1 | 0.000187 |
| 90 | 0.996037 | 0.996037 | 1.11E−16 | 1 | −0.00396 |

FIG. 25 illustrates the Anisotropy Function of Monte Carlo calculated value for Thermobrachytherapy Seed#1 and the Monte Carlo calculated value for the Best Model 2301 $^{125}$I in liquid water at 1 cm radii. The plot is fitted with a 6th order polynomial function.

FIG. 26 illustrates the Anisotropy Function of Monte Carlo calculated value for Thermobrachytherapy Seed#1 and the Book Value for the Best Model 2301 $^{125}$I in liquid water at 1 cm radii. The plot is fitted with a 6th order polynomial function.

Table 24b illustrates the Monte Carlo calculated Anisotropy Function of the Thermobrachytherapy Seed#1 in liquid water for Radial Distances of 2 cm. A comparison between calculated and book values of the Best Model 2301 $^{125}$I Seed is also calculated.

TABLE 24b

Monte Carlo calculated Anisotropy Function of the Thermobrachytherapy Seed#1 in liquid water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 0 | 0.965729 | 0.986817 | −0.02184 | 0.854 | 0.130831 |
| 5 | 0.791594 | 0.810992 | −0.0245 | 0.72 | 0.099436 |
| 10 | 0.701235 | 0.724824 | −0.03364 | 0.671 | 0.04506 |
| 15 | 0.697762 | 0.718106 | −0.02916 | 0.734 | −0.04937 |
| 20 | 0.796005 | 0.819861 | −0.02997 | 0.794 | 0.002526 |
| 25 | 0.826486 | 0.853352 | −0.03251 | 0.847 | −0.02422 |
| 30 | 0.848773 | 0.858304 | −0.01123 | 0.89 | −0.04632 |
| 35 | 0.809979 | 0.821552 | −0.01429 | 0.926 | −0.12529 |
| 40 | 0.917837 | 0.940464 | −0.02465 | 0.954 | −0.03791 |
| 45 | 0.367312 | 0.883125 | −0.01823 | 0.978 | −0.11318 |
| 50 | 0.893594 | 0.903854 | −0.01148 | 0.992 | −0.0992 |
| 55 | 0.931811 | 0.944112 | −0.0132 | 1.003 | −0.07098 |
| 60 | 0.94777 | 0.963059 | −0.01613 | 1.01 | −0.06161 |
| 65 | 0.953051 | 0.971319 | −0.01917 | 1.019 | −0.06472 |
| 70 | 0.985862 | 0.984718 | 0.001161 | 1.026 | −0.03912 |
| 75 | 0.989964 | 1.000409 | −0.01055 | 1.029 | −0.03794 |
| 80 | 1.014289 | 1.019994 | −0.00562 | 1.03 | −0.01525 |
| 85 | 0.971096 | 0.976201 | −0.00526 | 1.022 | −0.04981 |
| 90 | 1 | 1 | 0 | 1 | 0 |

FIG. 27 illustrates the Anisotropy Function of Monte Carlo calculated value for Thermobrachytherapy Seed#1 and the Monte Carlo calculated value for the Best Model 2301 $^{125}$I in liquid water at 2 cm radii. The plot is fitted with a 6th order polynomial function.

FIG. 28 illustrates the Anisotropy Function of Monte Carlo calculated value for Thermobrachytherapy Seed#1 and the Book Value for the Best Model 2301 $^{125}$I in liquid water at 2 cm radii. The plot is fitted with a 6th order polynomial function.

Table 24c illustrates the Monte Carlo calculated Anisotropy Function of the Thermobrachytherapy Seed#1 in liquid water for Radial Distances of 3 cm. A comparison between calculated and book values of the Best Model 2301 [125]I Seed is also calculated.

TABLE 24c

Monte Carlo calculated Anisotropy Function of the Thermobrachytherapy Seed#1 to liquid water for Radial Distances of 3 cm. A comparison between calculated and book values of the Best Model 2301 [125]I Seed is also calculated.

| An-gle | AF at 3 cm | Best Model 2301 [125]I Seed | Error | Book Value (Meigooni et al) | Error |
|---|---|---|---|---|---|
| 0 | 1.046749 | 1.081703 | −0.03339 | 0.922 | 0.135303 |
| 5 | 0.834596 | 0.827586 | 0.008398 | 0.726 | 0.149581 |
| 10 | 0.736561 | 0.750467 | −0.01888 | 0.699 | 0.053736 |
| 15 | 0.812837 | 0.833466 | −0.02538 | 0.756 | 0.075182 |
| 20 | 0.793065 | 0.808948 | −0.02003 | 0.809 | −0.0197 |
| 25 | 0.844568 | 0.872956 | −0.03361 | 0.852 | −0.00872 |
| 30 | 0.920348 | 0.930988 | −0.01156 | 0.885 | 0.039941 |
| 35 | 0.935357 | 0.953275 | −0.01916 | 0.919 | 0.017799 |
| 40 | 0.990214 | 0.987268 | 0.002976 | 0.947 | 0.045633 |
| 45 | 0.949857 | 0.95516 | −0.00558 | 0.968 | −0.01874 |
| 50 | 0.969268 | 0.973073 | −0.00393 | 0.985 | −0.01597 |
| 55 | 0.98734 | 1.008446 | −0.02138 | 0.997 | −0.00969 |
| 60 | 0.985163 | 0.988973 | −0.00387 | 1.009 | −0.02362 |
| 65 | 1.001282 | 1.000178 | 0.001103 | 1.012 | −0.01059 |
| 70 | 1.022119 | 1.030136 | −0.06784 | 1.016 | 0.006012 |
| 75 | 1.010293 | 1.018382 | −0.00801 | 1.018 | −0.00757 |
| 80 | 0.959631 | 0.960588 | −0.001 | 1.019 | −0.05826 |
| 85 | 0.994327 | 0.996809 | −0.0025 | 1.019 | −0.02421 |
| 90 | 1 | 1 | 0 | 1 | 0 |

FIG. 29 illustrates the Anisotropy Function of Monte Carlo calculated value for Thermobrachytherapy Seed#1 and the Book Value for the Best Model 2301 $^{125}$I in liquid water at 3 cm radii. The plot is fitted with a 6th order polynomial function.

FIG. 30 illustrates the Anisotropy Function of Monte Carlo calculated value for Thermobrachytherapy Seed#1 and the Book Value for the Best Model 2301 $^{125}$I in liquid water at 3 cm radii. The plot is fitted with a 6th order polynomial function.

Table 24d illustrates the Monte Carlo calculated Anisotropy Function of the Thermobrachytherapy Seed#1 in liquid water for Radial Distances of 4 cm. A comparison between calculated and book values of the Best Model 2301 [125]I Seed is also calculated.

TABLE 24d

Monte Carlo calculated Anisotropy Function of the Thermobrachytherapy Seed#1 in liquid water for Radial Distances of 4 cm. A comparison between calculated and book values of the Best Model 2301 [125]I Seed is also calculated.

| An-gle | AF at 4 cm | Best Model 2301 [125]I Seed | Error | Book Value (Meigooni et al) | Error |
|---|---|---|---|---|---|
| 0 | 1.044159 | 1.067157 | −0.02202 | 0.902 | 0.157605 |
| 5 | 0.843972 | 0.856189 | −0.01448 | 0.728 | 0.159303 |
| 10 | 0.846344 | 0.849553 | −0.00379 | 0.727 | 0.16416 |

TABLE 24d-continued

Monte Carlo calculated Anisotropy Function of the Thermobrachytherapy Seed#1 in liquid water for Radial Distances of 4 cm. A comparison between calculated and book values of the Best Model 2301 [125]I Seed is also calculated.

| An-gle | AF at 4 cm | Best Model 2301 [125]I Seed | Error | Book Value (Meigooni et al) | Error |
|---|---|---|---|---|---|
| 15 | 0.752004 | 0.762809 | −0.01437 | 0.779 | −0.03465 |
| 20 | 0.835638 | 0.843573 | −0.0095 | 0.814 | 0.026583 |
| 25 | 0.909071 | 0.917008 | −0.00873 | 0.863 | 0.053385 |
| 30 | 0.908464 | 0.921985 | −0.01488 | 0.892 | 0.018457 |
| 35 | 0.916856 | 0.927006 | −0.01107 | 0.918 | −0.00125 |
| 40 | 0.918556 | 0.928846 | −0.0112 | 0.939 | −0.02177 |
| 45 | 0.983039 | 0.992994 | −0.01013 | 0.976 | 0.007213 |
| 50 | 0.968012 | 0.968645 | −0.00065 | 0.991 | −0.0232 |
| 55 | 1.099604 | 1.028106 | −0.01833 | 1.004 | 0.005582 |
| 60 | 0.993738 | 1.000959 | −0.00727 | 1.007 | −0.01317 |
| 65 | 1.023079 | 1.017048 | 0.005895 | 1.009 | 0.013953 |
| 70 | 1.032431 | 1.020551 | 0.011507 | 1.023 | 0.009219 |
| 75 | 1.024549 | 1.009032 | 0.015145 | 1.017 | 0.007423 |
| 80 | 0.986329 | 0.975997 | 0.010475 | 1.017 | −0.03016 |
| 85 | 1.013189 | 0.998651 | 0.014348 | 1.018 | −0.00473 |
| 90 | 1 | 0.999983 | 1.73E−05 | 1 | 0 |

FIG. 31 illustrates the Anisotropy Function of Monte Carlo calculated value for Thermobrachytherapy Seed#1 and the Book Value for the Best Model 2301 $^{125}$I in liquid water at 4 cm radii. The plot is fitted with a 6th order polynomial function.

FIG. 32 illustrates the Anisotropy Function of Monte Carlo calculated value for Thermo Brachytherapy Seed#1 and the Book Value for the Best Model 2301 $^{125}$I in liquid water at 4 cm radii. The plot is fitted with a 6th order polynomial function.

Table 24e illustrates the Monte Carlo calculated Anisotropy Function of the Thermobrachytherapy Seed#1 in liquid water for Radial Distances of 5 cm. A comparison between calculated and book values of the Best Model 2301 [125]I Seed is also calculated.

TABLE 24e

Monte Carlo calculated Anisotropy Function of the Thermobrachytherapy Seed#1 in liquid water for Radial Distances of 5 cm. A comparison between calculated and book values of the Best Model 2301 [125]I Seed is also calculated

| An-gle | AF at 5 cm | Best Model 2301 [125]I Seed | Error | Book Value (Meigooni et al) | Error |
|---|---|---|---|---|---|
| 0 | 1.01337 | 1.037909 | −0.02422 | 0.894 | 0.133524 |
| 5 | 0.808504 | 0.126259 | −0.02196 | 0.753 | 0.07371 |
| 10 | 0.765679 | 0.781112 | −0.02016 | 0.732 | 0.04601 |
| 15 | 0.762468 | 0.785625 | −0.01037 | 0.795 | −0.04092 |
| 20 | 0.805936 | 0.814253 | −0.01032 | 0.825 | −0.02311 |
| 25 | 0.785503 | 0.790151 | −0.00592 | 0.865 | −0.0919 |
| 30 | 0.931303 | 0.93407 | −0.00297 | 0.899 | 0.035932 |
| 35 | 0.874852 | 0.880933 | −0.00695 | 0.92 | −0.04907 |
| 40 | 0.899968 | 0.909002 | −0.01004 | 0.943 | −0.04563 |
| 45 | 0.950244 | 0.965222 | −0.01576 | 0.968 | −0.01834 |
| 50 | 0.929789 | 0.921762 | 0.008633 | 0.997 | −0.06741 |
| 55 | 0.988796 | 1.00322 | −0.01459 | 0.993 | −0.00423 |
| 60 | 0.954913 | 0.972524 | −0.01844 | 1.01 | −0.05454 |
| 65 | 0.99748 | 0.982562 | 0.014956 | 1.024 | −0.0259 |
| 70 | 0.970803 | 0.959269 | 0.01188 | 1.011 | −0.03976 |
| 75 | 1.029805 | 1.020911 | 0.008636 | 1.02 | 0.009613 |
| 80 | 0.997893 | 0.991336 | 0.006571 | 1.01 | −0.01199 |
| 85 | 1.019 | 1.015815 | 0.003126 | 1.011 | 0.007913 |
| 90 | 1 | 1 | 0 | 1 | 0 |

FIG. 33 illustrates the Anisotropy Function of Monte Carlo calculated value for Thermobrachytherapy Seed#1 and the Book Value for the Best Model 2301 $^{125}$I in liquid water at 5 cm radii. The plot is fitted with a 6th order polynomial function.

FIG. 34 illustrates the Anisotropy Function of Monte Carlo calculated value for Thermobrachytherapy Seed#1 and the Book Value for the Best Model 2301 $^{125}$I in liquid water at 5 cm radii. The plot is fitted with a 6th order polynomial function.

Table 24f illustrates the Monte Carlo calculated Anisotropy Function of the Thermobrachytherapy Seed#1 in liquid water for Radial Distances of 6 cm. A comparison between calculated and book values of the Best Model 2301 $^{125}$I Seed is also calculated.

TABLE 24f

Monte Carlo calculated Anisotropy Function of the Thermobrachytherapy Seed#1 in liquid water for Radial Distances of 6 cm. A comparison between calculated and book values of the Best Model 2361 $^{125}$I Seed is also calculated

| Angle | AF at 6 cm | Best Model 2301 $^{125}$I Seed | Error | Book Value (Meigooni et al) | Error |
|---|---|---|---|---|---|
| 0 | 0.963271 | 1.002815 | −0.04105 | 0.893 | 0.078691 |
| 5 | 0.873686 | 0.888127 | −0.01653 | 0.771 | 0.133185 |
| 10 | 0.767832 | 0.782999 | −0.01975 | 0.764 | 0.005016 |
| 15 | 0.80553 | 0.819448 | −0.01728 | 0.805 | 0.000659 |
| 20 | 0.802787 | 0.817894 | −0.01882 | 0.852 | −0.05776 |
| 25 | 0.91588 | 0.936581 | −0.0226 | 0.89 | 0.029078 |
| 30 | 0.820472 | 0.833299 | −0.01563 | 0.915 | −0.10331 |
| 35 | 0.866345 | 0.886202 | −0.02292 | 0.964 | −0.1013 |
| 40 | 0.880596 | 0.904777 | −0.02746 | 0.976 | −0.09775 |
| 45 | 0.929708 | 0.948816 | −0.02055 | 0.979 | −0.05035 |
| 50 | 0.963876 | 0.976859 | −0.01347 | 0.989 | −0.0254 |
| 55 | 0.968881 | 0.98898 | −0.02075 | 1.011 | −0.04166 |
| 60 | 0.950198 | 0.967874 | −0.0186 | 1.019 | −0.06752 |
| 65 | 0.946892 | 0.960829 | −0.01472 | 1.034 | −0.08424 |
| 70 | 0.95177 | 0.948077 | 0.00388 | 1.035 | −0.08042 |
| 75 | 0.999705 | 1.01108 | −0.01138 | 1.043 | −0.04151 |
| 80 | 0.97142 | 0.972717 | −0.00133 | 1.02 | −0.04763 |
| 85 | 1.054951 | 1.053106 | 0.001749 | 1.031 | 0.023231 |
| 90 | 1 | 1 | 0 | 1 | 0 |

FIG. 35 illustrates the Anisotropy Function of Monte Carlo calculated value for Thermobrachytherapy Seed#1 and the Book Value for the Best Model 2301 $^{125}$I in liquid water at 6 cm radii. The plot is fitted with a 6th order polynomial function.

FIG. 36 illustrates the Anisotropy Function of Monte Carlo calculated value for Thermobrachytherapy Seed#1 and the Book Value for the Best Model 2301 $^{125}$I in liquid water at 6 cm radii. The plot is fitted with a 6th order polynomial function.

Table 24g illustrates the Monte Carlo calculated Anisotropy Function of the Thermobrachytherapy Seed#1 in liquid water for Radial Distances of 7 cm. A comparison between calculated and book values of the Best Model 2301 $^{125}$I Seed is also calculated.

TABLE 24g

Monte Carlo calculated Anisotropy Function of the Thermobrachytherapy Seed#1 in liquid water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 0 | 1.00207 | 1.044519 | −0.04236 | 0.858 | 0.167914 |
| 5 | 0.833197 | 0.872338 | −0.04698 | 0.8 | 0.041497 |
| 10 | 0.782894 | 0.814773 | −0.04072 | 0.782 | 0.001143 |
| 15 | 0.863295 | 0.89647 | −0.03843 | 0.812 | 0.063171 |
| 20 | 0.812335 | 0.839067 | −0.03291 | 0.821 | −0.01055 |
| 25 | 0.837071 | 0.857219 | −0.02407 | 0.86 | −0.02666 |
| 30 | 0.938672 | 0.968562 | −0.03184 | 0.873 | 0.075226 |
| 35 | 0.956463 | 0.965505 | −0.00945 | 0.924 | 0.035133 |
| 40 | 0.972739 | 1.010278 | −0.03859 | 0.937 | 0.038142 |
| 45 | 0.984548 | 1.008515 | −0.02434 | 0.954 | 0.032021 |
| 50 | 0.962371 | 0.983552 | −0.02201 | 0.961 | 0.001426 |
| 55 | 0.998295 | 1.020988 | −0.02273 | 0.99 | 0.008379 |
| 60 | 0.910017 | 0.920182 | −0.01117 | 1.002 | −0.0918 |
| 65 | 1.108344 | 1.14268 | −0.03098 | 1.03 | 0.076062 |
| 70 | 1.052193 | 1.069128 | −0.01609 | 1.01 | 0.041775 |
| 75 | 1.034983 | 1.039857 | −0.00471 | 1.02 | 0.01469 |
| 80 | 0.972257 | 0.991134 | −0.01942 | 1.005 | −0.03258 |
| 85 | 1.017453 | 1.029283 | −0.01163 | 1.021 | −0.00347 |
| 90 | 0.999979 | 0.999979 | 1.11E−16 | 1 | −2.1E−05 |

FIG. 37 illustrates the Anisotropy Function of Monte Carlo calculated value for Thermobrachytherapy Seed#1 and the Book Value for the Best Model 2301 $^{125}$I in liquid water at 7 cm radii. The plot is fitted with a 6th order polynomial function.

FIG. 38 illustrates the Anisotropy Function of Monte Carlo calculated value for Thermo Brachytherapy Seed#1 and the Book Value for the Best Model 2301 $^{125}$I in liquid water at 7 cm radii. The plot is fitted with a 6th order polynomial function.

Average Anisotropy Function:

The average anisotropy function is taken by taking an average of the calculated anisotropy functions for all the angles. Table 25a illustrates the Average Anisotropy Function calculated for radial distances of 1 cm in liquid water.

TABLE 25a

Average Anisotropy Function calculated for radial distances of 1 cm in liquid water

| | 1 cm | Best Model 2301 $^{125}$I Seed | Error | Book Value (Meigooni et al) | Error |
|---|---|---|---|---|---|
| Avg. Anisotropy Constant $\Phi_{an}(r)$ | −0.902 | 0.913 | −0.012 | 0.986 | −0.085 |

Table 25b illustrates the Average Anisotropy Function calculated for radial distances of 2 cm in liquid water.

TABLE 25b

Average Anisotropy Function calculated for
radial distances of 2 cm in liquid water

| 2 cm | Best Model 2301 $^{125}$I Seed | Error | Book Value (Meigooni et al) | Error |
|---|---|---|---|---|
| Avg. Anisotropy Constant $\Phi_{an}(r)$ | 0.89 | 0.904 | −0.016 | 0.976 | −0.0881 |

Table 25c illustrates the Average Anisotropy Function calculated for radial distances of 3 cm in liquid water.

TABLE 25e

Average Anisotropy Function calculated for
radial distances of 3 cm in liquid water

| 3 cm | Best Model 2301 $^{125}$I Seed | Error | Book Value (Meigooni et al) | Error |
|---|---|---|---|---|
| Avg. Anisotropy Constant $\Phi_{an}(r)$ | 0.937 | 0.946 | −0.01039 | 0.968 | −0.0325 |

Table 25d: Average Anisotropy Function calculated for radial distances of 4 cm in liquid water.

TABLE 25d

Average Anisotropy Function calculated for
radial distances of 4 cm in liquid water

| 4 cm | Best Model 2301 $^{125}$I Seed | Error | Book Value (Meigooni et al) | Error |
|---|---|---|---|---|
| Avg. Anisotropy Constant $\Phi_{an}(r)$ | 0.947 | 0.952 | −0.00428 | 0.971 | −0.0239 |

Table 25e illustrates the Average Anisotropy Function calculated for radial distances of 5 cm in liquid water.

TABLE 25e

Average Anisotropy Function calculated for
radial distances of 5 cm in liquid water

| 5 cm | Best Model 2301 $^{125}$I Seed | Error | Book Value (Meigooni et al) | Error |
|---|---|---|---|---|
| Avg. Anisotropy Constant $\Phi_{an}(r)$ | 0.920 | 0.926 | −0.006 | 0.969 | −0.05 |

Table 25f illustrates the Average Anisotropy Function calculated for radial distances of 6 cm in liquid water.

TABLE 25f

Average Anisotropy Function calculated for
radial distances of 6 cm in liquid water

| 6 cm | Best Model 2301 $^{125}$I Seed | Error | Book Value (Meigooni et al) | Error |
|---|---|---|---|---|
| Avg. Anisotropy Constant $\Phi_{an}(r)$ | 0.918 | 0.932 | −0.0153 | 0.991 | −0.0741 |

Table 25g illustrates the Average Anisotropy Function calculated for radial distances of 7 cm in liquid water.

TABLE 25g

Average Anisotropy Function calculated for
radial distances of 7 cm in liquid water

| 7 cm | Best Model 2301 $^{125}$I Seed | Error | Book Value (Meigooni et al) | Error |
|---|---|---|---|---|
| Avg. Anisotropy Constant $\Phi_{an}(r)$ | 0.949 | 0.972 | −0.024 | 0.969 | −0.0202 |

Source Anisotropy Constant:

The Source Anisotropy Constant is calculated by taking the average of all the Average Anisotropy Constants. Table 26 illustrates the Source Anisotropy Constant for Thermobrachytherapy Seed#1 in liquid water. The Source Anisotropy Constant is 0.923 and deviates from the Monte Carlo calculated Best Model 2301 $^{125}$I Seed by 1.28% book value by 4.6%

TABLE 26

Source Anisotropy Constant for Thermobrachytherapy
Seed#1 in liquid water.

| | Calculated value | Best Model 2301 $^{125}$I Seed | Error | Book value | Error |
|---|---|---|---|---|---|
| Source Anisotropy Constant $\Phi_{an}(r)$ | 0.923 | 0.935 | −0.0128 | 0.98 | −0.0582 |

1) Thermobrachytherapy Seed#1 in Solid Water i) Dose Rate (D):

Dose Rate was calculated for seed at 1 cm on the transverse plane (θ=90°) of the source (from the center of the source) in Solid Water. Therefore, for this measurement the phantom was taken to be Solid Water since it is the solid water measurement. Table 27 illustrates the Dose Rate for Thermobrachytherapy Seed#1 in Solid Water calculated using Monte Carlo. The error is calculated by using equation #16. Therefore, the error between the calculated thermobrachytherapy value and the calculated Best Model 2301 $^{125}$I seed is 6.0%. The measured value of Dose Rate is $0.245 \pm 4.99 \times 10^{-3}$ cGy*sec$^{-1}$*Ci$^{-1}$.

TABLE 27

Dose Rate for Thermobrachytherapy Seed#1 in
Solid Water calculated using Monte Carlo

| Calculated Dose Rate (cGy*sec$^{-1}$*Ci$^{-1}$) | Calculated Best Model 2301 $^{125}$I Seed (cGy*sec$^{-1}$*Ci$^{-1}$) | Error | Book Value (Meigooni et al) | Error |
|---|---|---|---|---|
| 0.244831 | 0.230994 | −0.0599 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials and Methods section) is used for SK. Table 28 illustrates the Air Kerma Strength for Thermobrachytherapy Seed#1 in Solid Water calculated using Monte Carlo. The error is calculated by using equation #16. Therefore, the error between the calculated thermobrachytherapy value and the calculated Best Model 2301 $^{125}$I seed is 6.0%. The measured value of Air Kerma Strength is 0.238±5.14*10$^{-3}$ cGy*cm$^2$*sec$^{-1}$*Ci$^{-1}$.

TABLE 28

Air Kerma Strength for Thermobrachytherapy Seed#1 in
Solid Water calculated using Monte Carlo

| Calculated Air Kerma Strength (cGy*cm$^2$* sec$^{-1}$*Ci$^{-1}$) | Calculated Best Model 2301 $^{125}$I Seed (cGy*cm$^2$* sec$^{-1}$*Ci$^{-1}$) | Error | Book Value (Meigooni et al) | Error |
|---|---|---|---|---|
| 0.237773 | 0.224332 | 0.0599 | N/A | NA | iii) Dose Rate Constant (Λ):

Dose rate constant is calculated using equation #4. In order to calculate it, the ratio of the dose rate and air kerma strength is taken. Table 29a illustrates the Monte Carlo calculated Dose Rate Constant Thermobrachytherapy Seed#1 in Solid Water. The error is calculated by using equation #. Therefore, the error between the calculated thermobrachytherapy value and the calculated Best Model 2301 $^{125}$I seed is 0.01%. Also, the error between the calculated thermobrachytherapy value and the Book Value for Best Model 2301 $^{125}$I seed is 5.1%. The measured value of Dose Rate Constant is 1.03±0.031cGy*h$^{-1}$U$^{-1}$.

TABLE 29

Monte Carlo calculated Dose Rate Constant
Thermobrachytherapy Seed#1 in Solid Water

| Calculated Dose Rate Constant (cGy*h$^{-1}$U$^{-1}$) | Best Model 2301 $^{125}$I Seed (cGy*h$^{-1}$U$^{-1}$) | Error | Book Value (Meigooni et al) (cGy*h$^{-1}$U$^{-1}$) | Error |
|---|---|---|---|---|
| 1.0297 | 1.02969 | 0.0001 | 0.98 | 0.051 | iv) Correction/Multiplicative Factor:

Meigooni et al calculated that a conversion factor of 1.05 was needed to convert the dose rate constant in solid water to liquid water.

The calculated Correction/Multiplicative factor obtained is 1.026.

iv) Radial Function:

Calculation of the radial function is a two fold process.

a) Geometry Function

The Geometry function is independent of the material content of the phantom. Also, the geometry (and dimension) of the source cell remains the same. Therefore, the geometry factor from Table 6 is applicable here.

b) Radial Function Using the Geometry Function

Radial Function was calculated using equation#8 incorporating the geometry function calculated in part a) above. Table 29b illustrates the Radial Function calculated at the transverse plane for the Thermobrachytherapy Seed#1 in Solid Water using Monte Carlo.

TABLE 29

Radial Function calculated at the tranverse plane for the Thermobrachytherapy
Seed#1 is Solid Water using Monte Carlo.

| Transverse distance (r) cm | Radial Function g(r, θ) | Best Model 2301 $^{125}$I Seed | Error | Book Value (Meigooni et al) | Error |
|---|---|---|---|---|---|
| 0.1 | 0.964876 | 0.9740849 | −0.00945 | | |
| 0.15 | 0.981422 | 0.9872727 | −0.00593 | | |
| 0.2 | 1.019521 | 1.0245773 | −0.00494 | | |
| 0.25 | 1.000004 | 0.997152 | 0.00286 | | |
| 0.3 | 1.000948 | 1.0106151 | −0.00957 | | |
| 0.4 | 0.994702 | 1.0024356 | −0.00771 | | |
| 0.5 | 0.992548 | 0.9962775 | −0.00374 | | |
| 0.6 | 0.951016 | 0.9601123 | −0.00947 | 1.044 | −0.08906 |
| 0.7 | 0.906666 | 0.9079231 | −0.00138 | | |
| 0.75 | 0.952771 | 0.9467391 | 0.006371 | | |
| 0.8 | 0.955798 | 0.9554107 | 0.000406 | | |
| 0.9 | 0.946121 | 0.9667486 | −0.02134 | | |
| 1 | 1.000001 | 1.0000005 | 0 | 1 | 5.07E−07 |
| 1.5 | 0.90524 | 0.9040619 | 0.001304 | 0.926 | −0.02242 |
| 2 | 0.813691 | 0.8129667 | 0.000891 | 0.842 | −0.03362 |
| 2.5 | 0.726495 | 0.728075 | −0.00217 | 0.752 | −0.03392 |
| 3 | 0.648377 | 0.6505947 | −0.00341 | 0.666 | −0.02646 |

TABLE 29-continued

Radial Function calculated at the tranverse plane for the Thermobrachytherapy Seed#1 is Solid Water using Monte Carlo.

| Transverse distance (r) cm | Radial Function g(r, θ) | Best Model 2301 125I Seed | Error | Book Value (Meigooni et al) | Error |
|---|---|---|---|---|---|
| 3.5 | 0.563752 | 0.5635308 | 0.000392 | 0.581 | −0.02969 |
| 4 | 0.512275 | 0.5125491 | −0.00054 | 0.509 | 0.006434 |
| 4.5 | 0.434328 | 0.4328601 | 0.003391 | 0.443 | −0.01958 |
| 5 | 0.380607 | 0.3817734 | −0.00306 | 0.386 | −0.01397 |
| 5.5 | 0.318492 | 0.3178485 | 0.002026 | 0.336 | −0.05211 |
| 6 | 0.27567 | 0.2753888 | 0.001021 | 0.286 | −0.03612 |
| 6.5 | 0.234263 | 0.2309718 | 0.014249 | 0.245 | −0.04382 |
| 7 | 0.206563 | 0.2041012 | 0.012064 | 0.207 | −0.00211 |
| 7.5 | 0.178336 | 0.176629 | 0.009665 | 0.178 | 0.001888 |
| 8 | 0.158985 | 0.1571086 | 0.011944 | 0.159 | −9.3E−05 |
| 8.5 | 0.12521 | 0.1246026 | 0.004876 | 0.14 | −0.10564 |
| 9 | 0.11154 | 0.1098135 | 0.015721 | 0.116 | −0.03845 |
| 9.5 | 0.094898 | 0.093497 | 0.014987 | 0.097 | −0.02167 |
| 10 | 0.080815 | 0.079492 | 0.016645 | 0.08 | 0.010189 |

FIG. 39 illustrates the Radial Function of Monte Carlo calculated value for Thermobrachytherapy Seed#1 and the Monte Carlo calculated value for the Best Model 2301 $^{125}$I in Solid Water. The plot is fitted with a 5th order polynomial function.

FIG. 40 illustrates the Radial Function of Monte Carlo calculated value for Thermobrachytherapy Seed#1 and the Book Value for the Best Model 2301 $^{125}$I in Solid Water. The plot is fitted with a 5th order polynomial function.

iv) Anisotropy Function:

Calculation of the radial function is a three fold process.

a) Calculating Geometry Function

The Geometry function is independent of the material content of the phantom and therefore, the geometry function from Table 7 is applicable here.

b) Calculating Coordinates for Detectors

The coordinates are independent of the material content of the phantom and therefore, the coordinates from Table 8 are applicable here.

c) Calculating Anisotropy Function Using the Data Accumulated in Tables 7 and 8

The Anisotropy Function was calculated using all the factors listed in equation #9. Table 7 was used to calculate the Geometry Function at various angles. Table 8 was used to find the coordinates needed to place the detectors at the various angles (and radial distances). Table 30a illustrates the Monte Carlo calculated Anisotropy Function of the Thermobrachytherapy Seed#1 in Solid Water for Radial Distances of 1 cm. A comparison between calculated values of the Best Model 2301 $^{125}$I Seed is also calculated.

TABLE 30a

Monte Carlo calculated Anisotropy Function of the Thermobrachytherapy Seed#1 in Solid Water for Radial Distances of 1 cm. A comparison between calculated values of the Best Model 2301 125I Seed is also calculated.

| Angle | AF at 1 cm | Best Model 2301 125I Seed | Error |
|---|---|---|---|
| 0 | 0.996494 | 1.026252 | −0.028996 |
| 5 | 0.847453 | 0.866304 | −0.02176 |
| 10 | 0.655995 | 0.672536 | −0.024595 |
| 15 | 0.24557 | 0.739002 | −0.019547 |
| 20 | 0.74101 | 0.75897 | −0.023664 |
| 25 | 0.777262 | 0.793086 | −0.019952 |
| 30 | 0.807494 | 0.822657 | −0.018432 |

TABLE 30a-continued

Monte Carlo calculated Anisotropy Function of the Thermobrachytherapy Seed#1 in Solid Water for Radial Distances of 1 cm. A comparison between calculated values of the Best Model 2301 125I Seed is also calculated.

| Angle | AF at 1 cm | Best Model 2301 125I Seed | Error |
|---|---|---|---|
| 35 | 0.884933 | 0.897361 | −0.013849 |
| 40 | 0.895856 | 0.906809 | −0.012078 |
| 45 | 0.946847 | 0.957336 | −0.010956 |
| 50 | 0.968148 | 0.971523 | −0.003474 |
| 55 | 0.986063 | 0.989839 | −0.003815 |
| 60 | 0.980092 | 0.987353 | −0.007354 |
| 65 | 0.990449 | 0.99135 | −0.000909 |
| 70 | 1.004312 | 0.998792 | 0.005527 |
| 75 | 1.041131 | 1.038309 | 0.002718 |
| 80 | 1.032423 | 1.032288 | 0.000131 |
| 85 | 0.994183 | 0.986828 | 0.007453 |
| 90 | 0.996037 | 0.996037 | 0 |

FIG. 41: Anisotropy Function of Monte Carlo calculated value for Thermobrachytherapy Seed#1 and the Monte Carlo for the Best Model 2301 $^{125}$I in Solid Water at 1 cm radii. The plot is fitted with a 6th order polynomial function.

Table 30b illustrates a Monte Carlo calculated Anisotropy Function of the Thermobrachytherapy Seed#1 in Solid Water for Radial Distances of 2 cm. A comparison between calculated and book values of the Best Model 2301 $^{125}$I Seed is also calculated.

TABLE 30b

Monte Carlo calculated Anisotropy Function of the Thermobrachytherapy Seed#1 in Solid Water for Radial Distances of 2 cm. A comparison between calculated and book values of the Best Model 2301 125I Seed in also calculated.

| Angle | AF at 2 cm | Best Model 2301 125I Seed | Error | Book Value (Meigooni et al) | Error |
|---|---|---|---|---|---|
| 0 | 0.98338 | 1.002986 | −0.019548 | 0.837 | 0.174887 |
| 5 | 0.807861 | 0.829332 | −0.02589 | | |
| 10 | 0.66456 | 0.677051 | −0.018449 | 0.659 | 0.008437 |
| 15 | 0.677366 | 0.689879 | −0.018139 | | |
| 20 | 0.759896 | 0.779294 | −0.024892 | 0.782 | −0.028266 |
| 25 | 0.798873 | 0.81592 | −0.020894 | | |
| 30 | 0.825427 | 0.83656 | −0.013307 | 0.882 | −0.064141 |
| 35 | 0.800079 | 0.803188 | −0.003871 | | |

TABLE 30b-continued

Monte Carlo calculated Anisotropy Function of the Thermobrachytherapy Seed#1 in Solid Water for Radial Distances of 2 cm. A comparison between calculated and book values of the Best Model 2301 $^{125}$I Seed in also calculated.

| Angle | AF at 2 cm | Best Model 2301 $^{125}$I Seed | Error | Book Value (Meigooni et al) | Error |
|---|---|---|---|---|---|
| 40 | 0.867128 | 0.876187 | −0.010339 | 0.946 | −0.083374 |
| 45 | 0.894279 | 0.901717 | −0.008249 | | |
| 50 | 0.924454 | 0.924023 | 0.000466 | 0.985 | −0.061468 |
| 55 | 0.948725 | 0.948227 | 0.000524 | | |
| 60 | 0.927232 | 0.928041 | −0.000871 | 1.007 | −0.079214 |
| 65 | 0.91481 | 0.912797 | 0.002205 | | |
| 70 | 0.960586 | 0.952063 | 0.008952 | 1.02 | −0.058249 |
| 75 | 0.991521 | 0.987641 | 0.003928 | | |
| 80 | 1.004723 | 1.004358 | 0.000363 | 1.027 | −0.021692 |
| 85 | 0.98388 | 0.984115 | −0.000239 | | |
| 90 | 1 | 1 | 0 | 1 | 0 |

FIG. 42 illustrates the Anisotropy Function of Monte Carlo calculated value for Thermobrachytherapy Seed#1 and the Monte Carlo for the Best Model 2301 $^{125}$I in Solid Water at 2 cm radii. The plot is fitted with a 6th order polynomial function.

FIG. 43 illustrates the Anisotropy Function of Monte Carlo calculated value for Thermobrachytherapy Seed#1 and the Book value for the Best Model 2301 $^{125}$I in Solid Water at 2 cm radii. The plot is fitted with a 6th order polynomial function.

Table 30c illustrates the Monte Carlo calculated Anisotropy Function of Thermobrachytherapy Seed#1 in Solid Water for Radial Distances of 3 cm. A comparison between calculated values of the Best Model 2301 $^{125}$I Seed is also calculated.

TABLE 30c

Monte Carlo calculated Anisotropy Function of Thermobrachytherapy Seed#1 in Solid Water for Radial Distances of 3 cm. A comparison between calculated values of the Best Model 2301 $^{125}$I Seed is also calculated.

| Angle | AF at 3 cm | Best Model 2301 $^{125}$I Seed | Error |
|---|---|---|---|
| 0 | 1.012225 | 1.045494 | −0.031821 |
| 5 | 0.756306 | 0.767353 | −0.014396 |
| 10 | 0.70105 | 0.06056 | −0.007091 |
| 15 | 0.736806 | 0.742168 | −0.007224 |
| 20 | 0.759654 | 0.769965 | −0.013391 |
| 25 | 0.846572 | 0.864285 | −0.020495 |
| 30 | 0.828748 | 0.835925 | −0.008586 |
| 35 | 0.875156 | 0.876294 | −0.001299 |
| 40 | 0.917407 | 0.919709 | −0.002503 |
| 45 | 0.899806 | 0.893813 | 0.006705 |
| 50 | 0.891812 | 0.89036 | 0.001631 |
| 55 | 0.911477 | 0.916484 | −0.005463 |
| 60 | 0.895706 | 0.900548 | −0.005377 |
| 65 | 0.884732 | 0.880534 | 0.004768 |
| 70 | 0.965355 | 0.97229 | −0.007132 |
| 75 | 0.958985 | 0.944857 | 0.014952 |
| 80 | 0.90757 | 0.899939 | 0.008479 |
| 85 | 0.95826 | 0.95404 | 0.004423 |
| 90 | 1 | 1 | 0 |

FIG. 44 illustrates the Anisotropy Function of Monte Carlo calculated value for Thermobrachytherapy Seed#1 and the Monte Carlo for the Best Model 2301 $^{125}$I in Solid Water at 3 cm radii. The plot is fitted with a 6th order polynomial function.

Table 30d illustrates the Monte Carlo calculated Anisotropy Function of Thermobrachytherapy Seed#1 in Solid Water for Radial Distances of 4 cm. A comparison between calculated values of the Best Model 2301 $^{125}$I Seed is also calculated.

TABLE 30d

Monte Carle calculated Anisotropy Function of Thermobrachytherapy Seed#1 in Solid Water for Radial Distances of 4 cm. A comparison between calculated values of the Best Model 2301 $^{125}$I Seed is also calculated.

| Angle | AF at 4 cm | Best Model 2301 $^{125}$I Seed | Error |
|---|---|---|---|
| 0 | 0.974327 | 0.996217 | −0.021973 |
| 5 | 0.788597 | 0.804645 | −0.019945 |
| 10 | 0.768105 | 0.786272 | −0.023105 |
| 15 | 0.751098 | 0.766287 | −0.019821 |
| 20 | 0.805114 | 0.821381 | −0.019805 |
| 25 | 0.836461 | 0.865759 | −0.03384 |
| 30 | 0.906229 | 0.928838 | −0.024341 |
| 35 | 0.9227 | 0.940615 | −0.019047 |
| 40 | 0.942636 | 0.956302 | −0.014291 |
| 45 | 0.954887 | 0.963304 | −0.008738 |
| 50 | 0.902201 | 0.909226 | −0.007726 |
| 55 | 0.999693 | 1.009165 | −0.009386 |
| 60 | 0.963996 | 0.967434 | −0.003553 |
| 65 | 0.966021 | 0.964955 | 0.001104 |
| 70 | 1.01121 | 1.007641 | 0.003542 |
| 75 | 0.978419 | 0.970099 | 0.008576 |
| 80 | 0.962388 | 0.956987 | 0.005643 |
| 85 | 1.006779 | 0.990027 | 0.016921 |
| 90 | 1 | 1 | 0 |

FIG. 45 illustrates the Anisotropy Function of Monte Carlo calculated value for Thermobrachytherapy Seed#1 and the Monte Carlo for the Best Model 2301 $^{125}$I in Solid Water at 4 cm radii. The plot is fitted with a 6th order polynomial function.

Table 30e illustrates the Monte Carlo calculated Anisotropy Function of Thermobrachytherapy Seed#1 in Solid Water for Radial Distances of 5 cm. A comparison between calculated and book values of the Best Model 2301 $^{125}$I Seed is also calculated.

TABLE 30e

Monte Carlo calculated Anisotropy Function of Thermobrachytherapy Seed#1 in Solid Water for Radial Distances of 5 cm. A comparison between calculated and book values of the Best Model 2301 $^{125}$I Seed is also calculated.

| Angle | AF at 5 cm | Best Model 2301 $^{125}$I Seed | Error | Book Value (Meigooni et al) | Error |
|---|---|---|---|---|---|
| 0 | 1.01337 | 1.06538 | −0.026421 | 0.886 | 0.17069 |
| 5 | 0.808504 | 0.863781 | −0.025047 | | |
| 10 | 0.765679 | 0.788669 | −0.019244 | 0.719 | 0.075788 |
| 15 | 0.762468 | 0.773249 | −0.024994 | | |
| 20 | 0.805936 | 0.817595 | −0.007523 | 0.801 | 0.013038 |
| 25 | 0.785503 | 0.879567 | −0.012514 | | |
| 30 | 0.931303 | 0.840307 | −0.011353 | 0.873 | −0.048377 |
| 35 | 0.874852 | 0.911502 | −0.015338 | | |
| 40 | 0.899968 | 0.949538 | −0.005609 | 0.938 | 0.006622 |
| 45 | 0.950244 | 0.936324 | 0.000441 | | |
| 50 | 0.929789 | 0.99784 | 0.010052 | 0.962 | 0.047682 |
| 55 | 0.988796 | 1.018567 | −0.003368 | | |
| 60 | 0.954913 | 0.948673 | −0.004997 | 0.99 | −0.046533 |
| 65 | 0.99748 | 1.02104 | 0.018982 | | |
| 70 | 0.970803 | 1.024804 | 0.007158 | 1.001 | 0.031108 |
| 75 | 1.029805 | 1.013883 | −0.000209 | | |
| 80 | 0.997893 | 1.06825 | 0.020662 | 1.011 | 0.078459 |
| 85 | 1.019 | 1.000983 | 0.021675 | | |
| 90 | 1 | 1 | 0 | 1 | 0 |

FIG. 46 illustrates the Anisotropy Function of Monte Carlo calculated value for Thermobrachytherapy Seed#1 and the Monte Carlo for the Best Model 2301 $^{125}$I in Solid Water at 5 cm radii. The plot is fitted with a 6th order polynomial function.

FIG. 47 illustrates the Anisotropy Function of Monte Carlo calculated value for Thermobrachytherapy Seed#1 and the Book value for the Best Model 2301 $^{125}$I in Solid Water at 5 cm radii. The plot is fitted with a 6th order polynomial function.

Table 30f illustrates the Monte Carlo calculated Anisotropy Function of Thermobrachytherapy Seed#1 in Solid Water for Radial Distances of 6 cm. A comparison between calculated values of the Best Model 2301 $^{125}$I Seed is also calculated.

TABLE 30f

Monte Carlo calculated Anisotropy Function of Thermobrachytherapy Seed#1 in Solid Water for Radial Distances of 6 cm. A comparison between calculated values of the Best Model 2301 $^{125}$I Seed is also calculated.

| Angle | AF at 6 cm | Best Model 2301 $^{125}$I Seed | Error |
| --- | --- | --- | --- |
| 0 | 0.939123 | 0.961176 | −0.022944 |
| 5 | 0.856811 | 0.869443 | −0.014529 |
| 10 | 0.74624 | 0.754599 | −0.011077 |
| 15 | 0.770177 | 0.77439 | −0.00544 |
| 20 | 0.749627 | 0.754773 | −0.006819 |
| 25 | 0.859541 | 0.868662 | −0.0105 |
| 30 | 0.824175 | 0.82609 | −0.002317 |
| 35 | 0.868763 | 0.864491 | 0.004942 |
| 40 | 0.848343 | 0.85658 | −0.009617 |
| 45 | 0.889552 | 0.878697 | 0.012354 |
| 50 | 0.863083 | 0.853307 | 0.011458 |
| 55 | 0.939138 | 0.938518 | 0.00066 |
| 60 | 0.910432 | 0.912431 | −0.00219 |
| 65 | 1.017911 | 1.005409 | 0.012434 |
| 70 | 0.974917 | 0.962483 | 0.012918 |
| 75 | 0.977531 | 0.972179 | 0.005505 |
| 80 | 1.039824 | 1.025741 | 0.013729 |
| 85 | 0.994157 | 0.987695 | 0.006542 |
| 90 | 1 | 1 | 0 |

FIG. 48 illustrates the Anisotropy Function of Monte Carlo calculated value for Thermobrachytherapy Seed#1 and the Monte Carlo for the Best Model 2301 $^{125}$I in Solid Water at 6 cm radii. The plot is fitted with a 6th order polynomial function.

Table 30g illustrates the Monte Carlo calculated Anisotropy Function of Thermobrachytherapy Seed#1 in Solid Water for Radial Distances of 7 cm. A comparison between calculated and book values of the Best Model 2301 $^{125}$I Seed is also calculated.

TABLE 30g

Monte Carlo calculated Anisotropy Function of Thermobrachytherapy Seed#1 in Solid Water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book value (Meigooni et al) | Error |
| --- | --- | --- | --- | --- | --- |
| 0 | 1.00207 | 1.044519 | −0.04236 | 0.888 | 0.222344 |
| 5 | 0.833197 | 0.872338 | −0.04698 | | |
| 10 | 0.782894 | 0.814773 | −0.04072 | 0.751 | 0.255709 |
| 15 | 0.863295 | 0.89647 | −0.03843 | | |
| 20 | 0.812335 | 0.839067 | −0.03291 | 0.82 | 0.085533 |
| 25 | 0.837071 | 0.857219 | −0.02407 | | |
| 30 | 0.938672 | 0.968562 | −0.03184 | 0.905 | 0.014884 |
| 35 | 0.956463 | 0.965505 | −0.00945 | | |
| 40 | 0.972739 | 1.010278 | −0.03859 | 0.952 | 0.043336 |

TABLE 30g-continued

Monte Carlo calculated Anisotropy Function of Thermobrachytherapy Seed#1 in Solid Water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book value (Meigooni et al) | Error |
| --- | --- | --- | --- | --- | --- |
| 45 | 0.984548 | 1.008515 | −0.02434 | | |
| 50 | 0.962371 | 0.983552 | −0.02201 | 0.972 | 0.025063 |
| 55 | 0.998295 | 1.020988 | −0.02273 | | |
| 60 | 0.910017 | 0.920182 | −0.01117 | 1.004 | 0.06859 |
| 65 | 1.108344 | 1.14268 | −0.03098 | | |
| 70 | 1.052193 | 1.069128 | −0.01609 | 0.999 | −0.019711 |
| 75 | 1.034983 | 1.039857 | −0.00471 | | |
| 80 | 0.972257 | 0.991134 | −0.01942 | 1.015 | 0.079653 |
| 85 | 1.017453 | 1.029283 | −0.01163 | | |
| 90 | 0.999979 | 0.999979 | 1.11E−16 | 1 | −2.1E−05 |

FIG. 49 illustrates the Anisotropy Function of Monte Carlo calculated value for Thermobrachytherapy Seed#1 and the Monte Carlo for the Best Model 2301 $^{125}$I in Solid Water at 7 cm radii. The plot is fitted with a 6th order polynomial function.

FIG. 50 illustrates the Anisotropy Function of Monte Carlo calculated value for Thermobrachytherapy Seed#1 and the Book value for the Best Model 2301 $^{125}$I in Solid Water at 7 cm radii. The plot is fitted with a 6th order polynomial function.

Average Anisotropy Function:

The average anisotropy function is taken by taking an average of the calculated anisotropy functions for all the angles. Table 31a illustrates the Average Anisotropy Constant calculated for radial distances of 1 cm in Solid Water.

TABLE 31a

Average Anisotropy Constant calculated for radial distances of 1 cm in Solid Water

| | 1 cm | Best Model 2301 $^{125}$I Seed | Error |
| --- | --- | --- | --- |
| Average Anisotropy Constant $\Phi_{an}(r)$ | 0.909 | 0.917 | −0.009 |

Table 31b illustrates the Average Anisotropy Constant calculated for radial distances of 2 cm in Solid Water.

TABLE 31b

Average Anisotropy Constant calculated for radial distances of 2 cm in Solid Water

| | 2 cm | Best Model 2301 $^{125}$I Seed | Error | Book Value (Meigooni et al) | Error |
| --- | --- | --- | --- | --- | --- |
| Average Anisotropy Constant $\Phi_{an}(r)$ | 0.881 | 0.898 | −0.01924 | 0.975 | −0.096 |

[Note NEXT TABLE IS TABLE 34C]

Table 34c illustrates the Average Anisotropy Constant calculated for radial distances of 3 cm in Solid Water.

TABLE 34c

Average Anisotropy Constant calculated for
radial distances of 3 cm in Solid Water

| | 3 cm | Best Model 2301 $^{125}$I Seed | Error |
|---|---|---|---|
| Average Anisotropy Constant $\Phi_{an}$ (r) | 0.879 | 0.883 | −0.0043 |

Table 34d illustrates the Average Anisotropy Constant calculated for radial distances of 4 cm in Solid water.

TABLE 34d

Average Anisotropy Constant calculated for
radial distances of 4 cm in Solid water

| | 4 cm | Best Model 2301 $^{125}$I Seed | Error |
|---|---|---|---|
| Average Anisotropy Constant $\Phi_{an}$ (r) | 0.918 | 0.928 | −0.0093 |

Table 34e illustrates the Average Anisotropy Constant calculated for radial distances of 5 cm in Solid Water.

TABLE 34e

Average Anisotropy Constant calculated for
radial distances of 5 cm in Solid Water

| | 5 cm | Best Model 2301 $^{125}$I Seed | Error | Book Value (Meigooni et al) | Error |
|---|---|---|---|---|---|
| Average Anisotropy Constant $\Phi_{an}$ (r) | 0.940 | 0.950 | −0.0105 | 0.965 | −0.0258 |

Table 34f illustrates the Average Anisotropy Constant calculated for radial distances of 6 cm in Solid Water.

TABLE 34f

Average Anisotropy Constant calculated for
radial distances of 6 cm in Solid Water

| | 6 cm | Best Model 2301 $^{125}$I Seed | Error |
|---|---|---|---|
| Average Anisotropy Constant $\Phi_{an}$ (r) | 0.8984 | 0.898 | −0.00015 |

Table 34g illustrates the Average Anisotropy Constant calculated for radial distances of 7 cm in Solid Water.

TABLE 34g

Average Anisotropy Constant calculated for
radial distances of 7 cm in Solid Water

| | 7 cm | Best Model 2301 $^{125}$I Seed | Error | Book Value (Meigooni et al) | Error |
|---|---|---|---|---|---|
| Average Anisotropy Constant $\Phi_{an}$ (r) | 1.006 | 1.01 | −0.005 | 0.977 | −0.03 |

Table 35 illustrates the Source Anisotropy Constant. The Source Anisotropy Constant is calculated by taking the average of all the Average Anisotropy Constants. The Source Anisotropy Constant is 0.918 and deviates from the Monte Carlo calculated Best Model 2301 $^{125}$I Seed by 0.08% and the Book value by 5.4%.

TABLE 35

Source Anisotropy Constant: The Source Anisotropy Constant is
calculated by taking the average of all the Average Anisotropy Constants

| | Calculated value | Best Model 2301 $^{125}$I Seed | Error | Book value | Error |
|---|---|---|---|---|---|
| Source Anisotropy Constant $\overline{\Phi_{an}}$ (r) | 0.918 | 0.926 | −0.008 | 0.97 | −0.0536 |

Thermobrachytherapy Seed#2 in Liquid Water i) Dose Rate (D):

Dose Rate was calculated for seed at 1 cm on the transverse plane (θ=90°) of the source (from the center of the source) in water. Therefore, for this measurement the phantom was taken to be liquid water since it is the liquid water measurement. Table 36 illustrates the Dose Rate for Thermobrachytherapy Seed#2 in liquid water calculated using Monte Carlo. The error is calculated by using equation #16. Therefore, the error between the calculated thermobrachytherapy value and the calculated Best Model 2301 $^{125}$I seed is 4.5%. The measured value of Dose Rate is 0.248±4.95*10$^{-3}$ cGy*sec$^{-1}$*Ci$^{-1}$.

TABLE 36

Dose Rate for Thermobrachytherapy Seed#2 in
liquid water calculated using Monte Carlo

| Calculated Dose Rate (cGy*sec$^{-1}$*Ci$^{-1}$) | Calculated Best Model 2301 $^{125}$I Seed (cGy*sec$^{-1}$*Ci$^{-1}$) | Error | Book Value (Meigooni et al) | Error |
|---|---|---|---|---|
| 0.247556 | 0.236993 | 0.0446 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 correction factor (as discussed in the Materials and Methods section) is used for SK.

Table 37 illustrates the Air Kerma Strength for Thermobrachytherapy Seed#2 in liquid water calculated using Monte Carlo. The error is calculated by using equation #16. Therefore, the error between the calculated thermobrachytherapy value and the calculated Best Model 2301 $^{125}$I seed is 4.3%. The measured value of Air Kerma Strength is 0.234±5.1*10$^{-3}$ cGy*cm$^2$sec$^{-1}$*Ci$^{-1}$.

TABLE 37

Air Kerma Strength for Thermobrachytherapy Seed#2 in liquid water calculated using Monte Carlo

| Calculated Air Kerma Strength (cGy*cm² sec⁻¹*Ci⁻¹) | Calculated Best Model 2301 ¹²⁵I Seed (cGy*cm² sec⁻¹*Ci⁻¹) | Error | Book Value (Meigooni et al) | Error |
|---|---|---|---|---|
| 0.234046 | 0.224332 | 0.0433 | N/A | N/A | iii) Dose Rate Constant (Λ):

Dose rate constant is calculated using equation #4. In order to calculate it, the ratio of the dose rate and air kerma strength is taken. Table 38 illustrates the Monte Carlo calculated Dose Rate Constant for Thermobrachytherapy Seed#2 in liquid water. The error is calculated by using equation #16. Therefore, the error between the calculated thermobrachytherapy value and the calculated Best Model 2301 $^{125}$I seed is 0.15%. Also, the error between the calculated thermobrachytherapy value and the Book Value for Best Model 2301 $^{125}$I seed is 4.75%. The measured value of Dose Rate is $1.058 \pm 0.031$ cGy*h⁻¹U⁻¹.

TABLE 38

Monte Carlo calculated Dose Rate Constant for Thermobrachytherapy Seed#2 in liquid water

| Calculated Dose Rate Constant (cGy*h⁻¹U⁻¹) | Best Model 2301 I¹²⁵ Seed Dose Rate Constant (cGy*h⁻¹U⁻¹) | Error | Book Value (Meigooni et al) | Error |
|---|---|---|---|---|
| 1.0577 | 1.05644 | 0.00148 | 1.01 | 0.0475 | iv) Radial Function:

Calculation of the radial function is a two fold process.

a) Geometry Function

The Geometry function is independent of the material content of the phantom. And also, the geometry (and dimension) of the source cell remains the same. Therefore, the geometry factor from Table 6 is applicable here.

b) Radial Function Using the Geometry Function.

Radial Function was calculated using equation# incorporating the geometry function calculated in part a) above. Table 39 illustrates the Radial Function calculated at the transverse plane for the Thermobrachytherapy Seed#2 in liquid water using Monte Carlo.

TABLE 39

Radial Function calculated at the transverse plane for the Thermobrachytherapy Seed#2 in liquid water using Monte Carlo.

| Transverse distance (r) cm | Radial Function g(r) | Best Model 2301 ¹²⁵I Seed | Error | Book Value (Meigooni et al) | Error |
|---|---|---|---|---|---|
| 0.1 | 0.891505 | 0.9456286 | −0.05724 | 1.033 | −0.09512 |
| 0.15 | 0.947105 | 0.972143 | −0.02575 | 1.029 | −0.06396 |
| 0.2 | 0.994958 | 1.0043252 | −0.00933 | 1.028 | −0.03105 |
| 0.25 | 0.979154 | 0.9786852 | 0.000479 | 1.027 | −0.05171 |
| 0.3 | 1.003378 | 0.9995776 | 0.003802 | 1.027 | −0.03944 |
| 0.4 | 1.030407 | 0.9913498 | 0.039398 | 1.027 | −0.04739 |
| 0.5 | 1.013596 | 1.0205403 | −0.0068 | 1.028 | −0.01474 |
| 0.6 | 1.008642 | 0.9631128 | 0.047273 | 1.034 | −0.0779 |
| 0.7 | 0.997534 | 0.9312438 | 0.071184 | 1.036 | −0.10966 |
| 0.75 | 0.975717 | 0.9597881 | 0.016596 | 1.03 | −0.06847 |
| 0.8 | 1.007574 | 0.9358905 | 0.076594 | 1.024 | −0.09 |
| 0.9 | 1.000351 | 1.0388782 | −0.03708 | 1.013 | 0.006 |
| 1 | 1.000001 | 1.0000005 | 2.22E-16 | 1 | 5.07E-07 |
| 1.5 | 0.937707 | 0.9266222 | 0.011962 | 0.938 | −0.01535 |
| 2 | 0.857589 | 0.8476955 | 0.011672 | 0.866 | −0.02708 |
| 2.5 | 0.077099 | 0.7624361 | −0.89888 | 0.79 | −0.04164 |
| 3 | 0.701005 | 0.6881108 | 0.018739 | 0.707 | −0.03494 |
| 3.5 | 0.623307 | 0.6073126 | 0.026336 | 0.635 | −0.04997 |
| 4 | 0.52286 | 0.5365308 | −0.02548 | 0.555 | −0.03966 |
| 4.5 | 0.468085 | 0.4829325 | −0.03074 | 0.488 | −0.01996 |
| 5 | 0.414212 | 0.4070779 | 0.017526 | 0.427 | −0.05126 |
| 5.5 | 0.364463 | 0.3609578 | 0.009711 | 0.372 | −0.03365 |
| 6 | 0.318889 | 0.2993458 | 0.065285 | 0.32 | −0.06271 |
| 6.5 | 0.28487 | 0.2680607 | 0.062708 | 0.285 | −0.05771 |
| 7 | 0.230912 | 0.2394946 | −0.03583 | 0.248 | −0.03223 |
| 7.5 | 0.203728 | 0.2032859 | 0.002173 | 0.215 | −0.05844 |
| 8 | 0.181191 | 0.1818156 | −0.00343 | 0.187 | −0.03885 |
| 8.5 | 0.16731 | 0.1542993 | 0.08432 | 0.16 | −0.04464 |
| 9 | 0.141106 | 0.1326667 | 0.063616 | 0.142 | −0.06087 |

TABLE 39-continued

Radial Function calculated at the transverse plane for the Thermobrachytherapy Seed#2 in liquid water using Monte Carlo.

| Transverse distance (r) cm | Radial Function g(r) | Best Model 2301 $^{125}$I Seed | Error | Book Value (Meigooni et al) | Error |
|---|---|---|---|---|---|
| 9.5 | 0.120217 | 0.1015704 | 0.183581 | 0.123 | −0.16272 |
| 10 | 0.089152 | 0.0994859 | −0.10388 | 0.103 | −0.01152 |

FIG. 51 illustrates the Radial Function of Monte Carlo calculated value for Thermobrachytherapy Seed#2 and the Monte Carlo calculated Value for the Best Model 2301 $^{125}$I in Liquid water. The plot is fitted with a 5th order polynomial function.

FIG. 52 illustrates the Radial Function of Monte Carlo calculated value for Thermobrachytherapy Seed#2 and the Book Value for the Best Model 2301 $^{125}$I in Liquid water. The plot is fitted with a 5th order polynomial function.

iv) Anisotropy Function:

Calculation of the radial function is a three fold process.

a) Calculating Geometry Function

The Geometry function is independent of the material content of the phantom and therefore, the geometry function from Table 8 is applicable here.

b) Calculating Coordinates for Detectors

The coordinates are independent of the material content of the phantom and therefore, the coordinates from Table 9 are applicable here.

c) Calculating Anisotropy Function Using the Data Accumulated in Tables 8a, 8b and 9

The Anisotropy Function was calculated using all the factors listed in equation #9. Tables 8a & 8b were used to calculate the Geometry Function at various angles. Table 9 was used to find the coordinates needed to place the detectors at the various angles (and radial distances). Table 40a illustrates the Monte Carlo calculated Anisotropy Function of Thermobrachytherapy Seed#2 in Liquid Water for Radial Distances of 1 cm. A comparison between calculated and book values of the Best Model 2301 $^{125}$I Seed is also calculated.

TABLE 40a

Monte Carlo calculated Anisotropy Function of Thermobrachytherapy Seed#2 in Liquid Water for Radial Distances of 1 cm. A comparison between calculated and book values of the Best Model 2301 $^{125}$I Seed is also calculated.

| Angle | AF at 1 cm | Best Model 2301 $^{125}$I Seed | Error | Book Value (Meigooni et al) | Error |
|---|---|---|---|---|---|
| 0 | 1.000033 | 1.016857 | −0.01655 | 0.867 | 0.15344 |
| 5 | 0.844234 | 0.857865 | −0.01589 | 0.724 | 0.16607 |
| 10 | 0.668452 | 0.677366 | −0.01307 | 0.653 | 0.023664 |
| 15 | 0.717345 | 0.725931 | −0.01183 | 0.721 | −0.00507 |
| 20 | 0.737649 | 0.7474 | −0.01305 | 0.785 | −0.060319 |
| 25 | 0.794388 | 0.803672 | −0.01155 | 0.85 | −0.065425 |
| 30 | 0.810683 | 0.821182 | −0.01278 | 0.9 | −0.099241 |
| 35 | 0.880462 | 0.890772 | −0.01157 | 0.946 | −0.069275 |
| 40 | 0.897858 | 0.906355 | −0.00937 | 0.982 | −0.085684 |
| 45 | 0.942573 | 0.953106 | −0.01105 | 1.001 | −0.058369 |
| 50 | 0.95692 | 0.959333 | −0.00251 | 1.014 | −0.056292 |
| 55 | 0.977092 | 0.978387 | −0.00132 | 1.024 | −0.045809 |
| 60 | 0.980928 | 0.98857 | −0.00773 | 1.03 | −0.047643 |
| 65 | 0.988725 | 0.988487 | 0.900241 | 1.033 | −0.04286 |
| 70 | 0.989279 | 0.986962 | 0.002348 | 1.036 | −0.045097 |
| 75 | 1.030734 | 1.031196 | −0.00045 | 1.039 | −0.007956 |
| 80 | 1.007915 | 1.009489 | −0.00156 | 1.1 | −0.083714 |

TABLE 40a-continued

Monte Carlo calculated Anisotropy Function of Thermobrachytherapy Seed#2 in Liquid Water for Radial Distances of 1 cm. A comparison between calculated and book values of the Best Model 2301 $^{125}$I Seed is also calculated.

| Angle | AF at 1 cm | Best Model 2301 $^{125}$I Seed | Error | Book Value (Meigooni et al) | Error |
|---|---|---|---|---|---|
| 85 | 1.00081 | 0.998686 | 0.002127 | 1 | 0.00081 |
| 90 | 0.996037 | 0.996037 | 0 | 1 | −0.003963 |

FIG. 53 illustrates the Anisotropy Function of Monte Carlo calculated value for Thermobrachytherapy Seed#2 and the Monte Carlo calculated value for the Best Model 2301 $^{125}$I in liquid water at 1 cm radii. The plot is fitted with a 6th order polynomial function.

FIG. 54 illustrates the Anisotropy Function of Monte Carlo calculated value for Thermobrachytherapy Seed#2 and the Book Value for the Best Model 2301 $^{125}$I in liquid water at 1 cm radii. The plot is fitted with a 6th order polynomial function.

Table 40b illustrates the Monte Carlo calculated Anisotropy Function of Thermobrachytherapy Seed#2 in liquid water for Radial Distances of 2 cm. A comparison between calculated and book values of the Best Model 2301 $^{125}$I Seed is also calculated.

TABLE 40b

Monte Carlo calculated Anisotropy Function of Thermobrachytherapy Seed#2 in liquid water for Radial Distances of 2 cm. A comparison between calculated and book values of the Best Model 2301 $^{125}$I Seed is also calculated

| Angle | AF at 2 cm | Best Model 2301 $^{125}$I Seed | Error | Book Value (Meigooni et al) | Error |
|---|---|---|---|---|---|
| 0 | 0.972591 | 0.986817 | −0.01442 | 0.854 | 0.138866 |
| 5 | 0.797157 | 0.810992 | −0.01706 | 0.72 | 0.107163 |
| 10 | 0.711869 | 0.724824 | −0.01787 | 0.671 | 0.060908 |
| 15 | 0.704106 | 0.718106 | −0.01949 | 0.734 | −0.040727 |
| 20 | 0.804406 | 0.819861 | −0.01885 | 0.794 | 0.013105 |
| 25 | 0.835115 | 0.853352 | −0.02137 | 0.847 | −0.014032 |
| 30 | 0.853212 | 0.858304 | −0.00593 | 0.89 | −0.041335 |
| 35 | 0.814789 | 0.821552 | −0.00823 | 0.926 | −0.120098 |
| 40 | 0.922932 | 0.940464 | −0.01864 | 0.954 | −0.032566 |
| 45 | 0.873368 | 0.883125 | −0.01105 | 0.978 | −0.106985 |
| 50 | 0.895748 | 0.903854 | −0.00897 | 0.992 | −0.097028 |
| 55 | 0.936683 | 0.944112 | −0.00787 | 1.003 | −0.066119 |
| 60 | 0.953816 | 0.963059 | −0.0096 | 1.01 | −0.055627 |
| 65 | 0.960706 | 0.971319 | −0.01093 | 1.019 | −0.057207 |
| 70 | 0.982271 | 0.984718 | −0.00248 | 1.026 | −0.04262 |
| 75 | 0.996574 | 1.000409 | −0.00383 | 1.029 | −0.031512 |
| 80 | 1.016478 | 1.019994 | −0.00345 | 1.03 | −0.013128 |
| 85 | 0.971341 | 0.976201 | −0.00498 | 1.022 | −0.049568 |
| 90 | 1 | 1 | 0 | 1 | 0 |

FIG. 55 illustrates the Anisotropy Function of Monte Carlo calculated value for Thermobrachytherapy Seed#2 and the Monte Carlo calculated for the Best Model 2301 $^{125}$I in liquid water at 2 cm radii. The plot is fitted with a 6th order polynomial function FIG. 56 illustrates the Anisotropy Function of Monte Carlo calculated value for Thermobrachytherapy Seed#2 and the Book Value for the Best Model 2301 $^{125}$I in liquid water at 2 cm radii. The plot is fitted with a 6th order polynomial function.

Table 40c illustrates the Monte Carlo calculated Anisotropy Function of Thermobrachytherapy Seed#2 in liquid water for Radial Distances of 3 cm. A comparison between calculated and book values of the Best Model 2301 $^{125}$I Seed is also calculated.

TABLE 40c

Monte Carlo calculated Anisotropy Function of Thermobrachytherapy Seed#2 in liquid water for Radial Distances of 3 cm. A comparison between calculated and book values of the Best Model 2301 $^{125}$I Seed is also calculated.

| Angle | AF at 3 cm | Best Model 2301 $^{125}$I Seed | Error | Book Value (Meigooni et al) | Error |
|---|---|---|---|---|---|
| 0 | 1.062729 | 1.081703 | −0.01754 | 0.922 | 0.152634 |
| 5 | 0.84505 | 0.827586 | 0.021103 | 0.726 | 0.163981 |
| 10 | 0.745824 | 0.750467 | −0.00619 | 0.699 | 0.066987 |
| 15 | 0.827248 | 0.833466 | −0.00746 | 0.756 | 0.094243 |
| 20 | 0.799849 | 0.808948 | −0.01125 | 0.809 | −0.011311 |
| 25 | 0.860543 | 0.872956 | −0.01422 | 0.852 | 0.010027 |
| 30 | 0.928153 | 0.930988 | −0.00304 | 0.885 | 0.04876 |
| 35 | 0.939299 | 0.953275 | −0.01466 | 0.919 | 0.022088 |
| 40 | 0.991368 | 0.987268 | 0.004153 | 0.947 | 0.046851 |
| 45 | 0.955833 | 0.95516 | 0.000705 | 0.968 | −0.012569 |
| 50 | 0.970277 | 0.973073 | −0.00287 | 0.985 | −0.014947 |
| 55 | 1.000539 | 1.008446 | −0.00784 | 0.997 | 0.00355 |
| 60 | 0.984424 | 0.988973 | −0.0046 | 1.009 | −0.024356 |
| 65 | 1.003341 | 1.000178 | 0.003162 | 1.012 | −0.008556 |
| 70 | 1.019852 | 1.030136 | −0.00998 | 1.016 | 0.003791 |
| 75 | 1.013856 | 1.018382 | −0.00444 | 1.018 | −0.004071 |
| 80 | 0.961765 | 0.960588 | 0.001225 | 1.019 | −0.056168 |
| 85 | 0.994766 | 0.996809 | −0.00205 | 1.019 | −0.023782 |
| 90 | 1 | 1 | 0 | 1 | 0 |

FIG. 57 illustrates the Anisotropy Function of Monte Carlo calculated value for Thermobrachytherapy Seed#2 and the Monte Carlo calculated for the Best Model 2301 $^{125}$I in liquid water at 3 cm radii. The plot is fitted with a 6th order polynomial function.

FIG. 58 illustrates the Anisotropy Function of Monte Carlo calculated value for Thermobrachytherapy Seed#2 and the Book value for the Best Model 2301 $^{125}$I in liquid water at 3 cm radii. The plot is fitted with a 6th order polynomial function.

Table 40d illustrates the Monte Carlo calculated Anisotropy Function of Thermobrachytherapy Seed#2 in liquid water for Radial Distances of 4 cm. A comparison between calculated and book values of the Best Model 2301 $^{125}$I Seed is also calculated.

TABLE 40d

Monte Carlo calculated Anisotropy Function of Thermobrachytherapy Seed#2 in liquid water for Radial Distances of 4 cm. A comparison between calculated and book values of the Best Model 2301 $^{125}$I Seed is also calculated.

| Angle | AF at 4 cm | Best Model 2301 $^{125}$I Seed | Error | Book Value (Meigooni et al) | Error |
|---|---|---|---|---|---|
| 0 | 1.047458 | 1.067157 | −0.01846 | 0.902 | 0.161262 |
| 5 | 0.848698 | 0.856189 | −0.00875 | 0.728 | 0.165794 |
| 10 | 0.843641 | 0.849553 | −0.00696 | 0.727 | 0.160441 |

TABLE 40d-continued

Monte Carlo calculated Anisotropy Function of Thermobrachytherapy Seed#2 in liquid water for Radial Distances of 4 cm. A comparison between calculated and book values of the Best Model 2301 $^{125}$I Seed is also calculated.

| Angle | AF at 4 cm | Best Model 2301 $^{125}$I Seed | Error | Book Value (Meigooni et al) | Error |
|---|---|---|---|---|---|
| 15 | 0.75386 | 0.762809 | −0.01173 | 0.779 | −0.032272 |
| 20 | 0.840591 | 0.843573 | −0.00353 | 0.814 | 0.032667 |
| 25 | 0.908304 | 0.917008 | −0.00949 | 0.863 | 0.052496 |
| 30 | 0.912712 | 0.921985 | −0.01006 | 0.892 | 0.02322 |
| 35 | 0.915824 | 0.927006 | −0.01206 | 0.918 | −0.00237 |
| 40 | 0.918773 | 0.928846 | −0.01085 | 0.939 | −0.021542 |
| 45 | 0.9845 | 0.992994 | −0.00855 | 0.976 | 0.008709 |
| 50 | 0.956752 | 0.968645 | −0.01228 | 0.991 | −0.034559 |
| 55 | 1.014113 | 1.028106 | −0.01361 | 1.004 | 0.010072 |
| 60 | 0.994831 | 1.006959 | −0.00612 | 1.007 | −0.012085 |
| 65 | 1.016231 | 1.017048 | −0.0008 | 1.009 | 0.007166 |
| 70 | 1.021108 | 1.020551 | 0.000546 | 1.023 | −0.001849 |
| 75 | 1.014378 | 1.009032 | 0.005298 | 1.017 | −0.002578 |
| 80 | 0.976854 | 0.975997 | 0.000878 | 1.017 | −0.039475 |
| 85 | 0.998467 | 0.998651 | −0.00018 | 1.018 | −0.019188 |
| 90 | 1 | 0.999983 | 1.73E−05 | 1 | 0 |

FIG. 59 illustrates the Anisotropy Function of Monte Carlo calculated value for Thermobrachytherapy Seed#2 and the Monte Carlo calculated for the Best Model 2301 $^{125}$I in liquid water at 4 cm radii. The plot is fitted with a 6th order polynomial function.

FIG. 60 illustrates the Anisotropy Function of Monte Carlo calculated value for Thermobrachytherapy Seed#2 and the Book Value calculated for the Best Model 2301 $^{125}$I in liquid water at 2 cm radii. The plot is fitted with a 6th order polynomial function.

Table 40e illustrates the Monte Carlo calculated Anisotropy Function of Thermobrachytherapy Seed#2 in liquid water for Radial Distances of 5 cm. A comparison between calculated and book values of the Best Model 2301 $^{125}$I Seed is also calculated.

TABLE 40e

Monte Carlo calculated Anisotropy Function of Thermobrachytherapy Seed#2 in liquid water for Radial Distances of 5 cm. A comparison between calculated and book values of the Best Model 2301 $^{125}$I Seed is also calculated.

| Angle | AF at 5 cm | Best Model 2301 $^{125}$Seed | Error | Book Value (Meigooni et al) | Error |
|---|---|---|---|---|---|
| 0 | 1.026903 | 1.037909 | −0.0106 | 0.894 | 0.148661 |
| 5 | 0.815129 | 0.826259 | −0.01347 | 0.753 | 0.082509 |
| 10 | 0.775649 | 0.781112 | −0.00699 | 0.732 | 0.05963 |
| 15 | 0.772767 | 0.785625 | −0.01637 | 0.795 | −0.027966 |
| 20 | 0.811832 | 0.814253 | −0.00297 | 0.825 | −0.015961 |
| 25 | 0.790539 | 0.790151 | 0.00049 | 0.865 | −0.086083 |
| 30 | 0.933794 | 0.93407 | −0.0003 | 0.899 | 0.038703 |
| 35 | 0.880013 | 0.880933 | −0.00104 | 0.92 | −0.043464 |
| 40 | 0.902171 | 0.909002 | −0.00752 | 0.943 | −0.043297 |
| 45 | 0.955933 | 0.965222 | −0.00962 | 0.968 | −0.012466 |
| 50 | 0.931583 | 0.921762 | 0.010654 | 0.997 | −0.065614 |
| 55 | 0.999427 | 1.00322 | −0.00378 | 0.993 | 0.006472 |
| 60 | 0.960247 | 0.972524 | −0.01262 | 1.01 | −0.049261 |
| 65 | 1.000826 | 0.982562 | 0.018588 | 1.024 | −0.022631 |
| 70 | 0.974142 | 0.959269 | 0.015504 | 1.011 | −0.036457 |
| 75 | 1.029715 | 1.020911 | 0.008623 | 1.02 | 0.009524 |
| 80 | 0.995538 | 0.991336 | 0.004238 | 1.01 | −0.014319 |
| 85 | 1.018132 | 1.015815 | 0.002281 | 1.011 | 0.007054 |
| 90 | 1 | 1 | 0 | 1 | 0 |

FIG. 61 illustrates the Anisotropy Function of Monte Carlo calculated value for Thermobrachytherapy Seed#2 and the Monte Carlo calculated for the Best Model 2301 $^{125}$I in liquid water at 5 cm radii. The plot is fitted with a 6th order polynomial function FIG. 62 illustrates the Anisotropy Function of Monte Carlo calculated value for Thermobrachytherapy Seed#2 and the Book Value for the Best Model 2301 $^{125}$I in liquid water at 5 cm radii. The plot is fitted with a 6th order polynomial function.

Table 40f illustrates the Monte Carlo calculated Anisotropy Function of Thermobrachytherapy Seed#2 in liquid water for Radial Distances of 6 cm. A comparison between calculated and book values of the Best Model 2301 $^{125}$I Seed is also calculated.

TABLE 40f

Monte Carlo calculated Anisotropy Function of Thermobrachytherapy Seed#2 in liquid water for Radial Distances of 6 cm. A comparison between calculated and book values of the Best Model 2301 $^{125}$I Seed is also calculated.

| Angle | AF at 6 cm | Best Model 2301 $^{125}$I Seed | Error | Book Value (Meigooni et al) | Error |
|---|---|---|---|---|---|
| 0 | 0.969181 | 1.002815 | −0.03354 | 0.893 | 0.085309 |
| 5 | 0.877846 | 0.888127 | −0.01158 | 0.771 | 0.138581 |
| 10 | 0.775889 | 0.782999 | −0.00908 | 0.764 | 0.015562 |
| 15 | 0.811767 | 0.819448 | −0.00937 | 0.805 | 0.008406 |
| 20 | 0.805201 | 0.817894 | −0.01552 | 0.852 | −0.054928 |
| 25 | 0.9137 | 0.936581 | −0.02443 | 0.89 | 0.026629 |
| 30 | 0.82033 | 0.833299 | −0.01556 | 0.915 | −0.103464 |
| 35 | 0.87206 | 0.886202 | −0.01596 | 0.964 | −0.095373 |
| 40 | 0.881475 | 0.904777 | −0.02575 | 0.976 | −0.096849 |
| 45 | 0.93567 | 0.948816 | −0.01386 | 0.979 | −0.04426 |
| 50 | 0.969154 | 0.976859 | −0.00789 | 0.989 | −0.020067 |
| 55 | 0.970141 | 0.98898 | −0.01905 | 1.011 | −0.040414 |
| 60 | 0.960045 | 0.967874 | −0.00809 | 1.019 | −0.057855 |
| 65 | 0.948985 | 0.960829 | −0.01233 | 1.034 | −0.08222 |
| 70 | 0.950045 | 0.948077 | 0.002075 | 1.035 | −0.082082 |
| 75 | 1.003345 | 1.01108 | −0.00765 | 1.043 | −0.03802 |
| 80 | 0.973936 | 0.972717 | 0.001253 | 1.02 | −0.045161 |
| 85 | 1.054661 | 1.053106 | 0.001477 | 1.031 | 0.02295 |
| 90 | 1 | 1 | 0 | 1 | 0 |

FIG. 63 illustrates the Anisotropy Function of Monte Carlo calculated value for Thermobrachytherapy Seed#2 and the Monte Carlo calculated for the Best Model 2301 $^{125}$I in liquid water at 6 cm radii. The plot is fitted with a 6th order polynomial function.

FIG. 64 illustrates the Anisotropy Function of Monte Carlo calculated value for Thermobrachytherapy Seed#2 and the Book value for the Best Model 2301 $^{125}$I in liquid water at 6 cm radii. The plot is fitted with a 6th order polynomial function.

Table 40g illustrates the Monte Carlo calculated Anisotropy Function of Thermobrachytherapy Seed#2 in liquid water for Radial Distances of 7 cm. A comparison between calculated and book values of the Best Model 2301 $^{125}$I Seed is also calculated.

TABLE 40g

Monte Carlo calculated Anisotropy Function of Thermobrachytherapy Seed#2 in liquid water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et at) | Error |
|---|---|---|---|---|---|
| 0 | 1.014464 | 1.044519 | −0.02877 | 0.858 | 0.182359 |
| 5 | 0.84554 | 0.872338 | −0.03072 | 0.8 | 0.056925 |
| 10 | 0.790712 | 0.814773 | −0.02953 | 0.782 | 0.011141 |
| 15 | 0.87651 | 0.89647 | −0.02226 | 0.812 | 0.079446 |
| 20 | 0.816902 | 0.839067 | −0.02642 | 0.821 | −0.004991 |
| 25 | 0.847151 | 0.857219 | −0.01174 | 0.86 | −0.014941 |
| 30 | 0.943176 | 0.968562 | −0.02621 | 0.873 | 0.080385 |
| 35 | 0.957799 | 0.965505 | −0.00798 | 0.924 | 0.036579 |
| 40 | 0.979902 | 1.010278 | −0.03007 | 0.937 | 0.045787 |
| 45 | 0.99091 | 1.008515 | −0.01746 | 0.954 | 0.03869 |
| 50 | 0.966233 | 0.983552 | −0.01761 | 0.961 | 0.005446 |
| 55 | 1.008051 | 1.020988 | −0.01267 | 0.99 | 0.018234 |
| 60 | 0.915609 | 0.920182 | −0.00497 | 1.002 | −0.086219 |
| 65 | 1.122188 | 1.14268 | −0.01793 | 1.03 | 0.089503 |
| 70 | 1.057438 | 1.069128 | −0.01093 | 1.01 | 0.046968 |
| 75 | 1.041891 | 1.039857 | 0.001956 | 1.02 | 0.021462 |
| 80 | 0.98055 | 0.991134 | −0.01068 | 1.005 | −0.024328 |
| 85 | 1.02353 | 1.029283 | −0.00559 | 1.021 | 0.002478 |
| 90 | 0.999979 | 0.999979 | 1.11E−16 | 1 | −2.1E−05 |

FIG. 65 illustrates the Anisotropy Function of Monte Carlo calculated value for Thermobrachytherapy Seed#2 and the Monte Carlo calculated for the Best Model 2301 $^{125}$I in liquid water at 7 cm radii. The plot is fitted with a 6th order polynomial function.

FIG. 66 illustrates the Anisotropy Function of Monte Carlo calculated value for Thermobrachytherapy Seed#2 and the Book value calculated for the Best Model 2301 $^{125}$I in liquid water at 7 cm radii. The plot is fitted with a 6th order polynomial function.

Average Anisotropy Function:

The average anisotropy function is taken by taking an average of the calculated anisotropy functions for all the angles. Table 41a illustrates the Average Anisotropy Constant calculated for radial distances of 1 cm in liquid water.

TABLE 41a

Average Asisotropy Constant calculated for radial distances of 1 cm in liquid water

| | 1 cm | Best Model 2301 $^{125}$I Seed | Error | Book Value (Meigooni et al) | Error |
|---|---|---|---|---|---|
| Average Anisotropy Constant $\Phi_{an}(r)$ | 0.906 | 0.913 | −0.00666 | 0.986 | −0.0807 |

Table 41b illustrates the Average Anisotropy Constant calculated for radial distances of 2 cm in liquid water.

TABLE 41b

Average Anisotropy Constant calculated for
radial distances of 2 cm in liquid water

| | 2 cm | Best Model 2301 $^{125}$I Seed | Error | Book Value (Meigooni et al) | Error |
|---|---|---|---|---|---|
| Average Anisotropy Constant $\Phi_{an}(r)$ | 0.895 | 0.904 | −0.01035 | 0.976 | −0.0831 |

Table 41c illustrates the Average Anisotropy Constant calculated for radial distances of 3 cm in liquid water.

TABLE 41c

Average Anisotropy Constant calculated for
radial distances of 3 cm in liquid water

| | 3 cm | Best Model 2301 $^{125}$I Seed | Error | Book Value (Meigooni et al) | Error |
|---|---|---|---|---|---|
| Average Asisotropy Constant $\Phi_{an}(r)$ | 0.942 | 0.946 | −0.0041 | 0.968 | −0.0264 |

Table 41d illustrates the Average Anisotropy Constant calculated for radial distances of 4 cm in liquid water.

TABLE 41d

Average Anisotropy Constant calculated for
radial distances of 4 cm in liquid water

| | 4 cm | Best Model 2301 $^{125}$I Seed | Error | Book Value (Meigooni et al) | Error |
|---|---|---|---|---|---|
| Average Anisotropy Constant $\Phi_{an}(r)$ | 0.945 | 0.952 | −0.0066 | 0.971 | −0.0261 |

Table 41e illustrates the Average Anisotropy Constant calculated for radial distances of 5 cm in liquid water.

TABLE 41e

Average Anisotropy Constant calculated for
radial distances of 5 cm in liquid water

| | 5 cm | Best Model 2301 $^{125}$I Seed | Error | Book Value (Mogooni et al) | Error |
|---|---|---|---|---|---|
| Average Anisotropy Constant $\Phi_{an}(r)$ | 0.925 | 0.926 | −0.001 | 0.969 | −0.0454 |

Table 41f illustrates the Average Anisotropy Constant calculated for radial distances of 6 cm in liquid water.

TABLE 41f

Average Anisotropy Constant calculated for
radial distances of 6 cm in liquid water

| | 6 cm | Best Model 2301 $^{125}$I Seed | Error | Book Value (Meigooni et al) | Error |
|---|---|---|---|---|---|
| Average Anisotropy Constant $\Phi_{an}(r)$ | 0.921 | 0.932 | −0.011 | 0.991 | −0.0709 |

Table 41g illustrates the Average Anisotropy Constant calculated for radial distances of 7 cm in liquid water.

TABLE 41g

Average Anisotropy Constant calculated for
radial distances of 7 cm in liquid water

| | 7 cm | Best Model 2301 $^{125}$I Seed | Error | Book Value (Meigooni et at) | Error |
|---|---|---|---|---|---|
| Average Anistropy Constant $\Phi_{an}(r)$ | 0.957 | 0.972 | −0.016 | 0.969 | −0.0126 |

Source Anisotropy Constant:

The Source Anisotropy Constant is calculated by taking the average of all the Average Anisotropy Constant. Table 42 illustrates the Source Anisotropy Function for Thermobrachytherapy Seed#2 liquid water.

TABLE 42

Source Anistropy Function for Thermobrachytherapy
Seed#2 liquid water

| | Calculated value | Best Model 2391 $^{125}$I Seed | Error | Book value | Error |
|---|---|---|---|---|---|
| Source Anistropy Constant $\overline{\Phi_{an}}(r)$ | 0.927 | 0.935 | −0.008 | 0.98 | −0.054 |

The Source Anisotropy Constant is 0.927 and deviates from the Monte Carlo calculated Best Model 2301 $^{125}$I Seed by 0.8% and the Book value by 5.4%

1) Thermobrachytherapy Seed#2 in Solid Water i) Dose Rate (D):

Dose Rate was calculated for seed at 1 cm on the transverse plane (θ=90°) of the source (from the center of the source) in Solid Water. Therefore, for this measurement the phantom was taken to be Solid Water since it is the solid water measurement. Table 43 illustrates the Dose Rate for Thermobrachytherapy Seed#2 in Solid Water calculated using Monte Carlo. The error is calculated by using equation #16. Therefore, the error between the calculated thermobrachytherapy value and the calculated Best Model 2301 $^{125}$I seed is 4.23%. The measured value of Dose Rate is $0.24 \pm 4.89*10^{-3}$ cGy*sec$^{-1}$*Ci$^{-1}$.

TABLE 43

Dose Rate for Thermobrachytherapy Seed#2 in
Solid Water calculated using Monte Carlo

| Calculated Dose Rate ($cGy*sec^{-1}*Ci^{-1}$) | Calculated Best Model 2301 $^{125}$I Seed ($cGy*sec^{-1}*Ci^{-1}$) | Error | Book Value (Meigooni et al) | Error |
|---|---|---|---|---|
| 0.240788 | 0.230994 | 0.0423 | N/A | | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials and Methods section) is used for SK. Table 44 illustrates the Air Kerma Strength for Thermobrachytherapy Seed#2 in Air calculated using Monte Carlo in Solid Water. The error is calculated by using equation #16. Therefore, the error between the calculated thermobrachytherapy value and the calculated Best Model 2301 $^{125}$I seed is 4.3%. The measured value of Air Kerma Strength is $0.234 \pm 5.1*10^{-3}$ $cGy*cm^2*sec^{-1}*Ci^{-1}$.

TABLE 44

Air Kerma Strength for Thermobrachytherapy Seed#2 in
Air calculated using Monte Carlo in Solid Water

| Calculated Air Kerma Strength ($cGy*sec^{-1}*Ci^{-1}$) | Calculated Best Model 2301 $^{125}$I Seed ($cGy*sec^{-1}*Ci^{-1}$) | Error | Book Value (Meigooni et al) | Error |
|---|---|---|---|---|
| 0.234046 | 0.224332 | 0.043 | N/A | NA | iii) Dose Rate Constant (Λ):

Dose rate constant is calculated using equation #4. In order to calculate it, the ratio of the dose rate and air kerma strength is taken. Table 45 illustrates the Monte Carlo calculated Dose Rate Constant for Thermobrachytherapy Seed#2 in Solid Water. The error is calculated by using equation #. Therefore, the error between the calculated thermobrachytherapy value and the calculated Best Model 2301 $^{125}$I seed is 0.09%. Also, the error between the calculated thermobrachytherapy value and the Book Value for Best Model 2301 $^{125}$I seed is 4.97%. The measured value of Dose Rate is $1.029 \pm 0.031$ $cGy*h^{-1}*U^{-1}$.

TABLE 45

Monte Carlo calculated Dose Raw Constant for
Thermobrachytherapy Seed#2 in Solid Water

| Calculated Dose Rate Constant ($cGy*h^{-1}*U^{-1}$) | Best Model 2301 $^{125}$I Seed ($cGy*h^{-1}*U^{-1}$) | Error | Book Value (Meigooni et al) ($cGy*h^{-1}*U^{-1}$) | Error |
|---|---|---|---|---|
| 1.0288 | 1.02969 | −0.0009 | 1.01 | 0.0497 | iv) Correction/Multiplicative Factor:

Meigooni et al calculated that a conversion factor of 1.05 was needed to convert the dose rate constant in solid water to liquid water. The calculated Correction/Multiplicative factor obtained is 1.028.

v) Radial Function:

Calculation of the radial function is a two fold process.

a) Geometry Function

The Geometry function is independent of the material content of the phantom. Also, the geometry (and dimension) of the source cell remains the same. Therefore, the geometry factor from Table 6 is applicable here.

b) Radial Function Using the Geometry Function

Radial Function was calculated using equation#8 incorporating the geometry function calculated in part a) above. Table 46 illustrates the Radial Function calculated at the transverse plane for the Thermobrachytherapy Seed#2 in Solid Water using Monte Carlo.

TABLE 46

Radial Function calculated at the transverse plane for the
Thermobrachytherapy Seed#2 in Solid Water using Monte Carlo.

| Transverse distance (r) cm | Radial Function g(r) | Best Model 2301 $^{125}$I Seed | Error | Book Value (Meigooni et al) | Error |
|---|---|---|---|---|---|
| 0.1 | 0.879539 | 0.9740849 | −0.09706 | | |
| 0.15 | 0.93508 | 0.9872727 | −0.05287 | | |
| 0.2 | 0.974717 | 1.0245773 | −0.04866 | | |
| 0.25 | 0.953075 | 0.997152 | −0.0442 | | |
| 0.3 | 0.968299 | 1.0106151 | −0.04187 | | |
| 0.4 | 1.03533 | 1.0024356 | 0.032815 | | |
| 0.5 | 1.030962 | 0.9962775 | 0.034814 | | |
| 0.6 | 0.991435 | 0.9601123 | 0.032624 | 1.044 | −0.089 |
| 0.7 | 0.964844 | 0.9079231 | 0.062694 | | |
| 0.75 | 0.969485 | 0.9467391 | 0.024026 | | |
| 0.8 | 0.93192 | 0.9554107 | −0.02459 | | |
| 0.9 | 0.966224 | 0.9667486 | −0.00054 | | |
| 1 | 1.000001 | 1.0000005 | 0 | 1 | 5.0669E−07 |
| 1.5 | 0.884876 | 0.9040619 | −0.02122 | 0.926 | −0.0444108 |
| 2 | 0.79886 | 0.8129667 | −0.01735 | 0.842 | −0.05123498 |
| 2.5 | 0.705464 | 0.728075 | −0.03106 | 0.752 | −0.06188283 |
| 3 | 0.607673 | 0.6505947 | −0.06597 | 0.666 | −0.08757784 |
| 3.5 | 0.541119 | 0.5635308 | −0.03977 | 0.581 | −0.0686426 |
| 4 | 0.45677 | 0.5125491 | −0.10883 | 0.509 | −0.10261204 |
| 4.5 | 0.394066 | 0.4328601 | −0.08962 | 0.443 | −0.11046108 |
| 5 | 0.359463 | 0.3817734 | −0.05844 | 0.386 | −0.06874904 |
| 5.5 | 0.305903 | 0.3178485 | −0.03758 | 0.336 | −0.08957374 |
| 6 | 0.26603 | 0.2753888 | −0.03398 | 0.286 | −0.06982505 |

TABLE 46-continued

Radial Function calculated at the transverse plane for the
Thermobrachytherapy Seed#2 in Solid Water using Monte Carlo.

| Transverse distance (r) cm | Radial Function g(r) | Best Model 2301 $^{125}$I Seed | Error | Book Value (Meigooni et al) | Error |
|---|---|---|---|---|---|
| 6.5 | 0.233636 | 0.2309718 | 0.011536 | 0.245 | −0.0463822 |
| 7 | 0.195227 | 0.2041012 | −0.04348 | 0.207 | −0.05687288 |
| 7.5 | 0.171557 | 0.176629 | −0.02871 | 0.178 | −0.03619428 |
| 8 | 0.139226 | 0.1571086 | −0.11382 | 0.159 | −0.12436229 |
| 8.5 | 0.125306 | 0.1246026 | 0.005648 | 0.14 | −0.10495467 |
| 9 | 0.107734 | 0.1098135 | −0.01893 | 0.116 | −0.07125574 |
| 9.5 | 0.104874 | 0.093497 | 0.121687 | 0.097 | 0.08117992 |
| 10 | 0.078577 | 0.079492 | −0.0115 | 0.08 | −0.01778224 |

FIG. 67 illustrates the Radial Function of Monte Carlo calculated value for Thermobrachytherapy Seed#2 and the Monte Carlo calculated value for the Best Model 2301 $^{125}$I in Solid Water. The plot is fitted with a 5th order polynomial function.

FIG. 68 illustrates the Radial Function of Monte Carlo calculated value for Thermobrachytherapy Seed#2 and the Book Value for the Best Model 2301 $^{125}$I in Solid Water. The plot is fitted with a 5th order polynomial function.

vi) Anisotropy Function:
Calculation of the radial function is a three fold process.
a) Calculating Geometry Function The Geometry function is independent of the material content of the phantom and therefore, the geometry function from Tables 8a and 8b are applicable here.

b) Calculating Coordinates for Detectors

The coordinates are independent of the material content of the phantom and therefore, the coordinates from Table 9 are applicable here.

c) Calculating Anisotropy Function Using the Data Accumulated in Tables 8a, 8b and Table 9

The Anisotropy Function was calculated using all the factors listed in equation #9. Tables 8a and 8b were used to calculate the Geometry Function at various angles. Table 9 was used to find the coordinates needed to place the detectors at the various angles (and radial distances).

Table 47a illustrates the Monte Carlo calculated Anisotropy Function of Thermobrachytherapy Seed#2 in Solid Water for Radial Distances of 1 cm. A comparison between calculated values of the Best Model 2301 $^{125}$I Seed is also calculated.

TABLE 47a

Monte Carlo calculated Anisotropy Function of Thermobrachytherapy
Seed#2 in Solid Water for Radial Distances of 1 cm.
A comparison between calculated valuesof the Best Model 2301
$^{125}$I Seed is also calculated.

| Angle | AF at 1 cm | Best Model 2301 $^{125}$I Seed | Error |
|---|---|---|---|
| 0 | 1.008107 | 1.026252 | −0.01768 |
| 5 | 0.856006 | 0.866304 | −0.01189 |
| 10 | 0.663249 | 0.672536 | −0.01381 |
| 15 | 0.730725 | 0.739002 | −0.0112 |
| 20 | 0.746872 | 0.75897 | −0.01594 |
| 25 | 0.783638 | 0.793086 | −0.01191 |
| 30 | 0.811896 | 0.822657 | −0.01308 |
| 35 | 0.888686 | 0.897361 | −0.00967 |
| 40 | 0.899904 | 0.906809 | −0.00761 |
| 45 | 0.949578 | 0.957336 | −0.0081 |
| 50 | 0.969195 | 0.971523 | −0.0024 |
| 55 | 0.986483 | 0.989839 | −0.00339 |

TABLE 47a-continued

Monte Carlo calculated Anisotropy Function of Thermobrachytherapy
Seed#2 in Solid Water for Radial Distances of 1 cm.
A comparison between calculated valuesof the Best Model 2301
$^{125}$I Seed is also calculated.

| Angle | AF at 1 cm | Best Model 2301 $^{125}$I Seed | Error |
|---|---|---|---|
| 60 | 0.98005 | 0.987353 | −0.0074 |
| 65 | 0.989675 | 0.99135 | −0.00169 |
| 70 | 1.002335 | 0.998792 | 0.003547 |
| 75 | 1.041047 | 1.038309 | 0.002637 |
| 80 | 1.032589 | 1.032288 | 0.000291 |
| 85 | 0.991752 | 0.986828 | 0.004989 |
| 90 | 0.996037 | 0.996037 | 0 |

FIG. 69 illustrates the Anisotropy Function of Monte Carlo calculated value for Thermobrachytherapy Seed#2 and the Monte Carlo calculated for the Best Model 2301 $^{125}$I in Solid Water at 1 cm radii. The plot is fitted with a 6th order polynomial function.

Table 47b illustrates the Monte Carlo calculated Anisotropy Function of the Best Model 2301 $I^{125}$ Seed in Solid Water for Radial Distances of 2 cm. A comparison between calculated and book values of the Best Model 2301 $^{125}$I Seed is also calculated.

TABLE 47b

Monte Carlo calculated Anisotropy Function of the Best Model
2301 $I^{125}$ Seed in Solid Water for Radial Distances of 2 cm.
A comparison between calculated and book values of the
Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 0 | 0.994972 | 1.002986 | −0.00799 | 0.837 | 0.188736 |
| 5 | 0.815758 | 0.829332 | −0.01637 | | |
| 10 | 0.670149 | 0.677051 | −0.01019 | 0.659 | 0.016918 |
| 15 | 0.684052 | 0.689879 | −0.00845 | | |
| 20 | 0.770323 | 0.779294 | −0.01151 | 0.782 | −0.014933 |
| 25 | 0.806397 | 0.81592 | −0.01167 | | |
| 30 | 0.830939 | 0.83656 | −0.00672 | 0.882 | −0.057892 |
| 35 | 0.801532 | 0.803188 | −0.00206 | | |
| 40 | 0.866698 | 0.876187 | −0.01083 | 0.946 | −0.083829 |
| 45 | 0.900694 | 0.901717 | −0.00113 | | |
| 50 | 0.925245 | 0.924023 | 0.001322 | 0.985 | −0.060665 |
| 55 | 0.953545 | 0.948227 | 0.005607 | | |
| 60 | 0.92931 | 0.928041 | 0.001367 | 1.007 | −0.07715 |
| 65 | 0.918041 | 0.912797 | 0.005745 | | |
| 70 | 0.958556 | 0.952063 | 0.006821 | 1.02 | −0.060239 |
| 75 | 0.996088 | 0.987641 | 0.008552 | | |

TABLE 47b-continued

Monte Carlo calculated Anisotropy Function of the Best Model 2301 I$^{125}$ Seed in Solid Water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 80 | 1.007711 | 1.004358 | 0.003338 | 1.027 | −0.018782 |
| 85 | 0.987205 | 0.984115 | 0.00314 | | |
| 90 | 1 | 1 | 0 | 1 | 0 |

FIG. 70 illustrates the Anisotropy Function of Monte Carlo calculated value for Thermobrachytherapy Seed#2 and the Monte Carlo calculated for the Best Model 2301 $^{125}$I in Solid Water at 2 cm radii. The plot is fitted with a 6th order polynomial function.

FIG. 71 illustrates the Anisotropy Function of Monte Carlo calculated value for Thermobrachytherapy Seed#2 and the Book value for the Best Model 2301 $^{125}$I in Solid Water at 2 cm radii. The plot is fitted with a 6th order polynomial function.

Table 47c illustrates the Monte Carlo calculated Anisotropy Function of the Best Model 2301 $^{125}$I Seed in Solid Water for Radial Distances of 3 cm. A comparison between calculated values of the Best Model 2301 $^{125}$I Seed is also calculated.

TABLE 47c

Monte Carlo calculated Anisotropy Function of the Best Model 2301 I$^{125}$ Seed in Solid Water for Radial Distances of 3 cm. A comparison between calculated values of the Best Model 2301 $^{125}$I Seed is also calculated.

| Angle | AF at 3 cm | Best Model 2301 $^{125}$I Seed | Error |
|---|---|---|---|
| 0 | 1.024838 | 1.045494 | −0.01976 |
| 5 | 0.765715 | 0.767353 | −0.00213 |
| 10 | 0.707137 | 0.706056 | 0.00153 |
| 15 | 0.743466 | 0.742168 | 0.001748 |
| 20 | 0.765973 | 0.769965 | −0.00518 |
| 25 | 0.84961 | 0.864285 | −0.01698 |
| 30 | 0.835195 | 0.835925 | −0.00087 |
| 35 | 0.87705 | 0.876294 | 0.000862 |
| 40 | 0.92078 | 0.919709 | 0.001164 |
| 45 | 0.904882 | 0.893813 | 0.012383 |
| 50 | 0.892654 | 0.89036 | 0.002576 |
| 55 | 0.920982 | 0.916484 | 0.004908 |
| 60 | 0.899397 | 0.900548 | −0.00128 |
| 65 | 0.88646 | 0.880534 | 0.006731 |
| 70 | 0.964466 | 0.97229 | −0.00805 |
| 75 | 0.955665 | 0.944857 | 0.011439 |
| 80 | 0.905628 | 0.899939 | 0.006321 |
| 85 | 0.950504 | 0.95404 | −0.00371 |
| 90 | 1 | 1 | 0 |

FIG. 72 illustrates the Anisotropy Function of Monte Carlo calculated value for Thermobrachytherapy Seed#2 and the Monte Carlo calculated for the Best Model 2301 $^{125}$I in Solid Water at 3 cm radii. The plot is fitted with a 6th order polynomial function.

Table 47d illustrates the Monte Carlo calculated Anisotropy Function of the Best Model 2301 $^{125}$I Seed in Solid Water for Radial Distances of 4 cm. A comparison between calculated values of the Best Model 2301 $^{125}$I Seed is also calculated.

TABLE 47d

Monte Carlo calculated Anisotropy Function of the Best Model 2301 I$^{125}$ Seed in Solid Water for Radial Distances of 4 cm. A comparison between calculated values of the Best Model 2301 $^{125}$I Seed is also calculated.

| Angle | AF at 4 cm | Best Model 2301 $^{125}$I Seed | Error |
|---|---|---|---|
| 0 | 0.984572 | 0.996217 | −0.01169 |
| 5 | 0.797341 | 0.804645 | −0.00908 |
| 10 | 0.776643 | 0.786272 | −0.01225 |
| 15 | 0.761371 | 0.766287 | −0.00642 |
| 20 | 0.816284 | 0.821381 | −0.00621 |
| 25 | 0.853665 | 0.865759 | −0.01397 |
| 30 | 0.91995 | 0.928838 | −0.00957 |
| 35 | 0.931786 | 0.940615 | −0.00939 |
| 40 | 0.949714 | 0.956302 | −0.00689 |
| 45 | 0.965179 | 0.963304 | 0.001946 |
| 50 | 0.910781 | 0.909226 | 0.00171 |
| 55 | 1.008934 | 1.009165 | −0.00023 |
| 60 | 0.967338 | 0.967434 | −1.E-04 |
| 65 | 0.975225 | 0.964955 | 0.010642 |
| 70 | 1.015545 | 1.007641 | 0.007844 |
| 75 | 0.976372 | 0.970099 | 9.006466 |
| 80 | 0.962731 | 0.956987 | 0.006001 |
| 85 | 1.003732 | 0.990027 | 0.013843 |
| 90 | 1 | 1 | 0 |

FIG. 73 illustrates the Anisotropy Function of Monte Carlo calculated value for Thermobrachytherapy Seed#2 and the Monte Carlo calculated for the Best Model 2301 $^{125}$I in Solid Water at 4 cm radii. The plot is fitted with a 6th order polynomial function.

Table 47e illustrates the Monte Carlo calculated Anisotropy Function of the Best Model 2301 $^{125}$I Seed in Solid Water for Radial Distances of 5 cm. A comparison between calculated and book values of the Best Model 2301 $^{125}$I Seed is also calculated.

TABLE 47e

Monte Carlo calculated Anisotropy Function of the Best Model 2301 I$^{125}$ Seed in Solid Water for Radial Distances of 5 cm. A comparison between calculated and book values of the Best Model 2301 $^{125}$I Seed is also calculated.

| Angle | AF at 5 cm | Best Model 2301 $^{125}$I Seed | Error | Book Value (Meigooni el al) | Error |
|---|---|---|---|---|---|
| 0 | 1.046664 | 1.96538 | −0.01757 | 0.886 | 0.181337 |
| 5 | 0.847794 | 0.863781 | −0.01851 | | |
| 10 | 0.781505 | 0.788669 | −0.00908 | 0.719 | 0.086933 |
| 15 | 0.757011 | 0.773249 | −0.021 | | |
| 20 | 0.81059 | 0.817595 | −0.00857 | 0.801 | 0.011973 |
| 25 | 0.865762 | 0.879567 | −0.0157 | | |
| 30 | 0.826843 | 0.840307 | −0.01602 | 0.873 | −0.052872 |
| 35 | 0.898924 | 0.911502 | −0.0138 | | |
| 40 | 0.940965 | 0.949538 | −0.00903 | 0.938 | 0.003161 |
| 45 | 0.936043 | 0.936324 | −0.0003 | | |
| 50 | 1.000119 | 0.99784 | 0.002284 | 0.962 | 0.039625 |
| 55 | 1.016749 | 1.018567 | −0.00178 | | |
| 60 | 0.942986 | 0.948673 | −0.00599 | 0.99 | −0.047489 |
| 65 | 1.031563 | 1.02104 | 0.010306 | | |
| 70 | 1.031741 | 1.024804 | 0.00677 | 1.001 | 0.030711 |
| 75 | 1.014544 | 1.013883 | 0.000652 | | |
| 80 | 1.080255 | 1.06825 | 0.011239 | 1.011 | 0.068502 |
| 85 | 1.011931 | 1.000983 | 0.010936 | | |
| 90 | 1 | 1 | 0 | 1 | 0 |

FIG. 74 illustrates the Anisotropy Function of Monte Carlo calculated value for Thermobrachytherapy Seed#2 and the Monte Carlo calculated for the Best Model 2301 $^{125}$I in Solid Water at 5 cm radii. The plot is fitted with a 6th order polynomial function.

FIG. 75 illustrates the Anisotropy Function of Monte Carlo calculated value for Thermobrachytherapy Seed#2 and the Book value for the Best Model 2301 $^{125}$I in Solid Water at 1 cm radii. The plot is fitted with a 6th order polynomial function.

Table 47f illustrates the Monte Carlo calculated Anisotropy Function of the Best Model 2301 $^{125}$I Seed in Solid Water for Radial Distances of 6 cm. A comparison between calculated values of the Best Model 2301 $^{125}$I Seed is also calculated.

TABLE 47f

Monte Carlo calculated Anisotropy Function of the Best Model 2301 I$^{125}$ Seed in Solid Water for Radial Distances of 6 cm. A comparison between calculated values of the Best Model 2301 $^{125}$I Seed is also calculated.

| Angle | AF at 6 cm | Best Model 2301 $^{125}$I Seed | Error |
|---|---|---|---|
| 0 | 0.950859 | 0.961176 | −0.022944 |
| 5 | 0.867337 | 0.869443 | −0.014529 |
| 10 | 0.751525 | 0.754599 | −0.011077 |
| 15 | 0.770497 | 0.77439 | −0.00544 |
| 20 | 0.754274 | 0.754773 | −0.006819 |
| 25 | 0.866324 | 0.868662 | −0.0105 |
| 30 | 0.829422 | 0.82609 | −0.002317 |
| 35 | 0.868055 | 0.864491 | 0.004942 |
| 40 | 0.853435 | 0.85658 | −0.009617 |
| 45 | 0.892122 | 0.878697 | 0.012354 |
| 50 | 0.862775 | 0.853307 | 0.011458 |
| 55 | 0.939576 | 0.938518 | 0.00066 |
| 60 | 0.918693 | 0.912431 | −0.00219 |
| 65 | 1.016373 | 1.005409 | 0.012434 |
| 70 | 0.97542 | 0.962483 | 0.012918 |
| 75 | 0.988762 | 0.972179 | 0.005505 |
| 80 | 1.035533 | 1.025741 | 0.013729 |
| 85 | 0.997364 | 0.987695 | 0.006542 |
| 90 | 1 | 1 | 0 |

FIG. 76 illustrates the Anisotropy Function of Monte Carlo calculated value for Thermobrachytherapy Seed#2 and the Monte Carlo calculated for the Best Model 2301 $^{125}$I in Solid Water at 6 cm radii. The plot is fitted with a 6th order polynomial function.

Table 47g illustrates the Monte Carlo calculated Anisotropy Function of the Best Model 2301 $^{125}$I Seed in Solid Water for Radial Distances of 7 cm. A comparison between calculated and book values of the Best Model 2301 $^{125}$I Seed is also calculated.

TABLE 47g

Monte Carlo calculated Anisotropy Function of the Best Model 2301 I$^{125}$ Seed in Solid Water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 0 | 1.098314 | 1.106333 | −0.00725 | 0.888 | 0.23684 |
| 5 | 0.851477 | 0.855329 | −0.0045 | | |
| 10 | 0.955089 | 0.96212 | −0.00731 | 0.751 | 0.271757 |
| 15 | 0.862468 | 0.860677 | 0.00208 | | |
| 20 | 0.905488 | 0.907204 | −0.00189 | 0.82 | 0.104253 |
| 25 | 0.93776 | 0.933333 | 0.004743 | | |
| 30 | 0.932488 | 0.944759 | −0.01299 | 0.905 | 0.030373 |
| 35 | 0.913629 | 0.904032 | 0.010617 | | |
| 40 | 1.010313 | 1.018978 | −0.0085 | 0.952 | 0.061253 |
| 45 | 1.093958 | 1.095808 | −0.00169 | | |
| 50 | 0.998124 | 1.006513 | −0.00833 | 0.972 | 0.026877 |
| 55 | 1.1273 | 1.133607 | −0.00556 | | |

TABLE 47g-continued

Monte Carlo calculated Anistropy Function of the Best Model 2301 I$^{125}$ Seed in Solid Water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 60 | 1.091075 | 1.091072 | 2.4E−06 | 1.004 | 0.086728 |
| 65 | 1.191029 | 1.189276 | 0.001474 | | |
| 70 | 0.99379 | 0.984267 | 0.009675 | 0.999 | −0.005215 |
| 75 | 1.095348 | 1.061721 | 0.031671 | | |
| 80 | 1.109199 | 1.096051 | 0.011996 | 1.015 | 0.092806 |
| 85 | 1.146705 | 1.141173 | 0.004848 | | |
| 90 | 0.999979 | 0.999979 | 1.11E−16 | 1 | −2.1E−05 |

FIG. 77 illustrates the Anisotropy Function of Monte Carlo calculated value for Thermobrachytherapy Seed#2 and the Monte Carlo calculated for the Best Model 2301 $^{125}$I in Solid Water at 7 cm radii. The plot is fitted with a 6th order polynomial function FIG. 78 illustrates the Anisotropy Function of Monte Carlo calculated value for Thermobrachytherapy Seed#2 and the Book value for the Best Model 2301 $^{125}$I in Solid Water at 7 cm radii. The plot is fitted with a 6th order polynomial function Average Anisotropy Function:

The average anisotropy function is taken by taking an average of the calculated anisotropy functions for all the angles. Table 48a illustrates the Average Anisotropy Constant calculated for radial distances of 1 cm in Solid Water.

TABLE 48a

Average Anisotropy Constant calculated for radial distances of 1 cm la Solid Water

| | 1 cm | Best Model 2301 $^{125}$I Seed | Error |
|---|---|---|---|
| Average Anisotropy Constant $\Phi_{an}$ (r) | 0.911 | 0.917 | −0.025 |

Table 48b illustrates the Average Anisotropy Function calculated for radial distances of 2 cm in Solid Water.

TABLE 48b

Average Anisotropy Function calculated for radial distances of 2 cm in Solid Water

| | 2 cm | Best Model 2301 $^{125}$I Seed | Error | Book Value (Meigooni et al) | Error |
|---|---|---|---|---|---|
| Average Anisotropy Constant $\Phi_{an}$ (r) | 0.885 | 0.898 | −0.014 | 0.975 | −0.092 |

Table 48c illustrates the Average Anisotropy Constant calculated for radial distances of 3 cm in Solid Water.

TABLE 48c

Average Anisotropy Constant calculated for
radial distances of 3 cm in Solid Water

| | 3 cm | Best Model 2301 $^{125}$I Seed | Error |
|---|---|---|---|
| Average Anisotropy Constant $\Phi_{an}$ (r) | 0.882 | 0.883 | −0.001 |

Table 48d illustrates the Average Anisotropy Constant calculated for radial distances of 4 cm in Solid water.

TABLE 48d

Average Anisotropy Constant calculated for
radial distances of 4 cm in Solid water

| | 4 cm | Best Model 2301 $^{125}$I Seed | Error |
|---|---|---|---|
| Average Anisotropy Constant $\Phi_{an}$ (r) | 0.925 | 0.928 | −0.002 |

Table 48e illustrates the Average Anisotropy Constant calculated for radial distances of 5 cm in Solid Water.

TABLE 48e

Average Anisotropy Constant calculated for
radial distances of 5 cm in Solid Water

| | 5 cm | Best Model 2301 $^{125}$I Seed | Error | Book Value (Meigooni et al) | Error |
|---|---|---|---|---|---|
| Average Anisotropy Constant $\Phi_{an}$ (r) | 0.940 | 0.950 | −0.0105 | 0.965 | −0.0259 |

Table 48f illustrates the Average Anisotropy Constant calculated for radial distances of 6 cm in Solid Water.

TABLE 48f

Average Anisotropy Constant calculated for
radial distances of 6 cm in Solid Water

| | 6 cm | Best Model 2301 $^{125}$I Seed | Error |
|---|---|---|---|
| Average Anisotropy Constant $\Phi_{an}$ (r) | 0.902 | 0.898 | −0.0045 |

Table 48g illustrates the Average Anisotropy Constant calculated for radial distances of 7 cm in Solid Water.

TABLE 48g

Average Anisotropy Constant calculated for
radial distances of 7 cm in Solid Water

| | 7 cm | Best Model 2301 $^{125}$I Seed | Error | Book Value (Meigooni et al) | Error |
|---|---|---|---|---|---|
| Average Anisotropy Constant $\Phi_{an}$ (r) | 1.017 | 1.01 | −0.004 | 0.977 | 0.04 |

The Source Anisotropy Constant was calculated where the Source Anisotropy Constant is calculated by taking the average of all the Average Anisotropy Constants.
[Note: there is no Table 49]

Table 50 illustrates the Source Anisotropy Function for the Source Anisotropy Constant is 0.923 and deviates from the Monte Carlo calculated Best Model 2301 $^{125}$I Seed by 0.3% and the Book value by 4.8%.

TABLE 50

Source Anisotropy Function for Thermobrachytherapy
Seed#2 in Solid Water

| | Calculated value | Best Model 2301 $^{125}$I Seed | Error | Book value | Error |
|---|---|---|---|---|---|
| Source Anisotropy Constant $\overline{\Phi_{an}}$ (r) | 0.923 | 0.926 | −0.003 | 0.97 | −0.048 |

Results
Dose Rate:

In liquid water, Best Model 2301 $^{125}$I seed has a dose rate of 0.237±4.84*10$^{-3}$ cGy*sec$^{-1}$*Ci$^{-1}$, thermobrachytherapy Seed#1 has a dose rate of 0.251±4.98*10$^{-3}$ cGy*sec$^{-1}$*Ci$^{-1}$ and thermobrachytherapy Seed#2 has a value of 0.248±4.99*10$^{-3}$ cGy*sec$^{-1}$*Ci$^{-1}$.

The percentage difference between thermobrachytherapy seed #1 and Best Model seed is 6.1%. Also, the percentage difference between thermobrachytherapy seed #2 and Best Model seed is 4.5%. The difference in percentages indicates that thermobrachytherapy seed#2 is closer to the Monte Carlo calculated value for Best Model 2301.

In Solid Water, Best Model has a dose rate of 0.231±4.78*10$^{-3}$ cGy*sec$^{-1}$*Ci$^{-1}$, thermobrachytherapy Seed#1 has a dose rate of 0.245±4.99*10$^{-3}$ cGy*sec$^{-1}$*Ci$^{-1}$ and thermobrachytherapy Seed#2 has a value of 0.241±4.89*10$^{-3}$ cGy*cm$^2$*sec$^{-1}$*Ci$^{-1}$.

The percentage difference between thermobrachytherapy seed #1 and Best Model seed is 6.0%. Also, the percentage difference between thermobrachytherapy seed #2 and Best Model seed is 4.23%.

It is to be noted that thermobrachytherapy seed#2 is closer to the dose rate calculated through Monte Carlo calculations for Best Model 2301.

Air Kerma Strength:

In liquid water, the air kerma strength obtained for the Best Model 2301 $^{125}$I seed is 0.224±4.98*10$^{-3}$ cGy*cm$^2$sec$^{-1}$*Ci$^{-1}$, the thermobrachytherapy seed #1 is 0.238±5.14*10$^{-3}$ cGy*cm$^2$ sec$^{-1}$*Ci$^{-1}$, and the thermobrachytherapy seed#2 is 0.234±5.1*10$^{-3}$ cGy*cm$^2$ sec$^{-1}$*Ci$^{-1}$.

The percentage difference between thermobrachytherapy seed #1 and Best Model seed is 6.0%. Also, the percentage difference between thermobrachytherapy seed #2 and Best Model seed is 4.3%.

It is to be noted that the percentage differences in liquid water are in good agreement with one another. The thermobrachytherapy seed#2 is closer than thermobrachytherapy seed#1 in terms of error percentage to the Monte Carlo calculations for the Best Model Seed.

In Solid Water, the air kerma strength obtained for Model 2301 $^{125}$I seed is 0.22±4.98*10$^{-3}$ cGy*cm$^2$sec$^{-1}$*Ci$^{-1}$, thermobrachytherapy seed #1 is 0.24±5.14*10$^{-3}$ cGy*cm$^2$*sec$^{-1}$*Ci$^{-1}$ and thermobrachytherapy seed#2 is 0.234±5.1*10$^{-3}$ cGy*sec$^{-1}$*Ci$^{-1}$.

The percentage difference between thermobrachytherapy seed #1 and Best Model seed is 6.0%. Also, the percentage difference between thermobrachytherapy seed #2 and Best Model seed is 4.3%. Like in liquid water, the percentage differences between the different seeds are in good agreement in Solid Water. The percentage difference with thermobrachytherapy seed#2 is closer to the Best Model measured value as opposed to the thermobrachytherapy seed#2.

Dose Rate Constant

In Liquid Water, the dose rate constant calculated for the Best model is $1.056\pm0.0055$ cGy*h$^{-1}$*U$^{-1}$ (Book value of 1.01: with a percentage difference of 4.6%). The value measured for thermobrachytherapy seed#1 $1.057\pm0.031$ cGy*h$^{-1}$U$^{-1}$, and thermobrachytherapy seed#2 is $1.058\pm0.031$ cGy*h$^{-1}$U$^{-1}$.

The value obtained for thermobrachytherapy Seed#1 varies by 0.091% from the calculated Best Model value and by 4.69% from Best Model book value. Continuing the comparison, the value obtained for thermobrachytherapy Seed#2 varies by 0.15% from the measured Best Model value and by 4.75% from Best Model book value.

It is to be noted that thermobrachytherapy seed#1 has a closer value to the calculated and the Book value for the Best Model 2301 Seed. In Solid Water, the dose rate constant calculated for the Best model is $1.03\pm0.031$ cGy*h$^{-1}$*U$^{-1}$ (Book value of 0.98: with a percentage difference of 5.1%). The value measured for thermobrachytherapy seed#1 $1.03\pm0.031$ cGy*h$^{-1}$U$^{-1}$ and thermobrachytherapy seeds#2 is $1.029\pm0.031$ cGy*h$^{-1}$*U$^{-1}$.

The value obtained for thermobrachytherapy Seed#1 varies by 0.01% from the measured Best Model value and by 5.1% from Best Model book value. The value obtained for thermobrachytherapy Seed#2 varies by 0.09% from the measured Best Model value and by 4.97% from Best Model book value. In Solid Water, both the seeds are relatively close to both the calculated Monte Carlo value and the Book value for the Best Model 2301 Seed. Thermobrachytherapy Seed#1 is closer to the calculated Best Model Value and Thermobrachytherapy Seed#2 is closer to the Best Model Book value.

Correction/Multiplicative Factor:

The Correction/Multiplicative Factor between the Solid Water and liquid water for the calculated Best Model 2301 $^{125}$I seed is 1.026 (Book Value of 1.05). Thermobrachytherapy Seed#1 has a factor of 1.026 and Thermobrachytherapy Seed#2 is 1.028.

Radial Dose Function:

Radial dose function was taken at 0.1 cm to 10 cm at 0.1 intervals to 1 cm and then a 0.5 cm interval to 10 cm. The figures for Radial functions can be compared and it shows superposition of the data points confirming good agreement between the measured value for Best Model and the book value. The radial function from the two brachytherapy seeds is further compared to the measured values and book values of the Best Model seed and again a good agreement is seen in the results. This is true for both the liquid water and solid water measurements. The data is fitted with a 5th order polynomial function.

Anisotropy Function

Anisotropy Function was calculated for all the three seeds in both Liquid and Solid Water. The function was calculated from 1 cm to 7 cm in 1 cm increments at 0°-90° at 10° increments. Similar to comparisons in the radial function, anisotropy function data points were superimposed confirming good agreement between the measured value for Best Model and the book value. The anisotropy function from the two brachytherapy seeds is further compared to the measured values and book values of the Best Model seed and again a good agreement is seen in the results. This is true for both the liquid water and solid water measurements. The data is fitted with a 6th order polynomial function. In liquid water, the Source Anisotropy Constant for Best Model 2301 Seed is 0.935, thermobrachytherapy seed#1 is 0.923 and thermobrachytherapy seed#2 is 0.927.

For the Best Model 2301, the value deviates by 4.6% from the Book value. The values for thermobrachytherapy seed#1 deviates from the Monte Carlo calculated Best Model 2301 $^{125}$I Seed by 1.28% and the Book value by 4.6%. Thermobrachytherapy seed#2 deviates from the Monte Carlo calculated Best Model 2301 $^{125}$I Seed by 0.8% and the Book value by 5.4%.

In analyzing the above results, it is to be noted that thermobrachytherapy seed#1 is closer to the Book value but thermobrachytherapy seed#2 is closer to the Monte Carlo calculated value for the Best Model 2301 seed in liquid water. In Solid Water, the Source Anisotropy Constant for Monte Carlo calculated Best Model 2301 Seed is 0.926. Thermobrachytherapy seed#1 has a value of 0.918 and thermobrachytherapy seed#2 has a value of 0.923. In terms of deviation, the Monte Carlo calculated Best Model seed deviates 4.5% from the book value for the same seed. Thermobrachytherapy seed#1 deviates from the Monte Carlo calculated Best Model 2301 $^{125}$I Seed by 0.08% and the Book value by 5.4%. Thermobrachytherapy seed#2 deviates from the Monte Carlo calculated Best Model 2301 $^{125}$I Seed by 0.3% and the Book value by 4.8%. It can be deciphered from the above results that, unlike the liquid water results, Thermobrachytherapy seed#1 is closer to the calculated Best Model 2301 seed values and Thermobrachytherapy seed#2 is closer to the Book Values.

CONCLUSIONS

The thermobrachytherapy seeds described herein exhibit a desired synergy between radiation and heat. The thermobrachytherapy seeds provide complementary treatment modalities, with brachytherapy killing oxygenated cells and hyperthermia killing hypoxic cells.

The thermobrachytherapy seeds have a ferromagnetic component along with the radioactive source to give concurrent treatments.

Two different thermobrachytherapy seeds were modeled with a Ni (70.4%)-Co (29.6%) ferromagnetic alloy. This alloy has a curie temperature of 48.2° C. and is appropriate around 50° C. Curie temperature (which is preferable for killing cancer cells and not overheating normal cells). The Ni—Cu alloy has a density of 8.92 g/cm$^3$ and is denser than bone. Therefore, it will be seen on films taken at kilo-voltage beams.

Thermobrachytherapy seed#1 has the radio-opaque Tungsten marker replaced by the nice alloy. Thermobrachytherapy seed#2 has the radio-opaque marker divided into three equal sections with one Tungsten marker in the middle and two outer Ni—Cu alloy sections. The results that are obtained are compared to both the Book values in the literature (Best Model 2301 $^{125}$I Seed) and measured Best Model 2301 $^{125}$I Seed, thus showing a two-fold comparison on how the thermobrachytherapy seeds can be favorably compared to Book values for radioactive seeds and also, to the measured values of the same seed.

When running the TG-43 factors in liquid water, the dose rate constant calculated for the Best model is $1.056\pm0.0055$ Gy*h$^{-1}$*U$^{-1}$ (Book value of 1.01: with a percentage difference of 4.6%).

Furthermore, the Dose Rate constant obtained for thermobrachytherapy Seed#1 (1.057±0.031 cGy*h$^{-1}$U$^{-1}$) varies by 0.091% from the measured Best Model value and by 4.69% from Best Model book value. Continuing the comparison, the value obtained for thermobrachytherapy Seed#2 (1.058±0.031 cGy*h$^{-1}$U$^{-1}$) varies by 0.15% from the measured Best Model value and by 4.75% from Best Model book value. The Solid Water measurements mirrored good agreement like in liquid water, the dose rate constant calculated for the Best model is 1.03±0.031 cGy*h$^{-1}$*U$^{-1}$ (Book value of 0.98: with a percentage difference of 5.1%). The value measured for thermobrachytherapy seed#1 1.03±0.031 cGy*h$^{-1}$U$^{-1}$ and thermobrachytherapy seeds#2 is 1.029±0.031 cGy*h$^{-1}$*U$^{-1}$.

The value obtained for thermobrachytherapy Seed#1 varies by 0.01% from the measured Best Model value and by 5.1% from Best Model book value. The value obtained for thermobrachytherapy Seed#2 varies by 0.09% from the measured Best Model value and by 4.97% from Best Model book value.

The Correction/Multiplicative Factor (conversion of dose rate constant) between the Solid Water and liquid water measurements for the calculated Best Model 2301 $^{125}$I seed is 1.026 (Book Value of 1.05). Thermobrachytherapy Seed#1 has a factor of 1.026 and Thermobrachytherapy Seed#2 is 1.028, which are in shows close agreement for both seeds.

The Radial Dose functions from the two thermobrachytherapy seeds are further compared to the measured values and book values of the Best Model seed and again a good agreement is seen in the results. This is evident in both liquid and Solid Water. Similar to comparisons in the radial function, anisotropy function data points were superimposed confirming good agreement between the measured value for Best Model and the book value. This extends to the data points for the thermobrachytherapy seeds #1 and #2 and the comparisons with the Best Model Seed (both measured and book values).

In liquid water, the Anisotropy Source Constant for Best Model Seed is 0.935 (deviates by 4.6% from the Book value), thermobrachytherapy seed#1 is 0.923 (deviates from calculated Best Model 2301 $^{125}$I Seed by 1.28% book value by 4.6%) and thermobrachytherapy seed#2 is 0.927 (deviates from calculated Best Model 2301 $^{125}$I Seed by 0.8% book value by 5.4%).

In Solid Water, the Anisotropy Source Constant for Best Model Seed is 0.926 (deviates by 4.5% from the Book value), thermobrachytherapy seed#1 is 0.918 (deviates from calculated Best Model 2301 $^{125}$I Seed by 0.08% book value by 5.4%) and thermobrachytherapy seed#2 is 0.923 (deviates from calculated Best Model 2301 $^{125}$I Seed by 0.3% book value by 4.8%).

The Anisotropy Source Constant is in good agreement for the two brachytherapy seeds #1 and #2 with both the Book value and measured value for the Best Model 2301 $^{125}$I Seed. This is true for both liquid and Solid Water data.

Analyzing the data, there is very little difference between thermobrachytherapy seed#1 and thermobrachytherapy seed#2 in comparison to one another. The data between the two thermobrachytherapy seeds is very comparable. Also, the results are quite similar, in terms of error percentage, between the Book values and measured value for the Best Model 2301 $^{125}$I Seed. It is also important to note that the thermobrachytherapy seed's TG-43 factors have not deviated too much from the established data on the Best Model Seed. This ensures that the radio-activity from the thermobrachytherapy seed is still established and there is no loss of activity around the thermobrachytherapy seed.

Prior Art FIG. 79 is a schematic top plan view of a Prior Art flat plate where a middle of the plate has a fairly larger temperature profile than the temperature profile of the peripheral areas of the plate. When such plate is used, however, the hyperthermia treatment can only be started during the last hour of brachytherapy. Referring now to FIG. 80, there is shown a schematic illustration of an embodiment where a dual-seed system 10 has an inner section 12 that is made of one or more magnetic materials. One non-limiting example of a magnetic material is Ni—Co, which is a ferromagnetic material with a curie temperature of 48.2° C. The dual-seed system 10 has at least one outer layer 14. The outer layer can be comprised on a material that is compatible with the human body. Non-limiting examples include that platinum, platinum alloys, or platinum-like materials.

Example 2

The thermo-brachytherapy seed described herein is especially useful for the treatment of prostate cancer.

This particular seed has several advantages over the existing approach of delivering the two modalities through separate implants.

The combination of I-125 and the ferromagnetic materials in a single seed can reduce trauma to the tissues compared to a circumstance where additional seeds are separately placed for magnetic heating. Already a typical prostate implant requires the placement of 80 to 100 seeds through 16-25 needles. Additional seeds just for heating would require additional trauma which can be avoided by the proposed design and use of a single seed providing both continuous gamma radiation and sensitizing heating when placed in a magnetic field.

The spacing of seeds for radioactive implant is generally about 1 cm apart. In an average implant designed to cover a volume of 30 to 40 cc, a total of about 80 seeds are typically used. With the Curie point of the alloy selected, such close spacing of the thermo-brachytherapy seed can give homogeneous heating and obviate the need for invasive thermometry. In this fashion, the patient can be spared additional trauma for the insertion of invasive thermometry. Since heating sessions will be multiple, the patient can be spared repeat trauma by the avoidance of interstitial thermometry and by the use of multiple seeds, all responding to the magnetic heating with a characteristic temperature generated which is a function of the alloy employed and the strength of the magnetic field.

Additional advantages of the combined function seed may be realized for patients who fail radiation and become resistant to hormonal manipulations, that are not at this time good choices for systemic cytotoxic chemotherapy. Response rates to chemotherapy are known to be very poor in prostate cancer. Hyperthermia has been shown to enhance the effects of at least some cytotoxic drugs. Drugs whose effects are known to be enhanced by heating include common agents Cisplatin, Adriamycin, Melphalan, Cyclophosphamide, and Vincristine. While not wishing to be bound by theory, the inventors herein believe that the mechanisms include: 1. Increased rates of alkylation; 2. Inhibition of repair of single strand DNA breaks; and 3. Enhanced drug uptake.

In certain treatment modalities, the seeds can remain in patient permanently, even after all radiation has been delivered by decay of the radioisotope. The seeds will maintain their heat producing characteristics and be readily available for fractionated heat treatments during cytotoxic chemotherapy.

In addition, a technical advantage is gained in post-implant CT verification since current techniques in post implant CT dosimetry requires identification of the exact locations of implanted seeds through CT imaging to verify adequate radiation dose distribution within the tumor volume. The post implant CT image of the patient anatomy is loaded into treatment planning system in order to project the resultant dose cloud in target volume and nearby critical structures, and to verify that prescribed dose sufficiently covers the planning target volume. If coverage is suboptimal, decision could be made in providing additional treatment if necessary.

In certain embodiments, the targeted range of temperatures needed for achievement of malignant cell apoptosis is between about 42 and about 46° C. A desired number of seeds are placed within the tumor volume, insuring uniform distribution of radiation and thermal fields, and producing approximately additive heating effect. The temperature increase produced by one seed was set lower than the targeted range for cell apoptosis. To achieve uniform isothermal distribution within the targeted volume, the therapeutic temperatures can be tunable based on the number of seeds used during the treatment, their locations, coil diameter, the amount of current through the induction coil and the frequency of the electro-magnetic field. See FIG. 81 which shows a temperature distribution (in ° C.) at the seed middle point for different frequencies of EM field.

Example 3

The thermo-brachytherapy seed combines a sealed radioactive source with a ferromagnetic core serving as a self regulating hyperthermia source when placed in an alternating electromagnetic field. The implantation of such a seed permits a radiation dose as presently commonly employed with permanent seed brachytherapy with the advantage of employing the same seed as a source for a series of radio-sensitizing hyperthermia sessions. Since the radiation is continuously released via the decay mechanism of the radioactive seed, the problem of time lapse between the two separate modalities is avoided. Moreover, the implanted seeds can be used for thermal re-treatment of the tumor in case of recurrence possibly as a sensitizer to systemic therapies without another invasive procedure.

In a method for the treatment of prostate cancer, internal radiation therapy, also known as interstitial implantation or brachytherapy is a treatment modality of choice for early stage prostate cancer or boost to external radiation. This method uses small (~0.5 cm) sealed radiation sources, implanted directly into the prostate gland and has the advantage of delivering a high dose of radiation to tumor tissues in the immediate area, minimizing damage to healthy nearby organs, such as the rectum and bladder. The following benefits compared to surgery or external beam radiation can be identified: less invasive, has fewer side effects, takes less time to perform, requires less time in the hospital, and finally, is less costly than either of the above therapies.

In broad terms it involves placing microscopic magnetic particles or macroscopic seeds within solid tumor tissue and subsequent application of alternating electro-magnetic (EM) field, causing heating via hysteretic loss, and/or induction of Eddy currents. This technique can be useful to address some of the shortcomings of other hyperthermia methods, in particular, achieving better temperature uniformity through relatively uniform placement of the particles or seeds, serving as heat sources in the targeted tissue. Complex invasive thermometry and feedback loops can be avoided via self-regulation of the heating in particles/seeds with the Curies temperature in the upper range of hyperthermia-relevant temperature interval. When magnetic material heats up to its Curies temperature, the second order phase transition occurring in the material causes drastic change in magnetic permeability and consequent decrease in response to the alternating EM field, preventing overheating.

In certain embodiments, the thermo-brachytherapy seeds can have cylindrical shape and are of the order of 1 mm in diameter and 1 to 7 cm in length, made of various alloys, including Ni—Cu, Fe—Pt, and Pd—Co, having Curie temperatures in a therapeutic range. The seeds are surgically placed in a regular pattern into malignant tissue under radiologic or ultrasound visual guidance, a procedure very similar to that of the interstitial radiation therapy.

Combining heating and radioactive properties into the one thermo-brachytherapy seed can thus provide local tumor control with minimized side effects and maximized treatment cost reduction.

Dosimetric characteristics of low-energy sources, such as $^{125}$I are very sensitive to the details of internal structure and encapsulating geometry of the seed due to self-absorption and filtration effects.

A standard radioactive interstitial implant models, BEST seed model 2301 $^{125}$I is schematically illustrated in FIG. 82A—Prior Art and has a solid tungsten core, serving as radiographic marker, coated by organic carbon layer impregnated with radioactive $^{125}$I.

FIG. 82B is a schematic illustration of a thermo-brachytherapy seed disclosed herein where a ferromagnetic material is used in place of the tungsten marker core and is expanded to fill the whole capsule. The ferromagnetic material is capable of producing heat when subjected to external alternating magnetic field. The thermo-brachytherapy seed can have an outer titanium capsule.

One advantage of thermo-brachytherapy seed is the temperature self-regulation, allowing the power production in the ferromagnetic material to "shut off" once the Curie temperature is reached, thus preventing the seed from overheating without a need for complicated feedback system. Non-limiting examples of useful materials having suitable Curie temperatures in the desirable therapeutic range include a nickel-copper (Ni—Cu) alloy, consisting of 70.4% Ni and 29.6% copper by weight, and a palladium-cobalt (Pd—Co), with concentrations of 93%-7% correspondingly.

Also, in certain embodiments, the targeted range of temperatures needed for achievement of malignant cell apoptosis is between 42C and 46C. From the physics prospective the magnetically mediated heat induction process can be divided in two parts: induction of Eddy and hysteretic currents in the ferromagnetic core under alternating electromagnetic field, and transfer of the induced heat from the core to the tumor cells.

As the first approximation we consider axially symmetrical 2D problem setup shown in FIG. 83. A seed is placed in the middle of a cylindrical water phantom surrounded by air, with an induction coil wrapped around the phantom.

A system of two equations, Ampere's law for vector potential $\vec{A}$ and heat conduction equation, governing the process, are simplified for the case of axial symmetry, since electric field $\vec{E} = -\partial \vec{A}/\partial t$ is present only in azimuthal direction:

$$(i\omega\sigma - \omega^2\varepsilon)\vec{A} + \nabla \times (\mu^{-1}\nabla \times \vec{A}) = 0$$

$$\rho C_P \frac{\partial T}{\partial t} - \nabla \cdot k\nabla T = Q(T, \vec{A})$$

Here time average of the inductive heating over one period $Q = \frac{1}{2}\sigma|\vec{E}|^2$ ω is frequency, σ—electric conductivity, ε and μ—electric permittivity and magnetic permeability, ρ—density, T—temperature, $C_P$—specific heat capacity, k—thermal conductivity.

The system is solved with appropriate boundary conditions in order to obtain a steady-state solution for a whole set of the system parameters.

FIG. 83 shows a model layout and resulting magnetic field distribution for 1 seed with ferromagnetic cores in alternating electro-magnetic field of w=100 kHz. The magnetic field distribution in the system points out to significant reduction in the strength of the field near the seed. This effect is taken into account when deciding on field parameters; efficient close coupling of the ferromagnetic core and a coil is not practically implemental as the distance is dictated by body anatomy.

Temperature distribution is shown in FIG. 84 for the frequency of 100 kHz. Self-regulation is implemented through temperature dependence of magnetic permeability μ of the ferromagnetic core material. The modeled temperature distribution (in ° C.) near the seed with ferromagnetic self-regulating core.

The processes of blood perfusion set a natural characteristic length that can be estimated for typical resting muscle as $$R_0 = \sqrt{\frac{K}{m\rho\rho_b C_b}} \sim 5 \text{ cm},$$

where m is volumetric blood flow per unit mass of tissue, ρ is the density of tissue, $\rho_b$ is the density of blood, $C_b$ is specific heat of blood and K is the thermal conductivity of tissue. $R_0$ has the meaning of temperature screening length, so that at distances smaller than $R_0$ from the seed the heat transfer is determined by thermal conduction and the temperature decays rather slowly (~1/r), while the blood perfusion dominates the heat transfer for $r>R_0$ and the temperature perturbation decays exponentially ($\sim e^{(-r/R0)}$).

In case of many seeds placed in the region $r<R_0$ their heating effects are approximately additive (not screened by blood perfusion). Therefore the preliminary estimate of temperature increase will be proportional to the number of seeds. As shown in FIG. 84, the seed is capable of producing enough heat to reach the therapeutic temperature range in the surrounding tissue. As the neighboring seed is often placed at a distance of about 1 cm, the effect of a system of heat sources will result in the desirable temperature distribution.

Also, in certain embodiments, different radionuclides such as I-125, Pd-103, Cs-131, and Au-198 can be used. The range of activities for seeds, total radiation delivered, and a reasonable range for total dose are as the following: I-125; 0.25-0.5 mCi and average radiation dose=145 Gy; Range from 100 Gy-180 Gy; Pd-103; 1.1-1.5 mCi, and average radiation for treatment=124 Gy; Range 85-150 Gy; and, Cs-131; activity similar as Pd-103; Average radiation dose=115 Gy; Range 80-145 Gy.

In certain embodiments, the radioactive material comprises one or more of I-125, Pd-103, Cs-131, or other radionuclides with similar half life and energy range.

In other embodiments, patients suffering from one or more cancers, such as, but not limited to: prostate, uterine, vaginal, uveal cancers, melanoma, or any solid tumor can be treated as described herein.

Example 4

In another aspect, there is provided herein a thermo-brachytherapy system for the treatment of a subject. The system generally includes an implantable medical seed or device that has a body having at least one outer surface. The implantable medical seed includes one or more magnetic energy-emitting elements configured to at least intermittently deliver a therapeutic dose of heat to at least a portion of tissue proximate the at least one outer surface of the implantable medical device. Also, the implantable medical seed includes one or more radiation-emitting elements configured to deliver a therapeutic dose of radiation to at least a portion of tissue proximate the at least one outer surface of the implantable medical device.

The system further includes a controller configured to apply an electro-magnetic or magnetic field to the one or more implantable medical devices. In certain embodiments, the system can include the one or more energy-emitting elements that are configured to provide a sensitizing heat pattern comprising one or more of: a region of tissue treated, intensity of magnetic energy, an ON-pulse duration, an OFF-pulse duration, and pulse frequency.

Also, in certain embodiments, the one or more magnetic energy-emitting elements can be operable to emit a sufficient amount of electromagnetic radiation to increase the temperature of at least a portion of the tissue proximate the at least one outer surface of the implantable medical device by about 5° C. to about 20° C. The seed can be a temperature self-regulating, allowing the power production in the magnetic material to "shut off" once a desired Curie temperature is reached, thus preventing the seed from overheating without a need for complicated feedback system.

FIG. 85 is a schematic illustration of a thermo-brachytherapy system having a Function Generator, a RF (Radio Frequency) Amplifier, an Electromagnetic Coil, a Fiber optic Temperature sensor and data collector, an oscilloscope, and a computer.

The function generator has the ability to produce several types of waves (sine, square, and triangle), with a wide range of frequencies ranging from 0.5 Hz to 5 MHz, with variable voltage control from 0V to 7V.

The RF Amplifier is a RF Power Amplifier. This is a 2000W amplifier, and would allow frequencies from 1 kHz to 500 kHz. The AC magnetic field induction system can be designed to have a desired coil diameter. Also, the AC magnetic field induction system can be configured to include a desired power supply and cooling components.

The inventors herein have determined that, due to the fact that standard thermocouples rely on current induction in dissimilar metals due to temperature gradients, and the fact that magnetic fields also induce current in conductors, it is not possible to use a standard thermocouple for temperature measurements. The magnetic field would induce the probe heating leading to incorrect readings. A Fiber optic temperature sensor, and data collector are used, such as Neoptix T1 optical temperature sensor, and a Nomad fiber optic portable thermometer, which has the capabilities of reading temperatures with an accuracy of ±0.5° C. Also, this device can be connected directly to the computer, and temperature and time values can be recorded.

In certain embodiments, it may be desirable to monitor in heat dissipation from the seeds due to physical movement of the blood, and related increase in blood flow in response to heat in a living organism. Also, fiber optic temperature sensors can be used to provide temperature readings at several points. Also, infrared thermal camera can be used for non-invasive real-time two-dimensional temperature assessment.

From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature referred to in this specification, are expressly incorporated by reference herein.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A thermobrachytherapy seed, comprising:
a seed having within an interior space thereof a magnetic material and at least one layer of radiation emission material that completely surrounds the magnetic material,
wherein the radiation emission material comprises one or more of I-125, Pd-103, or Cs-131 radionuclides,
wherein the radiation emission material has an activity in a range of from about 0.20 millicurie to about 0.5 millicurie,
wherein the seed exhibits a Curie point in a therapeutic range of from about 40° C. to about 60° C., and
wherein no void exists between the magnetic material within the interior space of the seed and the at least one layer of the radiation emission material.

2. The thermobrachytherapy seed of claim 1, wherein the magnetic material comprises one or more of a Ni (70.4%)-Co (29.6%) alloy or a Pd (93%)-Co (7%) palladium-cobalt (Pd—Co) alloy or a nickel-copper (Ni—Cu) alloy having 70.4% Ni and 29.6% copper by weight.

3. A system, comprising:
one or more implantable medical seeds, each implantable medical seed of the one or more implantable medical seeds including a body having an interior space and having at least one outer surface;
one or more magnetic energy-emitting elements comprising a magnetic material positioned within the interior space of each said implantable medical seed, the one or more magnetic energy-emitting elements configured to at least intermittently deliver a therapeutic dose of heat to tissue proximate to the at least one outer surface of each said implantable medical seed; and
one or more radiation-emitting elements positioned within the interior space of each said implantable medical seed, the one or more radiation-emitting elements forming at least one layer that completely surrounds the one or more magnetic energy-emitting elements positioned within the interior space of each said implantable medical seed, the one or more radiation-emitting elements configured to deliver a therapeutic dose of radiation to tissue proximate to the at least one outer surface of each said implantable medical seed,
wherein no void exists between the magnetic material within the interior space of each said implantable medical seed and the one or more radiation-emitting elements, and
wherein the system is adapted to include a controller configured to apply an electro-magnetic or magnetic field to the one or more implantable medical seeds.

4. The system of claim 3, wherein the one or more magnetic energy-emitting elements are configured to provide a sensitizing heat pattern comprising one or more of a region of tissue treated, intensity of magnetic energy, an ON-pulse duration, an OFF-pulse duration, and pulse frequency.

5. The system of claim 3, wherein the one or more magnetic energy-emitting elements are operable to emit an amount of electromagnetic radiation to increase a temperature of at least a portion of the tissue proximate to the at least one outer surface of each said implantable medical seed by at least one of a temperature of about 5° C. to about 20° C. or a temperature of between 42° C. and 46° C.

6. The system of claim 3, wherein each said implantable medical seed is temperature self-regulating, allowing a shut off of power production in the magnetic material comprising the one or more magnetic energy-emitting elements once a Curie temperature corresponding to the shut off of the power production is reached, wherein overheating of the one or more implantable medical seeds is substantially prevented.

7. The system of claim 3, wherein the one or more radiation-emitting elements comprise radiation emission material having an activity in a range of from about 0.2 millicurie to about 0.5 millicurie.

8. The system of claim 3, wherein the one or more radiation-emitting elements comprise radiation emission material including one or more of I-125, Pd-103, or Cs-131 radionuclides.

9. The system of claim 3, wherein each said implantable medical seed has at least one outer layer at least partially composed of platinum or platinum-like materials.

10. The system of claim 3, wherein each said implantable medical seed exhibits a Curie point in a therapeutic range between about 40° C. and about 60° C.

11. The system of claim 3, wherein the magnetic material comprises one or more of: a Ni (70.4%)-Co (29.6%) alloy or a Pd (93%)-Co(7%) palladium-cobalt (Pd—Co) alloy or a nickel-copper (Ni—Cu) alloy having 70.4% Ni and 29.6% copper by weight.

12. The thermobrachytherapy seed of claim 1, wherein the at least one layer of the radiation emission material comprises carbon containing $^{125}$I.

13. The system of claim 3, wherein the at least one layer of the one or more radiation-emitting elements comprises carbon containing $^{125}$I.

14. The thermobrachytherapy seed of claim 1, wherein the thermobrachytherapy seed is completely enclosed within a capsule.

15. The thermobrachytherapy seed of claim 14, wherein the capsule further comprises an inner capsule and an outer capsule that enclose the thermobrachytherapy seed.

16. The thermobrachytherapy seed of claim 14, wherein the capsule comprises a Titanium material.

17. The thermobrachytherapy seed of claim 1, wherein the thermobrachytherapy seed comprises an outer layer comprised of a material that is compatible with a human body.

18. The thermobrachytherapy seed of claim 1, wherein the at least one layer of the radiation emission material comprises a coating of the radiation emission material.

19. The system of claim 3, wherein each said implantable medical seed is completely enclosed within a capsule.

20. The system of claim 3, wherein each said implantable medical seed further comprises an inner capsule and an outer capsule that enclose the implantable medical seed.

21. The system of claim 3, wherein each said implantable medical seed is enclosed within a capsule comprising a Titanium material.

22. The system of claim 3, wherein the one or more radiation-emitting elements comprise a coating of radiation emission material.

23. A thermobrachytherapy seed, comprising:
   a seed, the seed including a body, the body having an outer surface and having an interior space, the interior space being completely surrounded by the outer surface of the body;
   magnetic material positioned within the interior space of the body;
   at least one layer of radiation emission material located within the interior space of the body, the at least one layer of the radiation emission material completely surrounding the magnetic material within the interior space of the body; and
   wherein no void exists between the magnetic material within the interior space of the body and the at least one layer of the radiation emission material.

24. The thermobrachytherapy seed of claim 23, wherein the at least one layer of the radiation emission material comprises a coating of the radiation emission material.

* * * * *